US011884978B2

(12) United States Patent
Brandon et al.

(10) Patent No.: US 11,884,978 B2
(45) Date of Patent: Jan. 30, 2024

(54) PATHOGEN BIOMARKERS AND USES THEREFOR

(71) Applicant: ImmuneXpress Pty Ltd, Boonah (AU)

(72) Inventors: Richard Bruce Brandon, Boonah (AU); Brian Andrew Fox, Seattle, WA (US); Leo Charles McHugh, Seattle, WA (US); Dayle Lorand Sampson, Seattle, WA (US)

(73) Assignee: IMMUNEXPRESS PTY LTD, Boonah (AU)

( * ) Notice: Subject to any disclaimer, the term of this patent is extended or adjusted under 35 U.S.C. 154(b) by 426 days.

(21) Appl. No.: 15/765,162

(22) PCT Filed: Sep. 30, 2016

(86) PCT No.: PCT/AU2016/050927
§ 371 (c)(1),
(2) Date: Mar. 30, 2018

(87) PCT Pub. No.: WO2017/054058
PCT Pub. Date: Apr. 6, 2017

(65) Prior Publication Data
US 2018/0305760 A1  Oct. 25, 2018

(30) Foreign Application Priority Data
Sep. 30, 2015 (AU) .................. 2015903986

(51) Int. Cl.
*C12Q 1/6883* (2018.01)
*G01N 33/68* (2006.01)
*C12Q 1/70* (2006.01)

(52) U.S. Cl.
CPC .......... *C12Q 1/6883* (2013.01); *C12Q 1/70* (2013.01); *C12Q 1/701* (2013.01); *G01N 33/6893* (2013.01); *C12Q 2600/106* (2013.01); *C12Q 2600/158* (2013.01); *G01N 2800/26* (2013.01)

(58) Field of Classification Search
None
See application file for complete search history.

(56) References Cited

U.S. PATENT DOCUMENTS

| | | |
|---|---|---|
| 2001/0051344 A1 | 12/2001 | Shalon et al. |
| 2004/0097460 A1 | 5/2004 | Ivey et al. |
| 2008/0070235 A1 | 3/2008 | Russwurm et al. |
| 2008/0286763 A1 | 11/2008 | Russwurm et al. |
| 2010/0068147 A1 | 3/2010 | Hibberd et al. |
| 2011/0076685 A1 | 3/2011 | Moeller et al. |
| 2011/0318738 A1 | 12/2011 | Jones et al. |
| 2015/0086570 A1 | 3/2015 | Violette et al. |
| 2018/0321242 A1 | 11/2018 | Brandon et al. |

FOREIGN PATENT DOCUMENTS

| | | |
|---|---|---|
| WO | WO 2012/174282 A2 | 12/2012 |
| WO | WO 2013/117746 A1 | 8/2013 |
| WO | WO 2014/201516 A2 | 12/2014 |
| WO | WO 2014/209238 | 12/2014 |
| WO | WO 2015/117204 A1 | 8/2015 |
| WO | WO 2015/121605 | 8/2015 |

OTHER PUBLICATIONS

Enard et al. (Science 2002 vol. 296 p. 340) (Year: 2002).*
Cobb et al (Crit Care Med 2002 vol. 30 p. 2711) (Year: 2002).*
Hu X. et al., 'Gene expression profiles in febrile children with defined viral and bacterial infection', Proceedings of the National Academy of Sciences of the United States of America. (2013), vol. 110, No. 31, pp. 12792-12797, 6 pages.
International Search Report dated Feb. 14, 2017, for PCT/AU2016/050927, 12 pages.
International Search Report and Written Opinion dated Feb. 27, 2017, for PCT/AU2016/051052, 24 pages.
Jamehdar S.A. et al., 'Herpes Simplex Virus Infection in Neonates and Young Infants with Sepsis', Iran Red Crescent Medical Journal. (2014), vol. 16, No. 2, article e14310.
Johnson S.B. et al., "Gene Expression Profiles Differentiate Between Sterile SIRS and Early Sepsis," Annals of Surgery. (2007), vol. 245, No. 4, pp. 611-621, 11 pages.
Kawada J. et al., 'Evaluation of Systemic Inflammatory Responses in Neonates with Herpes Simplex Virus Infection', The Journal of Infectious Diseases. (2004), vol. 190, pp. 494-498, 12 pages.
Kumar, S. et al., "Detection of 11 Common Viral and Bacterial Pathogens Causing Community-Acquired Pneumonia or Sepsis in Asymptomatic Patients by Using Multiplex Reverse Transcription-PCR Assay with Manual (Enzyme Hybridization) or Automated (Electronic Microarray) Detection," Journal of Clinical Microbiology. (2008), vol. 46, No. 9, pp. 3063-3072, 10 pages.
McHugh, Leo, et al. "A molecular host response assay to discriminate between sepsis and infection-negative systemic inflammation in critically ill patients: discovery and validation in independent cohorts." PLoS Med (2015); 12.12: e1001916, 35 pages.
Nagamori et al., "Sequential changes in pathophysiology of systemic inflammatory response in a disseminated neonatal herpes simplex virus (HSV) infection," Journal of Clinical Virology, 53 (2012) 265-267.
Parnell G.P. et al., "A distinct influenza signature in the blood transcriptome of patients with severe community-acquired pneumonia," Critical Care. (2012), vol. 16, 12 pages.

(Continued)

Primary Examiner — Katherine D Salmon
(74) Attorney, Agent, or Firm — Casimir Jones, S.C.; Mary Ann D. Brow

(57) ABSTRACT

Disclosed are compositions, methods and apparatus for diagnosing and/or monitoring a virus-associated systemic inflammation by measurement of a host immune response. The invention can be used for diagnosis including early diagnosis, monitoring, making treatment decisions, or management of subjects suspected of having systemic inflammation associated with an infection. More particularly, the present disclosure relates to peripheral blood RNA and protein biomarkers that are useful for specifically distinguishing between the host systemic immune response to viruses as compared to the host immune response to other causes of systemic inflammation.

13 Claims, 20 Drawing Sheets
Specification includes a Sequence Listing.

(56) References Cited

OTHER PUBLICATIONS

RayBiotech, 'RayBio® Label-based (L-Series) Human Antibody Array 1000 Membrane Kit: A combination of Human L-507 and Human L-493 Arrays—User Manual', (Feb. 2014) [online], [retrieved from the internet Feb. 20, 2017] <URL: http://www.raybiotech.com/files/manual/Antibody-Array/AAH-BLM-1000.pdf > pp. 15, 16, 18, 19.
Rendon-Ramirez E.J. et al., "TGF-ß Blood Levels Distinguish Between Influenza A (H1N1)pdm09 Virus Sepsis and Sepsis due to other Forms of Community-Acquired Pneumonia," Viral Immunology. (Jun. 2015), vol. 28, No. 5, pp. 248-254., 7 pages.
Tsalik E.L. et al., "An integrated transcriptome and expressed variant analysis of sepsis survival and death," Genome Medicine. (2014), vol. 6, article 111, 15 pages.
Tudor S. et al., "Cellular and Kaposi's sarcoma-associated herpes virus microRNAs in sepsis and surgical trauma," Cell Death and Disease. (2014), vol. 5, 10 pages.
Walton, A.H. et al., "Reactivation of Multiple Viruses in Patients with Sepsis," PLOS One. (2014), vol. 9, 13 pages.
Sampson D.L. et al., "A Four-Biomarker Blood Signature Discriminates Systemic Inflammation Due to Viral Infection Versus Other Etiologies," Scientific Reports, vol. 7, No. 2914, 2007. (18 pges).
Caraguel et al., "Selection of a cutoff value for real-time polymerase chain reaction results to fit a diagnostic purpose: analytical and epidemiologic approaches," J Vet Diagn Invest, 23:2-15 (2011).
Sampson D.L. et al., "A Four-Biomarker Blood Signature Discriminates Systemic Inflammation Due to Viral Infection Versus Other Etiologies," Scientific Reports, vol. 7, No. 2914, Jun. 6, 2017, 61 pages.

* cited by examiner

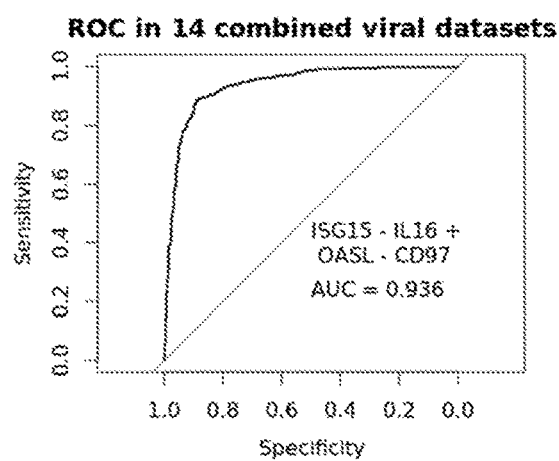 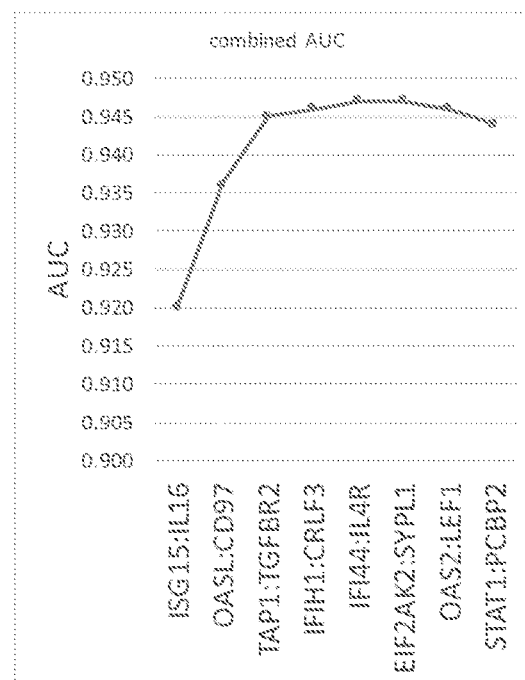
FIGURE 7
FIGURE 8

PATIENT REPORT

Immunexpress

SeptiCyte® Viral

| Patient Name | Medical Report # | Blood Collection Date | Sample ID |
|---|---|---|---|
| Jane Doe | 1000000 | 28-Jul-2014 | IXP100000 |

Score: 6 (0 – 5 – 10)

Score Interpretation Bands

| BAND | LIKELIHOOD | RATIO |
|---|---|---|
| Band 1 | Virus <10% likely | 0.05 |
| Band 2 | Virus >40% likely | 0.46 |
| Band 3 | Virus >80% likely | 6 |
| Band 4 | Virus >90% likely | 9 |

Probability of Viral Infection
>80%
73-86% (80% CI)

TEST DESCRIPTION:
The SeptiCyte® Viral test is an aid in the diagnosis of an active viral infection in patients with signs and symptoms consistent with local or systemic response to viral infections. Increasing values of the SeptiCyte® Viral Score is associated with an increased likelihood that systemic inflammation is attributable to an active viral infection and relative to other causes. The SeptiCyte® Viral Score is a quantitative blood test that combines the results of four RNA transcripts (ISG15, IL16, OASL and CD97) as a single numerical Patient Score.

TEST RESULT INFORMATION:
The SeptiCyte® Viral test should only be used in patients when active viral infection is suspected. Individual patient values should be interpreted only in the context of all other clinical and laboratory information.

LIMITATIONS:
The reported probability of a virus infection for the SeptiCyte® Viral test was determined in a sample of XX European and US patients aged – X assessed for herpes virus infection. Patients were classified by retrospective physician assessment in conjunction with specific virus detection or antibody assays (PCR, serum IgG, IgM).

ACTUAL PATIENT SCORE IN RELATION TO HISTORICAL DATA

PHYSICIAN COMMENTS:

Immunexpress
425 PONTIUS AVE N, SUITE 430
SEATTLE, WA 98104
P: 206.273.7975
www.immunexpress.com

FIGURE 12

PATHOGEN BIOMARKERS AND USES THEREFOR

FIELD OF THE INVENTION

This application is a U.S. national phase application of International PCT Patent Application NO. PCT/AU2016/050927, entitled "Pathogen biomarkers and uses therefor." filed Sep. 30, 2016, which claims priority to Australian Provisional Application No. 2015903986 entitled "Pathogen biomarkers and uses therefor" filed Sep. 30, 2015, the contents of which are incorporated herein by reference in their entirety.

This invention relates generally to compositions, methods and apparatus for diagnosing and/or monitoring a virus-associated systemic inflammation by measurement of a host immune response. The invention can be used for diagnosis including early diagnosis, monitoring, making treatment decisions, or management of subjects suspected of having systemic inflammation associated with an infection. More particularly, the present invention relates to peripheral blood RNA and protein biomarkers that are useful for specifically distinguishing between the host systemic immune response to viruses as compared to the host immune response to other causes of systemic inflammation.

BACKGROUND OF THE INVENTION

Fever and clinical signs of systemic inflammation (or SIRS) are commonly seen in patients presenting to medical services; either in general practice clinics, outpatient clinics, emergency rooms, hospital wards or intensive care units (Rangel-Frausto et al. (1995). The natural history of the systemic inflammatory response syndrome (SIRS). A prospective study. JAMA: the Journal of the American Medical Association, 273(2), 117-123; McGowan et al. (1987). Fever in hospitalized patients. With special reference to the medical service. The American Journal of Medicine, 82(3 Spec No), 580-586; Bor et al. (1988). Fever in hospitalized medical patients: characteristics and significance. Journal of General Internal Medicine, 3(2), 119-125; Finkelstein et al. (2000). Fever in pediatric primary care: occurrence, management, and outcomes. Pediatrics, 105(1 Pt 3), 260-266).

When SIRS is the result of a confirmed infectious process it is called infection-positive SIRS (ipSIRS), otherwise known as sepsis. Within this definition lies the following assumptions; the infectious process could be local or generalized; the infection could be bacterial, fungal/yeast, viral or parasitic; the infectious process could be in an otherwise sterile body compartment. Such a definition has been updated in Levy et al. 2003 ("2001 SCCM/ESICM/ACCP/ATS/SIS International Sepsis Definitions Conference," Critical Care Medicine 31, no. 4: 1250-1256) to accommodate clinical and research use of the definition. The revised definition allows that the infection be in a sterile or non-sterile site (e.g., overgrowth of a pathogen/commensal in the intestine) and that the infection can be either confirmed or suspected.

In many instances the use of the terms SIRS and sepsis, and what clinical conditions they do or do not include, are confusing in clinical situations. Such confusion leads to difficulties in clinical diagnosis and in making decisions on subsequent patient treatment and management. Difficulties in clinical diagnosis are based on the following questions: 1) what constitutes a "suspected" Infection given that many body organs/sites are naturally colonized by microbes (e.g., *Escherichia coli* in the intestines, *Staphylococcus epider-* *midis* in skin), viruses (e.g., latent viruses such as herpes) or parasites (e.g., *Toxoplasma*, Glardia); 2) what constitutes a pathological growth of an organism in a normally non-sterile body site?; 3) what contributions to SIRS are made by a viral/microbial/parasitic co-infection in a non-sterile body site (e.g., upper respiratory tract), and if such an infection is suspected then should the patient be put on antibiotics, anti-fungal, anti-viral or anti-parasitic compounds?

Patients with fever and SIRS need to be carefully assessed, and tested, to determine the cause of the presenting clinical signs as there are many possible differential diagnoses (Munro, N. (2014). Fever in acute and critical care: a diagnostic approach. AACN Adv Crit Care 25: 237-248). Possible differential diagnoses include infection (bacterial, fungal, viral, parasitic), trauma, allergy, drug reaction, autoimmunity, surgery, neutropenia, cancer, metabolic disorders, clotting disorders. Patients with fever and SIRS caused by bacterial or fungal infection often require immediate medical attention and it is therefore important to quickly differentiate such patients. Patients with fever and SIRS caused by viral infection need to be further assessed to determine 1) the degree of systemic inflammation due to viral infection, 2) the degree of involvement of microbes (commensals, microbiome, pathogens) to systemic inflammation 3) contributions that each of viruses, microbes and sterile injury are making to systemic inflammation 4) likelihood of the patient rapidly deteriorating. The results of such an assessment aids clinicians in making appropriate management and treatment decisions.

Whether or not a host responds to a viral infection through a SIRS depends largely upon the extent and type of exposure to viral antigen (Klimpel G R. Immune Defenses. In: Baron S, editor. Medical Microbiology. 4th edition. Galveston (Tex.): University of Texas Medical Branch at Galveston; 1996. Chapter 50). Factors that affect host immune system exposure to viral antigen include; 1) Host immune status, including vaccination, 2). Primary or secondary exposure to the same virus, 3). Stage of infection (early, late, re-activation), 4). Infection type (cytolytic, persistent, latent, integrated), 5). Mechanism of spread (primary hematogenous, secondary hematogenous, local, nervous), 6). Virus location (systemic or restricted to mucosal surface). Table 1 lists some example virus types (by family and Baltimore classification) and the means by which the host is exposed to viral antigen. Viruses have multiple methods of interacting with the host and its cells and if a host mounts a systemic inflammatory response to a viral infection it means that the immune system has been exposed to sufficient levels of novel viral antigens. Types of viral antigens include proteins (capsid, those involved in virus replication) and nucleic acids (RNA and/or DNA). Most viral proteins are specific to a particular type of virus and the host immune system will respond in a specific, adaptive, and usually delayed, manner. However, it is known that there are host receptors, called pattern recognition receptors (PRR), for foreign (microbial, viral) nucleic acid, including RNA and DNA (Perry, A. K., Chen, G., Zheng, D., Tang, H., & Cheng, G. (2005). The host type I interferon response to viral and bacterial infections. Cell Research, 15(6), 407-422). PRRs recognise, in a non-specific manner, conserved molecular motifs called Pathogen Associated Molecular Patterns, or PAMPs. The cellular pathways and conserved response to PRR stimulation are well documented and includes the production of Type I interferons (Type I IFNs). Whilst DNA and RNA viruses use different initial receptors they both activate the kinases TANK-binding kinase-1 (TBK1) and/or the inducible I B kinase (IKK-i), which ultimately leads to the production of Type I IFNs. The variable downstream effects of Type I IFNs are dependent upon a number of factors including, but not limited to, cell source, concentration, receptor density, receptor avidity and affinity, cell type Hall, J. C., & Rosen, A. (2010). Type I interferons: crucial participants in disease amplification in autoimmunity. Nature Reviews Rheumatology, 6(1), 40-49). Accordingly, the host immune system responds to a viral infection in both a generalized and specific manner.

Currently, diagnosis of viral conditions is challenging. In general, the conventional method for diagnosing viral infection is cell culture and isolation (growth of virus in cell culture, observation of cytopathic effect (CPE) or hemabsorption (HAD), and partial or complete identification by staining or biochemical or immunoassay (e.g. Immunofluorescence)) (Hsiung, G. D. 1984. Diagnostic virology: from animals to automation. Yale J. Biol. Med. 57:727-733; Leland D S, Ginocchio C C (2007) Role of Cell Culture for Virus Detection in the Age of Technology. Clinical Microbiology Reviews 20: 49-78). This method has limitations in that it requires; appropriate transport of the clinical sample in an appropriate virus-preservation medium, an initial strong suspicion of what the infecting virus might be (to select a suitable cell line that will grow the suspected virus), a laboratory having suitable expertise, equipment and cell lines, and, once these conditions are all in place, a lengthy incubation period (days to weeks) to grow the virus. The process is laborious and expensive.

With respect to improving the diagnosis of viral conditions, and more recently, sensitive and specific assays such as those using monoclonal antibodies or nucleic acid amplification have become available and are now widely available and used in diagnostic laboratories. Amplification of viral DNA and RNA (e.g., PCR) and viral antigen detection are fast and do not require the lengthy incubation period needed for viral isolation in cell cultures, may involve less technical expertise, and are sensitive enough to be useful for viruses that do not proliferate in standard cell cultures. Molecular detection of viral DNA and RNA also has its limitations in that an initial strong suspicion of what the infecting virus might be is also required (to use specific PCR primers and probes, for example), the method detects both live and dead virus, and that most molecular tests are designed to detect only one type of virus and, as such, will only detect one type of virus. By way of example, it has been shown that mixed respiratory infections occur in up to 15% of immunocompetent children and that such mixed infections lead to an increase in disease severity (Waner, J. L. 1994. Mixed viral infections: detection and management. Clin. Microbiol. Rev. 7:143-151). A PCR designed to only one type of virus will not detect a mixed infection if the primers and probes are not specific to all viruses present in the clinical specimen. To cover the possibility of a mixed infection, as well as to cover multiple possible viral causes or strains, there are some commercially available assays capable of detecting more than one virus and/or strain at a time (e.g., BioMerieux, BioFire, FilmArray®, Respiratory Panel; Luminex, xTAG® Respiratory Viral Panel). Such an approach is especially useful in confirming an infective agent if clinical signs are pathognomonic or if a particular body system is affected (e.g., respiratory tract or gastrointestinal tract). Further, there are techniques that allow for amplification of viral DNA of unknown sequence which could be useful in situations where the clinical signs are generalized, for viruses with high mutation rates, for new and emerging viruses, or for detecting biological weapons of man-made nature (Clem et al. (2007) Virus detection and identification using random multiplex (RT)-PCR with 3'-locked random primers. Virol J 4: 65; Liang et al. (1992) Differential display of eukaryotic messenger RNA by means of the polymerase chain reaction. Science 257(5072):967-971; Nie X et al. (2001) A novel usage of random primers for multiplex RT-PCR detection of virus and viroid in aphids, leaves, and tubers. J Virol Methods 91(1):37-49; Ralph et al. (1993) RNA fingerprinting using arbitrarily primed PCR identifies differentially regulated RNAs in mink lung (Mv1Lu) cells growth arrested by transforming growth factor beta 1. Proc Natl Acad Sci USA 90(22):10710-10714). However, it has been shown that the use of molecular detection methods, compared to conventional detection methods, in patients with lower respiratory tract infections did not significantly change the treatment regimen but led to an overall increase in cost of patient management (Oosterheert J J, van Loon A M, Schuurman R, Hoepelman A I M, Hak E, et al. (2005) Impact of rapid detection of viral and atypical bacterial pathogens by real-time polymerase chain reaction for patients with lower respiratory tract infection. Clinical Infectious Diseases 41: 1438-1444). Thus, the availability of faster and more sensitive molecular detection assays for pathogens does not necessarily positively impact clinical decision making, patient outcome, antibiotic use, adoption or hospital econometrics. Further, pathogen detection assays for viruses have limitations in that the results are often difficult to interpret in a clinical context when used in isolation. Thus, the diagnosis of a viral infection, and if a virus is isolated or identified whether it is pathogenic or not, cannot always be made simply by determining the presence of such an organism in a host sample.

In some instances, detection of host antibodies to an infecting virus remains the diagnostic gold standard, because either the virus cannot be grown, or the presence of virus in a biological fluid is transient (e.g., arboviral infections) and therefore cannot be detected at all times. Antibody detection also has limitations including: it usually takes at least 10 days for a host to generate detectable and specific immunoglobulin G antibodies in a primary infection, by which time the clinical signs have often abated; anti-viral antibodies following a primary infection can persist for a long period making it difficult to interpret the timing of an infection relapse for viruses that show latency; a specific test must be ordered to detect a specific virus. These limitations make it difficult to determine when the host was infected, whether high antibody titers to a particular virus means that a particular virus is the causative agent of the presenting clinical signs, and which test to order. In some instances the ratio of IgM to IgG antibodies can be used to determine the recency of virus infection. IgM is usually produced early in the immune response and is non-specific, whereas IgG is produced later in the immune response and is specific. Examples of the use of this approach include the diagnosis of hepatitis E (Tripathy et al. (2012). Cytokine Profiles, CTL Response and T Cell Frequencies in the Peripheral Blood of Acute Patients and Individuals Recovered from Hepatitis E Infection. PLoS ONE, 7(2), e31822), dengue (SA-Ngasang et al. (2005). Specific IgM and IgG responses in primary and secondary dengue virus infections determined by enzyme-linked immunosorbent assay. Epidemiology and Infection, 134(04), 820), and Epstein-Barr Virus (Hess, R. D. (2004). Routine Epstein-Barr Virus Diagnostics from the Laboratory Perspective: Still Challenging after 35 Years. Journal of Clinical Microbiology, 42(8), 3381-3387). The IgM/IgG ratio approach also suffers from the limitation that the clinician must know which specific test to order a priori.

A need, therefore, exists for better ways of detecting the presence of viral inflections, particularly systemic inflammation associated with viral infections, to permit early diagnosis, monitoring, making treatment decisions, or management of subjects having, or suspected of having, a systemic inflammation.

SUMMARY OF THE INVENTION

The present invention arises from the determination that certain host response peripheral blood expression products, including RNA transcripts (RNA markers), are commonly, specifically and differentially expressed across different mammals (humans, macaques, pigs) during systemic inflammations caused by different viral infections. Such RNA transcripts (biomarkers) are useful for diagnosis early in the infective process and over the course of an infection. These biomarkers are therefore useful in early diagnosis, diagnosis, monitoring, prognosis and determination of severity of systemic inflammation associated with viral infection. In particular, based on the known and demonstrated specificity to virus-associated systemic inflammation, such biomarkers are useful in determining the etiology of a systemic inflammatory response when caused by a viral infection.

Because such biomarkers are commonly, specifically and differentially expressed across species, and in response to a variety of different types of viruses covering examples from each of the Baltimore classification groups (I-VII), they are considered to be "pan-viral" inflammatory biomarkers in mammals. To ensure that the biomarkers described herein are truly pan-viral and also specific to a viral infection, the following procedures and methods were deliberately performed: 1). A mixture of both DNA and RNA viruses were included in the "discovery" core datasets—only those biomarkers with strong performance across all of these datasets were selected for further analysis, 2). A wide range of virus families, including both DNA and RNA viruses, were included in the various "validation" datasets, 3). A wide range of virus families causing a variety of clinical signs were included in the various datasets, 4). Viruses covering all of the Baltimore Classification categories were included in the various datasets, 5). Viruses and samples covering a variety of stage of infection, infection type, mechanism of spread and location were included in the various datasets, 6). Controlled and time-course datasets were selected to cover more than one species of mammal (humans, macaques, pigs), 7). In time-course studies samples early in the infection process were chosen, prior to peak clinical signs, to limit the possibility of a bacterial co-infection, 8). Biomarkers significant for other conditions that may induce the same biochemical pathways were subtracted (e.g., biomarkers for autoimmunity, asthma, bacterial infections, sarcoidosis, stress, anaphylaxis, trauma, age, obesity, gender and race), 9). Validation was performed in both adults and children with a variety of viral conditions. Following the stringent selection process only those biomarkers with an AUC greater than existing virus assays and clinical judgment were selected to ensure clinical utility.

Based on this determination, the present inventors have developed various methods, apparatus, compositions, and kits, which take advantage of differentially expressed biomarkers, including ratios thereof (derived biomarkers), to determine the presence, absence or degree of virus-associated inflammatory response syndrome (VaSIRS) in subjects presenting with fever or clinical signs of systemic inflammation. In certain embodiments, these methods, apparatus, compositions, and kits represent a significant advance over prior art processes and products, which have not been able to: 1) distinguish VaSIRS from other etiologies of systemic inflammation; and/or 2) determine the contribution of a viral infection (if any) to the presenting clinical signs and pathology.

Accordingly, in one aspect, the present invention provides methods for determining an indicator used in assessing a likelihood of a subject having a presence, absence or degree of VaSIRS. These methods generally comprise, consist or consist essentially of: (1) determining a biomarker value that is measured or derived for at least one (e.g., 1, 2, 3, 4, 5, 6, 7, 8, 9, 10, or more) corresponding VaSIRS biomarker in a sample taken from the subject and that is at least partially indicative of a level of the VaSIRS biomarker in the sample; and (2) determining the indicator using the biomarker value. Suitably, the subject has at least one clinical sign of SIRS. The at least one VaSIRS biomarker is suitably not a biomarker of at least one other SIRS condition (e.g., 1, 2, 3, 4 or 5 other SIRS conditions) selected from the group consisting of: bacterium associated SIRS, autoimmune disease associated SIRS, cancer associated SIRS and trauma associated SIRS. The sample is suitably a biological sample, representative examples of which include blood samples including peripheral blood samples, and leukocyte samples. In other embodiments, the sample is a tissue biopsy such as a liver tissue biopsy.

In specific embodiments, the at least one VaSIRS biomarker is an expression product of a gene selected from the group consisting of: ZBP1, TMEM62, CD38, ISG15, IFI44, RSAD2, HERC5, MX1, HERC6, OAS2, XAF1, IFI6, PARP12, EIF2AK2, DHX58, UBE2L6, DDX60, USP18, RTP4, PHF11, IFIH1, ZBP1, STAT1, LAP3, TAP1, C19orf66, CUL1, POLB, ZC3HAV1, IL16, ITPKB, CAMK2G, CTDSP2, DPEP2, LTB, CBX7, FNBP1, FOXO1, MAST3, LDLRAP1, TMEM204, FAIM3, RGS14, IKBKB, ZXDC, PHF20, DGKA, XPC, PPARD, C2orf58, NLRP1, IL27RA, ABLIM1, JAK1, METTL3, SAFB2, PPM1F, TYK2, BANP, CRTC3, ATM, PAFAH1B1, PIK3IP1, WDR37, TGFBR2, ZNF274, STAT5B, MAML1, SATB1, DOCK9, CHMP7, BRD1, BTG1, ATF7IP2, DIDO1, LEF1, TNRC6B, SERTAD2, CEP68, BCL2, VPS8, CHD3, PUM2, TGOLN2, NDE1, CCR7, PSTPIP1, TIAM1, PECAM1, PDE3B, MYC, FOXJ2, PRMT2, CSNK1D, RPL10A, SERINC5, ARHGEF2, HGSNAT, TRAK1, PHF2, PBX3, SESN1, DPF2, IL4R, NOSIP, MPPE1, NR3C1, ABAT, GCC2, ZFC3H1, SETD2, ITSN2, R3HDM2, ARHGAP15, PCF11, MAPRE2, ST3GAL1, NACA, WDR47, SSBP2, CLK4, EIF3H, FRY, ZNF238, PTGER4, PCNX, NECAP2, CASC3, MSL1, VEZF1, KIAA0232, RASSF2, RPL22, ACAA1, MAP4K4, BEX4, NCBP2, LRMP, CAMK1D, UTP14A, STX6, RPS6KA3, PRKAA1, GOLGA7, ZNF143, SNRK, SYPL1, CYLD, PRUNE, CRLF3, CD93, GPS2, FBXO11, UBE2D2, USP10, CCNG2, SOS2, ARRB1, CEP170, SMAD4, CIAPIN1, KLF7, PHF20L1, ALDH3A2, PDCD6IP, WASF2, TGFBI, GPBP1L1, PCBP2, DCP2, LYST, ERBB2IP, ANKRD49, NDFIP1, ATAD2B, ZNF292, CCNT2, MARCH7, ACAP2, MED13, IL6ST, PHF3, SP3, SEC62, ZFYVE16, NEK7, POLD4, GNA12, TRIB2, YTHDF3, PPP2R5A, PPP1R2, ZDHHC17, STK38L, ST13, FAM134A, PFDN5, MARCH8, POLR1D, OASL, N4BP1, NOD2, RNF19B, PRKAG2, IGSF6, MEF2A, LPIN2, PPP1R11, USP15, BACH1, SSFA2, MKLN1, FYB, NSUN3, MAX, STAM2, HHEX, CLEC4A, ZFAND5, ABI1, MORC3, RC3H2, MAP1LC3B, TM2D3, CHST11, NAB1, KLF3, YPEL5, MXI1, CD97, CYTH4, HCK, ARHGAP26, RARA, XPO6, TNFRSF1A, SLCO3A1, ICAM3, PTPN6, PRKCD, RAB11FIP1, CSF2RB, LCP2, TYROBP, PHC2, RHOG, PSAP, LYN, TMEM127, LILRA2, AOAH, FGR, PLEKHO2, ARAP1, RBM23, PTPRE, KLF6, LIMK2, LILRB3, TLR2, GPR97, GMIP, SIRPA, LRP10, LPAR2, TREM1, IL13RA1, ITGAX, ARHGAP25, SIRPB1, ZDHHC18, TLE3, ITGB2, SNX27, PGS1, ATP6V1B2, RAB31, MAP3K11, PACSIN2, KIAA0513, EMR2, RERE, NUMB, RALB, ETS2, STAT5A, LST1, RIN3, TNK2, IQSEC1, PISD, SORL1, FES, KIAA0247, IL6R, LAPTM5, VAMP3, FAM65B, MAP3K5, TRIM8, ZYX, MAPK14, PLEKHO1, NCOA1, RNASET2, APBB1IP, RXRA, PTAFR, CNPY3, TNFSF13, RPS6KA1, OSBPL2, MTMR3, TMBIM1, TFEB, TFE3, RAF1, STX3, LAT2, GRB2, NDEL1, SEMA4D, FCGRT, DOK3, HIP1, UBN1, PLXNC1, NRBF2, INPP5D, SH2D3C, MMP25, IL10RB, FLOT2, PIAS1, PITPNA, APLP2, CTBP2, GPSM3, RNF130, DGCR2, ZMIZ1, CAP1, GSK3B, RGS19, RAB7A, CREBBP, RBMS1, IL1RAP, RTN3, PPP4R1, TRI-OBP, GABARAP, MCTP2, NFKB1, CST3, ABHD2, SH2B3, STX10, TSC22D3, TLE4, HAL, ARRB2, MAP3K3, NPL, CCND3, SERINC3, GNAQ, USP4, PSEN1, KBTBD2, LYL1, AIF1, MBP, ACVR1B, RAB4B, PTEN, ASAP1, MANSC1, RYBP, CSAD, UBXN2B, TNIP1, WBP2, OGFRL1, SNN, HPCAL1, CD37, RNF146, RAB14, TOPORS, NFYA, FOXO3, CREB1, MAPK1, SOAT1, UBQLN2, OSBPL11, KLHL2, VAV3, BRD4, MARK3, BAZ2B, ZNF148, CASP8, CHMP1B, HPS1, RNF141, MOSPD2, PINK1, CDIPT, NCOA4, PPP3R1, MKRN1, GYPC, BMP2K and FBXO9. Non-limiting examples of nucleotide sequences for these VaSIRS biomarkers are listed in SEQ ID NOs: 1-415 (see, Table 19 for sequence ID numbers, biomarker gene symbols, Ensembl transcript IDs). Non-limiting examples of amino acid sequences for these VaSIRS biomarkers are listed in SEQ ID NOs: 416-830. In illustrative examples, an individual VaSIRS biomarker is selected from the group consisting of:
(a) a polynucleotide expression product comprising a nucleotide sequence that shares at least 70% (or at least 71% to at least 99% and all integer percentages in between) sequence identity with the sequence set forth in any one of SEQ ID NO: 1-415, or a complement thereof; (b) a polynucleotide expression product comprising a nucleotide sequence that encodes a polypeptide comprising the amino acid sequence set forth in any one of SEQ ID NO: 416-830; (c) a polynucleotide expression product comprising a nucleotide sequence that encodes a polypeptide that shares at least 70% (or at least 71% to at least 99% and all integer percentages in between) sequence similarity or identity with at least a portion of the sequence set forth in SEQ ID NO: 416-830; (d) a polynucleotide expression product comprising a nucleotide sequence that hybridizes to the sequence of (a), (b), (c) or a complement thereof, under medium or high stringency conditions; (e) a polypeptide expression product comprising the amino acid sequence set forth in any one of SEQ ID NO: 416-830; and (f) a polypeptide expression product comprising an amino acid sequence that shares at least 70% (or at least 71% to at least 99% and all integer percentages in between) sequence similarity or identity with the sequence set forth in any one of SEQ ID NO: 416-830 (see, Table 20 for sequence ID numbers and GenBank Accession Numbers).

Certain VaSIRS biomarkers of the present invention have strong diagnostic performance on their own (as measured, for example, using area under curve (AUC)) for detecting VaSIRS and are referred to herein as "Group A VaSIRS biomarkers". Thus, in specific embodiments, the at least one VaSIRS biomarker is selected from Group A VaSIRS biomarkers, wherein an individual Group A VaSIRS biomarker is an expression product of a gene selected from the group consisting of: ZBP1, TMEM62 and CD38. Suitably, the biomarker value is measured or derived for a single Group A VaSIRS biomarker and the indicator is determined using the biomarker value. Alternatively, biomarker values are measured or derived for at least 2 or each of the Group A VaSIRS biomarkers, and the indicator is determined by combining the biomarker values.

Other VaSIRS biomarkers have strong diagnostic performance when combined with one or more other VaSIRS biomarkers. In some embodiments, pairs of biomarkers are used to determine the indicator. In illustrative examples of this type, one biomarker of a biomarker pair is selected from Group B VaSIRS biomarkers and the other is selected from Group C VaSIRS biomarkers, wherein an individual Group B VaSIRS biomarker is an expression product of a gene selected from the group consisting of: ISG15, IFI44, RSAD2, HERC5, MX1, HERC6, OAS2, XAF1, IFI6, PARP12, EIF2AK2, DHX58, UBE2L6, DDX60, USP18, RTP4, PHF11, IFIH1, ZBP1, STAT1, LAP3, TAP1, C19orf66, CUL1, POLB and ZC3HAV1, and wherein an individual Group C VaSIRS biomarker is an expression product of a gene selected from the group consisting of: IL16, ITPKB, CAMK2G, CTDSP2, DPEP2, LTB, CBX7, FNBP1, FOXO1, MAST3, LDLRAP1, TMEM204, FAIM3, RGS14, IKBKB, ZXDC, PHF20, DGKA, XPC, PPARD, C2orf58, NLRP1, IL27RA, ABLIM1, JAK1, METTL3, SAFB2, PPM1F, TYK2, BANP, CRTC3, ATM, PAFAH1B1, PIK3IP1, WDR37, TGFBR2, ZNF274, STAT5B, MAML1, SATB1, DOCK9, CHMP7, BRD1, BTG1, ATF7IP2, DIDO1, LEF1, TNRC6B, SERTAD2, CEP68, BCL2, VPS8, CHD3, PUM2, TGOLN2, NDE1, CCR7, PSTPIP1, TIAM1, PECAM1, PDE3B, MYC, FOXJ2, PRMT2, CSNK1D, RPL10A, SERINC5, ARHGEF2, HGSNAT, TRAK1, PHF2, PBX3, SESN1, DPF2, IL4R, NOSIP, MPPE1, NR3C1, ABAT, GCC2, ZFC3H1, SETD2, ITSN2, R3HDM2, ARHGAP15, PCF11, MAPRE2, ST3GAL1, NACA, WDR47, SSBP2, CLK4, EIF3H, FRY, ZNF238, PTGER4, PCNX, NECAP2, CASC3, MSL1, VEZF1, KIAA0232, RASSF2, RPL22, ACAA1, MAP4K4, BEX4, NCBP2, LRMP, CAMK1D, UTP14A, STX6, RPS6KA3, PRKAA1, GOLGA7, ZNF143, SNRK, SYPL1, CYLD, PRUNE, CRLF3, CD93, GPS2, FBXO11, UBE2D2, USP10, CCNG2, SOS2, ARRB1, CEP170, SMAD4, CIAPIN1, KLF7, PHF20L1, ALDH3A2, PDCD6IP, WASF2, TGFBI, GPBP1L1, PCBP2, DCP2, LYST, ERBB2IP, ANKRD49, NDFIP1, ATAD2B, ZNF292, CCNT2, MARCH7, ACAP2, MED13, IL6ST, PHF3, SP3, SEC62, ZFYVE16, NEK7, POLD4, GNA12, TRIB2, YTHDF3, PPP2R5A, PPP1R2, ZDHHC17, STK38L, ST13, FAM134A, PFDN5, MARCH8 and POLR1D.

In other illustrative examples, one biomarker of a biomarker pair is selected from Group D VaSIRS biomarkers and the other is selected from Group E VaSIRS biomarkers, wherein an individual Group D VaSIRS biomarker is an expression product of a gene selected from the group consisting of: OASL, N4BP1, NOD2, RNF19B, PRKAG2, IGSF6, MEF2A, LPIN2, PPP1R11, USP15, BACH1, SSFA2, MKLN1, FYB, NSUN3, MAX, STAM2, HHEX, CLEC4A, ZFAND5, ABI1, MORC3, RC3H2, MAP1LC3B, TM2D3, CHST11, NAB1, KLF3, YPEL5 and MXI1, and wherein an individual Group E VaSIRS biomarker is an expression product of a gene selected from the group consisting of: CD97, CYTH4, HCK, ARHGAP26, RARA, XPO6, TNFRSF1A, SLCO3A1, ICAM3, PTPN6, PRKCD, RAB11FIP1, CSF2RB, LCP2, TYROBP, PHC2, RHOG, PSAP, LYN, TMEM127, LILRA2, AOAH, FGR, PLEKHO2, ARAP1, RBM23, PTPRE, KLF6, LIMK2, LILRB3, TLR2, GPR97, GMIP, SIRPA, LRP10, LPAR2, TREM1, IL13RA1, ITGAX, ARHGAP25, SIRPB1, ZDHHC18, TLE3, ITGB2, SNX27, PGS1, ATP6V1B2, RAB31, MAP3K11, PACSIN2, KIAA0513, EMR2, RERE, NUMB, RALB, ETS2, STAT5A, LST1, RIN3, TNK2, IQSEC1, PISD, SORL1, FES, KIAA0247, IL6R, LAPTM5, VAMP3, FAM65B, MAP3K5, TRIM8, ZYX, MAPK14, PLEKHO1, NCOA1, RNASET2, APBB1IP, RXRA, PTAFR, CNPY3, TNFSF13, RPS6KA1, OSBPL2, MTMR3, TMBIM1, TFEB, TFE3, RAF1, STX3, LAT2, GRB2, NDEL1, SEMA4D, FCGRT, DOK3, HIP1, UBN1, PLXNC1, NRBF2, INPP5D, SH2D3C, MMP25, IL10RB, FLOT2, PIAS1, PITPNA, APLP2, CTBP2, GPSM3, RNF130, DGCR2, ZMIZ1, CAP1, GSK3B, RGS19, RAB7A, CREBBP, RBMS1, IL1RAP, RTN3, PPP4R1, TRIOBP, GABARAP, MCTP2, NFKB1, CST3, ABHD2, SH2B3, STX10, TSC22D3, TLE4, HAL, ARRB2, MAP3K3, NPL, CCND3, SERINC3, GNAQ, USP4, PSEN1, KBTBD2, LYL1, AIF1, MBP, ACVR1B, RAB4B, PTEN, ASAP1, MANSC1, RYBP, CSAD, UBXN2B, TNIP1, WBP2, OGFRL1, SNN, HPCAL1, CD37, RNF146, RAB14, TOPORS, NFYA, FOXO3, CREB1, MAPK1, SOAT1, UBQLN2, OSBPL11, KLHL2, VAV3, BRD4, MARK3, BAZ2B, ZNF148, CASP8, CHMP1B, HPS1, RNF141, MOSPD2, PINK1, CDIPT, NCOA4, PPP3R1, MKRN1, GYPC, BMP2K and FBXO9.

In some embodiments, biomarker values are measured or derived for a Group B VaSIRS biomarker and for a Group C VaSIRS biomarker, and the indicator is determined by combining the biomarker values. In some embodiments, biomarker values are measured or derived for a Group D VaSIRS biomarker and for a Group E VaSIRS biomarker, and the indicator is determined by combining the biomarker values. In other embodiments, biomarker values are measured or derived for a Group B VaSIRS biomarker, for a Group C VaSIRS biomarker, for a Group D VaSIRS biomarker and for a Group E VaSIRS biomarker, and the indicator is determined by combining the biomarker values. Suitably, in the above embodiments, the methods comprise combining the biomarker values using a combining function, wherein the combining function is at least one of: an additive model; a linear model; a support vector machine; a neural network model; a random forest model; a regression model; a genetic algorithm; an annealing algorithm; a weighted sum; a nearest neighbor model; and a probabilistic model.

In some embodiments, the methods comprise: (a) determining a pair of biomarker values, each biomarker value being a value measured or derived for at least one corresponding VaSIRS biomarker; (b) determining a derived biomarker value using the pair of biomarker values, the derived biomarker value being indicative of a ratio of concentrations of the pair of VaSIRS biomarkers; and determining the indicator using the derived marker value. In illustrative examples of this type, biomarker values are measured or derived for a Group B VaSIRS biomarker and for a Group C VaSIRS biomarker to obtain the pair of biomarker values and the derived biomarker value is determined using the pair of biomarker values. In other illustrative examples, biomarker values are measured or derived for a Group D VaSIRS biomarker and for a Group E VaSIRS biomarker to obtain the pair of biomarker values and the derived biomarker value is determined using the pair of biomarker values.

In some embodiments, the methods comprise: (a) determining a first derived biomarker value using a first pair of biomarker values, the first derived biomarker value being indicative of a ratio of concentrations of first and second VaSIRS biomarkers; (b) determining a second derived biomarker value using a second pair of biomarker values, the second derived biomarker value being indicative of a ratio of concentrations of third and fourth VaSIRS biomarkers; and (c) determining the indicator by combining the first and second derived biomarker values. Suitably, the first VaSIRS biomarker is selected from Group B VaSIRS biomarkers, the second VaSIRS biomarker is selected from Group C VaSIRS biomarkers, the third VaSIRS biomarker is selected from Group D VaSIRS biomarkers, and the fourth VaSIRS biomarker is selected from Group E VaSIRS biomarkers. In illustrative examples of this type, the methods comprise combining the biomarker values using a combining function, wherein the combining function is at least one of: an additive model; a linear model; a support vector machine; a neural network model; a random forest model; a regression model; a genetic algorithm; an annealing algorithm; a weighted sum; a nearest neighbor model; and a probabilistic model.

Suitably, in embodiments that utilize pairs of VaSIRS biomarkers as broadly described above and elsewhere herein, an individual pair of VaSIRS biomarkers has a mutual correlation in respect of VaSIRS that lies within a mutual correlation range, the mutual correlation range being between ±0.9 (or between ±0.8, ±0.7, ±0.6, ±0.5, ±0.4, ±0.3, ±0.2 or ±0.1) and the indicator has a performance value greater than or equal to a performance threshold representing the ability of the indicator to diagnose the presence, absence or degree of VaSIRS, wherein the performance threshold is indicative of an explained variance of at least 0.3. In illustrative examples of this type, an individual VaSIRS biomarker has a condition correlation with the presence, absence or degree of VaSIRS that lies outside a condition correlation range, wherein the condition correlation range is between ±0.3. In other illustrative examples, an individual VaSIRS biomarker has a condition correlation with the presence, absence or degree of VaSIRS that lies outside a condition correlation range, wherein the condition correlation range is at least one of ±0.9, ±0.8, ±0.7, ±0.6, ±0.5 or ±0.4. In specific embodiments, the performance threshold is indicative of an explained variance of at least one of 0.4, 0.5, 0.6, 0.7, 0.8 and 0.9.

In certain embodiments that utilize pairs of VaSIRS biomarkers as broadly described above and elsewhere herein the Group B VaSIRS biomarker is suitably an expression product of ISG15, the Group C VaSIRS biomarker is suitably an expression product of IL16, the Group D VaSIRS biomarker is suitably an expression product of OASL, and the Group E VaSIRS biomarker is suitably an expression product of CD97.

The virus associated with the VaSIRS is suitably selected from any one of Baltimore virus classification Groups I, II, III, IV, V, VI and VII, which is capable of inducing at least one of the clinical signs of SIRS.

Another aspect of the present invention provides apparatus for determining an indicator used in assessing a likelihood of a subject having a presence, absence or degree of VaSIRS. This apparatus generally comprises at least one electronic processing device that:

determines a pair of biomarker values, each biomarker value being a value measured or derived for at least one corresponding VaSIRS biomarker, as broadly described above and elsewhere herein, of a sample taken from the subject and being at least partially indicative of a concentration of the VaSIRS biomarker in the sample;

determines a derived biomarker value using the pair of biomarker values, the derived biomarker value being indicative of a ratio of concentrations of the pair of VaSIRS biomarkers; and determines the indicator using the derived biomarker value.

In specific embodiments, the pairs of VaSIRS biomarkers are selected from the biomarker pairs listed in Table 13 or Table 14.

In yet another aspect, the present invention provides compositions for determining an indicator used in assessing a likelihood of a subject having a presence, absence or degree of VaSIRS. These compositions generally comprise, consist or consist essentially of at least one pair of cDNAs and at least one oligonucleotide primer or probe that hybridizes to an individual one of the cDNAs, wherein the at least one pair of cDNAs is selected from pairs of cDNA including a first pair and a second pair of cDNAs, wherein the first pair comprises a Group B VaSIRS biomarker cDNA and a Group C VaSIRS biomarker cDNA and wherein the second pair comprises a Group D VaSIRS biomarker cDNA and a Group E VaSIRS biomarker cDNA. Suitably, the compositions comprise a population of cDNAs corresponding to mRNA derived from a cell or cell population. In some embodiments, the cell is a cell of the immune system, suitably a leukocyte. In some embodiments, the cell population is blood, suitably peripheral blood. In some embodiments, the at least one oligonucleotide primer or probe is hybridized to an individual one of the cDNAs. In any of the above embodiments, the composition may further comprise a labeled reagent for detecting the cDNA. In illustrative examples of this type, the labeled reagent is a labeled said at least one oligonucleotide primer or probe. In other embodiments, the labeled reagent is a labeled said cDNA. In some embodiments, the at least one oligonucleotide primer or probe is in a form other than a high-density array. In some embodiments, the composition comprises a pair of primers that hybridize to opposite strands of the cDNA and that permit nucleic acid amplification of an amplicon with homology to the cDNA. In specific examples of this type, the composition further comprises a probe that hybridizes to the amplicon. In these embodiments, at least one of the pair of primer and probe is labeled.

Still another aspect of the present invention provides kits for determining an indicator indicative of the likelihood of the presence, absence or degree of VaSIRS. The kits generally comprise, consist or consist essentially of at least one pair of reagents selected from reagent pairs including a first pair of reagents and a second pair of reagents, wherein the first pair of reagents comprises (i) a reagent that allows quantification of a Group B VaSIRS biomarker; and (ii) a reagent that allows quantification of a Group C VaSIRS biomarker, wherein the second pair of reagents comprises: (iii) a reagent that allows quantification of a Group D VaSIRS biomarker; and (iv) a reagent that allows quantification of a Group E VaSIRS biomarker.

In a further aspect, the present invention provides methods for managing a subject with VaSIRS. These methods generally comprise, consist or consist essentially of: exposing the subject to a treatment regimen for treating VaSIRS, or avoiding exposing the subject to a treatment regimen for treating a SIRS other than VaSIRS based on an indicator obtained from an indicator-determining method, wherein the indicator is indicative of the presence of VaSIRS in the subject, and wherein the indicator-determining method is an indicator-determining method as broadly described above and elsewhere herein. In some embodiments, the methods further comprise taking a sample from the subject and determining an indicator indicative of the likelihood of the presence, absence or degree of VaSIRS using the an indicator-determining method. In other embodiments, the methods further comprise sending a sample taken from the subject to a laboratory at which the indicator is determined according to the indicator-determining method. In these embodiments, the methods suitably further comprise receiving the indicator from the laboratory.

Yet another aspect of the present invention provides methods of monitoring the efficacy of a particular treatment regimen in a subject towards a desired health state (e.g., absence of VaSIRS). These methods generally comprise, consist or consist essentially of: (1) determining a biomarker value that is measured or derived for at least one (e.g., 1, 2, 3, 4, 5, 6, 7, 8, 9, 10, or more) corresponding VaSIRS biomarker as broadly defined above in a sample taken from the subject and that is at least partially indicative of a level of the VaSIRS biomarker in the sample, wherein the sample is taken after treatment of the subject with the treatment regimen; (2) determining an indicator using the biomarker value, wherein the indicator is used in assessing a likelihood of the subject having a presence, absence or degree of VaSIRS, and (3) assessing the likelihood of the subject having a presence, absence or degree of VaSIRS using the indicator to thereby determine whether the treatment regimen is effective for changing the health status of the subject to the desired health state.

In another aspect, the present invention provides methods of determining whether a treatment regimen is effective for treating a subject with VaSIRS. These methods generally comprise, consist or consist essentially of: (a) correlating a biomarker value that is measured or derived for at least one (e.g., 1, 2, 3, 4, 5, 6, 7, 8, 9, 10, or more) corresponding VaSIRS biomarker as broadly defined above with an effective treatment regimen; (b) determining a biomarker value that is measured or derived for the at least one corresponding VaSIRS biomarker in a sample taken from the subject after treatment with the treatment regimen; (c) determining an indicator using the biomarker value, wherein the indicator is used in assessing a likelihood of the subject having a presence, absence or degree of VaSIRS, (d) assessing the likelihood of the subject having a presence, absence or degree of VaSIRS using the indicator to thereby determine whether the treatment regimen is effective for treating VaSIRS in the subject.

A further aspect of the present invention provides methods of correlating a biomarker value that is measured or derived for at least one (e.g., 1, 2, 3, 4, 5, 6, 7, 8, 9, 10, or more) corresponding VaSIRS biomarker as broadly defined above with a positive or negative response to a treatment regimen. These methods generally comprise, consist or consist essentially of: (a) determining a biomarker value for the at least one corresponding VaSIRS biomarker in a sample taken from a subject with VaSIRS following commencement of the treatment regimen, wherein the biomarker value is at least partially indicative of a level of the VaSIRS biomarker in the sample; and (c) correlating the sample VaSIRS biomarker value with a positive or negative response to the treatment regimen.

Another aspect of the present invention provides methods of determining a positive or negative response to a treatment regimen by a subject with VaSIRS. These methods generally comprise, consist or consist essentially of: (a) correlating a reference biomarker value that is measured or derived for at least one (e.g., 1, 2, 3, 4, 5, 6, 7, 8, 9, 10, or more) corresponding VaSIRS biomarker as broadly defined above with a positive or negative response to the treatment regimen; and (b) determining a biomarker value for the at least one corresponding VaSIRS biomarker in a sample taken from a subject with VaSIRS, wherein the sample biomarker value indicates whether the subject is responding to the treatment regimen.

In some embodiments, the methods of determining a positive or negative response to a treatment regimen further comprise: (i) determining a first sample biomarker value for the at least one corresponding VaSIRS biomarker as broadly defined above in a sample taken from the subject prior to commencing the treatment regimen; and (ii) comparing the first sample biomarker value with a second sample biomarker value for the at least one corresponding VaSIRS biomarker taken from the subject after commencement of the treatment regimen, to thereby determine a positive or negative response to the treatment regimen.

Another aspect of the present invention provides methods of treating, preventing or inhibiting the development of VaSIRS in a subject. These methods generally comprise, consist or consist essentially of: exposing the subject to a treatment regimen for treating VaSIRS, or avoiding exposing the subject to a treatment regimen for treating a SIRS other than VaSIRS based on an indicator obtained from an indicator-determining method, the indicator-determining method comprising, consisting or consisting essentially of: (a) determining a plurality of biomarker values, each biomarker value being indicative of a value measured or derived for at least one VaSIRS biomarker as broadly defined above of the subject; (b) determining an indicator using a combination of the plurality of biomarker values, the indicator being at least partially indicative of the presence, absence or degree of VaSIRS, wherein: (i) at least two (e.g., 2, 3, 4, 5, 6, 7, 8, 9, 10, or more) VaSIRS biomarkers have a mutual correlation in respect of VaSIRS that lies within a mutual correlation range, the mutual correlation range being between ±0.9; and (ii) the indicator has a performance value greater than or equal to a performance threshold representing the ability of the indicator to diagnose the presence, absence or degree of VaSIRS, the performance threshold being indicative of an explained variance of at least 0.3.

Suitably, the method further comprises: (1) determining a plurality of measured biomarker values, each measured biomarker value being a measured value of VaSIRS biomarker of the subject; and (2) applying a function to at least one of the measured biomarker values to determine at least one derived biomarker value, the at least one derived biomarker value being indicative of a value of a corresponding derived VaSIRS biomarker.

Suitably, the function includes at least one of: (a) multiplying two biomarker values; (b) dividing two biomarker values; (c) adding two biomarker values; (d) subtracting two biomarker values; (e) a weighted sum of at least two biomarker values; (f) a log sum of at least two biomarker values; and (g) a sigmoidal function of at least two biomarker values.

In another aspect of the present invention, methods are provided for monitoring the efficacy of a particular treatment regimen in a subject towards a desired health state. These methods generally comprise, consist or consist essentially of: (a) determining a plurality of biomarker values, each biomarker value being indicative of a value measured or derived for at least one VaSIRS biomarker as broadly defined above of the subject after treatment with a treatment regimen; (b) determining an indicator using a combination of the plurality of biomarker values, the indicator being at least partially indicative of the presence, absence or degree of VaSIRS, wherein: (i) at least two (e.g., 2, 3, 4, 5, 6, 7, 8, 9, 10, or more) VaSIRS biomarkers have a mutual correlation in respect of VaSIRS that lies within a mutual correlation range, the mutual correlation range being between ±0.9; and (ii) the indicator has a performance value greater than or equal to a performance threshold representing the ability of the indicator to diagnose the presence, absence or degree of VaSIRS, or to provide a prognosis for a VaSIRS, the performance threshold being indicative of an explained variance of at least 0.3, and (c) determining that the treatment regimen is effective for changing the health status of the subject to the desired health state on the basis that the indicator indicates the presence of VaSIRS or the presence of VaSIRS of a lower degree relative to the degree of VaSIRS in the subject before treatment with the treatment regimen.

Still other aspects of the present invention contemplate the use of the indicator-determining methods as broadly described above and elsewhere herein in methods for correlating a biomarker profile with an effective treatment regimen for VaSIRS, or for determining whether a treatment regimen is effective for treating a subject with VaSIRS, or for correlating a biomarker profile with a positive or negative response to a treatment regimen, or for determining a positive or negative response to a treatment regimen by a subject with VaSIRS.

BRIEF DESCRIPTION OF THE DRAWINGS

FIG. 7 shows a ROC plot for the best performing combination of derived biomarkers (ISG15:IL16/OASL:CD97) across a combination of 14 different viral datasets.

FIG. 8 shows a plot of area under curve obtained across a combination of 14 different viral datasets when sequentially adding derived biomarkers to the best performing single derived biomarker (IL16/ISG15). The combination of ISG15:IL16/OASL:CD97 is considered to have the optimal commercial utility with the lowest risk of introduction of noise.

FIG. 12 is an example output depicting an indicator that is useful for assessing the presence of VaSIRS in a patient.

DETAILED DESCRIPTION OF THE INVENTION

1. Definitions

Figure 1:
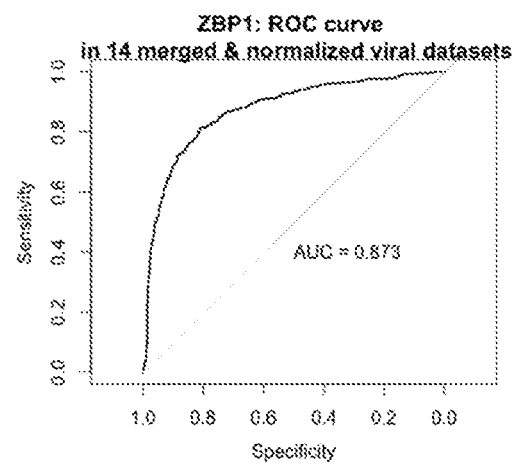
FIG. 1 is a ROC plot of the performance (AUC) of ZBP1 In the merged and normalized dataset (14 Individual datasets).

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e., to at least one) of the grammatical object of the article. By way of example, "an element" means one element or more than one element.

As used herein, the term "amplicon" refers to a nucleic acid that is the product of amplification. Thus an amplicon may be homologous to a reference sequence, a target sequence, or any sequence of nucleic acid that has been subjected to amplification. Generally, within a reaction sample, the concentration of amplicon sequence will be significantly greater than the concentration of original (template) nucleic acid sequence.

As used herein, "and/or" refers to and encompasses any and all possible combinations of one or more of the associated listed Items, as well as the lack of combinations when interpreted in the alternative (or).

The term "biomarker" broadly refers to any detectable compound, such as a protein, a peptide, a proteoglycan, a glycoprotein, a lipoprotein, a carbohydrate, a lipid, a nucleic acid (e.g., DNA, such as cDNA or amplified DNA, or RNA, such as mRNA), an organic or inorganic chemical, a natural or synthetic polymer, a small molecule (e.g., a metabolite), or a discriminating molecule or discriminating fragment of any of the foregoing, that is present in or derived from a sample. "Derived from" as used in this context refers to a compound that, when detected, is Indicative of a particular molecule being present in the sample. For example, detection of a particular cDNA can be indicative of the presence of a particular RNA transcript in the sample. As another example, detection of or binding to a particular antibody can be indicative of the presence of a particular antigen (e.g., protein) in the sample. Here, a discriminating molecule or fragment is a molecule or fragment that, when detected, indicates presence or abundance of an above-identified compound. A biomarker can, for example, be isolated from a sample, directly measured in a sample, or detected in or determined to be in a sample. A biomarker can, for example, be functional, partially functional, or non-functional. In specific embodiments, the "biomarkers" include "immune system biomarkers", which are described in more detail below.

The term "biomarker value" refers to a value measured or derived for at least one corresponding biomarker of a subject and which is typically at least partially indicative of an abundance or concentration of a biomarker in a sample taken from the subject. Thus, the biomarker values could be measured biomarker values, which are values of biomarkers measured for the subject, or alternatively could be derived biomarker values, which are values that have been derived from one or more measured biomarker values, for example by applying a function to the one or more measured biomarker values. Biomarker values can be of any appropriate form depending on the manner in which the values are determined. For example, the biomarker values could be determined using high-throughput technologies such as mass spectrometry, sequencing platforms, array and hybridization platforms, immunoassays, flow cytometry, or any combination of such technologies and in one preferred example, the biomarker values relate to a level of activity or abundance of an expression product or other measurable molecule, quantified using a technique such as PCR, sequencing or the like. In this case, the biomarker values can be in the form of amplification amounts, or cycle times, which are a logarithmic representation of the concentration of the biomarker within a sample, as will be appreciated by persons skilled in the art and as will be described in more detail below.

The term "biomarker profile" refers to one or a plurality of one or more types of biomarkers (e.g., an mRNA molecule, a cDNA molecule and/or a protein, etc.), or an indication thereof, together with a feature, such as a measurable aspect (e.g., biomarker value) of the biomarker(s). A biomarker profile may comprise a single biomarker whole level, abundance or amount correlates with the presence, absence or degree of a condition (e.g., a healthy condition or VaSIRS). Alternatively, a biomarker profile may comprise at least two such biomarkers or indications thereof, where the biomarkers can be in the same or different classes, such as, for example, a nucleic acid and a polypeptide. Thus, a biomarker profile may comprise at least 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 or more biomarkers or indications thereof. In some embodiments, a biomarker profile comprises hundreds, or even thousands, of biomarkers or indications thereof. A biomarker profile can further comprise one or more controls or internal standards. In certain embodiments, the biomarker profile comprises at least one biomarker, or indication thereof, that serves as an internal standard. In other embodiments, a biomarker profile comprises an indication of one or more types of biomarkers. The term "indication" as used herein in this context merely refers to a situation where the biomarker profile contains symbols, data, abbreviations or other similar indicia for a biomarker, rather than the biomarker molecular entity itself. The term "biomarker profile" is also used herein to refer to a biomarker value or combination of at least two biomarker values, wherein individual biomarker values correspond to values of biomarkers that can be measured or derived from one or more subjects, which combination is characteristic of a discrete condition, stage of condition, subtype of condition or a prognosis for a discrete condition, stage of condition, subtype of condition. The term "profile biomarkers" is used to refer to a subset of the biomarkers that have been identified for use in a biomarker profile that can be used in performing a clinical assessment, such as to rule in or rule out a specific condition, different stages or severity of conditions, subtypes of different conditions or different prognoses. The number of profile biomarkers will vary, but is typically of the order of 10 or less.

The terms "complementary" and "complementarity" refer to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands.

Throughout this specification, unless the context requires otherwise, the words "comprise," "comprises" and "comprising" will be understood to imply the inclusion of a stated step or element or group of steps or elements but not the exclusion of any other step or element or group of steps or elements. Thus, use of the term "comprising" and the like Indicates that the listed elements are required or mandatory, but that other elements are optional and may or may not be present. By "consisting of" is meant including, and limited to, whatever follows the phrase "consisting of". Thus, the phrase "consisting of" Indicates that the listed elements are required or mandatory, and that no other elements may be present. By "consisting essentially of" is meant including any elements listed after the phrase, and limited to other elements that do not Interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

The term "correlating" refers to determining a relationship between one type of data with another or with a state.

The term "degree" of VaSIRS, as used herein, refers to the seriousness, severity, stage or state of a VaSIRS. For example, a VaSIRS may be characterized as mild, moderate or severe. A person of skill in the art would be able to determine or assess the degree of a particular VaSIRS. For example, the degree of a VaSIRS may be determined by comparing the likelihood or length of survival of a subject having a VaSIRS with the likelihood or length of survival in other subjects having VaSIRS. In other embodiments, the degree of a VaSIRS may be determined by comparing the clinical signs of a subject having a condition with the degree of the clinical signs in other subjects having VaSIRS.

As used herein, the terms "diagnosis", "diagnosing" and the like are used Interchangeably herein to encompass determining the likelihood that a subject will develop a condition, or the existence or nature of a condition in a subject. These terms also encompass determining the severity of disease or episode of disease, as well as in the context of rational therapy, in which the diagnosis guides therapy, including initial selection of therapy, modification of therapy (e.g., adjustment of dose or dosage regimen), and the like. By "likelihood" Is meant a measure of whether a subject with particular measured or derived biomarker values actually has a condition (or not) based on a given mathematical model. An increased likelihood for example may be relative or absolute and may be expressed qualitatively or quantitatively. For instance, an increased likelihood may be determined simply by determining the subject's measured or derived biomarker values for at least two VaSIRS biomarkers and placing the subject in an "increased likelihood" category, based upon previous population studies. The term "likelihood" is also used interchangeably herein with the term "probability". The term "risk" relates to the possibility or probability of a particular event occurring at some point in the future. "Risk stratification" refers to an arraying of known clinical risk factors to allow physicians to classify patients into a low, moderate, high or highest risk of developing a particular disease or condition.

The term "gene", as used herein, refers to a stretch of nucleic acid that codes for a polypeptide or for an RNA chain that has a function. While it is the exon region of a gene that is transcribed to form mRNA, the term "gene" also includes regulatory regions such as promoters and enhancers that govern expression of the exon region.

The term "high-density array" refers to a substrate or collection of substrates or surfaces bearing a plurality of array elements (e.g., discrete regions having particular moieties, e.g., proteins (e.g., antibodies), nucleic acids (e.g., oligonucleotide probes), etc., immobilized thereto), where the array elements are present at a density of about 100 elements/$cm^2$ or more, about 1,000 elements/$cm^2$ or more, about 10,000 elements/$cm^2$ or more, or about 100,000 elements/$cm^2$ or more. In specific embodiments, a "high-density array" is one that comprises a plurality of array elements for detecting about 100 or more different biomarkers, about 1,000 or more different biomarkers, about 10,000 or more different biomarkers, or about 100,000 or more different biomarkers. In representative example of these embodiments, a "high-density array" is one that comprises a plurality of array elements for detecting biomarkers of about 100 or more different genes, of about 1,000 or more different genes, of about 10,000 or more different genes, or of about 100,000 or more different genes. Generally, the elements of a high-density array are not labeled. The term "low-density array" refers to a substrate or collection of substrates or surfaces bearing a plurality of array elements (e.g., discrete regions having particular moieties, e.g., proteins (e.g., antibodies), nucleic acids (e.g., oligonucleotide probes), etc., immobilized thereto), where the array elements are present at a density of about 100 elements/$cm^2$ or less, about 50 elements/$cm^2$ or less, about 20 elements/$cm^2$ or less, or about 10 elements/$cm^2$ or less. In specific embodiments, a "low-density array" is one that comprises a plurality of array elements for detecting about 100 or less different biomarkers, about 50 or less different biomarkers, about 20 or less different biomarkers, or about 10 or less different biomarkers. In representative example of these embodiments, a "low-density array" is one that comprises a plurality of array elements for detecting biomarkers of about 100 or less different genes, of about 50 or less different genes, of about 20 or less different genes, or of about 10 or less different genes. Generally, the elements of a low-density array are not labeled.

As used herein the terms "homology", "homologous" and the like refer to the level of similarity between two or more nucleic acid sequences in terms of percent of sequence identity. Generally, homologous sequences or sequences with homology refer to nucleic acid sequences that exhibit at least 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% sequence identity to one another. Alternatively, or in addition, homologs, homologous sequences or sequences with homology refer to nucleic acid sequences that hybridize under high stringency conditions to one another. High stringency conditions include and encompass from at least about 31% v/v to at least about 50% v/v formamide and from at least about 0.01 M to at least about 0.15 M salt for hybridization at 42° C., and at least about 0.01 M to at least about 0.15 M salt for washing at 42° C. High stringency conditions also may include 1% BSA, 1 mM EDTA, 0.5 M $NaHPO_4$ (pH 7.2), 7% SDS for hybridization at 65° C., and (i) 0.2×SSC, 0.1% SDS; or (ii) 0.5%

BSA, 1 mM EDTA, 40 mM NaHPO$_4$ (pH 7.2), 1% SDS for washing at a temperature in excess of 65° C.

The term "indicator" as used herein refers to a result or representation of a result, including any information, number, ratio, signal, sign, mark, or note by which a skilled artisan can estimate and/or determine a likelihood or risk of whether or not a subject is suffering from a given disease or condition. In the case of the present invention, the "indicator" may optionally be used together with other clinical characteristics, to arrive at a diagnosis (that is, the occurrence or nonoccurrence) of VaSIRS or a prognosis for a VaSIRS in a subject. That such an indicator is "determined" is not meant to imply that the indicator is 100% accurate. The skilled clinician may use the indicator together with other clinical indicia to arrive at a diagnosis.

The term "immobilized" means that a molecular species of interest is fixed to a solid support, suitably by covalent linkage. This covalent linkage can be achieved by different means depending on the molecular nature of the molecular species. Moreover, the molecular species may be also fixed on the solid support by electrostatic forces, hydrophobic or hydrophilic interactions or Van-der-Waals forces. The above described physico-chemical interactions typically occur in interactions between molecules. In particular embodiments, all that is required is that the molecules (e.g., nucleic acids or polypeptides) remain immobilized or attached to a support under conditions in which it is intended to use the support, for example in applications requiring nucleic acid amplification and/or sequencing or in in antibody-binding assays. For example, oligonucleotides or primers are immobilized such that a 3' end is available for enzymatic extension and/or at least a portion of the sequence is capable of hybridizing to a complementary sequence. In some embodiments, immobilization can occur via hybridization to a surface attached primer, in which case the immobilized primer or oligonucleotide may be in the 3'-5' orientation. In other embodiments, immobilization can occur by means other than base-pairing hybridization, such as the covalent attachment.

The term "immune system", as used herein, refers to cells, molecular components and mechanisms, including antigen-specific and non-specific categories of the adaptive and innate immune systems, respectively, that provide a defense against damage and insults resulting from a viral infection. The term "innate immune system" refers to a host's non-specific reaction to insult to include antigen-nonspecific defense cells, molecular components and mechanisms that come into action immediately or within several hours after exposure to almost any insult or antigen. Elements of the innate immunity include for example phagocytic cells (monocytes, macrophages, dendritic cells, polymorphonuclear leukocytes such as neutrophils, reticuloendothelial cells such as Küpffer cells, and microglia), cells that release inflammatory mediators (basophils, mast cells and eosinophils), natural killer cells (NK cells) and physical barriers and molecules such as keratin, mucous, secretions, complement proteins, immunoglobulin M (IgM), acute phase proteins, fibrinogen and molecules of the clotting cascade, and cytokines. Effector compounds of the innate immune system include chemicals such as lysozymes, IgM, mucous and chemoattractants (e.g., cytokines or histamine), complement and clotting proteins. The term "adaptive immune system" refers to antigen-specific cells, molecular components and mechanisms that emerge over several days, and react with and remove a specific antigen. The adaptive immune system develops throughout a host's lifetime. The adaptive immune system is based on leukocytes, and is divided into two major sections: the humoral immune system, which acts mainly via Immunoglobulins produced by B cells, and the cell-mediated immune system, which functions mainly via T cells.

Reference herein to "immuno-interactive" includes reference to any interaction, reaction, or other form of association between molecules and in particular where one of the molecules is, or mimics, a component of the immune system.

The term "label" is used herein in a broad sense to refer to an agent that is capable of providing a detectable signal, either directly or through interaction with one or more additional members of a signal producing system and that has been artificially added, linked or attached via chemical manipulation to a molecule. Labels can be visual, optical, photonic, electronic, acoustic, opto-acoustic, by mass, electro-chemical, electro-optical, spectrometry, enzymatic, or otherwise chemically, biochemically hydrodynamically, electrically or physically detectable. Labels can be, for example tailed reporter, marker or adapter molecules. In specific embodiments, a molecule such as a nucleic acid molecule is labeled with a detectable molecule selected form the group consisting of radioisotopes, fluorescent compounds, bioluminescent compounds, chemiluminescent compounds, metal chelators or enzymes. Examples of labels include, but are not limited to, the following radioisotopes (e.g., $^3$H, $^{14}$C, $^{35}$S, $^{125}$I, $^{131}$I), fluorescent labels (e.g., FITC, rhodamine, lanthanide phosphors), luminescent labels such as luminol; enzymatic labels (e.g., horseradish peroxidase, beta-galactosidase, luciferase, alkaline phosphatase, acetylcholinesterase), biotinyl groups (which can be detected by marked avidin, e.g., streptavidin containing a fluorescent marker or enzymatic activity that can be detected by optical or calorimetric methods), predetermined polypeptide epitopes recognized by a secondary reporter (e.g., leucine zipper pair sequences, binding sites for secondary antibodies, metal binding domains, epitope tags).

The term "microarray" refers to an arrangement of array elements, e.g., probes (including primers), ligands, biomarker nucleic acid sequence or protein sequences on a substrate. The term "microarray" Includes within its scope "high-density arrays" and "low-density arrays".

The term "nucleic acid" or "polynucleotide" as used herein includes RNA, mRNA, miRNA, cRNA, cDNA mtDNA, or DNA. The term typically refers to a polymeric form of nucleotides of at least 10 bases in length, either ribonucleotides or deoxynucleotides or a modified form of either type of nucleotide. The term includes single and double stranded forms of DNA or RNA.

By "obtained" is meant to come into possession. Samples so obtained include, for example, nucleic acid extracts or polypeptide extracts isolated or derived from a particular source. For instance, the extract may be isolated directly from a biological fluid or tissue of a subject.

As used herein, the term "positive response" means that the result of a treatment regimen includes some clinically significant benefit, such as the prevention, or reduction of severity, of symptoms, or a slowing of the progression of the condition. By contrast, the term "negative response" means that a treatment regimen provides no clinically significant benefit, such as the prevention, or reduction of severity, of symptoms, or increases the rate of progression of the condition.

"Protein", "polypeptide" and "peptide" are used interchangeably herein to refer to a polymer of amino acid residues and to variants and synthetic analogues of the same.

By "primer" is meant an oligonucleotide which, when paired with a strand of DNA, is capable of initiating the synthesis of a primer extension product in the presence of a suitable polymerizing agent. The primer is preferably single-stranded for maximum efficiency in amplification but can alternatively be double-stranded. A primer must be sufficiently long to prime the synthesis of extension products in the presence of the polymerization agent. The length of the primer depends on many factors, including application, temperature to be employed, template reaction conditions, other reagents, and source of primers. For example, depending on the complexity of the target sequence, the primer may be at least about 5, 6, 7, 8, 9, 10, 11, 12, 13, 14, 15, 16, 17, 18, 19, 20, 21, 22, 23, 24, 25, 26, 27, 28, 29, 30, 35, 40, 50, 75, 100, 150, 200, 300, 400, 500, to one base shorter in length than the template sequence at the 3' end of the primer to allow extension of a nucleic acid chain, though the 5' end of the primer may extend in length beyond the 3' end of the template sequence. In certain embodiments, primers can be large polynucleotides, such as from about 35 nucleotides to several kilobases or more. Primers can be selected to be "substantially complementary" to the sequence on the template to which it is designed to hybridize and serve as a site for the initiation of synthesis. By "substantially complementary", it is meant that the primer is sufficiently complementary to hybridize with a target polynucleotide. Desirably, the primer contains no mismatches with the template to which it is designed to hybridize but this is not essential. For example, non-complementary nucleotide residues can be attached to the 5' end of the primer, with the remainder of the primer sequence being complementary to the template. Alternatively, non-complementary nucleotide residues or a stretch of non-complementary nucleotide residues can be interspersed into a primer, provided that the primer sequence has sufficient complementarity with the sequence of the template to hybridize therewith and thereby form a template for synthesis of the extension product of the primer.

As used herein, the term "probe" refers to a molecule that binds to a specific sequence or sub-sequence or other moiety of another molecule. Unless otherwise indicated, the term "probe" typically refers to a nucleic acid probe that binds to another nucleic acid, also referred to herein as a "target polynucleotide", through complementary base pairing. Probes can bind target polynucleotides lacking complete sequence complementarity with the probe, depending on the stringency of the hybridization conditions. Probes can be labeled directly or indirectly and include primers within their scope.

The term "prognosis" as used herein refers to a prediction of the probable course and outcome of a clinical condition or disease. A prognosis is usually made by evaluating factors or symptoms of a disease that are indicative of a favorable or unfavorable course or outcome of the disease. The skilled artisan will understand that the term "prognosis" refers to an increased probability that a certain course or outcome will occur; that is, that a course or outcome is more likely to occur in a subject exhibiting a given condition, when compared to those individuals not exhibiting the condition.

The term "sample" as used herein includes any biological specimen that may be extracted, untreated, treated, diluted or concentrated from a subject. Samples may include, without limitation, biological fluids such as whole blood, serum, red blood cells, white blood cells, plasma, saliva, urine, stool (i.e., feces), tears, sweat, sebum, nipple aspirate, ductal lavage, tumor exudates, synovial fluid, ascitic fluid, peritoneal fluid, amniotic fluid, cerebrospinal fluid, lymph, fine needle aspirate, amniotic fluid, any other bodily fluid, cell lysates, cellular secretion products, inflammation fluid, semen and vaginal secretions. Samples may include tissue samples and biopsies, tissue homogenates and the like. Advantageous samples may include ones comprising any one or more biomarkers as taught herein in detectable quantities. Suitably, the sample is readily obtainable by minimally invasive methods, allowing the removal or isolation of the sample from the subject. In certain embodiments, the sample contains blood, especially peripheral blood, or a fraction or extract thereof. Typically, the sample comprises blood cells such as mature, immature or developing leukocytes, including lymphocytes, polymorphonuclear leukocytes, neutrophils, monocytes, reticulocytes, basophils, coelomocytes, hemocytes, eosinophils, megakaryocytes, macrophages, dendritic cells natural killer cells, or fraction of such cells (e.g., a nucleic acid or protein fraction). In specific embodiments, the sample comprises leukocytes including peripheral blood mononuclear cells (PBMC).

The term "solid support" as used herein refers to a solid inert surface or body to which a molecular species, such as a nucleic acid and polypeptides can be immobilized. Non-limiting examples of solid supports include glass surfaces, plastic surfaces, latex, dextran, polystyrene surfaces, polypropylene surfaces, polyacrylamide gels, gold surfaces, and silicon wafers. In some embodiments, the solid supports are in the form of membranes, chips or particles. For example, the solid support may be a glass surface (e.g., a planar surface of a flow cell channel). In some embodiments, the solid support may comprise an inert substrate or matrix which has been "functionalized", such as by applying a layer or coating of an intermediate material comprising reactive groups which permit covalent attachment to molecules such as polynucleotides. By way of non-limiting example, such supports can include polyacrylamide hydrogels supported on an inert substrate such as glass. The molecules (e.g., polynucleotides) can be directly covalently attached to the intermediate material (e.g., a hydrogel) but the intermediate material can itself be non-covalently attached to the substrate or matrix (e.g., a glass substrate). The support can include a plurality of particles or beads each having a different attached molecular species.

As used herein, the term SIRS ("systemic inflammatory response syndrome") refers to a clinical response arising from a non-specific insult with two or more of the following measureable clinical characteristics; a body temperature greater than 38° C. or less than 36° C., a heart rate greater than 90 beats per minute, a respiratory rate greater than 20 per minute, a white blood cell count (total leukocytes) greater than 12,000 per $mm^3$ or less than 4,000 per $mm^3$, or a band neutrophil percentage greater than 10%. From an immunological perspective, it may be seen as representing a systemic response to insult (e.g., major surgery) or systemic inflammation. As used herein, "VaSIRS" includes any one or more (e.g., 1, 2, 3, 4, 5) of the clinical responses noted above but with underlying viral infection etiology. Confirmation of infection can be determined using any suitable procedure known in the art, illustrative examples of which include nucleic acid detection (e.g., polymerase chain reaction (PCR), immunological detection (e.g., ELISA), isolation of virus from infected cells, cell lysis and imaging techniques such as electron microscopy. From an immunological perspective, VaSIRS may be seen as a systemic response to viral infection, whether it is a local, peripheral or systemic infection.

The terms "subject", "individual" and "patient" are used interchangeably herein to refer to an animal subject, particularly a vertebrate subject, and even more particularly a mammalian subject. Suitable vertebrate animals that fall within the scope of the invention include, but are not restricted to, any member of the phylum Chordata, subphylum vertebrata including primates, rodents (e.g., mice rats, guinea pigs), lagomorphs (e.g., rabbits, hares), bovines (e.g., cattle), ovines (e.g., sheep), caprines (e.g., goats), porcines (e.g., pigs), equines (e.g., horses), canines (e.g., dogs), felines (e.g., cats), avians (e.g., chickens, turkeys, ducks, geese, companion birds such as *canaries*, budgerigars etc.), marine mammals (e.g., dolphins, whales), reptiles (snakes, frogs, lizards, etc.), and fish. A preferred subject is a primate (e.g., a human, ape, monkey, chimpanzee). The subject suitably has at least one (e.g., 1, 2, 3, 4, 5 or more) clinical sign of SIRS.

As used herein, the term "treatment regimen" refers to prophylactic and/or therapeutic (i.e., after onset of a specified condition) treatments, unless the context specifically indicates otherwise. The term "treatment regimen" encompasses natural substances and pharmaceutical agents (i.e., "drugs") as well as any other treatment regimen including but not limited to dietary treatments, physical therapy or exercise regimens, surgical interventions, and combinations thereof.

It will be appreciated that the terms used herein and associated definitions are used for the purpose of explanation only and are not intended to be limiting.

2. Pan-Viral Systemic Inflammation Biomarkers and their Use for Identifying Subjects with VaSIRS The present invention concerns methods, apparatus, compositions and kits for identifying subjects with VaSIRS or for providing a prognosis for subjects with VaSIRS. In particular, VaSIRS biomarkers are disclosed for use in these modalities to assess the likelihood of the presence, absence or degree of VaSIRS in subjects, or for providing a prognosis for subjects with VaSIRS. The methods, apparatus, compositions and kits of the invention are useful for early detection of VaSIRS, thus allowing better treatment interventions for subjects with symptoms of SIRS that stem at least in part from a viral infection.

The present inventors have determined that certain expression products are commonly, specifically and differentially expressed in humans, macaques and pigs during systemic inflammations with a range of viral etiologies (e.g., Groups I, II, III, IV, V, VI and VII viruses), underscoring the conserved nature of the host response to a VaSIRS. The results presented herein provide clear evidence that a unique biologically-relevant biomarker profile predicts VaSIRS with a remarkable degree of accuracy. This "pan-viral" systemic inflammation biomarker profile was validated in two independently derived external datasets (MARS, pediatric) and two publicly available datasets (HIV and PCV) (see, Table 4 for details) and used to distinguish VaSIRS from other SIRS conditions including bacterium associated SIRS (BaSIRS), autoimmune disease associated SIRS (ADaSIRS), cancer associated SIRS (CaSIRS) and trauma associated SIRS (TaSIRS). Overall, these findings provide compelling evidence that the expression products disclosed herein can function as biomarkers for VaSIRS and may potentially serve as a useful diagnostic for triaging treatment decisions for SIRS-affected subjects. In this regard, it is proposed that the methods, apparatus, compositions and kits disclosed herein that are based on these biomarkers may serve in the point-of-care diagnostics that allow for rapid and inexpensive screening for VaSIRS, which may result in significant cost savings to the medical system as VaSIRS-affected subjects can be exposed to therapeutic agents that are suitable for treating VaSIRS as opposed to therapeutic agents for other SIRS conditions.

Thus, specific expression products are disclosed herein as VaSIRS biomarkers that provide a means for identifying VaSIRS and/or for distinguishing VaSIRS from other SIRS conditions including BaSIRS, ADaSIRS, CaSIRS and TaSIRS, and/or for providing a prognosis for a subject with VaSIRS. Evaluation of these VaSIRS biomarkers through analysis of their levels in a subject or in a sample taken from a subject provides a measured or derived biomarker value for determining an indicator that can be used for assessing the presence, absence or degree of VaSIRS in a subject or for providing a prognosis for VaSIRS in a subject.

Accordingly, biomarker values can be measured biomarker values, which are values of biomarkers measured for the subject, or alternatively could be derived biomarker values, which are values that have been derived from one or more measured biomarker values, for example by applying a function to the one or more measured biomarker values. As used herein, biomarkers to which a function has been applied are referred to as "derived markers".

The biomarker values may be determined in any one of a number of ways. An exemplary method of determining biomarker values is described by the present inventors in WO 2015/117204, which is incorporated herein by reference in its entirety. In one example, the process of determining biomarker values can include measuring the biomarker values, for example by performing tests on the subject or on sample(s) taken from the subject. More typically however, the step of determining the biomarker values includes having an electronic processing device receive or otherwise obtain biomarker values that have been previously measured or derived. This could include for example, retrieving the biomarker values from a data store such as a remote database, obtaining biomarker values that have been manually input, using an input device, or the like. The indicator is determined using a combination of the plurality of biomarker values, the indicator being at least partially indicative of the presence, absence, degree or prognosis of VaSIRS. Assuming the method is performed using an electronic processing device, an indication of the indicator is optionally displayed or otherwise provided to the user. In this regard, the indication could be a graphical or alphanumeric representation of an indicator value. Alternatively however, the indication could be the result of a comparison of the indicator value to predefined thresholds or ranges, or alternatively could be an indication of the presence, absence, degree of a VaSIRS or prognosis for a VaSIRS, derived using the indicator.

In some embodiments, biomarker values are combined, for example by adding, multiplying, subtracting, or dividing biomarker values to determine an indicator value. This step is performed so that multiple biomarker values can be combined into a single indicator value, providing a more useful and straightforward mechanism for allowing the indicator to be interpreted and hence used in diagnosing the presence, absence or degree of VaSIRS in the subject, or providing a prognosis for a VaSIRS in the subject.

In some embodiments in which a plurality of biomarkers and biomarker values are used, in order to ensure that an effective diagnosis or prognosis can be determined, at least two of the biomarkers have a mutual correlation in respect of VaSIRS that lies within a mutual correlation range, the mutual correlation range being between ±0.9. This requirement means that the two biomarkers are not entirely correlated in respect of each other when considered in the context of the VaSIRS being diagnosed or prognosed. In other words, at least two of the biomarkers in the combination respond differently as the condition changes, which adds significantly to their ability when combined to discriminate between at least two conditions, to diagnose the presence, absence or degree of VaSIRS, and/or to provide a prognosis for the VaSIRS in or of the subject.

Typically, the requirement that biomarkers have a low mutual correlation means that the biomarkers may relate to different biological attributes or domains such as, but not limited, to different molecular functions, different biological processes and different cellular components. Illustrative examples of molecular function include addition of, or removal of, one of more of the following moieties to, or from, a protein, polypeptide, peptide, nucleic acid (e.g., DNA, RNA): linear, branched, saturated or unsaturated alkyl (e.g., $C_1$-$C_{24}$ alkyl); phosphate; ubiquitin; acyl; fatty acid, lipid, phospholipid; nucleotide base; hydroxyl and the like. Molecular functions also include signaling pathways, including without limitation, receptor signaling pathways and nuclear signaling pathways. Non-limiting examples of molecular functions also include cleavage of a nucleic acid, peptide, polypeptide or protein at one or more sites; polymerization of a nucleic acid, peptide, polypeptide or protein; translocation through a cell membrane (e.g., outer cell membrane; nuclear membrane); translocation into or out of a cell organelle (e.g., Golgi apparatus, lysosome, endoplasmic reticulum, nucleus, mitochondria); receptor binding, receptor signaling, membrane channel binding, membrane channel influx or efflux; and the like.

Illustrative examples of biological processes include: stages of the cell cycle such as meiosis, mitosis, cell division, prophase, metaphase, anaphase, telophase and interphase, stages of cell differentiation; apoptosis; necrosis; chemotaxis; immune responses including adaptive and innate immune responses, pro-inflammatory immune responses, autoimmune responses, tolerogenic responses and the like. Other illustrative examples of biological processes include generating or breaking down adenosine triphosphate (ATP), saccharides, polysaccharides, fatty acids, lipids, phospholipids, sphingolipids, glycolipids, cholesterol, nucleotides, nucleic acids, membranes (e.g., cell plasma membrane, nuclear membrane), amino acids, peptides, polypeptides, proteins and the like. Representative examples of cellular components include organelles, membranes, as for example noted above, and others.

It will be understood that the use of biomarkers that have different biological attributes or domains provides further information than if the biomarkers were related to the same or common biological attributes or domains. In this regard, it will be appreciated if the at least two biomarkers are highly correlated to each other, the use of both biomarkers would add little diagnostic/prognostic improvement compared to the use of a single one of the biomarkers. Accordingly, an indicator-determining method of the present invention in which a plurality of biomarkers and biomarker values are used preferably employ biomarkers that are not well correlated with each other, thereby ensuring that the inclusion of each biomarker in the method adds significantly to the discriminative ability of the indicator.

Despite this, in order to ensure that the indicator can accurately be used in performing the discrimination between at least two conditions (e.g., VaSIRS and healthy condition) or the diagnosis of the presence, absence or degree of VaSIRS or the provision of a prognosis for the VaSIRS, the indicator has a performance value that is greater than or equal to a performance threshold. The performance threshold may be of any suitable form but is to be typically indicative of an explained variance of at least 0.3, or an equivalent value of another performance measure.

Suitably, a combination of biomarkers is employed, which biomarkers have a mutual correlation between ±0.9 and which combination provides an explained variance of at least 0.3. This typically allows an indicator to be defined that is suitable for ensuring that an accurate discrimination, diagnosis or prognosis can be obtained whilst minimizing the number of biomarkers that are required. Typically the mutual correlation range is one of ±0.8; ±0.7; ±0.6; ±0.5; ±0.4; ±0.3; ±0.2; and, ±0.1. Typically each VaSIRS biomarker has a condition correlation with the presence, absence or degree of VaSIRS, or with a prognosis for a VaSIRS that lies outside a condition correlation range, the condition correlation range being between ±0.3 and more typically ±0.9; ±0.8; ±0.7; ±0.6; ±0.5; and, ±0.4. Typically the performance threshold is indicative of an explained variance of at least one of 0.4; 0.5; 0.6; 0.7; 0.8; and 0.9.

It will be understood that in this context, the biomarkers used within the above-described method can define a biomarker profile for a VaSIRS, which includes a minimal number of biomarkers, whilst maintaining sufficient performance to allow the biomarker profile to be used in making a clinically relevant diagnosis, prognosis, or differentiation. Minimizing the number of biomarkers used minimizes the costs associated with performing diagnostic or prognostic tests and in the case of nucleic acid expression products, allows the test to be performed utilizing relatively straightforward techniques such as nucleic acid array, and polymerase chain reaction (PCR) processes, or the like, allowing the test to be performed rapidly in a clinical environment.

Furthermore, producing a single indicator value allows the results of the test to be easily interpreted by a clinician or other medical practitioner, so that test can be used for reliable diagnosis in a clinical environment.

Processes for generating suitable biomarker profiles are described for example in WO 2015/117204, which uses the term "biomarker signature" in place of "biomarker profile" as defined herein. It will be understood, therefore, that terms "biomarker profile" and "biomarker signature" are equivalent in scope. The biomarker profile-generating processes disclosed in WO 2015/117204 provide mechanisms for selecting a combination of biomarkers, and more typically derived biomarkers, that can be used to form a biomarker profile, which in turn can be used in diagnosing the presence, absence or degree of VaSIRS or in providing a prognosis for a VaSIRS. In this regard, the biomarker profile defines the biomarkers that should be measured (i.e., the profile biomarkers), how derived biomarker values should be determined for measured biomarker values, and then how biomarker values should be subsequently combined to generate an indicator value. The biomarker profile can also specify defined indicator value ranges that indicate a particular presence, absence or degree of VaSIRS or that provide a prognosis for a VaSIRS.

Using the above-described methods a number of biomarkers have been identified that are particularly useful for assessing a likelihood that a subject has a presence, absence or degree of VaSIRS or for providing a prognosis for a VaSIRS in a subject. These biomarkers are referred to herein as "VaSIRS biomarkers". As used herein, the term "VaSIRS biomarker" refers to a biomarker of the host, generally a biomarker of the host's immune system, which is altered, or whose level of expression is altered, as part of an inflammatory response to damage or insult resulting from a viral infection. The VaSIRS biomarkers are suitably expression products of genes (also referred to interchangeably herein as "VaSIRS biomarker genes"), including polynucleotide and polypeptide expression products. As used herein, polynucleotide expression products of VaSIRS biomarker genes are referred to herein as "VaSIRS biomarker polynucleotides." Polypeptide expression products of the VaSIRS biomarker genes are referred to herein as "VaSIRS biomarker polypeptides."

VaSIRS biomarker are suitably selected from expression products of any one or more of the following VaSIRS genes: ZBP1, TMEM62, CD38, ISG15, IFI44, RSAD2, HERC5, MX1, HERC6, OAS2, XAF1, IFI6, PARP12, EIF2AK2, DHX58, UBE2L6, DDX60, USP18, RTP4, PHF11, IFIH1, ZBP1, STAT1, LAP3, TAP1, C19orf66, CUL1, POLB, ZC3HAV1, IL16, ITPKB, CAMK2G, CTDSP2, DPEP2, LTB, CBX7, FNBP1, FOXO1, MAST3, LDLRAP1, TMEM204, FAIM3, RGS14, IKBKB, ZXDC, PHF20, DGKA, XPC, PPARD, C2orf58, NLRP1, IL27RA, ABLIM1, JAK1, METTL3, SAFB2, PPM1F, TYK2, BANP, CRTC3, ATM, PAFAH1B1, PIK3IP1, WDR37, TGFBR2, ZNF274, STAT5B, MAML1, SATB1, DOCK9, CHMP7, BRD1, BTG1, ATF7IP2, DIDO1, LEF1, TNRC6B, SERTAD2, CEP68, BCL2, VPS8, CHD3, PUM2, TGOLN2, NDE1, CCR7, PSTPIP1, TIAM1, PECAM1, PDE3B, MYC, FOXJ2, PRMT2, CSNK1D, RPL10A, SERINC5, ARHGEF2, HGSNAT, TRAK1, PHF2, PBX3, SESN1, DPF2, IL4R, NOSIP, MPPE1, NR3C1, ABAT, GCC2, ZFC3H1, SETD2, ITSN2, R3HDM2, ARHGAP15, PCF11, MAPRE2, ST3GAL1, NACA, WDR47, SSBP2, CLK4, EIF3H, FRY, ZNF238, PTGER4, PCNX, NECAP2, CASC3, MSL1, VEZF1, KIAA0232, RASSF2, RPL22, ACAA1, MAP4K4, BEX4, NCBP2, LRMP, CAMK1D, UTP14A, STX6, RPS6KA3, PRKAA1, GOLGA7, ZNF143, SNRK, SYPL1, CYLD, PRUNE, CRLF3, CD93, GPS2, FBXO11, UBE2D2, USP10, CCNG2, SOS2, ARRB1, CEP170, SMAD4, CIAPIN1, KLF7, PHF20L1, ALDH3A2, PDCD6IP, WASF2, TGFBI, GPBP1L1, PCBP2, DCP2, LYST, ERBB2IP, ANKRD49, NDFIP1, ATAD2B, ZNF292, CCNT2, MARCH7, ACAP2, MED13, IL6ST, PHF3, SP3, SEC62, ZFYVE16, NEK7, POLD4, GNA12, TRIB2, YTHDF3, PPP2R5A, PPP1R2, ZDHHC17, STK38L, ST13, FAM134A, PFDN5, MARCH8, POLR1D, OASL, N4BP1, NOD2, RNF19B, PRKAG2, IGSF6, MEF2A, LPIN2, PPP1R11, USP15, BACH1, SSFA2, MKLN1, FYB, NSUN3, MAX, STAM2, HHEX, CLEC4A, ZFAND5, ABI1, MORC3, RC3H2, MAP1LC3B, TM2D3, CHST11, NAB1, KLF3, YPEL5, MXI1, CD97, CYTH4, HCK, ARHGAP26, RARA, XPO6, TNFRSF1A, SLCO3A1, ICAM3, PTPN6, PRKCD, RAB11FIP1, CSF2RB, LCP2, TYROBP, PHC2, RHOG, PSAP, LYN, TMEM127, LILRA2, AOAH, FGR, PLEKHO2, ARAP1, RBM23, PTPRE, KLF6, LIMK2, LILRB3, TLR2, GPR97, GMIP, SIRPA, LRP10, LPAR2, TREM1, IL13RA1, ITGAX, ARHGAP25, SIRPB1, ZDHHC18, TLE3, ITGB2, SNX27, PGS1, ATP6V1B2, RAB31, MAP3K11, PACSIN2, KIAA0513, EMR2, RERE, NUMB, RALB, ETS2, STAT5A, LST1, RIN3, TNK2, IQSEC1, PISD, SORL1, FES, KIAA0247, IL6R, LAPTM5, VAMP3, FAM65B, MAP3K5, TRIM5, ZYX, MAPK14, PLEKHO1, NCOA1, RNASET2, APBB1IP, RXRA, PTAFR, CNPY3, TNFSF13, RPS6KA1, OSBPL2, MTMR3, TMBIM1, TFEB, TFE3, RAF1, STX3, LAT2, GRB2, NDEL1, SEMA4D, FCGRT, DOK3, HIP1, UBN1, PLXNC1, NRBF2, INPP5D, SH2D3C, MMP25, IL10RB, FLOT2, PIAS1, PITPNA, APLP2, CTBP2, GPSM3, RNF130, DGCR2, ZMIZ1, CAP1, GSK3B, RGS19, RAB7A, CREBBP, RBMS1, IL1RAP, RTN3, PPP4R1, TRIOBP, GABARAP, MCTP2, NFKB1, CST3, ABHD2, SH2B3, STX10, TSC22D3, TLE4, HAL, ARRB2, MAP3K3, NPL, CCND3, SERINC3, GNAQ, USP4, PSEN1, KBTBD2, LYL1, AIF1, MBP, ACVR1B, RAB4B, PTEN, ASAP1, MANSC1, RYBP, CSAD, UBXN2B, TNIP1, WBP2, OGFRL1, SNN, HPCAL1, CD37, RNF146, RAB14, TOPORS, NFYA, FOXO3, CREB1, MAPK1, SOAT1, UBQLN2, OSBPL11, KLHL2, VAV3, BRD4, MARK3, BAZ2B, ZNF148, CASP8, CHMP1B, HPS1, RNF141, MOSPD2, PINK1, CDIPT, NCOA4, PPP3R1, MKRN1, GYPC, BMP2K and FBXO9. Non-limiting examples of nucleotide sequences for these VaSIRS biomarkers are listed in SEQ ID NOs: 1-415. Non-limiting examples of amino acid sequences for these VaSIRS biomarkers are listed in SEQ ID NOs: 416-830.

Of the above VaSIRS biomarkers, expression products of ZBP1, TMEM62 and CD38 (e.g., RNA transcripts of these genes) have been found to have strong diagnostic performance on their own (as measured, for example, using area under curve (AUC)) for detecting VaSIRS, or for providing a prognosis for a VaSIRS and are referred to herein as "Group A VaSIRS biomarkers". Thus, in specific embodiments, Group A VaSIRS biomarkers, may be used either by themselves or in combination with other VaSIRS biomarkers including other Group A VaSIRS biomarkers for the determination of the indicator. Suitably, in these embodiments, a biomarker value is measured or derived for the Group A VaSIRS biomarker and optionally for the other VaSIRS biomarker(s) to determine the indicator.

The present inventors have also determined that other VaSIRS biomarkers have strong diagnostic performance when combined with one or more other VaSIRS biomarkers. In advantageous embodiments, pairs of VaSIRS biomarkers have been identified that can be used to determine the indicator. Accordingly, in representative examples of this type, an indicator is determined that correlates to a ratio of VaSIRS biomarkers, which can be used in assessing a likelihood of a subject having a presence, absence or degree of VaSIRS, or in providing a prognosis for a subject with VaSIRS.

In these examples, the indicator-determining methods suitably include determining a pair of biomarker values, wherein each biomarker value is a value measured or derived for at least one corresponding VaSIRS biomarker of the subject and is at least partially indicative of a concentration of the VaSIRS biomarker in a sample taken from the subject. The biomarker values are typically used to determine a derived biomarker value using the pair of biomarker values, wherein the derived biomarker value is indicative of a ratio of concentrations of the pair of VaSIRS biomarkers. Thus, if the biomarker values denote the concentrations of the VaSIRS biomarkers, then the derived biomarker value will be based on a ratio of the biomarker values. However, if the biomarker values are related to the concentrations of the biomarkers, for example if they are logarithmically related by virtue of the biomarker values being based on PCR cycle times, or the like, then the biomarker values may be combined in some other manner, such as by subtracting the cycle times to determine a derived biomarker value indicative of a ratio of the concentrations of the VaSIRS biomarkers.

The derived biomarker value is then used to determine the indicator, either by using the derived biomarker value as an indicator value, or by performing additional processing, such as comparing the derived biomarker value to a reference or the like, as will be described in more detail below.

In some embodiments in which pairs of VaSIRS biomarkers are used to determine a derived biomarker value, one biomarker of a biomarker pair is selected from Group B VaSIRS biomarkers and the other is selected from Group C VaSIRS biomarkers, wherein an individual Group B VaSIRS biomarker is an expression product of a gene selected from the group consisting of: ISG15, IFI44, RSAD2, HERC5, MX1, HERC6, OAS2, XAF1, IFI6, PARP12, EIF2AK2, DHX58, UBE2L6, DDX60, USP18, RTP4, PHF11, IFIH1, ZBP1, STAT, LAP3, TAP1, C19orf66, CUL1, POLB and ZC3HAV1, and wherein an individual Group C VaSIRS biomarker is an expression product of a gene selected from the group consisting of: IL16, ITPKB, CAMK2G, CTDSP2, DPEP2, LTB, CBX7, FNBP1, FOXO1, MAST3, LDL-RAP1, TMEM204, FAIM3, RGS14, IKBKB, ZXDC, PHF20, DGKA, XPC, PPARD, C2orf68, NLRP1, IL27RA, ABLIM1, JAK1, METTL3, SAFB2, PPM1F, TYK2, BANP, CRTC3, ATM, PAFAH1B1, PIK3IP1, WDR37, TGFBR2, ZNF274, STAT5B, MAML1, SATB1, DOCK9, CHMP7, BRD1, BTG1, ATF7IP2, DIDO1, LEF1, TNRC6B, SER-TAD2, CEP68, BCL2, VPS8, CHD3, PUM2, TGOLN2, NDE1, CCR7, PSTPIP1, TIAM1, PECAM1, PDE3B, MYC, FOXJ2, PRMT2, CSNK1D, RPL10A, SERINC5, ARHGEF2, HGSNAT, TRAK1, PHF2, PBX3, SESN1, DPF2, IL4R, NOSIP, MPPE1, NR3C1, ABAT, GCC2, ZFC3H1, SETD2, ITSN2, R3HDM2, ARHGAP15, PCF11, MAPRE2, ST3GAL1, NACA, WDR47, SSBP2, CLK4, EIF3H, FRY, ZNF238, PTGER4, PCNX, NECAP2, CASC3, MSL1, VEZF1, KIAA0232, RASSF2, RPL22, ACAA1, MAP4K4, BEX4, NCBP2, LRMP, CAMK1D, UTP14A, STX6, RPS6KA3, PRKAA1, GOLGA7, ZNF143, SNRK, SYPL1, CYLD, PRUNE, CRLF3, CD93, GPS2, FBXO11, UBE2D2, USP10, CCNG2, SOS2, ARRB1, CEP170, SMAD4, CIAPIN1, KLF7, PHF20L1, ALDH3A2, PDCD6IP, WASF2, TGFBI, GPBP1L1, PCBP2, DCP2, LYST, ERBB2IP, ANKRD49, NDFIP1, ATAD2B, ZNF292, CCNT2, MARCH7, ACAP2, MED13, IL6ST, PHF3, SP3, SEC62, ZFYVE16, NEK7, POLD4, GNA12, TRIB2, YTHDF3, PPP2R5A, PPP1R2, ZDHHC17, STK38L, ST13, FAM134A, PFDN5, MARCH8 and POLR1D.

In other embodiments in which pairs of VaSIRS biomarkers are used to determine a derived biomarker value, one biomarker of a biomarker pair is selected from Group D VaSIRS biomarkers and the other is selected from Group E VaSIRS biomarkers, wherein an individual Group D VaSIRS biomarker is an expression product of a gene selected from the group consisting of: OASL, N4BP1, NOD2, RNF19B, PRKAG2, IGSF6, MEF2A, LPIN2, PPP1R11, USP15, BACH1, SSFA2, MKLN1, FYB, NSUN3, MAX, STAM2, HHEX, CLEC4A, ZFAND5, ABI1, MORC3, RC3H2, MAP1LC3B, TM2D3, CHST11, NAB1, KLF3, YPEL5 and MXI1, and wherein an individual Group E VaSIRS biomarker is an expression product of a gene selected from the group consisting of: CD97, CYTH4, HCK, ARHGAP26, RARA, XPO6, TNFRSF1A, SLCO3A1, ICAM3, PTPN6, PRKCD, RAB11FIP1, CSF2RB, LCP2, TYROBP, PHC2, RHOG, PSAP, LYN, TMEM127, LILRA2, AOAH, FGR, PLEKHO2, ARAP1, RBM23, PTPRE, KLF6, LIMK2, LILRB3, TLR2, GPR97, GMIP, SIRPA, LRP10, LPAR2, TREM1, IL13RA1, ITGAX, ARHGAP25, SIRPB1, ZDHHC18, TLE3, ITGB2, SNX27, PGS1, ATP6V1B2, RAB31, MAP3K11, PACSIN2, KIAA0513, EMR2, RERE, NUMB, RALB, ETS2, STAT5A, LST1, RIN3, TNK2, IQSEC1, PISD, SORL1, FES, KIAA0247, IL6R, LAPTM5, VAMP3, FAM65B, MAP3K5, TRIMS, ZYX, MAPK14, PLEKHO1, NCOA1, RNASET2, APBB1IP, RXRA, PTAFR, CNPY3, TNFSF13, RPS6KA1, OSBPL2, MTMR3, TMBIM1, TFEB, TFE3, RAF1, STX3, LAT2, GRB2, NDEL1, SEMA4D, FCGRT, DOK3, HIP1, UBN1, PLXNC1, NRBF2, INPP5D, SH2D3C, MMP25, IL10RB, FLOT2, PIAS1, PITPNA, APLP2, CTBP2, GPSM3, RNF130, DGCR2, ZMIZ1, CAP1, GSK3B, RGS19, RAB7A, CREBBP, RBMS1, IL1RAP, RTN3, PPP4R1, TRIOBP, GABARAP, MCTP2, NFKB1, CST3, ABHD2, SH2B3, STX10, TSC22D3, TLE4, HAL, ARRB2, MAP3K3, NPL, CCND3, SERINC3, GNAQ, USP4, PSEN1, KBTBD2, LYL1, AIF1, MBP, ACVR1B, RAB4B, PTEN, ASAP1, MANSC1, RYBP, CSAD, UBXN2B, TNIP1, WBP2, OGFRL1, SNN, HPCAL1, CD37, RNF146, RAB14, TOPORS, NFYA, FOXO3, CREB1, MAPK1, SOAT1, UBQLN2, OSBPL11, KLHL2, VAV3, BRD4, MARK3, BAZ2B, ZNF148, CASP8, CHMP1B, HPS1, RNF141, MOSPD2, PINK1, CDIPT, NCOA4, PPP3R1, MKRN1, GYPC, BMP2K and FBXO9.

In specific embodiments, the indicator-determining methods involve determining a first derived biomarker value using a first pair of biomarker values, the first derived biomarker value being indicative of a ratio of concentrations of first and second VaSIRS biomarkers, determining a second derived biomarker value using a second pair of biomarker values, the second derived biomarker value being indicative of a ratio of concentrations of third and fourth VaSIRS biomarkers and determining the indicator by combining the first and second derived biomarker values. Thus, in these embodiments, two pairs of derived biomarker values can be used, which can assist in increasing the ability of the indicator to reliably determine the likelihood of a subject having or not having VaSIRS.

The derived biomarker values could be combined using a combining function such as an additive model; a linear model; a support vector machine; a neural network model; a random forest model; a regression model; a genetic algorithm; an annealing algorithm; a weighted sum; a nearest neighbor model; and a probabilistic model. In some embodiments, biomarker values are measured or derived for a Group B VaSIRS biomarker and for a Group C VaSIRS biomarker, and the indicator is determined by combining the biomarker values. In some embodiments, biomarker values are measured or derived for a Group D VaSIRS biomarker and for a Group E VaSIRS biomarker, and the indicator is determined by combining the biomarker values. In still other in some embodiments, biomarker values are measured or derived for a Group B VaSIRS biomarker, for a Group C VaSIRS biomarker, for a Group D VaSIRS biomarker and for a Group E VaSIRS biomarker, and the indicator is determined by combining the biomarker values.

In some embodiments, the indicator is compared to an indicator reference, with a likelihood being determined in accordance with results of the comparison. The indicator reference may be derived from indicators determined for a number of individuals in a reference population. The reference population typically includes individuals having different characteristics, such as a plurality of individuals of different sexes; and/or ethnicities, with different groups being defined based on different characteristics, with the subject's indicator being compared to indicator references derived from individuals with similar characteristics. The reference population can also include a plurality of healthy individuals, a plurality of individuals suffering from VaSIRS, a plurality of individuals suffering from a SIRS other than VaSIRS (e.g., ADaSIRS, CaSIRS and TaSIRS), a plurality of individuals showing clinical signs of VaSIRS, a plurality of individuals showing clinical signs of a SIRS other than VaSIRS (e.g., ADaSIRS, CaSIRS and TaSIRS), and/or first and second groups of individuals, each group of individuals suffering from a respective diagnosed SIRS.

The indicator can also be used for determining a likelihood of the subject having a first or second condition, wherein the first condition is VaSIRS and the second condition is a healthy condition or another SIRS (e.g., ADaSIRS, CaSIRS and TaSIRS); in other words to distinguish between these conditions. In this case, this would typically be achieved by comparing the indicator to first and second indicator references, the first and second indicator references being indicative of first and second conditions and determining the likelihood in accordance with the results of the comparison. In particular, this can include determining first and second indicator probabilities using the results of the comparisons and combining the first and second indicator probabilities, for example using a Bayes method, to determine a condition probability corresponding to the likelihood of the subject having one of the conditions. In this situation the first and second conditions could include VaSIRS and another SIRS conditions, or VaSIRS and a healthy condition. In this case, the first and second indicator references are distributions of indicators determined for first and second groups of a reference population, the first and second group consisting of individuals diagnosed with the first or second condition respectively.

In specific embodiments, the indicator-determining methods of the present invention are performed using at least one electronic processing device, such as a suitably programmed computer system or the like. In this case, the electronic processing device typically obtains at least two pairs of measured biomarker values, either by receiving these from a measuring or other quantifying device, or by retrieving these from a database or the like. The processing device then determines a first derived biomarker value indicative of a ratio of concentrations of first and second immune system biomarkers and a second derived biomarker value indicative of a ratio of third and fourth immune system biomarkers. The processing device then determines the indicator by combining the first and second derived biomarker values.

The processing device can then generate a representation of the indicator, for example by generating an alphanumeric indication of the indicator, a graphical indication of a comparison of the indicator to one or more indicator references or an alphanumeric indication of a likelihood of the subject having at least one medical condition.

The indicator-determining methods of the present invention typically include obtaining a sample from a subject, who typically has at least one clinical sign of SIRS, wherein the sample includes one or more VaSIRS biomarkers (e.g., polynucleotide or polypeptide expression products of VaSIRS genes) and quantifying at least one (e.g., 1, 2, 3, 4, 5, 6, 7, 8, 9, 10 or more) of the VaSIRS biomarkers within the sample to determine biomarker values. This can be achieved using any suitable technique, and will depend on the nature of the VaSIRS biomarkers. Suitably, an individual measured or derived VaSIRS biomarker value corresponds to the level, abundance or amount of a respective VaSIRS biomarker or to a function that is applied to that level or amount. As used herein the terms "level", "abundance" and "amount" are used interchangeably herein to refer to a quantitative amount (e.g., weight or moles), a semi-quantitative amount, a relative amount (e.g., weight % or mole % within class), a concentration, and the like. Thus, these terms encompass absolute or relative amounts or concentrations of VaSIRS biomarkers in a sample. For example, if the indicator in some embodiments of the indicator-determining method of the present invention, which uses a plurality of VaSIRS biomarkers, is based on a ratio of concentrations of the polynucleotide expression products, this process would typically include quantifying polynucleotide expression products by amplifying at least some polynucleotide expression products in the sample, determining an amplification amount representing a degree of amplification required to obtain a defined level of each of a pair of polynucleotide expression products and determining the indicator by determining a difference between the amplification amounts. In this regard, the amplification amount is generally a cycle time, a number of cycles, a cycle threshold and an amplification time. In this case, the method includes determining a first derived biomarker value by determining a difference between the amplification amounts of a first pair of polynucleotide expression products, determining a second derived biomarker value by determining a difference between the amplification amounts of a second pair of polynucleotide expression products and determining the indicator by adding the first and second derived biomarker values.

In some embodiments, the presence, absence or degree of VaSIRS or prognosis for a VaSIRS in a subject is established by determining one or more of VaSIRS biomarker values, wherein an individual VaSIRS biomarker value is indicative of a value measured or derived for a VaSIRS biomarker in a subject or in a sample taken from the subject. These biomarkers are referred to herein as "sample VaSIRS biomarkers". In accordance with the present invention, a sample VaSIRS biomarker corresponds to a reference VaSIRS biomarker (also referred to herein as a "corresponding VaSIRS biomarker"). By "corresponding VaSIRS biomarker" is meant a VaSIRS biomarker that is structurally and/or functionally similar to a reference VaSIRS biomarker as set forth for example in SEQ ID NOs: 1-830. Representative corresponding VaSIRS biomarkers include expression products of allelic variants (same locus), homologues (different locus), and orthologues (different organism) of reference VaSIRS biomarker genes. Nucleic acid variants of reference VaSIRS biomarker genes and encoded VaSIRS biomarker polynucleotide expression products can contain nucleotide substitutions, deletions, inversions and/or insertions. Variation can occur in either or both the coding and non-coding regions. The variations can produce both conservative and non-conservative amino acid substitutions (as compared in the encoded product). For nucleotide sequences, conservative variants include those sequences that, because of the degeneracy of the genetic code, encode the amino acid sequence of a reference VaSIRS polypeptide.

Generally, variants of a particular VaSIRS biomarker gene or polynucleotide will have at least about 40%, 45%, 50%, 51%, 52%, 53%, 54%, 55%, 56%, 57%, 58%, 59% 60%, 61%, 62%, 63%, 64%, 65%, 66%, 67%, 68%, 69% 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or more sequence identity to that particular nucleotide sequence as determined by sequence alignment programs known in the art using default parameters. In some embodiments, the VaSIRS biomarker gene or polynucleotide displays at least about 40%, 45%, 50%, 51%, 52%, 53%, 54%, 55%, 56%, 57%, 58%, 59% 60%, 61%, 62%, 63%, 64%, 65%, 66%, 67%, 68%, 69% 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or more sequence identity to a nucleotide sequence selected from any one of SEQ ID NO: 1-415.

Corresponding VaSIRS biomarkers also include amino acid sequences that display substantial sequence similarity or identity to the amino acid sequence of a reference VaSIRS biomarker polypeptide. In general, an amino acid sequence that corresponds to a reference amino acid sequence will display at least about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 97, 88, 89, 90, 91, 92, 93, 94, 95, 96, 97, 98, 99% or even up to 100% sequence similarity or identity to a reference amino acid sequence selected from any one of SEQ ID NO: 416-830.

In some embodiments, calculations of sequence similarity or sequence identity between sequences are performed as follows:

To determine the percentage identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In some embodiments, the length of a reference sequence aligned for comparison purposes is at least 30%, usually at least 40%, more usually at least 50%, 60%, and even more usually at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide at the corresponding position in the second sequence, then the molecules are identical at that position. For amino acid sequence comparison, when a position in the first sequence is occupied by the same or similar amino acid residue (i.e., conservative substitution) at the corresponding position in the second sequence, then the molecules are similar at that position.

The percentage identity between the two sequences is a function of the number of identical amino acid residues shared by the sequences at individual positions, taking into account the number of gaps, and the length of each gap, which need to be introduced for optimal alignment of the two sequences. By contrast, the percentage similarity between the two sequences is a function of the number of identical and similar amino acid residues shared by the sequences at individual positions, taking into account the number of gaps, and the length of each gap, which need to be introduced for optimal alignment of the two sequences.

The comparison of sequences and determination of percentage identity or percentage similarity between sequences can be accomplished using a mathematical algorithm. In certain embodiments, the percentage identity or similarity between amino acid sequences is determined using the Needleman and Wünsch, (1970, J. Mol. Biol. 48: 444-453) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6. In specific embodiments, the percent identity between nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. An non-limiting set of parameters (and the one that should be used unless otherwise specified) includes a Blossum 62 scoring matrix with a gap penalty of 12, a gap extend penalty of 4, and a frameshift gap penalty of 5.

In some embodiments, the percentage identity or similarity between amino acid or nucleotide sequences can be determined using the algorithm of E. Meyers and W. Miller (1989, Cabios, 4: 11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al., (1990, J Mol Biol., 215: 403-10). BLAST nucleotide searches can be performed with the NBLAST program, score=100, wordlength=12 to obtain nucleotide sequences homologous to 53010 nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997, Nucleic Acids Res, 25: 3389-3402). When utilizing BLAST and Gapped BLAST programs, the default parameters of the respective programs (e.g., XBLAST and NBLAST) can be used.

Corresponding VaSIRS biomarker polynucleotides also include nucleic acid sequences that hybridize to reference VaSIRS biomarker polynucleotides, or to their complements, under stringency conditions described below. As used herein, the term "hybridizes under low stringency, medium stringency, high stringency, or very high stringency conditions" describes conditions for hybridization and washing. "Hybridization" is used herein to denote the pairing of complementary nucleotide sequences to produce a DNA-DNA hybrid or a DNA-RNA hybrid. Complementary base sequences are those sequences that are related by the base-pairing rules. In DNA, A pairs with T and C pairs with G. In RNA, U pairs with A and C pairs with G. In this regard, the terms "match" and "mismatch" as used herein refer to the hybridization potential of paired nucleotides in complementary nucleic acid strands. Matched nucleotides hybridize efficiently, such as the classical A-T and G-C base pair mentioned above. Mismatches are other combinations of nucleotides that do not hybridize efficiently.

Guidance for performing hybridization reactions can be found in Ausubel et al., (1998, supra), Sections 6.3.1-6.3.6. Aqueous and non-aqueous methods are described in that reference and either can be used. Reference herein to low stringency conditions include and encompass from at least about 1% v/v to at least about 15% v/v formamide and from at least about 1 M to at least about 2 M salt for hybridization at 42° C., and at least about 1 M to at least about 2 M salt for washing at 42° C. Low stringency conditions also may include 1% Bovine Serum Albumin (BSA), 1 mM EDTA, 0.5 M NaHPO$_4$ (pH 7.2), 7% SDS for hybridization at 65° C., and (i) 2×SSC, 0.1% SDS; or (ii) 0.5% BSA, 1 mM EDTA, 40 mM NaHPO$_4$ (pH 7.2), 5% SDS for washing at room temperature. One embodiment of low stringency conditions includes hybridization in 6× sodium chloride/sodium citrate (SSC) at about 45° C., followed by two washes in 0.2×SSC, 0.1% SDS at least at 50° C. (the temperature of the washes can be increased to 55° C. for low stringency conditions). Medium stringency conditions include and encompass from at least about 16% v/v to at least about 30% v/v formamide and from at least about 0.5 M to at least about 0.9 M salt for hybridization at 42° C., and at least about 0.1 M to at least about 0.2 M salt for washing at 55° C. Medium stringency conditions also may include 1% Bovine Serum Albumin (BSA), 1 mM EDTA, 0.5 M NaHPO$_4$ (pH 7.2), 7% SDS for hybridization at 65° C., and (i) 2×SSC, 0.1% SDS; or (ii) 0.5% BSA, 1 mM EDTA, 40 mM NaHPO$_4$ (pH 7.2), 5% SDS for washing at 60-65° C. One embodiment of medium stringency conditions includes hybridizing in 6×SSC at about 45° C., followed by one or more washes in 0.2×SSC, 0.1% SDS at 60° C. High stringency conditions include and encompass from at least about 31% v/v to at least about 50% v/v formamide and from about 0.01 M to about 0.15 M salt for hybridization at 42° C., and about 0.01 M to about 0.02 M salt for washing at 55° C. High stringency conditions also may include 1% BSA, 1 mM EDTA, 0.5 M NaHPO$_4$ (pH 7.2), 7% SDS for hybridization at 65° C., and (i) 0.2×SSC, 0.1% SDS; or (ii) 0.5% BSA, 1 mM EDTA, 40 mM NaHPO$_4$ (pH 7.2), 1% SDS for washing at a temperature in excess of 65° C. One embodiment of high stringency conditions includes hybridizing in 6×SSC at about 45° C., followed by one or more washes in 0.2×SSC, 0.1% SDS at 65° C.

In certain embodiments, a corresponding VaSIRS biomarker polynucleotide is one that hybridizes to a disclosed nucleotide sequence under very high stringency conditions. One embodiment of very high stringency conditions includes hybridizing 0.5 M sodium phosphate, 7% SDS at 65° C., followed by one or more washes at 0.2×SSC, 1% SDS at 65° C.

Other stringency conditions are well known in the art and a skilled addressee will recognize that various factors can be manipulated to optimize the specificity of the hybridization. Optimization of the stringency of the final washes can serve to ensure a high degree of hybridization. For detailed examples, see Ausubel et al., supra at pages 2.10.1 to 2.10.16 and Sambrook et al. (1989, supra) at sections 1.101 to 1.104.

Generally, a sample is processed prior to VaSIRS biomarker detection or quantification. For example, nucleic acid and/or proteins may be extracted, Isolated, and/or purified from a sample prior to analysis. Various DNA, mRNA, and/or protein extraction techniques are well known to those skilled in the art. Processing may include centrifugation, ultracentrifugation, ethanol precipitation, filtration, fractionation, resuspension, dilution, concentration, etc. In some embodiments, methods and systems provide analysis (e.g., quantification of RNA or protein biomarkers) from raw sample (e.g., biological fluid such as blood, serum, etc.) without or with limited processing.

Methods may comprise steps of homogenizing a sample in a suitable buffer, removal of contaminants and/or assay inhibitors, adding a VaSIRS biomarker capture reagent (e.g., a magnetic bead to which is linked an oligonucleotide complementary to a target VaSIRS nucleic acid biomarker), incubated under conditions that promote the association (e.g., by hybridization) of the target biomarker with the capture reagent to produce a target biomarker:capture reagent complex, incubating the target biomarker:capture complex under target biomarker-release conditions. In some embodiments, multiple VaSIRS biomarkers are isolated in each round of isolation by adding multiple VaSIRS biomarkers capture reagents (e.g., specific to the desired biomarkers) to the solution. For example, multiple VaSIRS biomarker capture reagents, each comprising an oligonucleotide specific for a different target VaSIRS biomarker can be added to the sample for isolation of multiple VaSIRS biomarker. It is contemplated that the methods encompass multiple experimental designs that vary both in the number of capture steps and in the number of target VaSIRS biomarker captured in each capture step. In some embodiments, capture reagents are molecules, moieties, substances, or compositions that preferentially (e.g., specifically and selectively) interact with a particular biomarker sought to be isolated, purified, detected, and/or quantified. Any capture reagent having desired binding affinity and/or specificity to the particular VaSIRS biomarker can be used in the present technology. For example, the capture reagent can be a macromolecule such as a peptide, a protein (e.g., an antibody or receptor), an oligonucleotide, a nucleic acid, (e.g., nucleic acids capable of hybridizing with the VaSIRS biomarkers), vitamins, oligosaccharides, carbohydrates, lipids, or small molecules, or a complex thereof. As illustrative and non-limiting examples, an avidin target capture reagent may be used to isolate and purify targets comprising a biotin moiety, an antibody may be used to isolate and purify targets comprising the appropriate antigen or epitope, and an oligonucleotide may be used to isolate and purify a complementary oligonucleotide.

Any nucleic acids, including single-stranded and double-stranded nucleic acids, that are capable of binding, or specifically binding, to a target VaSIRS biomarker can be used as the capture reagent. Examples of such nucleic acids include DNA, RNA, aptamers, peptide nucleic acids, and other modifications to the sugar, phosphate, or nucleoside base. Thus, there are many strategies for capturing a target and accordingly many types of capture reagents are known to those in the art.

In addition, VaSIRS biomarker capture reagents may comprise a functionality to localize, concentrate, aggregate, etc. the capture reagent and thus provide a way to isolate and purify the target VaSIRS biomarker when captured (e.g., bound, hybridized, etc.) to the capture reagent (e.g., when a target:capture reagent complex is formed). For example, in some embodiments the portion of the capture reagent that interacts with the VaSIRS biomarker (e.g., an oligonucleotide) is linked to a solid support (e.g., a bead, surface, resin, column, and the like) that allows manipulation by the user on a macroscopic scale. Often, the solid support allows the use of a mechanical means to isolate and purify the target: capture reagent complex from a heterogeneous solution. For example, when linked to a bead, separation is achieved by removing the bead from the heterogeneous solution, e.g., by physical movement. In embodiments in which the bead is magnetic or paramagnetic, a magnetic field is used to achieve physical separation of the capture reagent (and thus the target VaSIRS biomarker) from the heterogeneous solution.

The VaSIRS biomarkers may be quantified or detected using any suitable technique. In specific embodiments, the VaSIRS biomarkers are quantified using reagents that determine the level, abundance or amount of individual VaSIRS biomarkers. Non-limiting reagents of this type include reagents for use in nucleic acid- and protein-based assays.

In illustrative nucleic acid-based assays, nucleic acid is isolated from cells contained in the biological sample according to standard methodologies (Sambrook, et al., 1989, supra; and Ausubel et al., 1994, supra). The nucleic acid is typically fractionated (e.g., poly A$^+$ RNA) or whole cell RNA. Where RNA is used as the subject of detection, it may be desired to convert the RNA to a complementary DNA. In some embodiments, the nucleic acid is amplified by a template-dependent nucleic acid amplification technique. A number of template dependent processes are available to amplify the VaSIRS biomarker sequences present in a given template sample. An exemplary nucleic acid amplification technique is the polymerase chain reaction (referred to as PCR), which is described in detail in U.S. Pat. Nos. 4,683,195, 4,683,202 and 4,800,159, Ausubel et al. (supra), and in Innis et al., ("PCR Protocols", Academic Press, Inc., San Diego Calif., 1990). Briefly, in PCR, two primer sequences are prepared that are complementary to regions on opposite complementary strands of the biomarker sequence. An excess of deoxynucleotide triphosphates are added to a reaction mixture along with a DNA polymerase, e.g., Taq polymerase. If a cognate VaSIRS biomarker sequence is present in a sample, the primers will bind to the biomarker and the polymerase will cause the primers to be extended along the biomarker sequence by adding on nucleotides. By raising and lowering the temperature of the reaction mixture, the extended primers will dissociate from the biomarker to form reaction products, excess primers will bind to the biomarker and to the reaction products and the process is repeated. A reverse transcriptase PCR amplification procedure may be performed in order to quantify the amount of mRNA amplified. Methods of reverse transcribing RNA into cDNA are well known and described in Sambrook et al., 1989, supra. Alternative methods for reverse transcription utilize thermostable, RNA-dependent DNA polymerases. These methods are described in WO 90/07641. Polymerase chain reaction methodologies are well known in the art. In specific embodiments in which whole cell RNA is used, cDNA synthesis using whole cell RNA as a sample produces whole cell cDNA.

In certain advantageous embodiments, the template-dependent amplification involves quantification of transcripts in real-time. For example, RNA or DNA may be quantified using the Real-Time PCR technique (Higuchi, 1992, et al., *Biotechnology* 10: 413-417). By determining the concentration of the amplified products of the target DNA in PCR reactions that have completed the same number of cycles and are in their linear ranges, it is possible to determine the relative concentrations of the specific target sequence in the original DNA mixture. If the DNA mixtures are cDNAs synthesized from RNAs isolated from different tissues or cells, the relative abundance of the specific mRNA from which the target sequence was derived can be determined for the respective tissues or cells. This direct proportionality between the concentration of the PCR products and the relative mRNA abundance is only true in the linear range of the PCR reaction. The final concentration of the target DNA in the plateau portion of the curve is determined by the availability of reagents in the reaction mix and is independent of the original concentration of target DNA. In specific embodiments, multiplexed, tandem PCR (MT-PCR) is employed, which uses a two-step process for gene expression profiling from small quantities of RNA or DNA, as described for example in US Pat. Appl. Pub. No. 20070190540. In the first step, RNA is converted into cDNA and amplified using multiplexed gene specific primers. In the second step each individual gene is quantitated by real time PCR.

In certain embodiments, target nucleic acids are quantified using blotting techniques, which are well known to those of skill in the art. Southern blotting involves the use of DNA as a target, whereas Northern blotting involves the use of RNA as a target. Each provides different types of information, although cDNA blotting is analogous, in many aspects, to blotting or RNA species. Briefly, a probe is used to target a DNA or RNA species that has been immobilized on a suitable matrix, often a filter of nitrocellulose. The different species should be spatially separated to facilitate analysis. This often is accomplished by gel electrophoresis of nucleic acid species followed by "blotting" on to the filter. Subsequently, the blotted target is incubated with a probe (usually labeled) under conditions that promote denaturation and rehybridization. Because the probe is designed to base pair with the target, the probe will bind a portion of the target sequence under renaturing conditions. Unbound probe is then removed, and detection is accomplished as described above. Following detection/quantification, one may compare the results seen in a given subject with a control reaction or a statistically significant reference group or population of control subjects as defined herein. In this way, it is possible to correlate the amount of VaSIRS biomarker nucleic acid detected with the progression or severity of the disease.

Also contemplated are biochip-based technologies such as those described by Hacia et al. (1996, *Nature Genetics* 14: 441-447) and Shoemaker et al. (1996, *Nature Genetics* 14: 450-456). Briefly, these techniques involve quantitative methods for analyzing large numbers of genes rapidly and accurately. By tagging genes with oligonucleotides or using fixed nucleic acid probe arrays, one can employ biochip technology to segregate target molecules as high-density arrays and screen these molecules on the basis of hybridization. See also Pease et al. (1994, *Proc. Natl. Acad. Sci. U.S.A.* 91: 5022-5026); Fodor et al. (1991, *Science* 251: 767-773). Briefly, nucleic acid probes to VaSIRS biomarker polynucleotides are made and attached to biochips to be used in screening and diagnostic methods, as outlined herein. The nucleic acid probes attached to the biochip are designed to be substantially complementary to specific expressed VaSIRS biomarker nucleic acids, i.e., the target sequence (either the target sequence of the sample or to other probe sequences, for example in sandwich assays), such that hybridization of the target sequence and the probes of the present invention occur. This complementarity need not be perfect; there may be any number of base pair mismatches, which will interfere with hybridization between the target sequence and the nucleic acid probes of the present invention. However, if the number of mismatches is so great that no hybridization can occur under even the least stringent of hybridization conditions, the sequence is not a complementary target sequence. In certain embodiments, more than one probe per sequence is used, with either overlapping probes or probes to different sections of the target being used. That is, two, three, four or more probes, with three being desirable, are used to build in a redundancy for a particular target. The probes can be overlapping (i.e. have some sequence in common), or separate.

In an illustrative biochip analysis, oligonucleotide probes on the biochip are exposed to or contacted with a nucleic acid sample suspected of containing one or more VaSIRS biomarker polynucleotides under conditions favoring specific hybridization. Sample extracts of DNA or RNA, either single or double-stranded, may be prepared from fluid suspensions of biological materials, or by grinding biological materials, or following a cell lysis step which includes, but is not limited to, lysis effected by treatment with SDS (or other detergents), osmotic shock, guanidinium isothiocyanate and lysozyme. Suitable DNA, which may be used in the method of the invention, includes cDNA. Such DNA may be prepared by any one of a number of commonly used protocols as for example described in Ausubel, et al., 1994, supra, and Sambrook, et al., 1989, supra.

Suitable RNA, which may be used in the method of the invention, includes messenger RNA, complementary RNA transcribed from DNA (cRNA) or genomic or subgenomic RNA. Such RNA may be prepared using standard protocols as for example described in the relevant sections of Ausubel, et al. 1994, supra and Sambrook, et al. 1989, supra).

cDNA may be fragmented, for example, by sonication or by treatment with restriction endonucleases. Suitably, cDNA is fragmented such that resultant DNA fragments are of a length greater than the length of the immobilized oligonucleotide probe(s) but small enough to allow rapid access thereto under suitable hybridization conditions. Alternatively, fragments of cDNA may be selected and amplified using a suitable nucleotide amplification technique, as described for example above, Involving appropriate random or specific primers.

Usually the target VaSIRS biomarker polynucleotides are detectably labeled so that their hybridization to individual probes can be determined. The target polynucleotides are typically detectably labeled with a reporter molecule illustrative examples of which include chromogens, catalysts, enzymes, fluorochromes, chemiluminescent molecules, bioluminescent molecules, lanthanide ions (e.g., $Eu^{34}$), a radioisotope and a direct visual label. In the case of a direct visual label, use may be made of a colloidal metallic or non-metallic particle, a dye particle, an enzyme or a substrate, an organic polymer, a latex particle, a liposome, or other vesicle containing a signal producing substance and the like. Illustrative labels of this type include large colloids, for example, metal colloids such as those from gold, selenium, silver, tin and titanium oxide. In some embodiments in which an enzyme is used as a direct visual label, biotinylated bases are incorporated into a target polynucleotide.

The hybrid-forming step can be performed under suitable conditions for hybridizing oligonucleotide probes to test nucleic acid including DNA or RNA. In this regard, reference may be made, for example, to NUCLEIC ACID HYBRIDIZATION, A PRACTICAL APPROACH (Homes and Higgins, eds.) (IRL press, Washington D.C., 1985). In general, whether hybridization takes place is influenced by the length of the oligonucleotide probe and the polynucleotide sequence under test, the pH, the temperature, the concentration of mono- and divalent cations, the proportion of G and C nucleotides in the hybrid-forming region, the viscosity of the medium and the possible presence of denaturants. Such variables also influence the time required for hybridization. The preferred conditions will therefore depend upon the particular application. Such empirical conditions, however, can be routinely determined without undue experimentation.

After the hybrid-forming step, the probes are washed to remove any unbound nucleic acid with a hybridization buffer. This washing step leaves only bound target polynucleotides. The probes are then examined to identify which probes have hybridized to a target polynucleotide.

The hybridization reactions are then detected to determine which of the probes has hybridized to a corresponding target sequence. Depending on the nature of the reporter molecule associated with a target polynucleotide, a signal may be instrumentally detected by irradiating a fluorescent label with light and detecting fluorescence in a fluorimeter; by providing for an enzyme system to produce a dye which could be detected using a spectrophotometer; or detection of a dye particle or a colored colloidal metallic or non-metallic particle using a reflectometer; in the case of using a radioactive label or chemiluminescent molecule employing a radiation counter or autoradiography. Accordingly, a detection means may be adapted to detect or scan light associated with the label which light may include fluorescent, luminescent, focused beam or laser light. In such a case, a charge couple device (CCD) or a photocell can be used to scan for emission of light from a probe:target polynucleotide hybrid from each location in the micro-array and record the data directly in a digital computer. In some cases, electronic detection of the signal may not be necessary. For example, with enzymatically generated color spots associated with nucleic acid array format, visual examination of the array will allow interpretation of the pattern on the array. In the case of a nucleic acid array, the detection means is suitably interfaced with pattern recognition software to convert the pattern of signals from the array into a plain language genetic profile. In certain embodiments, oligonucleotide probes specific for different VaSIRS biomarker polynucleotides are in the form of a nucleic acid array and detection of a signal generated from a reporter molecule on the array is performed using a 'chip reader'. A detection system that can be used by a 'chip reader' is described for example by Pirrung et al. (U.S. Pat. No. 5,143,854). The chip reader will typically also incorporate some signal processing to determine whether the signal at a particular array position or feature is a true positive or maybe a spurious signal. Exemplary chip readers are described for example by Fodor et al. (U.S. Pat. No. 5,925,525). Alternatively, when the array is made using a mixture of individually addressable kinds of labeled microbeads, the reaction may be detected using flow cytometry.

In certain embodiments, the VaSIRS biomarker is a target RNA (e.g., mRNA) or a DNA copy of the target RNA whose level or abundance is measured using at least one nucleic acid probe that hybridizes under at least low, medium, or high stringency conditions to the target RNA or to the DNA copy, wherein the nucleic acid probe comprises at least 15 (e.g., 15, 16, 17, 18, 19, 20, 21, 22, 23, 24, 25, 26, 27, 28, 29, 30, or more) contiguous nucleotides of VaSIRS biomarker polynucleotide. In some embodiments, the measured level or abundance of the target RNA or its DNA copy is normalized to the level or abundance of a reference RNA or a DNA copy of the reference RNA. Suitably, the nucleic acid probe is immobilized on a solid or semi-solid support. In illustrative examples of this type, the nucleic acid probe forms part of a spatial array of nucleic acid probes. In some embodiments, the level of nucleic acid probe that is bound to the target RNA or to the DNA copy is measured by hybridization (e.g., using a nucleic acid array). In other embodiments, the level of nucleic acid probe that is bound to the target RNA or to the DNA copy is measured by nucleic acid amplification (e.g., using a polymerase chain reaction (PCR)). In still other embodiments, the level of nucleic acid probe that is bound to the target RNA or to the DNA copy is measured by nuclease protection assay.

Sequencing technologies such as Sanger sequencing, pyrosequencing, sequencing by ligation, massively parallel sequencing, also called "Next-generation sequencing" (NGS), and other high-throughput sequencing approaches with or without sequence amplification of the target can also be used to detect or quantify the presence of VaSIRS nucleic acid biomarker in a sample. Sequence-based methods can provide further information regarding alternative splicing and sequence variation in previously identified genes. Sequencing technologies include a number of steps that are grouped broadly as template preparation, sequencing, detection and data analysis. Current methods for template preparation involve randomly breaking genomic DNA into smaller sizes from which each fragment is immobilized to a support. The immobilization of spatially separated fragment allows thousands to billions of sequencing reaction to be performed simultaneously. A sequencing step may use any of a variety of methods that are commonly known in the art. One specific example of a sequencing step uses the addition of nucleotides to the complementary strand to provide the DNA sequence. The detection steps range from measuring bioluminescent signal of a synthesized fragment to four-color imaging of single molecule. In some embodiments in which NGS is used to detect or quantify the presence of VaSIRS nucleic acid biomarker in a sample, the methods are suitably selected from semiconductor sequencing (Ion Torrent; Personal Genome Machine); Helicos True Single Molecule Sequencing (tSMS) (Harris et al. 2008, *Science* 320: 106-109); 454 sequencing (Roche) (Margulies et al. 2005, *Nature*, 437, 376-380); SOLID technology (Applied Biosystems); SOLEXA sequencing (Illumina); single molecule, real-time (SMRT™) technology of Pacific Biosciences; nanopore sequencing (Soni and Meller, 2007. *Clin Chem* 53: 1996-2001); DNA nanoball sequencing; sequencing using technology from Dover Systems (Polonator), and technologies that do not require amplification or otherwise transform native DNA prior to sequencing (e.g., Pacific Biosciences and Helicos), such as nanopore-based strategies (e.g., Oxford Nanopore, Genia Technologies, and Nabsys).

In other embodiments, VaSIRS biomarker protein levels are assayed using protein-based assays known in the art. For example, when VaSIRS biomarker protein is an enzyme, the protein can be quantified based upon its catalytic activity or based upon the number of molecules of the protein contained in a sample. Antibody-based techniques may be employed including, for example, immunoassays, such as the enzyme-linked immunosorbent assay (ELISA) and the radioimmunoassay (RIA).

In specific embodiments, protein-capture arrays that permit simultaneous detection and/or quantification of a large number of proteins are employed. For example, low-density protein arrays on filter membranes, such as the universal protein array system (Ge, 2000 *Nucleic Acids Res.* 28(2):e3) allow imaging of arrayed antigens using standard ELISA techniques and a scanning charge-coupled device (CCD) detector. Immuno-sensor arrays have also been developed that enable the simultaneous detection of clinical analytes. It is now possible using protein arrays, to profile protein expression in bodily fluids, such as in sera of healthy or diseased subjects, as well as in subjects pre- and post-drug treatment.

Exemplary protein capture arrays include arrays comprising spatially addressed antigen-binding molecules, commonly referred to as antibody arrays, which can facilitate extensive parallel analysis of numerous proteins defining a proteome or subproteome. Antibody arrays have been shown to have the required properties of specificity and acceptable background, and some are available commercially (e.g., BD Biosciences, Clontech, Bio-Rad and Sigma). Various methods for the preparation of antibody arrays have been reported (see, e.g., Lopez et al., 2003 *J. Chromatogram. B* 787:19-27; Cahill, 2000 *Trends in Biotechnology* 7:47-51; U.S. Pat. App. Pub. 2002/0055186; U.S. Pat. App. Pub. 2003/0003599; PCT publication WO 03/062444; PCT publication WO 03/077851; PCT publication WO 02/59601; PCT publication WO 02/39120; PCT publication WO 01/79849; PCT publication WO 99/39210). The antigen-binding molecules of such arrays may recognize at least a subset of proteins expressed by a cell or population of cells, illustrative examples of which include growth factor receptors, hormone receptors, neurotransmitter receptors, catecholamine receptors, amino acid derivative receptors, cytokine receptors, extracellular matrix receptors, antibodies, lectins, cytokines, serpins, proteases, kinases, phosphatases, ras-like GTPases, hydrolases, steroid hormone receptors, transcription factors, heat-shock transcription factors, DNA-binding proteins, zinc-finger proteins, leucine-zipper proteins, homeodomain proteins, intracellular signal transduction modulators and effectors, apoptosis-related factors, DNA synthesis factors, DNA repair factors, DNA recombination factors and cell-surface antigens.

Individual spatially distinct protein-capture agents are typically attached to a support surface, which is generally planar or contoured. Common physical supports include glass slides, silicon, microwells, nitrocellulose or PVDF membranes, and magnetic and other microbeads.

Particles in suspension can also be used as the basis of arrays, providing they are coded for identification; systems include color coding for microbeads (e.g., available from Luminex, Bio-Rad and Nanomics Biosystems) and semiconductor nanocrystals (e.g., QDots™, available from Quantum Dots), and barcoding for beads (UltraPlexm, available from Smartbeads) and multimetal microrods (Nanobarcodes™ particles, available from Surromed). Beads can also be assembled into planar arrays on semiconductor chips (e.g., available from LEAPS technology and BioArray Solutions). Where particles are used, individual protein-capture agents are typically attached to an individual particle to provide the spatial definition or separation of the array. The particles may then be assayed separately, but in parallel, in a compartmentalized way, for example in the wells of a microtiter plate or in separate test tubes.

In operation, a protein sample, which is optionally fragmented to form peptide fragments (see, e.g., U.S. Pat. App. Pub. 2002/0055186), is delivered to a protein-capture array under conditions suitable for protein or peptide binding, and the array is washed to remove unbound or non-specifically bound components of the sample from the array. Next, the presence or amount of protein or peptide bound to each feature of the array is detected using a suitable detection system. The amount of protein bound to a feature of the array may be determined relative to the amount of a second protein bound to a second feature of the array. In certain embodiments, the amount of the second protein in the sample is already known or known to be invariant.

In specific embodiments, the VaSIRS biomarker is a target polypeptide whose level is measured using at least one antigen-binding molecule that is immuno-interactive with the target polypeptide. In these embodiments, the measured level of the target polypeptide is normalized to the level of a reference polypeptide. Suitably, the antigen-binding molecule is immobilized on a solid or semi-solid support. In illustrative examples of this type, the antigen-binding molecule forms part of a spatial array of antigen-binding molecule. In some embodiments, the level of antigen-binding molecule that is bound to the target polypeptide is measured by immunoassay (e.g., using an ELISA).

All the essential reagents required for detecting and quantifying the VaSIRS biomarkers of the invention may be assembled together in a kit. In some embodiments, the kit comprises a reagent that permits quantification of at least one VaSIRS biomarker. In some embodiments the kit comprises: (I) a reagent that allows quantification (e.g., determining the level or abundance) of a first VaSIRS biomarker; and (ii) a reagent that allows quantification (e.g., determining the level or abundance) of a second VaSIRS biomarker, wherein the first and second biomarkers have a mutual correlation in respect of VaSIRS that lies within a mutual correlation range of between ±0.9, and wherein a combination of respective biomarker values for the first and second VaSIRS biomarkers that are measured for or derived from a subject has a performance value greater than or equal to a performance threshold representing the ability of the combination of the first and second VaSIRS biomarkers to diagnose the presence, absence or degree of the at least one condition, or to provide a prognosis for the at least one condition, the performance threshold being a variance explained of at least 0.3. In some embodiments, the kit further comprises (iii) a reagent that allows quantification (e.g., determining the level or abundance) of a third VaSIRS biomarker; and (iv) a reagent that allows quantification (e.g., determining the level or abundance) of a fourth VaSIRS biomarker, wherein the third and fourth VaSIRS biomarkers have a mutual correlation in respect of VaSIRS that lies within a mutual correlation range of between ±0.9, and wherein a combination of respective biomarker values for the third and fourth VaSIRS biomarkers that are measured for or derived from a subject has a performance value greater than or equal to a performance threshold representing the ability of the combination of the third and fourth VaSIRS biomarkers to diagnose the presence, absence or degree of VaSIRS, or to provide a prognosis for a VaSIRS, the performance threshold being a variance explained of at least 0.3.

In the context of the present invention, "kit" Is understood to mean a product containing the different reagents necessary for carrying out the methods of the invention packed so as to allow their transport and storage. Materials suitable for packing the components of the kit include crystal, plastic (polyethylene, polypropylene, polycarbonate and the like), bottles, vials, paper, envelopes and the like. Additionally, the kits of the invention can contain instructions for the simultaneous, sequential or separate use of the different components contained in the kit. The instructions can be in the form of printed material or in the form of an electronic support capable of storing instructions such that they can be read by a subject, such as electronic storage media (magnetic disks, tapes and the like), optical media (CD-ROM, DVD) and the like. Alternatively or in addition, the media can contain Internet addresses that provide the instructions.

Reagents that allow quantification of a VaSIRS biomarker include compounds or materials, or sets of compounds or materials, which allow quantification of the VaSIRS biomarker. In specific embodiments, the compounds, materials or sets of compounds or materials permit determining the expression level of a gene (e.g., VaSIRS biomarker gene), including without limitation the extraction of RNA material, the determination of the level of a corresponding RNA, etc., primers for the synthesis of a corresponding cDNA, primers for amplification of DNA, and/or probes capable of specifically hybridizing with the RNAs (or the corresponding cDNAs) encoded by the genes, TaqMan probes, etc.

The kits may also optionally include appropriate reagents for detection of labels, positive and negative controls, washing solutions, blotting membranes, microtiter plates, dilution buffers and the like. For example, a nucleic acid-based detection kit may include (i) a VaSIRS biomarker polynucleotide (which may be used as a positive control), (ii) a primer or probe that specifically hybridizes to a VaSIRS biomarker polynucleotide. Also included may be enzymes suitable for amplifying nucleic acids including various polymerases (reverse transcriptase, Taq, Sequenase™, DNA ligase etc. depending on the nucleic acid amplification technique employed), deoxynucleotides and buffers to provide the necessary reaction mixture for amplification. Such kits also generally will comprise, in suitable means, distinct containers for each individual reagent and enzyme as well as for each primer or probe. Alternatively, a protein-based detection kit may include (I) a VaSIRS biomarker polypeptide (which may be used as a positive control), (ii) an antibody that binds specifically to a VaSIRS biomarker polypeptide. The kit can also feature various devices (e.g., one or more) and reagents (e.g., one or more) for performing one of the assays described herein; and/or printed instructions for using the kit to quantify the expression of a VaSIRS biomarker gene.

The reagents described herein, which may be optionally associated with detectable labels, can be presented in the format of a microfluidics card, a chip or chamber, a microarray or a kit adapted for use with the assays described in the examples or below, e.g., RT-PCR or Q PCR techniques described herein.

The reagents also have utility in compositions for detecting and quantifying the biomarkers of the invention. For example, a reverse transcriptase may be used to reverse transcribe RNA transcripts, including mRNA, in a nucleic acid sample, to produce reverse transcribed transcripts, including reverse transcribed mRNA (also referred to as "cDNA"). In specific embodiments, the reverse transcribed mRNA is whole cell reverse transcribed mRNA (also referred to herein as "whole cell cDNA"). The nucleic acid sample is suitably derived from components of the immune system, representative examples of which include components of the innate and adaptive immune systems as broadly discussed for example above. In specific embodiments, the reverse transcribed RNA is derived blood cells (e.g., peripheral blood cells). Suitably, the reverse transcribed RNA is derived leukocytes.

The reagents are suitably used to quantify the reverse transcribed transcripts. For example, oligonucleotide primers that hybridize to the reverse transcribed transcript can be used to amplify at least a portion of the reverse transcribed transcript via a suitable nucleic acid amplification technique, e.g., RT-PCR or qPCR techniques described herein. Alternatively, oligonucleotide probes may be used to hybridize to the reverse transcribed transcript for the quantification, using a nucleic acid hybridization analysis technique (e.g., microarray analysis), as described for example above. Thus, in some embodiments, a respective oligonucleotide primer or probe is hybridized to a complementary nucleic acid sequence of a reverse transcribed transcript in the compositions of the invention. The compositions typically comprise labeled reagents for detecting and/or quantifying the reverse transcribed transcripts. Representative reagents of this type include labeled oligonucleotide primers or probes that hybridize to RNA transcripts or reverse transcribed RNA, labeled RNA, labeled reverse transcribed RNA as well as labeled oligonucleotide linkers or tags (e.g., a labeled RNA or DNA linker or tag) for labeling (e.g., end labeling such as 3' end labeling) RNA or reverse transcribed RNA. The primers, probes, RNA or reverse transcribed RNA (i.e., cDNA) (whether labeled or non-labeled) may be immobilized or free in solution. Representative reagents of this type include labeled oligonucleotide primers or probes that hybridize to reverse transcribed and transcripts as well as labeled reverse transcribed transcripts. The label can be any agent that is capable of providing a detectable signal or reporter molecule as known in the art, illustrative examples of which are described above and elsewhere herein.

The present invention also encompasses non-reverse transcribed RNA embodiments in which cDNA is not made and the RNA transcripts are directly the subject of the analysis. Thus, in other embodiments, reagents are suitably used to quantify RNA transcripts directly. For example, oligonucleotide probes can be used to hybridize to transcripts for quantification of immune system biomarkers of the invention, using a nucleic acid hybridization analysis technique (e.g., microarray analysis), as described for example above. Thus, in some embodiments, a respective oligonucleotide probe is hybridized to a complementary nucleic acid sequence of an immune system biomarker transcript in the compositions of the invention. In illustrative examples of this type, the compositions may comprise labeled reagents that hybridize to transcripts for detecting and/or quantifying the transcripts. Representative reagents of this type include labeled oligonucleotide probes that hybridize to transcripts as well as labeled transcripts. The primers or probes may be immobilized or free in solution.

The present invention also extends to the management of VaSIRS, or prevention of further progression of VaSIRS, or assessment of the efficacy of therapies in subjects following positive diagnosis for the presence of VaSIRS, in a subject. Once a subject is positively identified as having VaSIRS, the subject may be administered a therapeutic agent for treating the VaSIRS such as an anti-viral agent, illustrative examples of which include abacavir, acyclovir, acyclovir, adefovir, amantadine, amprenavir, ampligen, arbidol, asunaprevir, atazanavir, atripla, boceprevir, cidofovir, combivir, complera, daclatasvir, darunavir, delavirdine, didanosine, docosanol, dolutegravir, edoxudine, efavirenz, emtricitabine, enfuvirtide, entecavir, famciclovir, fomivirsen, fosamprenavir, foscarnet, fosfonet, ganciclovir, ibacitabine, immunovir, idoxuridine, imiquimod, indinavir, inosine, interferon type III, interferon type II, interferon type I, lamivudine, lopinavir, loviride, maraviroc, moroxydine, methisazone, nelfinavir, nevirapine, nexavir, neuraminidase blocking agents, oseltamivir, peginterferon alfa-2a, penciclovir, peramivir, pleconaril, podofilox, podophyllin, podophyllotoxin, raltegravir, monoclonal antibody respigams, ribavirin, inhaled rhibovirons, rimantadine, ritonavir, pyrimidine, saquinavir, stavudine, stribild, tenofovir, tenofovir disoproxil, tenofovir alafenamide fumarate (TAF), tipranavir, trifluridine, trizivir, tromantadine, truvada, valaciclovir, valganciclovir, vicriviroc, vidarabine, viperin, viramidine, zalcitabine, zanamivir, zidovudine, or salts and combinations thereof.

Typically, the therapeutic agents will be administered in pharmaceutical (or veterinary) compositions together with a pharmaceutically acceptable carrier and in an effective amount to achieve their intended purpose. The dose of active compounds administered to a subject should be sufficient to achieve a beneficial response in the subject over time such as a reduction in, or relief from, the symptoms of VaSIRS. The quantity of the pharmaceutically active compounds(s) to be administered may depend on the subject to be treated inclusive of the age, sex, weight and general health condition thereof. In this regard, precise amounts of the active compound(s) for administration will depend on the judgment of the practitioner. In determining the effective amount of the active compound(s) to be administered in the treatment or prevention of VaSIRS, the medical practitioner or veterinarian may evaluate severity of any symptom or clinical sign associated with the presence of VaSIRS or degree of VaSIRS including, inflammation, blood pressure anomaly, tachycardia, tachypnea fever, chills, vomiting, diarrhea, skin rash, headaches, confusion, muscle aches, seizures. In any event, those of skill in the art may readily determine suitable dosages of the therapeutic agents and suitable treatment regimens without undue experimentation.

The therapeutic agents may be administered in concert with adjunctive (palliative) therapies to increase oxygen supply to major organs, increase blood flow to major organs and/or to reduce the inflammatory response. Illustrative examples of such adjunctive therapies include non-steroidal-anti-inflammatory drugs (NSAIDs), intravenous saline and oxygen.

The present invention also contemplates the use of the indicator-determining methods, apparatus, compositions and kits disclosed herein in methods of treating, preventing or inhibiting the development of VaSIRS in a subject. These methods (also referred to herein as "treatment methods") generally comprise: exposing the subject to a treatment regimen for treating VaSIRS, or avoiding exposing the subject to a treatment regimen for treating a SIRS other than VaSIRS based on an indicator obtained from an indicator-determining method as disclosed herein. In specific embodiments, these treatment methods comprise: (1) determining a biomarker value that is measured or derived for at least one (e.g., 1, 2, 3, 4, 5, 6, 7, 8, 9, 10, or more) corresponding VaSIRS biomarker of the subject; (2) determining the indicator using the biomarker value; and (3) administering to the subject, on the basis that the indicator indicates the presence of VaSIRS, an effective amount of an agent that treats or ameliorates the symptoms or reverses or inhibits the development of VaSIRS. In other embodiments, the treatment methods comprise: (a) determining a plurality of biomarker values, each biomarker value being indicative of a value measured or derived for at least one (e.g., 1, 2, 3, 4, 5, 6, 7, 8, 9, 10, or more) VaSIRS biomarker of the subject; (b) determining an indicator using a combination of the plurality of biomarker values, the indicator being at least partially indicative of the presence, absence or degree of VaSIRS, wherein: (i) at least two (e.g., 2, 3, 4, 5, 6, 7, 8, 9, 10, or more) VaSIRS biomarkers have a mutual correlation in respect of the at least one condition that lies within a mutual correlation range, the mutual correlation range being between ±0.9; and (ii) the indicator has a performance value greater than or equal to a performance threshold representing the ability of the indicator to diagnose the presence, absence or degree of VaSIRS, the performance threshold being indicative of an explained variance of at least 0.3; and (c) administering to the subject, on the basis that the indicator indicates the presence of VaSIRS, an effective amount of an agent that treats or ameliorates the symptoms or reverses or inhibits the development of VaSIRS.

In advantageous embodiments, the treatment methods comprise: (1) determining a plurality of measured biomarker values, each measured biomarker value being a measured value of a VaSIRS biomarker of the subject; and (2) applying a function to at least one of the measured biomarker values to determine at least one derived biomarker value, the at least one derived biomarker value being indicative of a value of a corresponding derived VaSIRS biomarker. The function suitably includes at least one of: (a) multiplying two biomarker values; (b) dividing two biomarker values; (c) adding two biomarker values; (d) subtracting two biomarker values; (e) a weighted sum of at least two biomarker values; (f) a log sum of at least two biomarker values; and (g) a sigmoidal function of at least two biomarker values.

The present invention can be practiced in the field of predictive medicine for the purpose of diagnosis or monitoring the presence or development of VaSIRS in a subject, and/or monitoring response to therapy efficacy. The biomarker profiles and corresponding indicators of the present invention further enable determination of endpoints in pharmacotranslational studies. For example, clinical trials can take many months or even years to establish the pharmacological parameters for a medicament to be used in treating or preventing VaSIRS. However, these parameters may be associated with a biomarker profile and corresponding indicator of a health state (e.g., a healthy condition). Hence, the clinical trial can be expedited by selecting a treatment regimen (e.g., medicament and pharmaceutical parameters), which results in a biomarker profile associated with a desired health state (e.g., healthy condition). This may be determined for example by: (1) determining a biomarker value that is measured or derived for at least one (e.g., 1, 2, 3, 4, 5, 6, 7, 8, 9, 10, or more) corresponding VaSIRS biomarker of a subject after treatment with a treatment regimen; (2) determining the indicator using the biomarker value; and (3) determining that the treatment regimen is effective for changing the health status of the subject to the desired health state (e.g., healthy condition) on the basis that the indicator indicates the presence of a healthy condition or the presence of a condition of a lower degree relative to the degree of the condition in the subject before treatment with the treatment regimen. As used herein, the term "degree" refers to the extent or stage of a condition. Alternatively, selection of the treatment regimen may be determined by: (a) determining a plurality of biomarker values, each biomarker value being indicative of a value measured or derived for at least one (e.g., 1, 2, 3, 4, 5, 6, 7, 8, 9, 10, or more) VaSIRS biomarker of a subject after treatment with a treatment regimen; (b) determining an indicator using a combination of the plurality of VaSIRS biomarker values, the indicator being at least partially indicative of the presence, absence or degree of at least one condition selected from a healthy condition, inSIRS, ipSIRS or a particular stage of ipSIRS, wherein: (i) at least two (e.g., 2, 3, 4, 5, 6, 7, 8, 9, 10, or more) VaSIRS biomarkers have a mutual correlation in respect of the at least one condition that lies within a mutual correlation range, the mutual correlation range being between ±0.9; and (ii) the indicator has a performance value greater than or equal to a performance threshold representing the ability of the indicator to diagnose the presence, absence or degree of the at least one condition, or to provide a prognosis for the at least one condition, the performance threshold being indicative of an explained variance of at least 0.3, and (c) determining that the treatment regimen is effective for changing the health status of the subject to the desired health state (e.g., healthy condition) on the basis that the indicator indicates the presence of a healthy condition or the presence of a condition of a lower degree relative to the degree of the condition in the subject before treatment with the treatment regimen. Accordingly, this aspect of the present invention advantageously provides methods of monitoring the efficacy of a particular treatment regimen in a subject (for example, in the context of a clinical trial) already diagnosed with VaSIRS. These methods take advantage of measured or derived biomarker values that correlate with treatment efficacy to determine, for example, whether measured or derived biomarker values of a subject undergoing treatment partially or completely normalize during the course of or following therapy or otherwise shows changes associated with responsiveness to the therapy.

Accordingly, the invention provides methods of correlating a biomarker profile with an effective treatment regimen for VaSIRS. In some embodiments, these methods comprise: (1) determining a biomarker profile defining a biomarker value that is measured or derived for at least one (e.g., 1, 2, 3, 4, 5, 6, 7, 8, 9, 10, or more) corresponding VaSIRS biomarker of a subject with VaSIRS and for whom an effective treatment has been identified; and (2) correlating the biomarker profile so determined with an effective treatment regimen for VaSIRS. In other embodiments, the biomarker profile-correlating methods comprise: (a) determining a biomarker profile defining a combination of at least two (e.g., 2, 3, 4, 5, 6, 7, 8, 9, 10, or more) biomarker values corresponding to values of at least two VaSIRS biomarkers that can be measured for or derived from a subject with VaSIRS and for whom an effective treatment has been identified, wherein: (i) the at least two VaSIRS biomarkers have a mutual correlation in respect of the condition that lies within a mutual correlation range, the mutual correlation range being between ±0.9; and (ii) the combination of at least two biomarker values has a performance value greater than or equal to a performance threshold representing the ability of the combination of at least two biomarker values to diagnose the presence, absence or degree of VaSIRS, or to provide a prognosis for the VaSIRS, the performance threshold being indicative of an explained variance of at least 0.3; and (b) correlating the biomarker profile so determined with an effective treatment regimen for the condition. In specific embodiments, an indicator or biomarker profile is correlated to a global probability or a particular outcome, using receiver operating characteristic (ROC) curves.

The invention further provides methods of determining whether a treatment regimen is effective for treating a subject with VaSIRS. In some embodiments, these methods comprise: (1) determining a post-treatment biomarker value that is measured or derived for at least one (e.g., 1, 2, 3, 4, 5, 6, 7, 8, 9, 10, or more) corresponding VaSIRS biomarker of a subject after treatment with a treatment regimen; (2) determining a post-treatment indicator using the post-treatment biomarker value, wherein the post-treatment indicator is at least partially indicative of the presence, absence or degree of VaSIRS, wherein the post-treatment indicator indicates whether the treatment regimen is effective for treating VaSIRS in the subject on the basis that post-treatment indicator indicates the presence of a healthy condition or the presence of VaSIRS of a lower degree relative to the degree of VaSIRS in the subject before treatment with the treatment regimen. In other embodiments, these methods comprise: (a) determining a plurality of post-treatment biomarker values, each post-treatment VaSIRS biomarker value being indicative of a value measured or derived for at least one (e.g., 1, 2, 3, 4, 5, 6, 7, 8, 9, 10, or more) VaSIRS biomarker of a subject after treatment with the treatment regimen; (b) determining a post-treatment indicator using a combination of the plurality of post-treatment biomarker values, the post-treatment indicator being at least partially indicative of the presence, absence or degree of VaSIRS, wherein: (i) the at least two (e.g., 2, 3, 4, 5, 6, 7, 8, 9, 10, or more) VaSIRS biomarkers have a mutual correlation in respect of the at least one condition that lies within a mutual correlation range, the mutual correlation range being between ±0.9; and (ii) the post-treatment indicator has a performance value greater than or equal to a performance threshold representing the ability of the post-treatment indicator to diagnose the presence, absence or degree of VaSIRS, the performance threshold being indicative of an explained variance of at least 0.3, wherein the post-treatment indicator indicates whether the treatment regimen is effective for treating the VaSIRS in the subject on the basis that post-treatment indicator indicates the presence of a healthy condition or the presence of VaSIRS of a lower degree relative to the degree of VaSIRS in the subject before treatment with the treatment regimen.

The invention can also be practiced to evaluate whether a subject is responding (i.e., a positive response) or not responding (i.e., a negative response) to a treatment regimen. This aspect of the invention provides methods of correlating a biomarker profile with a positive or negative response to a treatment regimen. In some embodiments, these methods comprise: (1) determining a biomarker profile defining a biomarker value that is measured or derived for at least one (e.g., 1, 2, 3, 4, 5, 6, 7, 8, 9, 10, or more) corresponding VaSIRS biomarker of a subject following commencement of the treatment regimen; and (2) correlating the biomarker profile so determined with a positive or negative response to the treatment regimen. In other embodiments, these methods comprise: (a) determining a biomarker profile defining a combination of at least two (e.g., 2, 3, 4, 5, 6, 7, 8, 9, 10, or more) biomarker values corresponding to values of at least two VaSIRS biomarkers that can be measured for or derived from a subject following commencement of the treatment regimen, wherein: (i) the at least two VaSIRS biomarkers have a mutual correlation in respect of VaSIRS, which lies within a mutual correlation range, the mutual correlation range being between ±0.9; and (ii) the combination of at least two biomarker values has a performance value greater than or equal to a performance threshold representing the ability of the combination of at least two biomarker values to diagnose the presence, absence or degree of VaSIRS, or to provide a prognosis for the VaSIRS, the performance threshold being indicative of an explained variance of at least 0.3; and (b) correlating the biomarker profile so determined with a positive or negative response to the treatment regimen.

The invention also encompasses methods of determining a positive or negative response to a treatment regimen by a subject with VaSIRS. In some embodiments, these methods comprise: (1) correlating a reference biomarker profile with a positive or negative response to the treatment regimen, wherein the biomarker profile defines a biomarker value that is measured or derived for at least one (e.g., 1, 2, 3, 4, 5, 6, 7, 8, 9, 10, or more) corresponding VaSIRS biomarker of a control subject or control group; (2) determining a sample biomarker profile defining a biomarker value that is measured or derived for the at least one (e.g., 1, 2, 3, 4, 5, 6, 7, 8, 9, 10, or more) corresponding VaSIRS biomarker of the subject following commencement of the treatment regimen, wherein the sample biomarker profile indicates whether the subject is responding positively or negatively to the treatment regimen, based on the correlation of the reference biomarker signature with the positive or negative response to the treatment regimen. In other embodiments, the methods comprise: (a) correlating a reference biomarker profile with a positive or negative response to the treatment regimen, wherein the biomarker profile defines a combination of at least two (e.g., 2, 3, 4, 5, 6, 7, 8, 9, 10, or more) biomarker values corresponding to values of at least two VaSIRS biomarkers that are measured for or derived from a control subject or control group, wherein: (i) the at least two VaSIRS biomarkers have a mutual correlation in respect of VaSIRS, which lies within a mutual correlation range, the mutual correlation range being between ±0.9; and (ii) the combination of at least two biomarker values has a performance value greater than or equal to a performance threshold representing the ability of the combination of at least two biomarker values to diagnose the presence, absence or degree of VaSIRS, or to provide a prognosis for the VaSIRS, the performance threshold being indicative of an explained variance of at least 0.3; (b) determining a sample biomarker profile defining a combination of at least two (e.g., 2, 3, 4, 5, 6, 7, 8, 9, 10, or more) biomarker values corresponding to values of the at least two VaSIRS biomarkers that are measured or derived from the subject following commencement of the treatment regimen, wherein the sample biomarker profile indicates whether the subject is responding positively or negatively to the treatment regimen, based on the correlation of the reference biomarker profile with the positive or negative response to the treatment regimen.

In related embodiments, the present invention further contemplates methods of determining a positive or negative response to a treatment regimen by a subject. In some embodiments, these methods comprise: (1) determining a sample biomarker profile defining a biomarker value that is measured or derived for at least one (e.g., 1, 2, 3, 4, 5, 6, 7, 8, 9, 10, or more) corresponding VaSIRS biomarker of a subject following commencement of the treatment regimen, wherein the sample biomarker profile is correlated with a positive or negative response to the treatment regimen; and (2) determining whether the subject is responding positively or negatively to the treatment regimen based on the sample biomarker profile. In other embodiments, these methods comprise: (a) determining a sample biomarker profile defining a combination of at least two (e.g., 2, 3, 4, 5, 6, 7, 8, 9, 10, or more) biomarker values corresponding to values of at least two VaSIRS biomarkers that are measured for or derived from a subject following commencement of the treatment regimen, wherein: (i) the at least two VaSIRS biomarkers have a mutual correlation in respect of VaSIRS, which lies within a mutual correlation range, the mutual correlation range being between ±0.9; and (ii) the combination of at least two biomarker values has a performance value greater than or equal to a performance threshold representing the ability of the combination of at least two biomarker values to diagnose the presence, absence or degree of VaSIRS, or to provide a prognosis for the VaSIRS, the performance threshold being indicative of an explained variance of at least 0.3, wherein the sample biomarker profile is correlated with a positive or negative response to the treatment regimen; and (b) determining whether the subject is responding positively or negatively to the treatment regimen based on the sample biomarker profile.

The above methods can be practiced to identify responders or non-responders relatively early in the treatment process, i.e., before clinical manifestations of efficacy. In this way, the treatment regimen can optionally be discontinued, a different treatment protocol can be implemented and/or supplemental therapy can be administered. Thus, in some embodiments, a sample VaSIRS biomarker profile is obtained within about 2 hours, 4 hours, 6 hours, 12 hours, 1 day, 2 days, 3 days, 4 days, 5 days, 1 week, 2 weeks, 3 weeks, 4 weeks, 6 weeks, 8 weeks, 10 weeks, 12 weeks, 4 months, six months or longer of commencing therapy.

The present invention also contemplates methods in which the indicator-determining method of the invention is implemented using one or more processing devices. In some embodiments, these methods comprise: (1) determining a pair of biomarker values, the pair of biomarker values being selected from the group consisting of: (a) a first pair of biomarker values indicative of a concentration of polynucleotide expression products of a Group B VaSIRS biomarker gene (e.g., ISG15) and a Group C VaSIRS biomarker gene (e.g., IL16); and (b) a second pair of biomarker values indicative of a concentration of polynucleotide expression products of a Group D VaSIRS biomarker gene (e.g., OASL) gene and a Group E VaSIRS biomarker gene (e.g., CD97); (2) determining an indicator indicative of a ratio of the concentrations of the polynucleotide expression products using the pair of biomarker values; (3) retrieving previously determined first and second indicator references from a database, the first and second indicator references being determined based on indicators determined from first and second groups of a reference population, one of the groups consisting of individuals diagnosed with VaSIRS; (4) comparing the indicator to the first and second indicator references; (5) using the results of the comparison to determine a probability indicative of the subject having or not having VaSIRS; and (6) generating a representation of the probability, the representation being displayed to a user to allow the user to assess the likelihood of a subject having VaSIRS.

Similarly apparatus can be provided for determining the likelihood of a subject having VaSIRS, the apparatus including: (A) a sampling device that obtains a sample taken from a subject, the sample including polynucleotide expression products; (B) a measuring device that quantifies polynucleotide expression products within the sample to determine a pair of biomarker values, the pair of biomarker values being selected from the group consisting of: (a) a first pair of biomarker values indicative of a concentration of polynucleotide expression products of a Group B VaSIRS biomarker gene (e.g., ISG15) and a Group C VaSIRS biomarker gene (e.g., IL16); and (b) a second pair of biomarker values indicative of a concentration of polynucleotide expression products of a Group D VaSIRS biomarker gene (e.g., OASL) gene and a Group E VaSIRS biomarker gene (e.g., CD97); (C) at least one processing device that: (I) receives an indication of the pair of biomarker values from the measuring device; (ii) determines an indicator using a ratio of the concentration of the first and second polynucleotide expression products using the biomarker values; (iii) compares the indicator to at least one indicator reference; (iv) determines a likelihood of the subject having or not having VaSIRS condition using the results of the comparison; and (v) generates a representation of the indicator and the likelihood for display to a user.

The present invention also encompasses methods for differentiating between VaSIRS and another SIRS other than VaSIRS in a subject. These methods suitably comprise: (a) obtaining a sample taken from a subject showing a clinical sign of SIRS, the sample including polynucleotide expression products; (b) in a measuring device: (i) amplifying at least some polynucleotide expression products in the sample; (ii) determining an amplification amount representing a degree of amplification required to obtain a defined level of polynucleotide expression products including: amplification amounts for a first pair of polynucleotide expression products of a Group B VaSIRS biomarker gene (e.g., ISG15) and a Group C VaSIRS biomarker gene (e.g., IL16); and amplification amounts for a second pair of polynucleotide expression products of a Group D VaSIRS biomarker gene (e.g., OASL) gene and a Group E VaSIRS biomarker gene (e.g., CD97); (c) in a processing system: (i) retrieving the amplification amounts; (ii) determining an indicator by: determining a first derived biomarker value indicative of a ratio of concentrations of the first pair of polynucleotide expression products by determining a difference between the amplification amounts for the first pair; determining a second derived biomarker value indicative of a ratio of concentrations of the second pair of polynucleotide expression products by determining a difference between the amplification amounts for the second pair; (d) determining the indicator by adding the first and second derived biomarker values; (e) retrieving previously determined first and second indicator references from a database, wherein the first and second indicator references are distributions of indicators determined for first and second groups of a reference population, the first and second group consisting of individuals diagnosed with VaSIRS and the other SIRS, respectively; (f) comparing the indicator to the first and second indicator references; (g) using the results of the comparison to determine a probability of the subject being classified within the first or second group; (h) generating a representation at least partially indicative of the indicator and the probability; and (i) providing the representation to a user to allow the user to assess the likelihood of a subject having or not having VaSIRS or the other SIRS.

Additionally, methods can be provided for determining an indicator used in assessing a likelihood of a subject having a presence, absence or degree of VaSIRS, or in providing a prognosis for a VaSIRS. These methods suitably include: (1) determining a plurality of biomarker values, each biomarker value being indicative of a value measured or derived for at least one corresponding VaSIRS biomarker of the subject and being at least partially indicative of a concentration of the VaSIRS biomarker in a sample taken from the subject; (2) determining the indicator using a combination of the plurality of biomarker values, wherein: at least two biomarkers have a mutual correlation in respect of VaSIRS that lies within a mutual correlation range, the mutual correlation range being between ±0.9; and the indicator has a performance value greater than or equal to a performance threshold representing the ability of the indicator to diagnose the presence, absence or degree of VaSIRS, or to provide a prognosis for the VaSIRS, the performance threshold being indicative of an explained variance of at least 0.3.

In order that the invention may be readily understood and put into practical effect, particular preferred embodiments will now be described by way of the following non-limiting examples.

EXAMPLES

Example 1

Group A Biomarkers and their Diagnostic Performance Across Various Datasets

Three Individual biomarkers were discovered that had strong diagnostic performance (as measured using area under curve (AUC)) across all viral datasets, including ZBP1 (DNA SEQ ID NO: 399), TMEM62 (DNA SEQ ID NO: 414) and CD38 (DNA SEQ ID NO: 415). These biomarkers were discovered using four "core viral" datasets including dengue, Lassa fever, Influenza and herpes virus infections. Ten "validation viral" datasets were then used to validate these biomarkers. These datasets included samples taken from patients with a broad range of virus infections including adenovirus, herpesvirus, enterovirus, rhinovirus, hepatitis C virus, measles, rotavirus and respiratory syncytial virus. "Non-viral inflammation" datasets included conditions that cause a systemic inflammation including, amongst others; bacterial Infection, anaphylaxis and trauma, and potentially confounding factors such as obesity, age, gender and race. The AUC for each biomarker in each dataset is listed in Table 2., the three right hand columns.

Example 2

Groups B, C, D and E Biomarkers. Biomarkers are Grouped Based on their Correlation to ISG15, IL16, OASL and CD97

Two pairs of derived biomarkers (IL16/ISG15; CD97/OASL) were discovered that provided the highest AUC across all of the viral datasets studied. Biomarkers as ratios that provided AUC>0.8 (see Table 13 for full list of derived biomarkers) were then allocated to one of four Groups, as individual biomarkers, based on their correlation to either ISG15 (Group B), IL16 (Group C), OASL (Group D) or CD97 (Group E), as presented in Table 10.

Example 3

VaSIRS Biomarker Derivation (Single and Derived Biomarkers)

An illustrative process for the identification of VaSIRS biomarkers for use in diagnostic algorithms will now be described.

Gene expression data (derived from clinical trials performed by the inventors or from Gene Expression Omnibus) were analyzed using a variety of statistical approaches to identify individual and derived biomarkers (ratios) but largely follows the method described in WO 2015/117204. Individual and derived markers were graded based on performance (Area Under Curve).

Datasets used for training were derived from GEO (which are all MIAME-compliant) with the following restrictions; peripheral blood samples were used, appropriate controls were used, an appropriate number of samples were used to provide significance following False-Discovery Rate (FDR) adjustment, all data passed standard quality control metrics, principle component analysis did not reveal any artifacts or potential biases. The datasets were divided into two groups—"discovery" and "validation" listed in Table 3 and Table 4. Details of the types of viruses studied are included in Table 5. The datasets in the "discovery" group were deliberately chosen to enable the identification of a specific VaSIRS biomarker profile that could be used for all viruses and across different species, and therefore included studies of; DNA and RNA viruses, multiple mammalian species (human and macaque), experimentally-Infected subjects where a control sample was taken prior to inoculation, samples taken over time, in particular early-stage samples.

Prior to analysis each dataset was filtered to include only the top 6000 genes as measured by the mean gene expression level across all samples in the dataset. This ensured that only those genes with relatively strong expression were analysed and that a limited number of candidates were taken forward to the next compute-time intensive step. Receiver Operator Curve (ROC) and Area Under Curve (AUC) were then calculated across all derived biomarkers using the difference in the log 2 of the expression values for each derived biomarker. This resulted in approximately 36,000,000 derived biomarkers per dataset. An AUC>0.5 was defined as a derived biomarker value being higher in cases than controls, i.e. where the numerator is potentially up-regulated in cases and/or the denominator is potentially down-regulated in cases. All four "discovery" datasets were combined by taking the mean AUC for each derived biomarker. Resulting derived biomarkers were then filtered by keeping only those with a mean AUC greater than or equal to 0.92 across all four datasets. The number of remaining derived biomarkers after this step was 856 (~0.003% of the original number). This same process was repeated except the search was performed using single biomarkers (rather than as derived biomarkers) and an AUC filter of 0.70 was applied. The number of remaining single biomarkers after this process was 11 (~0.18% of the original number of single biomarkers).

The 856 derived biomarkers were then tested (AUC calculated) on an additional 10 viral datasets ("validation" datasets—see Table 4).

To ensure that these 856 derived biomarkers were specific to viral inflammation (were not indicative of inflammation associated with bacterial infection, trauma, autoimmune disease, other non-viral systemic inflammatory conditions) a number of additional datasets (n=21, listed in Table 6) were used to identify derived biomarkers of generalized, non-viral inflammation. These datasets were subject to the same restrictions as the "discovery" and "validation" datasets including; peripheral blood samples were used, appropriate controls were used, an appropriate number of samples were used to provide significance following False-Discovery Rate (FDR) adjustment, all data passed standard quality control metrics, principle component analysis did not reveal any artifacts or potential biases. Only those samples relating to non-viral inflammation were analysed as part of this process of identifying derived biomarkers of generalized, non-viral inflammation. Derived biomarkers that had strong performance (based on AUC>0.8 In more than 3 of the 21 datasets) were removed (subtracted) from the list of identified pan-viral derived biomarkers (856) to ensure specificity.

A further filtering step was then applied. Only derived biomarkers with an AUC greater than 0.75 In at least 11 of the 14 viral datasets (the 4 discovery datasets and the 10 validation sets) were retained. A cut-off AUC of 0.75 was chosen for the following four reasons: 1). simple diagnostic heuristics for the diagnosis of influenza have an AUC between 0.7 and 0.79 (Ebell, M. H., & Afonso, A. (2011). A Systematic Review of Clinical Decision Rules for the Diagnosis of influenza. The Annals of Family Medicine, 9(1), 69-77); 2). clinicians can predict patients that are ultimately blood culture positive from those with suspected infection with an AUC of 0.77 (Fischer, J. E., Harbarth, S., Agthe, A. G., Benn, A., Ringer, S. A., Goldmann, D. A., & Fanconi, S. (2004). Quantifying uncertainty: physicians' estimates of infection in critically ill neonates and children. Clinical Infectious Diseases: an Official Publication of the infectious Diseases Society of America, 38(10), 1383-1390); 3). the use of polymerase chain reaction-based tests, compared to conventional tests, for respiratory pathogens in patients with suspected lower respiratory tract infections (LRTI) increased the diagnostic yield from 21% to 43% of cases (that is, molecular-based pathogen tests in this study only detected a pathogen in 43% of suspected LRTI) (Oosterheert, J. J., van Loon, A. M., Schuurman, R., Hoepelman, A. I. M., Hak, E., Thijsen, S., et al. (2005). Impact of rapid detection of viral and atypical bacterial pathogens by real-time polymerase chain reaction for patients with lower respiratory tract infection. Clinical Infectious Diseases, 41(10), 1438-1444); 4). the sensitivity of point-of-care tests for influenza is about 70% (Foo, H., & Dwyer, D. E. (2009). Rapid tests for the diagnosis of influenza. Australian Prescriber 32:64-67). Thus, current existing diagnostic procedures and tests for viral infections do not have good diagnostic performance, and in many instances no pathogen or antibody response is detected in samples taken at the time the patient presents with clinical signs. A pan-viral signature with an AUC of at least 0.75 will therefore have greater clinical utility than most existing viral diagnostic assays, and at the critical time when the patient presents with clinical signs. Following this filtering step, 473 derived biomarkers remained.

Example 4

VaSIRS Biomarker Derivation (Combination of Derived Biomarkers)

Next, a search for the best combination and number of derived biomarkers was performed with the aim of finding a minimal set of derived biomarkers with optimal commercial utility. Optimal commercial utility in this instance means consideration of the following non-limiting factors; diagnostic performance, clinical utility, diagnostic noise (introduced by using too many derived biomarkers), transferability to available molecular chemistries (e.g. PCR, microarray, DNA sequencing), transferability to available point-of-care platforms (e.g. Biocartis Idylla, Cepheid GeneXpert, Becton Dickinson BD Max, Curetis Unyvero, Oxford Nanopore Technologies MinION), cost of assay manufacture (the more reagents and biomarkers the larger the cost), ability to multiplex biomarkers, availability of suitable reporter dyes, complexity of results interpretation.

To be able to determine the best combination of derived markers all study datasets needed to be combined. As such, all 14 viral datasets were normalized individually using mean centering to zero and variance set to one. The mean of a biomarker in a dataset was calculated in three steps: (a) calculation of the mean of the cases, (b) calculation of the mean of the controls, and (c) calculation of the mean of the preceding two values. Once the mean for each biomarker had been calculated, the expression values for that biomarker in each sample was adjusted by subtracting the mean value. The values were further adjusted by dividing by the variance. This was performed for all biomarker expression values for every sample in every dataset. All 14 viral datasets were then combined into a single expression matrix.

Following normalization, a search (greedy) for the best performing pair of derived biomarkers was performed (by AUC in the normalized dataset). This was accomplished by first identifying the best performing derived biomarker. Each of the other remaining derived biomarkers was then added and, as long as neither biomarker in the newly added derived biomarker was already part of the first derived biomarker, the AUC was calculated. This process continued and an AUC plot was generated based on sequential adding of derived biomarkers.

Example 5

VaSIRS Biomarker Performance (Single, Derived Biomarkers and Combined Derived Biomarkers)

Figure 2:
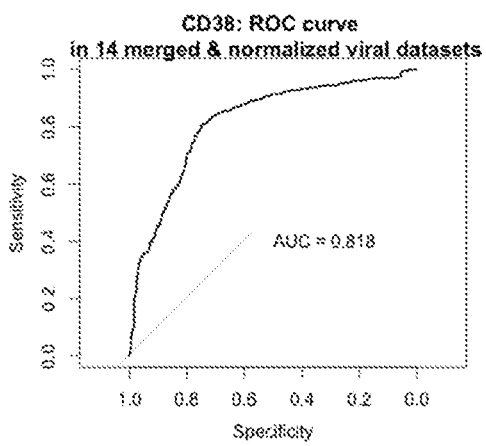
FIG. 2 is a plot of the performance (AUC) of CD38 In the merged and normalized dataset (14 Individual datasets).
Figure 3:
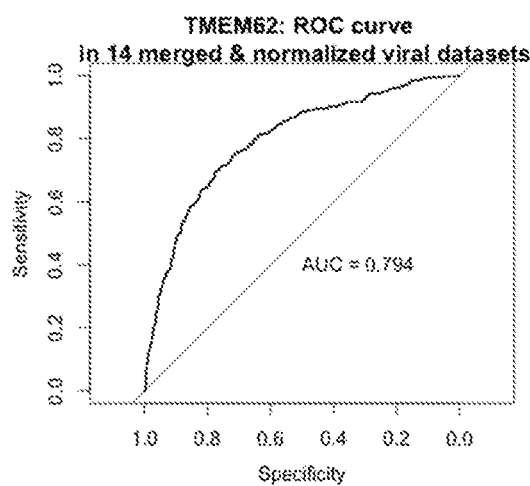
FIG. 3 is a plot of the performance (AUC) of TMEM62 In the merged and normalized dataset (14 Individual datasets).
Figure 4:
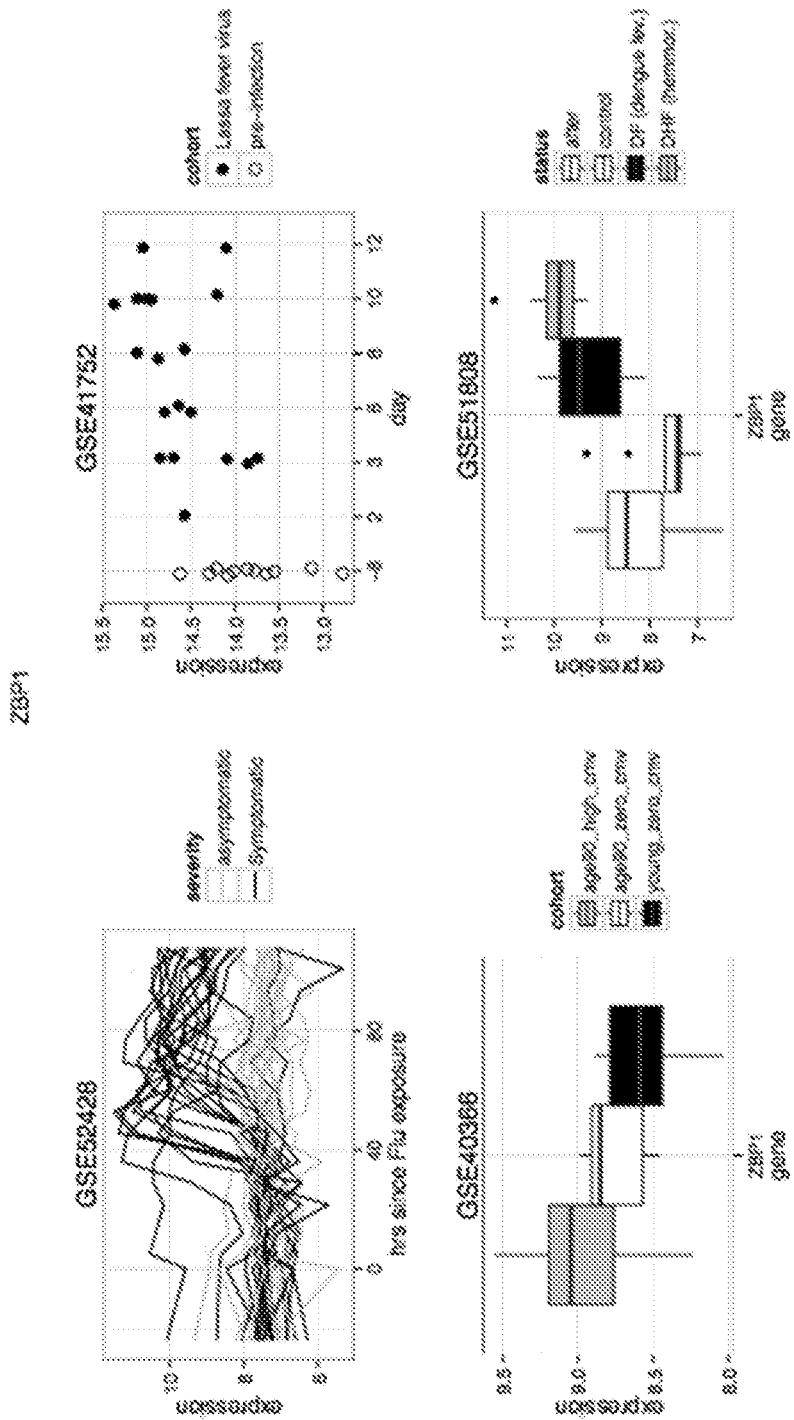
FIG. 4 shows plots of the performance of the individual biomarker ZBP1 In the four "core" viral datasets, including influenza virus, Lassa fever virus, cytomegalovirus and dengue fever virus.
Figure 5:
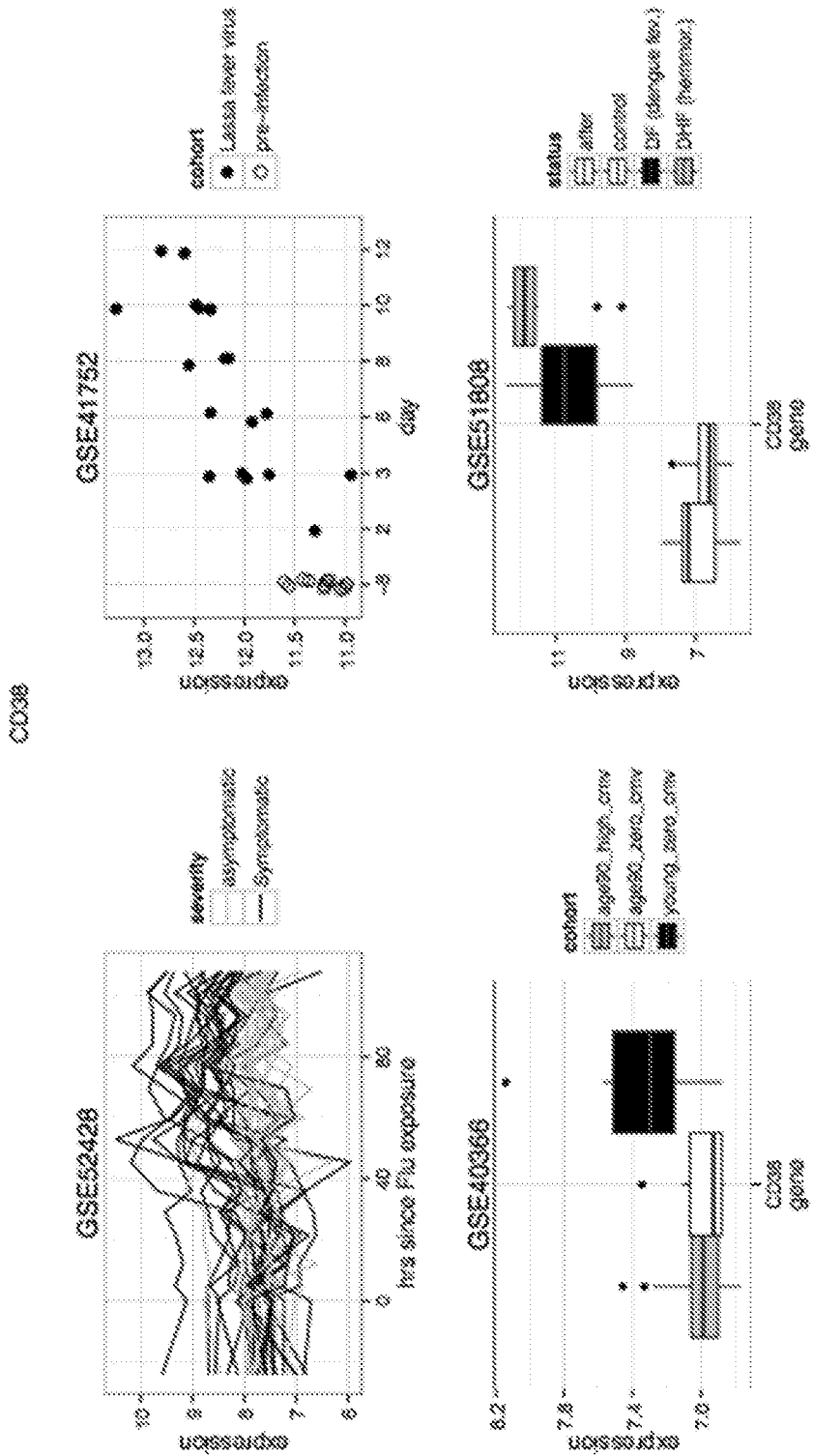
FIG. 5 shows plots of the performance of the individual biomarker CD38 In the four "core" viral datasets, including influenza virus, Lassa fever virus, cytomegalovirus and dengue fever virus.
Figure 6:
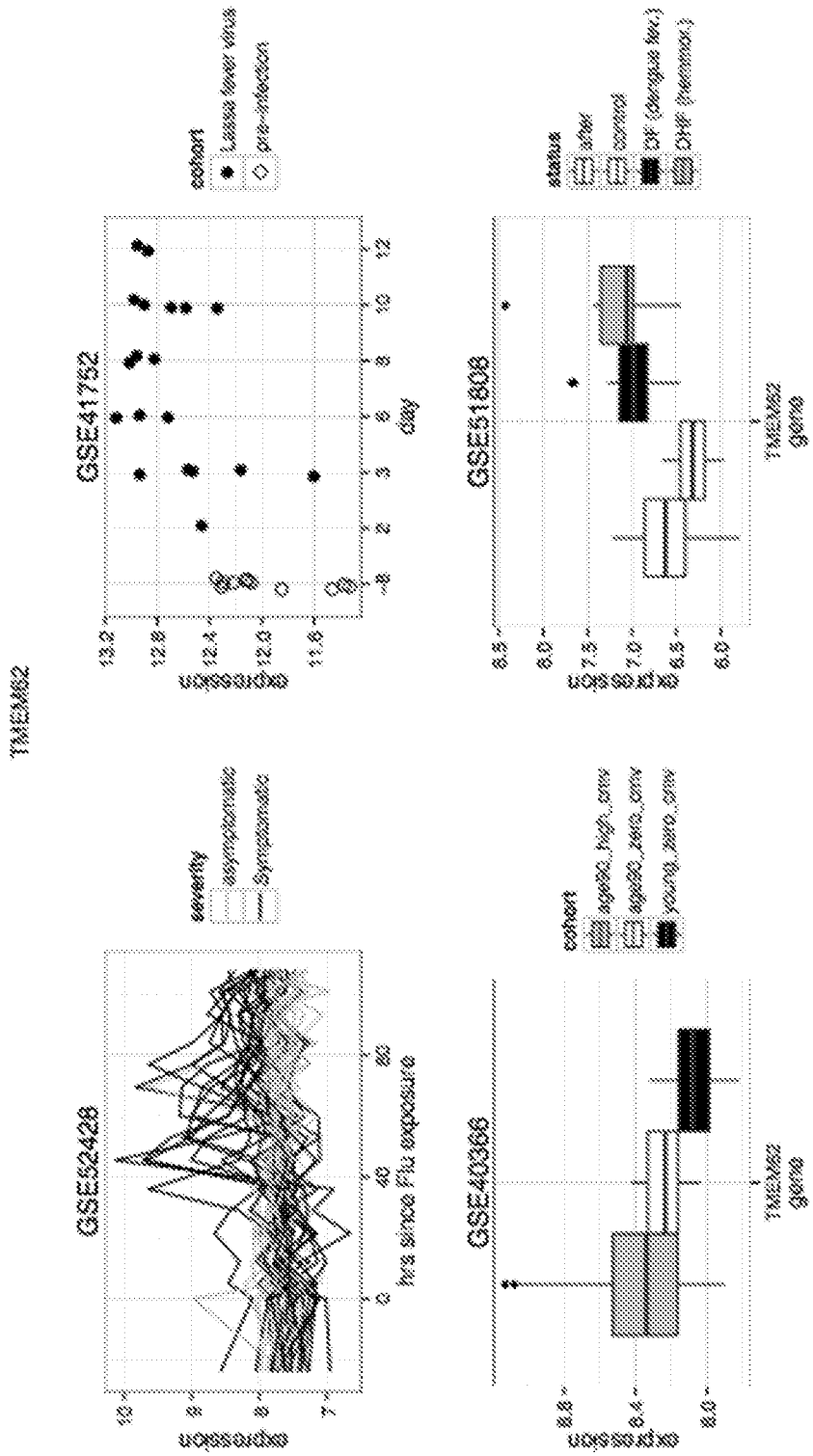
FIG. 6 shows plots of the performance of the individual biomarker TMEM62 in the four "core" viral datasets, including influenza virus, Lassa fever virus, cytomegalovirus and dengue fever virus.

Following filtering of single biomarkers based on a mean AUC of 0.75 in at least 9 of the 14 viral data sets (instead of 11 for derived biomarkers) a total of three individual biomarkers with good performance in the combined dataset remained, including: TMEM62, ZBP1 and CD38 (FIGS. 1, 2 and 3). Performance of these three individual biomarkers in each of the core datasets is depicted in FIGS. 4, 5 and 6.

As discussed, following the final filtering step based on a mean AUC of 0.8 In at least 11 of the 14 viral datasets, 473 derived biomarkers remained. The performance of each of these 473 derived biomarkers, based on the decreasing mean AUC across 14 individual datasets, is shown in Table 7. The performance of an example eight derived biomarkers (with reduced redundancy—that is, unique numerators and denominators) across the various individual datasets (not combined) ("discovery", "validation", "non-viral") is shown in Table 8.

Following normalization of all datasets and a greedy search the best performing individual derived biomarker was ISG15:IL16 with an AUC of 0.92. Note: the best performing derived biomarker for the combined, normalized dataset is different to the best performing derived biomarker listed in Table 7 because of the way in which AUC was calculated (mean of individual datasets versus mean of combined datasets). The best second unique derived biomarker to add to the first derived biomarker was OASL:CD97. The AUC obtained across the normalized dataset using these two derived biomarkers was 0.936, an 0.016 Improvement over the use of a single derived biomarker (see FIG. 7). The addition of a third derived biomarker (TAP1:TGFBR2) only improved the AUC by 0.009 and it is possible that this third derived biomarker created overfitting and noise. Thus, it was considered that the optimal commercial VIR "pan-viral" signature consists of the following two derived biomarkers: ISG15:IL16/OASL:CD97. FIG. 8 shows the effect on the overall AUC of sequentially adding derived biomarkers to ISG15:IL16.

Table 9 shows the performance (AUC) of the top eight derived biomarkers individually and when added sequentially to the top performing derived biomarkers for the combined datasets.

Figure 9:
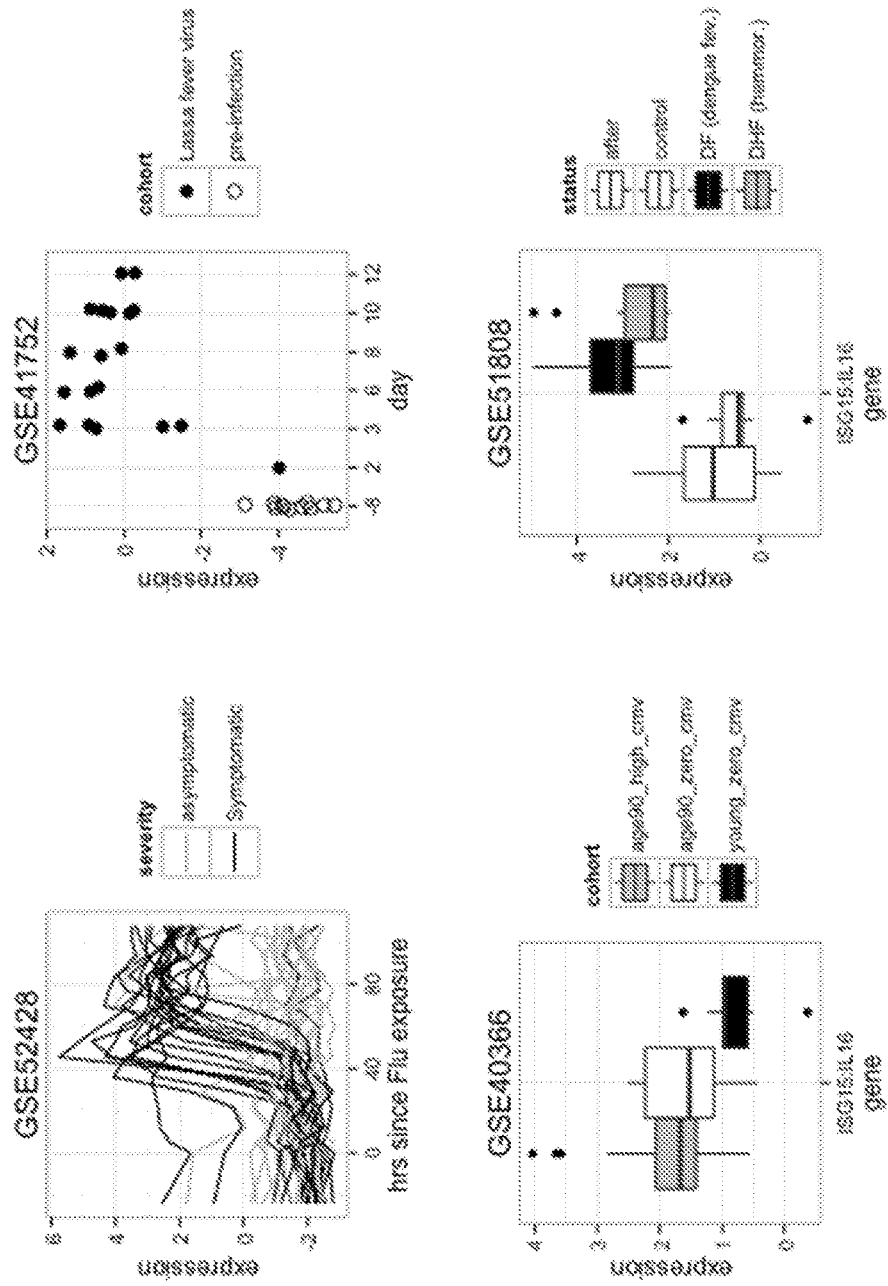
FIG. 9 shows plots of the performance of the derived biomarker IL16/ISG15 in the four "core" viral datasets, including influenza virus, Lassa fever virus, cytomegalovirus and dengue fever virus.
Figure 10:
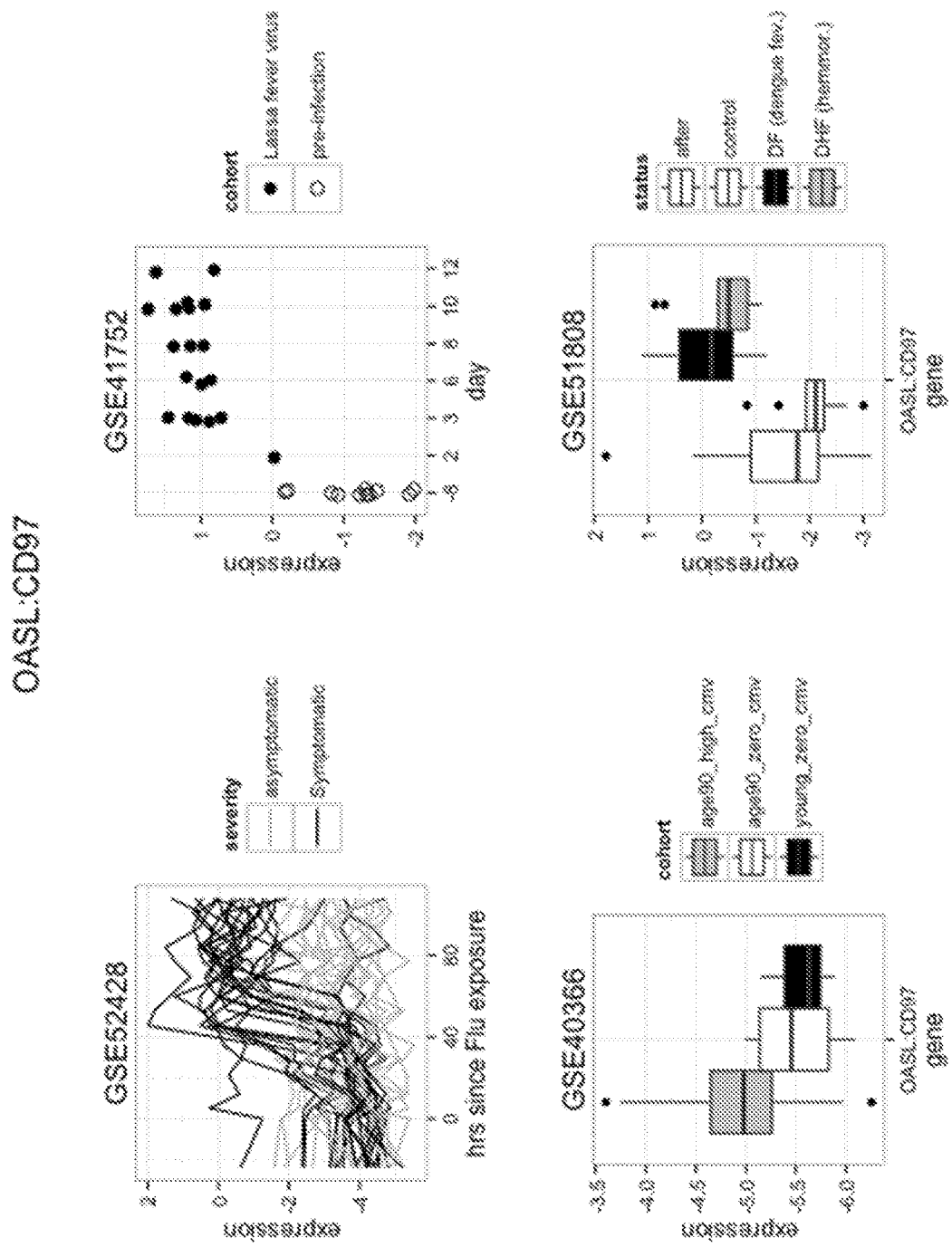
FIG. 10 shows plots of the performance of the derived CD97/OASL in the four "core" viral datasets, including influenza virus, Lassa fever virus, cytomegalovirus and dengue fever virus.

FIGS. 9 and 10 contain plots demonstrating the performance of the two top derived biomarkers in the "core" four datasets consisting of influenza virus-, Lassa fever virus-, cytomegalovirus- and dengue fever virus-infected subjects, and respective controls. In the influenza virus and Lassa virus time course studies, subjects with and without clinical signs post-inoculation are clearly separated based on the expression index of IL16/ISG15 and CD97/OASL independently. In these two time course studies these specific gene expression changes were apparent prior to the onset of peak clinical signs and persisted beyond the final sample collection time point of 100 hours ('flu) or 12 days (Lassa). For influenza virus infection, the signature for both derived biomarkers peaks quickly and between 20 and 60 hours post-inoculation, whereas peak clinical signs were reported between 40 and 100 hours post-inoculation (Huang, Y., Zaas, A. K., Rao, A., Dobigeon, N., Woolf, P. J., Veldman, T., et al. (2011). Temporal Dynamics of Host Molecular Responses Differentiate Symptomatic and Asymptomatic Influenza A Infection. PLoS Genetics, 7(8), e1002234). Similarly, for the Lassa fever virus infection, the signature for both derived biomarkers peaks quickly on Day 3 post-inoculation, whereas peak clinical signs (anorexia, neurological) were reported from Day 9 post-inoculation (Malhotra, S., Yen, J. Y., Honko, A. N., Garamszegi, S., Caballero, I. S., Johnson, J. C., et al. (2013). Transcriptional Profiling of the Circulating Immune Response to Lassa Virus in an Aerosol Model of Exposure. PLoS Neglected Tropical Diseases, 7(4), e2171). For Lassa fever virus infection the signature for both derived biomarkers also peaks prior to the detection of either viremia (4-12 days) or the presence of serum AST (aspartate transaminase) (5-12 days). In the dengue fever virus study subjects with fulminant dengue fever or hemorrhagic dengue fever are clearly separated from either convalescent or control subjects. Nonagenarian subjects with and without a titer to cytomegalovirus are less clearly separated using IL16/ISG15 compared to CD97/OASL, emphasizing the clinical utility and power of the combination of the two derived biomarkers as a VaSIRS biomarker profiles.

Example 6

VaSIRS Biomarker Profiles (Grouping)

The VaSIRS biomarker profiles can be grouped: individual biomarkers, derived biomarkers, combinations of derived biomarkers.

The three individual biomarkers are ZBP1, TMEM62, and CD38 (Group A).

There are four biomarkers in the best performing two derived biomarker signature: ISG15, IL16, OASL and CD97 and 413 unique biomarkers in the list of 473 biomarkers with an AUC>0.7. For each unique biomarker, a correlation coefficient was calculated. Table 10 lists 413 unique biomarkers and their correlation to each of the four biomarkers in the top performing two-derived biomarker signature. Each set of biomarkers make up Groups B, C, D and E respectively.

The best combination of derived biomarkers was determined to be: IL16/ISG15 and CD97/OASL (Group F).

Numerators and denominators that occur more than twice in the total 473 derived biomarkers are listed in Table 11 and Table 12 respectively.

Example 7

Analysis of Derived Biomarkers

Of the 473 derived biomarkers some individual biomarkers occur more frequently as either numerators or denominators in a derived biomarker. Tables 10 and 11 show the frequency of individual biomarkers in the numerator and denominator positions of the 473 derived biomarkers respectively. OASL and USP18 are the most frequent numerators appearing 344 and 50 times respectively, and ABLIM and IL16 are the most frequent denominators appearing 12 and 9 times respectively.

Performance (AUC) of the 473 derived biomarkers across the four core datasets is shown in Table 13. This set of derived biomarkers had a mean AUC>0.92 across the four core datasets following removal of top performing derived biomarkers in non-viral inflammation.

Example 7

Further Validation of Derived Biomarkers

Figure 11:
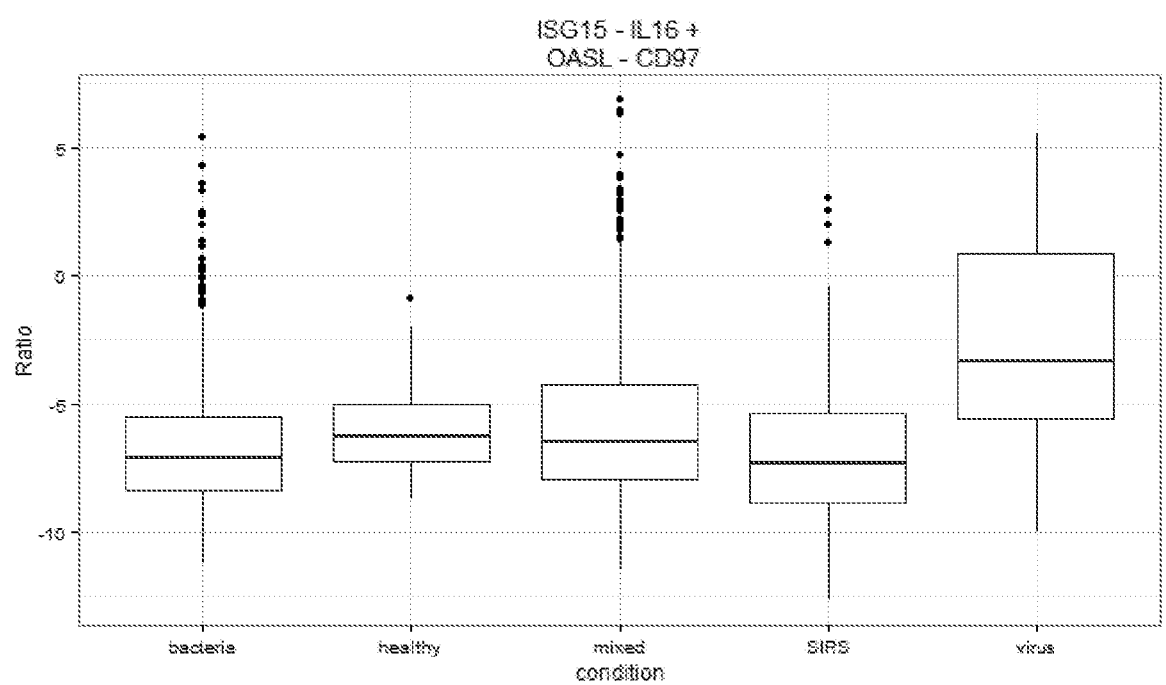
FIG. 11 shows box and whisker plots of the gene expression ratio index for combination of derived biomarkers IL16/ISG15 and CD97/OASL for 624 patients with suspected sepsis. Patients are grouped based on whether a pathogenic organism was isolated (bacteria, mixed condition, virus) or not (healthy, SIRS).

The two derived-biomarker signature (IL16/ISG15; CD97/OASL) was then further validated for its ability to identify human patients in a sepsis clinical trial that had evidence of a viral infection (Molecular Diagnosis and Risk Stratification of Sepsis (MARS) study (ClinicalTrials.gov Identifier NCT01905033)). In this trial, peripheral blood samples were obtained from 624 patients retrospectively diagnosed with either inSIRS or sepsis. Some patients, but not all, suspected of having a viral infection, were also tested for the presence of specific viral nucleic acid using PCR in body fluid samples, including blood, or the presence of specific anti-viral antibodies in plasma. It was known a priori that the detection of the presence of viral nucleic acid or plasma antibodies does not necessarily mean that such patients had an active viral infection at the time the sample was taken or that the detection of virus correlated to the presenting clinical signs (Jansen, R. R., Wieringa, J., Koekkoek, S. M., Visser, C. E., Pajkrt, D., Molenkamp, R., et al. (2011). Frequent detection of respiratory viruses without symptoms: toward defining clinically relevant cutoff values. Journal of Clinical Microbiology, 49(7), 2631-2636). Results of this further validation in samples from the independent MARS clinical trial are presented in the box and whisker plots in FIG. 11 where the gene expression ratio index is plotted against patient groups for which gene expression data were available. Patients were categorized into five groups including;
- Virus: patients with viral infection only—those patients suspected of having a viral infection who were tested and were positive (30). No other positive microbiology,
- SIRS: those patients who were clinically diagnosed as having no infection and for which there were no positive microbiology results,
- Mixed condition: those patients who were clinically diagnosed as having possible, probable or definite infection and for which there were no positive microbiology results,
- Bacteria: Gram positive or Gram negative results—patients who had at least one positive microbiology results from any sample,
- Healthy: healthy subjects.

A large proportion of those patients positive for the presence of a virus are also positive using gene expression of IL16/ISG15 and CD97/OASL, with an AUC of 0.79. Again, it should be noted that detection of viral DNA, or antibodies to virus, does not necessarily mean that a patient has an active viral infection present.

A total of 38 biomarker ratios had an AUC above 0.80 in the MARS viral set—see Table 14. Approximately 70 of the total of 473 biomarker ratios have AUCs under 0.70 in this MARS dataset, and 358 biomarker ratios had an AUC between 0.70 and 0.80.

Example 8

Example Applications of VaSIRS Biomarker Profiles

Use of the above described biomarkers and resulting VaSIRS biomarker profiles in patient populations and benefits in respect of differentiating various conditions, will now be described.

An assay capable of differentiating patients with any viral infection can be used in multiple patient populations, and in conjunction with presenting clinical signs, including those patients located in: Intensive Care Units (medical and surgical ICU), medical wards, Emergency Departments (ED), medical clinics. An assay capable of differentiating patients with any viral infection can also be used to identify those patients that need to be isolated from others as part of managing spread of disease. Such an assay can also be used as part of efforts to ensure judicious use of antibiotics, detection of re-activation of latent viruses, determination of the severity of a VaSIRS, and determination of the etiology of a viral infection causing the presenting systemic inflammation.

Detecting an Immune Response to Key Viral Pathogens in Conjunction with Clinical Signs Not all viruses can infect humans and, of those that can, many cause clinical signs that are restricted to certain organs. Table 15 lists key human viral pathogens (and virus type) based on major presenting clinical signs. Those virus types included in this patent as either part of the discovery or validation datasets are underlined. The biomarkers described herein may be used in conjunction with clinical signs to determine the presence and extent of a VaSIRS.

Detecting an Immune Response to Key Viral Pathogens when Patients Present

There are a limited number of human viruses that cause viremia and of those that do a viremia is usually only present in blood for a short period as part of the pathogenesis, making direct detection of the pathogen difficult using blood as a sample. Further, it takes 10-14 days following an infection for specific immunoglobulin G antibodies to appear in blood. Infection with a pathogenic virus causes a detectable systemic immune response (VaSIRS) prior to, and during, the development of peak clinical signs. As such, VaSIRS biomarkers are useful for early diagnosis, diagnosis and monitoring in the key periods of viral incubation, and when patients present with clinical signs. Table 16 lists common human viruses that are known to cause SIRS and a viremia along with a supporting scientific reference.

Detecting an Immune Response to Key Viral Pathogens for which them are Tailored Anti-Viral Therapies Those viruses that cause a viremia and can be treated with an anti-viral agent, Illustrative examples of which are listed in Table 17. It is important that viruses, as for example shown in Table 17, be detected and identified because 1) they can be treated with anti-viral medication 2) most other viral infections cause transient clinical signs and are not life-threatening. In such viral infections it is also important to know if there is a co-infection with bacteria so that antibiotics can be prescribed. The VaSIRS biomarkers described herein can determine the extent of systemic inflammation due to a viral infection and, as such, judgment can be made as to whether antibiotic prescription is appropriate. Further, once it has been determined that systemic inflammation Is due to a virus, other more specific viral diagnostic tests can be used downstream to identify the pathogen.

Detecting an Immune Response to Key Viral Pathogens that Cause Respiratory Disease Some of the most common viruses that cause infection in humans are respiratory viruses including, rhinovirus, influenza, respiratory syncytial virus and parainfluenza virus— see Table 18 (Peltola V, Waris M, Osterback R, Susi P, Ruuskanen O, Hyypia T. Rhinovirus transmission within families with children: incidence of symptomatic and asymptomatic infections. 3 Infect Dis 2008; 197:382-389). Most adults experience at least one rhinovirus infection per year (Arruda E, Pitkaranta A, Witek T J Jr. Doyle C A, Hayden F G. Frequency and natural history of rhinovirus infections in adults during autumn. J Clin Microbiol 1997; 35:2864-2868). Influenza infection remains seasonal and common, and places a significant burden on both healthcare and society (Thompson W W, Comanor L, Shay D K (2006) Epidemiology of seasonal influenza: use of surveillance data and statistical models to estimate the burden of disease. J Infect Dis 194 Suppl 2: S82-S91). Respiratory syncytial virus is ubiquitous, most infants have been infected by the age of two, and there are no effective vaccines available (Paes B A, Mitchell I, BanerjI A, Lanctôt K L, Langley J M (2011) A decade of respiratory syncytial virus epidemiology and prophylaxis: translating evidence into everyday clinical practice. Canadian respiratory journal: journal of the Canadian Thoracic Society 18: e10). Fortunately most respiratory virus infections are self-limiting because there are few treatment options other than palliative care and the use of some anti-viral drugs early in the course of infection (e.g. ribavirin for respiratory syncytial virus; oseltamivir and amantadine for influenza). However, in some instances respiratory viral infections can lead to complications, including exacerbation of existing pathologies, or concurrent or subsequent viral or bacterial infections. Thus, patients presenting to medical facilities with respiratory virus infection(s) need to be differentiated from those with bacterial infection, or at least a determination has to be made as to whether a viral or a bacterial infection is contributing to the presenting clinical signs so that appropriate anti-viral or antibiotic therapy can be administered. A list of common viral pathogens that cause community acquired pneumonia in adults and children can be found in Table 18 (based on Pavia A T (2013) What is the Role of Respiratory Viruses in Community-Acquired Pneumonia? Infectious Disease Clinics of North America 27: 157-175). The biomarkers described in this patent can determine the presence and extent of systemic inflammation due to a respiratory viral infection and, as such, judgment can be made regarding appropriate management procedures, specific anti-viral treatments and/or antibiotic treatments.

Differentiating Patients with a Viral Condition in ICU

It has been shown that greater than 50% of patients in medical ICUs have SIRS and greater than 80% in surgical ICUs have infection-negative SIRS (inSIRS) (Brun-Buisson C (2000) The epidemiology of the systemic inflammatory response. Intensive Care Med 26 Suppl 1: S64-S74). From a clinician's perspective these patients present with non-specific clinical signs and the source and type of infection, if there is one, must be determined quickly so that appropriate therapies can be administered. Patients with inSIRS have a higher likelihood of being infected with bacteria or fungi (compared to patients without SIRS), and have a much higher 28-day mortality (Comstedt P, Storgaard M, Lassen A T (2009) The Systemic Inflammatory Response Syndrome (SIRS) in acutely hospitalised medical patients: a cohort study. Scand J Trauma Resusc Emerg Med 17: 67. doi: 10.1186/1757-7241-17-67). Further, patients with prolonged sepsis (BaSIRS) have a higher frequency of viral infections, possibly due to reactivation of latent viruses as a result of immunosuppression (Walton, A. H., Muenzer, J. T., Rasche, D., Boomer, J. S., & Sato, B. (2014). Reactivation of multiple viruses in patients with sepsis. PLoS ONE). The higher the prevalence of SIRS in ICU, the higher the risk of infection and death will be in SIRS-affected patients. The re-activation of viruses in ICU patients with BaSIRS, and the benefits of early intervention in patients with BaSIRS (Rivers E P (2010) Point: Adherence to Early Goal-Directed Therapy: Does It Really Matter? Yes. After a Decade, the Scientific Proof Speaks for Itself. Chest 138: 476-480) creates a need for triaging patients with clinical signs of SIRS to determine whether they have a viral or bacterial infection, or both. Monitoring intensive care patients on a regular basis with biomarkers of the present invention will allow medical practitioners to determine the presence, or absence, of a viral infection. If positive, further diagnostic tests could then be performed on appropriate clinical samples to determine the type of viral infection so that appropriate therapy can be administered. For example, if a patient tested positive for a viral infection, and further testing demonstrated the presence of a herpes virus, then appropriate anti-herpes viral therapies could be administered.

In pediatric ICUs the incidence of viral infections is reportedly low (1%), consisting mostly of enterovirus, parechovirus and respiratory syncytial virus infections (Verboon-Maciolek, M. A., Krediet, T. G., Gerards, L. J., Fleer, A., & van Loon, T. M. (2005). Clinical and epidemiologic characteristics of viral infections in a neonatal intensive care unit during a 12-year period. The Pediatric Infectious Disease Journal, 24(10), 901-904). However, because the mortality rate of virus-infected patients is high, and they present with similar clinical signs to those with bacterial or fungal infections, it is important to rule out the possibility of a viral infection in pediatric patients so that other appropriate therapies can be administered, or to rule in a viral infection so that further, more specific, virus testing and therapy management can be performed.

Determining which patients have viral infections in the ICU will allow for early intervention, appropriate choice of therapies, when to start and stop therapies, whether a patient needs to be isolated, when to start and stop appropriate patient management procedures, and in determining how a patient is responding to therapy. Information provided by the VaSIRS biomarkers of the present invention will therefore allow medical intensivists to tailor and modify therapies and management procedures to ensure infected patients survive and spend less time in intensive care. Less time in intensive care leads to considerable savings in medical expenses including through less occupancy time and through appropriate use and timing of medications.

Differentiating Patients with a Viral Condition in Hospital Wards

Viruses are an important cause of nosocomial infections in hospital where it has been reported that between 5 and 32% of all nosocomial infections are due to viruses, depending upon the hospital location and patient type (Aitken, C., & Jeffries, D. J. (2001). Nosocomial spread of viral disease. Clinical Microbiology Reviews, 14(3), 528-546); Valenti, W. M., Menegus, M. A., Hall, C. B., Pincus, P. H., & Douglas, R. G. 3. (1980). Nosocomial viral infections: I. Epidemiology and significance. Infection Control: IC, 1(1), 33-37). Identification of those patients with a VaSIRS, especially early in the course of infection when there are non-specific clinical signs, would assist clinicians and hospital staff in determining appropriate measures (e.g quarantine, hygiene methods) to be put in place to reduce the risk of virus spread to other non-infected patients.

In a study in a US hospital of over 4000 inpatients over an 11 week period at least one episode of fever occurred in 1,194 patients (29%) (McGowan J E J, Rose R C, Jacobs N F, Schaberg D R, Haley R W (1987) Fever in hospitalized patients. With special reference to the medical service. Am J Med 82: 580-586). The rate of fever was highest on medical and surgical services and the authors found that both infectious and non-infectious processes played important roles in the cause. However, determining the cause of fever was complicated by the fact that over 390 different factors were identified. In this study, a review of 341 episodes of fever in 302 patients on the medical service identified a single potential cause in 56%, multiple factors were present in 26%, and no potential causes were found in 18%. Of all factors identified, 44% were community-acquired infections, 9% were nosocomial infections, 20% possibly involved infection, and 26% were non-infectious processes. Thus, fever is common in hospital surgical and medical wards, there are many causes including infectious and non-infectious, diagnosis is difficult and in many instances a cause is not found. The biomarkers outlined herein can differentiate viral infections from other causes of SIRS which will assist medical practitioners in determining the cause of fever, ensuring that resources are not wasted on unnecessary diagnostic procedures and that patients are managed and treated appropriately.

Differentiating Patients with a Viral Condition in Emergency Departments

In 2010, approximately 130 million people presented to emergency departments in the USA and the third most common primary reason for the visit was fever (5.6 million people had a fever (>38° C.) and for 5 million people it was the primary reason for the visit) (Niska R, Bhuiya F, Xu J (2010) National hospital ambulatory medical care survey: 2007 emergency department summary. Natl Health Stat Report 26: 1-31). Of those patients with a fever, 664,000 had a fever of unknown origin—that is, the cause of the fever was not obvious at presentation. As part of diagnosing the reason for the emergency department visit 48,614,000 complete blood counts (CBC) were performed and 5.3 million blood cultures were taken. In 3.65 million patients presenting the primary diagnosis was "infectious" and in approximately 25% of cases (32.4 million) antibiotics were administered. 13.5% of all people presenting to emergency were admitted to hospital. Clinicians in emergency need to determine the answer to a number of questions quickly, including: what is the reason for the visit, is the reason for the visit an infection, does the patient need to be admitted? The diagnosis, treatment and management of patients with a fever, inSIRS, VaSIRS or BaSIRS are different. By way of example, a patient with a fever without other SIRS clinical signs and no obvious source of viral, or microbial infection may be sent home, or provided with other non-hospital services, without further hospital treatment. However, a patient with a fever may have early BaSIRS, and not admitting such a patient and aggressively treating with antibiotics may put their life at risk. Such a patient may also have VaSIRS and quickly deteriorate, or progress to BaSIRS without appropriate hospital care and/or the use of anti-viral agents. The difference in the number of patients presenting to emergency that are ultimately diagnosed with an "infection" (3.65 million) and the number treated with antibiotics (32.4 million) suggests the following; 1) diagnostic tools that determine the presence of an infection are not available, or are not being used, or are not accurate enough, or do not provide strong enough negative predictive value, or are not providing accurate information that can be acted on within a reasonable timeframe 2) when it comes to suspected infection, and because of the acute nature of infections, clinicians err on the side of caution by administering antibiotics. Further, in a study performed in the Netherlands on patients presenting to emergency with fever, 36.6% of patients admitted to hospital had a suspected bacterial infection (that is, it was not confirmed) (Limper M, Eeftinck Schattenkerk D, de Kruif M D, van Wissen M, Brandjes D P M, et al. (2011) One-year epidemiology of fever at the Emergency Department. Neth J Med 69: 124-128). This suggests that a large proportion of patients presenting to emergency are admitted to hospital without a diagnosis. The VaSIRS biomarkers described herein can identify those patients with a VaSIRS from those without a VaSIRS, assisting medical practitioners in triaging patients with fever or SIRS. Such effective triage tools make best use of scarce hospital resources, including staff, equipment and therapies. Accurate triage decision-making also ensures that patients requiring hospital treatment are given it, and those that don't are provided with other appropriate services.

In a study performed in Argentina in patients presenting to emergency with influenza-like symptoms, only 37% of samples taken and analysed for the presence of viruses (using immunofluorescence, RT-PCR and virus culture) were positive (Santamaria, C., Uruena, A., Videla, C., Suarez, A., Ganduglia, C., Carballal, G., et al. (2008). Epidemiological study of influenza virus infections in young adult outpatients from Buenos Aires, Argentina. Influenza and Other Respiratory Viruses, 2(4), 131-134). In a study based in Boston, USA, acute respiratory infections were a common reason children presented to emergency departments in Winter (Bourgeois, F. T., Valim, C., Wei, 3. C., McAdam, A. J., & Mandl, K. D. (2006). Influenza and other respiratory virus-related emergency department visits among young children. Pediatrics, 118(1), e1-8). Using a respiratory classifier (based on clinical signs) these authors found that in children less than, or equal to, 7 years of age an acute respiratory infection was suspected in 39.8% of all emergency department visits (less at a whole city or state level). In this latter study only 55.5% of these patients had a virus isolated. Thus, a large percentage of patients with influenza-like symptoms presenting to emergency are likely not being diagnosed as having a viral infection using laboratory-based tests. The VaSIRS biomarkers outlined herein can identify those patients with a VaSIRS from those without a VaSIRS, assisting medical practitioners in making an accurate diagnosis of a viral infection in patients with influenza-like symptoms. Such patients can then be further tested to determine the presence of specific viruses amenable to anti-viral therapies. Accurate diagnosis of a VaSIRS also assists in ensuring that only those patients that need either anti-viral treatment or antibiotics receive them which may lead to fewer side effects and fewer days on antibiotics (Adcock, P. M., Stout, G. G., Hauck, M. A., & Marshall, G. S. (1997). Effect of rapid viral diagnosis on the management of children hospitalized with lower respiratory tract infection. The Pediatric Infectious Disease Journal, 16(9), 842-846).

Differentiating Patents with a Viral Condition in Medical Clinics

Patients presenting to medical clinics as outpatients often have clinical signs of SIRS including abnormal temperature, heart rate or respiratory rate and there are many causes of these clinical signs. Such patients need to be assessed thoroughly to determine the cause of the clinical signs because in some instances it could be a medical emergency. By way of example, a patient with colic might present with clinical signs of increased heart rate. Differential diagnoses could be (but not limited to) appendicitis, urolithiasis, cholecystitis, pancreatitis, enterocolitis. In each of these conditions it would be important to determine if there was a non-infectious systemic inflammatory response (inSIRS) or whether an infection was contributing to the systemic response. The treatment and management of patients with non-infectious systemic inflammation and/or SIRS due to infectious causes are different. The VaSIRS biomarkers detailed herein can differentiate a VaSIRS from other causes of SIRS so that a medical practitioner can either rule in or rule out a systemic inflammation of viral etiology. As a result medical practitioners can more easily determine the next medical actions and procedure(s) to perform to satisfactorily resolve the patient issue.

Detection of Reactivation of Latent Viruses

Reactivation of latent viruses is common in patients that are immunocompromised, including those with prolonged sepsis and those on immunosuppressive therapy (Walton A H, Muenzer I T, Rasche D, Boomer I S, Sato B, et al. (2014) Reactivation of multiple viruses in patients with sepsis. PLoS ONE 9: e98819; Andersen, H. K., and E. S. Spencer. 1969. Cytomegalovirus infection among renal allograft recipients. Acta Med. Scand. 186:7-19; Bustamante C I, Wade J C (1991) Herpes simplex virus infection in the immunocompromised cancer patient. J Clin Oncol 9: 1903-1915). For patients with sepsis (Walton et al., 2014), cytomegalovirus (CMV), Epstein-Barr (EBV), herpes-simplex (HSV), human herpes virus-6 (HHV-6), and anellovirus TTV were all detectable in blood at higher rates compared to control patients, and those patients with detectable CMV had higher 90-day mortality. However, because these viruses have only been detected in sepsis patients it is not known whether reactivated latent viruses contribute to pathology, morbidity and mortality.

Determining the Extent of Systemic Inflammation in Patients with a VaSIRS

Patients presenting to medical facilities often have any one of the four clinical signs of SIRS. However, many different conditions can present with one of the four clinical signs of SIRS and such patients need to be assessed to determine if they have inSIRS, and if so the extent of inSIRS, or VaSIRS, and if so the extent of VaSIRS, and to exclude other differential diagnoses.

By way of example, a patient with respiratory distress is likely to present with clinical signs of increased respiratory rate. Differential diagnoses could be (but not limited to) asthma, viral or bacterial pneumonia, congestive heart failure, physical blockage of airways, allergic reaction, collapsed lung, pneumothorax. In this instance it would be important to determine if there was a systemic inflammatory response (inSIRS) or whether an infection (viral, bacterial, fungal or parasitic) was contributing to the condition. The treatment and management of patients with and without systemic inflammation and/or viral, bacterial, fungal or parasitic infections are different. Because the biomarkers described herein can determine the degree of systemic involvement, the use of them will allow medical practitioners to determine the next medical procedure(s) to perform to satisfactorily resolve the patient issue. Patients with a collapsed lung, pneumothorax or a physical blockage are unlikely to have a systemic inflammatory response and patients with congestive heart failure, allergic reaction or asthma may have a large systemic inflammatory response but not due to infection. The extent of VaSIRS, as indicated by biomarkers presented herein, allows clinicians to determine a cause of the respiratory distress, to rule out other possible causes and provides them with information to assist in decision making on next treatment and management steps. For example, a patient with respiratory distress and a strong marker response indicating VaSIRS is likely to be hospitalized and specific viral diagnostic tests performed to ensure that appropriate anti-viral therapy is administered.

Antibiotic Stewardship

In patients suspected of having a systemic infection (inSIRS, BaSIRS, VaSIRS) a clinical diagnosis and treatment regimen is provided by the physician(s) at the time the patient presents and often in the absence of any results from diagnostic tests. This is done in the interests of rapid treatment and positive patient outcomes. However, such an approach leads to over-prescribing of antibiotics irrespective of whether the patient has a microbial infection or not. Clinician diagnosis of BIR is reasonably reliable (0.88) in children but only with respect to differentiating between patients ultimately shown to be blood culture positive and those that were judged to be unlikely to have an infection at the time antibiotics were administered (Fischer, J. E. et al. Quantifying uncertainty: physicians' estimates of infection in critically ill neonates and children. Clin. Infect. Dis. 38, 1383-1390 (2004)). In Fischer et al., (2004), 54% of critically ill children were put on antibiotics during their hospital stay, of which only 14% and 16% had proven systemic bacterial infection or localized infection respectively. In this study, 53% of antibiotic treatment courses for critically ill children were for those that had an unlikely infection and 38% were antibiotic treatment courses for critically ill children as a rule-out treatment episode. Clearly, pediatric physicians err on the side of caution with respect to treating critically ill patients by placing all patients suspected of an infection on antibiotics—38% of all antibiotics used in critically Ill children are used on the basis of ruling out BIR, that is, are used as a precaution. Antibiotics are also widely prescribed and overused in adult patients as reported in Braykov et al., 2014 (Braykov, N. P., Morgan, D. J., Schweizer, M. L., Uslan, D. Z., Kelesidis, T., Weisenberg, S. A., et al. (2014). Assessment of empirical antibiotic therapy optimisation in six hospitals: an observational cohort study. The Lancet Infectious Diseases, 14(12), 1220-1227). In this study, across six US hospitals over four days in 2009 and 2010, 60% of all patients admitted received antibiotics. Of those patients prescribed antibiotics 30% were afebrile and had a normal white blood cell count and where therefore prescribed antibiotics as a precaution. As such, an assay that can accurately diagnose any VaSIRS in patients presenting with non-pathognomonic clinical signs of infection would be clinically useful and may lead to more appropriate use of antibiotics and anti-viral therapies.

Controlling the Spread of a Virus

For serious viral diseases that have no current treatment (e.g., Severe Acute Respiratory Syndrome (SARS, coronavirus); Ebola virus) the best method of limiting viral spread is through a combination of accurate diagnosis and patient isolation (Chowell, G., Castillo-Chavez, C., Fenimore, P. W., Kribs-Zaleta, C. M., Arriola, L., & Hyman, J. M. (2004). Model parameters and outbreak control for SARS. Emerging infectious Diseases, 10(7), 1258-1263; Centers for Disease Control, Interim U.S. Guidance for Monitoring and Movement of Persons with Potential Ebola Virus Exposure, Dec. 24, 2014). The VaSIRS biomarkers detailed herein can be used to identify those people with early clinical signs that actually have a VaSIRS resulting from an active viral infection amongst the population at risk. For those people identified as having a VaSIRS appropriate testing and procedures can then be performed to obtain an accurate and specific diagnosis and to limit viral spread through isolation of patients and the use of appropriate protective measures.

Example 9

First Example Workflow for Determining Host Response

A first example workflow for measuring host response to VaSIRS will now be described. The workflow involves a number of steps depending upon availability of automated platforms. The assay uses quantitative, real-time determination of the amount of each host immune cell RNA transcript in the sample based on the detection of fluorescence on a qRT-PCR instrument (e.g. Applied Biosystems 7500 Fast Dx Real-Time PCR Instrument, Applied Biosystems, Foster City, Calif., catalogue number 440685; K082562). Transcripts are each reverse-transcribed, amplified, detected, and quantified in a separate reaction well using a probe that is visualized in the FAM channel (by example). Such reactions can be run as single-plexes (one probe for one transcript per tube), multiplexed (multiple probes for multiple transcripts in one tube), one-step (reverse transcription and PCR are performed in the same tube), or two-step (reverse transcription and PCR performed as two separate reactions in two tubes). A score is calculated using interpretive software provided separately to the kit but designed to integrate with RT-PCR machines.

The workflow below describes the use of manual processing and a pre-prepared kit.
Pre-Analytical
Blood collection
Total RNA isolation
Analytical
Reverse transcription (generation of cDNA)
qPCR preparation
qPCR
Software, Interpretation of Results and Quality Control
Output.
Kit Contents
Diluent
RT Buffer
RT Enzyme Mix
qPCR Buffer
Primer/Probe Mix
AmpliTaq Gold® (or similar)
High Positive Control
Low Positive Control
Negative Control
Blood Collection The specimen used is a 2.5 mL sample of blood collected by venipuncture using the PAXgene® collection tubes within the PAXgene® Blood RNA System (Qiagen, kit catalogue #762164; Becton Dickinson, Collection Tubes catalogue number 762165; K042613). An alternate collection tube is Tempus® (Life Technologies).
Total RNA Isolation Blood (2.5 mL) collected into a PAXgene RNA tube is processed according to the manufacturer's instructions. Briefly, 2.5 mL sample of blood collected by venipuncture using the PAXgene™ collection tubes within the PAXgene™ Blood RNA System (Qiagen, kit catalogue #762164; Becton Dickinson, Collection Tubes catalogue number 762165; K042613). Total RNA isolation is performed using the procedures specified in the PAXgene™ Blood RNA kit (a component of the PAXgene™ Blood RNA System). The extracted RNA is then tested for purity and yield (for example by running an $A_{260/280}$ ratio using a Nanodrop® (Thermo Scientific)) for which a minimum quality must be (ratio >1.6). RNA should be adjusted in concentration to allow for a constant input volume to the reverse transcription reaction (below). RNA should be processed immediately or stored in single-use volumes at or below −70° C. for later processing.
Reverse Transcription Determine the appropriate number of reaction equivalents to be prepared (master mix formulation) based on a plate map and the information provided directly below. Each clinical specimen is run in singleton.

Each batch run desirably includes the following specimens:
High Control, Low Control, Negative Control, and No Template Control (Test Diluent instead of sample) in singleton each
Program the ABI 7500 Fast Dx Instrument as detailed below.
Launch the software.
Click Create New Document In the New Document Wizard, select the following options:
  i. Assay: Standard Curve (Absolute Quantitation)
  ii. Container: 96-Well Clear
  iii. Template: Blank Document (or select a laboratory-defined template)
  iv. Run Mode: Standard 7500
  v. Operator: Enter operator's initials
  vi. Plate name: [default]
Click Finish
Select the instrument tab in the upper left
In the Thermal Cycler Protocol area, Thermal Profile tab, enter the following times:
  i. 25° C. for 10 minutes
  ii. 45° C. for 45 minutes
  iii. 93° C. for 10 minutes
  iv. Hold at 25° C. for 60 minutes In a template-free area, remove the test Diluent and RT-qPCR Test RT Buffer to room temperature to thaw. Leave the RT-qPCR Test RT Enzyme mix in the freezer and/or on a cold block.

In a template-free area, assemble the master mix in the order listed below.

| RT Master Mix - Calculation: | | |
| --- | --- | --- |
|  | Per well | ×N |
| RT-qPCR Test RT Buffer | 3.5 μL | 3.5 × N |
| RT-qPCR Test RT Enzyme mix | 1.5 μL | 1.5 × N |
| Total Volume | 5 μL | 5 × N |

Gently vortex the master mix then pulse spin. Add the appropriate volume (5 μL) of the RT Master Mix Into each well at room temperature.

Remove clinical specimens and control RNAs to thaw. (If the specimens routinely take longer to thaw, this step may be moved upstream in the validated method.)

Vortex the clinical specimens and control RNAs, then pulse spin. Add 10 μL of control RNA or RT-qPCR Test Diluent to each respective control or negative well.

Add 10 μL of sample RNA to each respective sample well (150 ng total input for RT; $OD_{260}/OD_{280}$ ratio greater than 1.6). Add 10 μL of RT-qPCR Test Diluent to the respective NTC well.

Note: The final reaction volume per well is 15 μL.

|  | Samples |
| --- | --- |
| RT Master Mix | 5 μL |
| RNA sample | 10 μL |
| Total Volume (per well) | 15 μL |

Mix by gentle pipetting. Avoid forming bubbles in the wells.

Cover wells with a seal.

Spin the plate to remove any bubbles (1 minute at 400×g).

Rapidly transfer to ABI 7500 Fast Dx Instrument pre-programmed as detailed above.

Click Start. Click Save and Continue. Before leaving the instrument, it is recommended to verify that the run started successfully by displaying a time under Estimated Time Remaining.

qPCR master mix may be prepared to coincide roughly with the end of the RT reaction. For example, start about 15 minutes before this time. See below.

When RT is complete (i.e. resting at 25° C.; stop the hold at any time before 60 minutes is complete), spin the plate to collect condensation (1 minute at 400×g).

qPCR Preparation

Determine the appropriate number of reaction equivalents to be prepared (master mix formulation) based on a plate map and the information provided in RT Preparation above.

Program the ABI 7500 Fast Dx with the settings below.
a) Launch the software.
b) Click Create New Document
c) In the New Document Wizard, select the following options:
  i. Assay: Standard Curve (Absolute Quantitation)
  ii. Container: 96-Well Clear
  iii. Template: Blank Document (or select a laboratory-defined template)
  iv. Run Mode: Standard 7500
  v. Operator: Enter operator's initials
  vi. Plate name: Enter desired file name
d) Click Next
e) In the Select Detectors dialog box:
  i. Select the detector for the first biomarker, and then click Add>>.
  ii. Select the detector second biomarker, and then click Add>>, etc.
  iii. Passive Reference: ROX
f) Click Next
g) Assign detectors to appropriate wells according to plate map.
  i. Highlight wells in which the first biomarker assay will be assigned
  ii. Click use for the first biomarker detector
  iii. Repeat the previous two steps for the other biomarkers
  iv. Click Finish
h) Ensure that the Setup and Plate tabs are selected
i) Select the instrument tab in the upper left
j) In the Thermal Cycler Protocol area, Thermal Profile tab, perform the following actions, with the results shown in Figure XX:
  i. Delete Stage 1 (unless this was completed in a laboratory-defined template).
  ii. Enter sample volume of 25 μL.
  iii. 95° C. 10 minutes
  iv. 40 cycles of 95° C. for 15 seconds, 63° C. for 1 minute
  v. Run Mode: Standard 7500
  vi. Collect data using the "stage 2, step 2 (63.0@1:00)" setting
k) Label the wells as below using this process: Right click over the plate map, then select Well Inspector. With the Well Inspector open, select a well or wells. Click back into the Well Inspector and enter the Sample Name. Close the Well Inspector when completed.
  i. CONH for High Control
  ii. CONL for Low Control
  iii. CONN for Negative Control
  iv. NTC for No Template Control
  v. [Accession ID] for clinical specimens
l) Ensure that detectors and quenchers are selected as listed below.
  i. FAM for ISG15 biomarker 1; quencher=none
  ii. FAM for IL16 biomarker 2; quencher=none
  iii. FAM for OASL; biomarker 3; quencher=none iv. FAM for CD97; biomarker 4; quencher=none
v. Select "ROX" for passive reference
qPCR In a template-free area, remove the assay qPCR Buffer and assay Primer/Probe Mixes for each target to room temperature to thaw. Leave the assay AmpliTaq Gold in the freezer and/or on a cold block.

Still in a template-free area, prepare qPCR Master Mixes for each target in the listed order at room temperature.

qPCR Master Mixes—Calculation Per Sample

|  | Per well | ×N |
|---|---|---|
| qPCR Buffer | 11 μL | 11 × N |
| Primer/Probe Mix | 3.4 μL | 3.4 × N |
| AmpliTaq Gold ® | 0.6 μL | 0.6 × N |
| Total Volume | 15 μL | 15 × N |

Example forward (F) and reverse (R) primers and probes (P) and their final reaction concentration for measuring four host response transcripts to viral biomarkers are contained in the following table (F, forward; R, reverse; P, probe).

| Reagent | 5'-3' Sequence | Reaction mM |
|---|---|---|
| ISG15-F | CTTCGAGGGGAAGCCCCTGGAG | 360 |
| ISG15-R | CCTGCTCGGATGCTGGTGGAGC | 360 |
| ISG15-P | CATGAATCTGCGCCTGCGGGG | 50 |
| IL16-F | GCCCAGTGACCCAAACATCCCC | 360 |
| 1L16-R | CAAAGCTATAGTCCATCCGAGCCTCG | 360 |
| IL16-P | GATAAAACACCCACTGCTTAAG | 50 |
| OASL-F | CCCTGGGGCCTTCTCTTCCCA | 360 |
| OASL-R | CCGCAGGCCTTGATCAGGC | 360 |
| OASL-P | CCCAGCCACCCCCTGAGGTC | 50 |
| CD97-F | CCATCCAGAATGTCATCAAATTGGTGGA | 360 |
| CD97-R | GGACAGGTGGCGCCAGGG | 360 |
| CD97-P | GAACTGATGGAAGCTCCTGGAGAC | 50 |

Gently mix the master mixes by flicking or by vortexing, and then pulse spin. Add 15 μL of qPCR Master Mix to each well at room temperature.

In a template area, add 130 μL of SeptiCyte Lab Test Diluent to each cDNA product from the RT Reaction. Reseal the plate tightly and vortex the plate to mix thoroughly.

Add 10 μL of diluted cDNA product to each well according to the plate layout.

Mix by gentle pipetting. Avoid forming bubbles in the wells.

Cover wells with an optical seal.

Spin the plate to remove any bubbles (1 minute at 400×g).

Place on real-time thermal cycler pre-programmed with the settings above.

Click Start. Click Save and Continue. Before leaving the instrument, it is recommended to verify that the run started successfully by displaying a time under Estimated Time Remaining.

Note: Do not open the qPCR plate at any point after amplification has begun.

When amplification has completed, discard the unopened plate.

Software, Interpretation of Results and Quality Control

Software is specifically designed to integrate with the output of PCR machines and to apply an algorithm based on the use of multiple biomarkers. The software takes into account appropriate controls and reports results in a desired format.

When the run has completed on the ABI 7500 Fast Dx Instrument, complete the steps below in the application 7500 Fast System with 21 CFR Part 11 Software, ABI software SDS v1.4.

Click on the Results tab in the upper left corner.

Click on the Amplification Plot tab in the upper left corner.

In the Analysis Settings area, select an auto baseline and manual threshold for all targets. Enter 0.01 as the threshold.

Click on the Analyse button on the right in the Analysis Settings area.

From the menu bar in the upper left, select File then Close.

Complete the form in the dialog box that requests a reason for the change. Click OK.

Transfer the data file (.sds) to a separate computer running the specific assay RT-qPCR Test Software.

Launch the assay RT-qPCR Test Software. Log in.

From the menu bar in the upper left, select File then Open. Browse to the location of the transferred data file (.sds). Click OK.

The data file will then be analysed using the assay's software application for interpretation of results.

Interpretation of Results and Quality Control

Results

Launch the interpretation software. Software application instructions are provided separately.

Following upload of the .sds file, the Software will automatically generate classifier scores for controls and clinical specimens.

Controls

The Software compares each CON (control) specimen (CONH, CONL, CONN) to its expected result. The controls are run in singleton.

| Control specimen | | |
|---|---|---|
| Designation | Name | Expected result |
| CONH | High Control | Score range |
| CONL | Low Control | Score range |
| CONN | Negative Control | Score range |
| NTC | No Template Control | Fail (no Ct for all targets) |

If CONH, CONL, and/or CONN fall the batch run is invalid and no data will be reported for the clinical specimens. This determination is made automatically by the interpretive software. The batch run should be repeated starting with either a new RNA preparation or starting at the RT reaction step.

If NTC yields a result other than Fail (no Ct for all targets), the batch run is invalid and no data may be reported for the clinical specimens. This determination is made by visual inspection of the run data. The batch run should be repeated starting with either a new RNA preparation or starting at the RT reaction step.

If a second batch run fails, please contact technical services. If both the calibrations and all controls are valid, then the batch run is valid and specimen results will be reported.

Specimens

Note that a valid batch run may contain both valid and invalid specimen results.

Analytical criteria (e.g. Ct values) that qualify each specimen as passing or failing (using pre-determined data) are called automatically by the software.

Scores out of range—reported.

Quality Control

Singletons each of the Negative Control, Low Positive Control, and High Positive Control must be included in each batch run. The batch is valid if no flags appear for any of these controls.

A singleton of the No Template Control Is included in each batch run and Fail (no Ct for all targets) is a valid result indicating no ampliflable material was detectable in the well.

The negative control must yield a Negative result. If the negative control is flagged as Invalid, then the entire batch run is invalid.

The low positive and high positive controls must fall within the assigned ranges. If one or both of the positive controls are flagged as Invalid, then the entire batch run is invalid.

Example 10

Example Output

A possible example output from the software for a VaSIRS assay is presented below in FIG. 12. The format of such a report depends on many factors including; quality control, regulatory authorities, cut-off values, the algorithm used, laboratory and clinician requirements, likelihood of misinterpretation.

In this instance the assay is called "SeptiCyte Viral". The result is reported as a number (6), a position on a 0-10 scale, and a probability of the patient having a VIR based on historical results and the use of a pre-determined cut-off (using results from clinical studies). Results of controls within the assay may also be reported. Other information that could be reported might include: previous results and date and time of such results, a prognosis, a scale that provides cut-off values for historical testing results that separate the conditions of healthy, inSIRS and VaSIRS such that those patients with higher scores are considered to have more severe VaSIRS.

Example 11

Second Example Workflow

A second example workflow will now be described. Machines have been, and are being, developed that are capable of processing a patient sample at point-of-care, or near point-of-care. Such machines require few molecular biology skills to run and are aimed at non-technical users. The idea is that the sample would be pipetted directly into a disposable cartridge(s) that is/are then inserted into the machine. For determining a specific host response the cartridge will need to extract high quality RNA from the cells in the sample for use in reverse transcription followed by RT-PCR. The machines are designed for minimum user interaction such that the user presses "Start" and within 1-3 hours results are generated. The cartridges contains all of the required reagents to perform host cell nucleic acid extraction (RNA), reverse transcription, and qRT-PCR, and the machine has appropriate software incorporated to allow use of algorithms to interpret each result and combine results, and final interpretation and printing of results.

Fresh, whole, anti-coagulated blood can be pipetted into a specialized cartridge (e.g. cartridges designed for Enigma ML machine by Enigma Diagnostics Limited (Enigma Diagnostics Limited, Building 224, Tetricus Science Park, Dstl, Porton Down, Salisbury, Wiltshire SP4 0JQ) or similar (Unyvero, Curetis AG, Max-Eyth-Str. 42 71088 Holzgerlingen, Germany)), and on-screen instructions followed to test for differentiating a VIR from other forms of SIRS. Inside the machine RNA is first extracted from the whole blood and is then converted into cDNA. The cDNA is then used in qRT-PCR reactions. The reactions are followed in real time and Ct values calculated. On-board software generates a result output (see, FIG. 12). Appropriate quality control measures for RNA quality, no template controls, high and low template controls and expected Ct ranges ensure that results are not reported erroneously.

Example 12

Example Algorithm Combining Derived Biomarkers for Assessing a VaSIRS

Derived biomarkers can be used in combination to increase the diagnostic power for separating various conditions. Determining which markers to use, and how many, for separating various conditions can be achieved by calculating Area Under Curve (AUC).

As such, and by example, a 4-VaSIRS polynucleotide biomarker profile (AUC 0.936) offers the appropriate balance between simplicity, practicality and commercial risk for diagnosing VaSIRS. Further, an equation using four biomarkers weighs each biomarker equally which also provides additional robustness in cases of analytical or clinical variability.

One example equation (amongst others) that provides good diagnostic power for diagnosing a VaSIRS is:

$$\text{Diagnostic Score} = (IL16 - ISG15) + (CD97 - OASL)$$

Note: each marker in the Diagnostic Score above is the Log 2 transformed concentration of the marker in the sample.

Example 13

Figure 13:
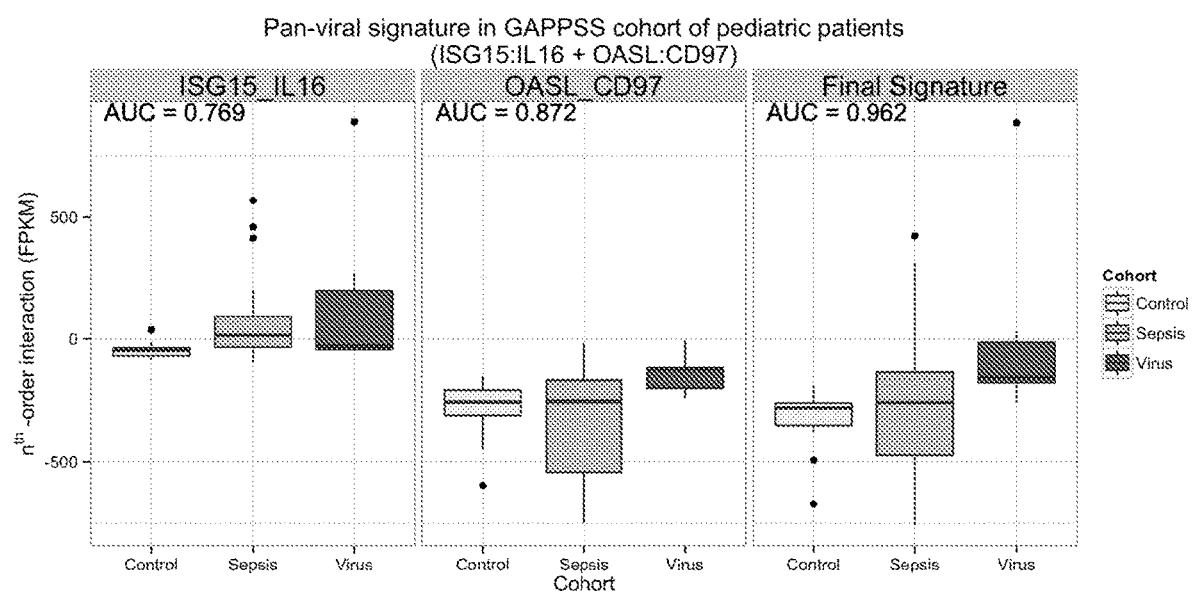
FIG. 13 shows box and whisker plots of the gene expression ratio index for combination of derived biomarkers IL16/ISG15 and CD97/OASL for pediatric patients. Patients are grouped based on whether they were healthy (Control) or whether they were positively diagnosed with BaSIRS (Sepsis) of VaSIRS (Virus).

Validation of Derived Biomarkers IL16/ISG15 and CD97/OASL on Pediatric Patient Sample Set The best performing pair of pan-viral biomarker ratios (IL16/ISG15+CD97/OASL) was further validated on an independent pediatric patient sample set. In this study, samples were collected from three groups of patients including 1). SIRS following cardiopulmonary bypass surgery (n=12), 2). Sepsis (SIRS+confirmed or strongly suspected bacterial infection) (n=28), 3). severe respiratory virus-infected (n=6). For SIRS patients, samples were taken within the first 24 hours following surgery and when the patient had at least two clinical signs of SIRS. Sepsis patients were retrospectively diagnosed by a panel of clinicians using all available clinical and diagnostic data. Virus-infected patients were also retrospectively diagnosed by a panel of clinicians using all available clinical and diagnostic data including the use of a viral PCR panel used on nasal or nasal/pharyngeal swabs (Biofire, FilmArray, Respiratory Panel, Biomerieux, 390 Wakara Way Salt Lake City, UT 84108 USA). The respiratory viruses detected in these patients were: rhinovirus/enterovirus, parainfluenza 3, respiratory syncytial virus and coronavirus HKU1. It should be noted that three of the six patients with a confirmed virus infection also had a confirmed or suspected bacterial infection. It should also be noted that sepsis patients that were not suspected of having a viral infection were also tested with the Biofire FilmArray and nine of the 28 sepsis patients had a positive viral PCR. Thus, there is some overlapping etiologies/pathologies in the sepsis and viral groups. FIG. 13 below shows box and whisker plots for each patient group (SIRS (control), sepsis and virus-infected). Performance of IL16/ISG15 alone, CD97/OASL alone and in combination ("Final Signature") is shown in the left, middle and right columns respectively. "FPKM" refers to "fragments per kilobase per million mapped reads" based on Next Generation Sequencing results. Area Under Curve (AUC) for the combined biomarker ratios is 0.962 when comparing virus-infected to SIRS patients. Some overlap is seen between the sepsis and virus patients, as would be expected based on the known presence of virus in "sepsis" patients and bacterial infection in "virus" patients.

Example 14

Figure 14:
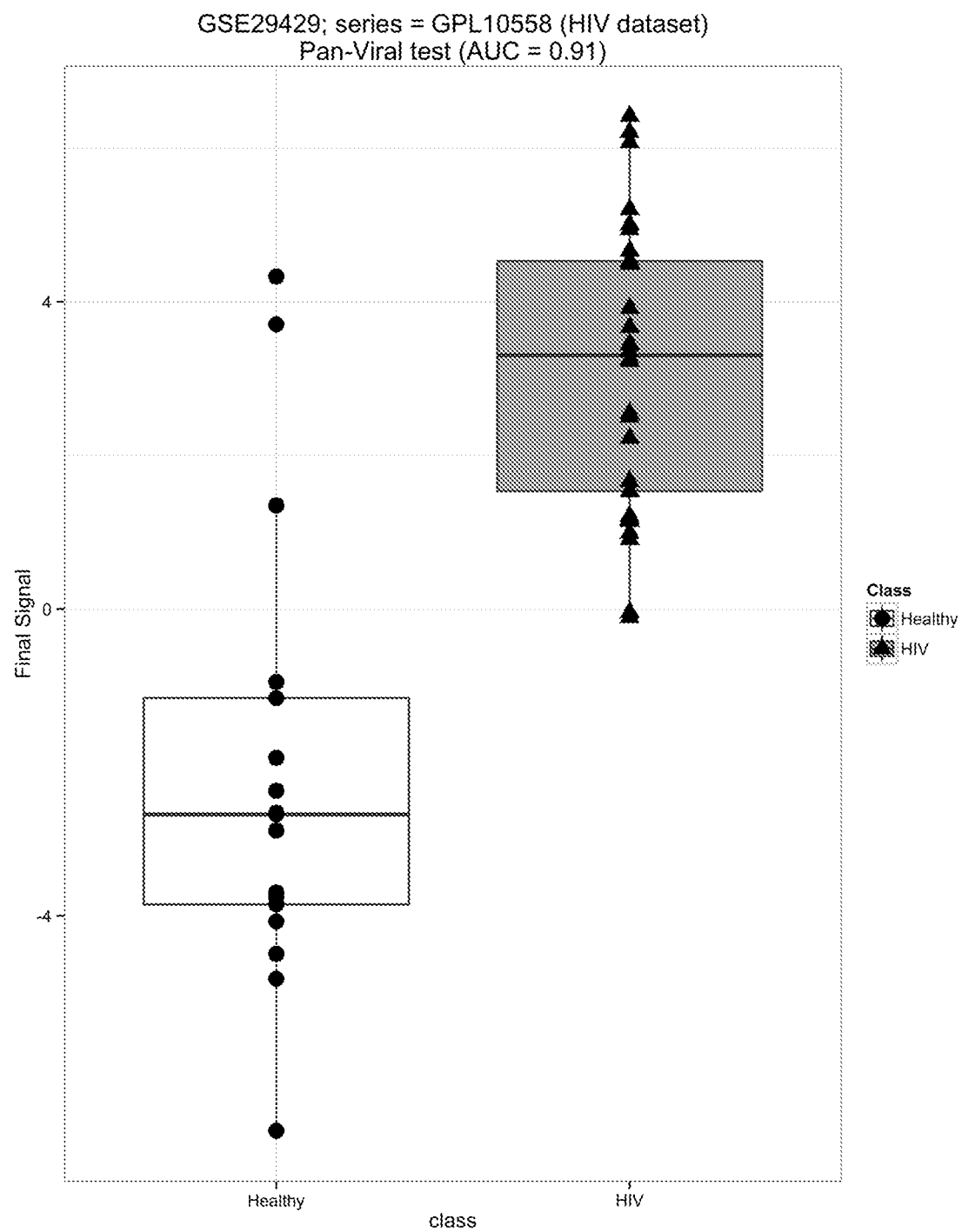
FIG. 14 shows a box and whisker plot of the results of a comparison of two groups of subjects, including 17 healthy controls and 30 patients infected with HIV. Samples analysed were taken from both healthy subjects and patients at the time of study enrolment. The Area Under Curve (AUC) using the combination of derived biomarkers IL16/ISG15 and CD97/OASL was 0.91.

Validation of Derived Biomarkers IL16/ISG15 and CD97/OASL on an Adult Patient Sample Set with HIV Infection The best performing pair of pan-viral biomarker ratios (IL16/ISG15+CD97/OASL) was further validated on an independent sample set consisting of adult patients with human immunodeficiency virus infection (GSE29429 using platform GPL10558). HIV is a member of the Baltimore virus classification Group VII. A subset of GSE29429 patients (run on the platform GPL10558) was deliberately chosen for the following reasons: 1). It contained samples taken at an appropriate timepoint of infection when at least one clinical sign of SIRS might be present (at presentation or trial enrolment); 2). None of the patients were on antiviral medication; 3). Appropriate healthy control patients were available. As such, a comparison was made between gene expression profiles of the derived biomarker combination of IL16/ISG15+CD97/OASL for 17 healthy controls versus 30 patients with confirmed HIV infection at enrolment. FIG. 14 shows a box and whisker plot of the results of this analysis. Area Under Curve (AUC) for the combined derived biomarkers is 0.91 when comparing HIV-Infected patients (right hand side) to healthy subjects (left hand side).

Example 15

Figure 15:
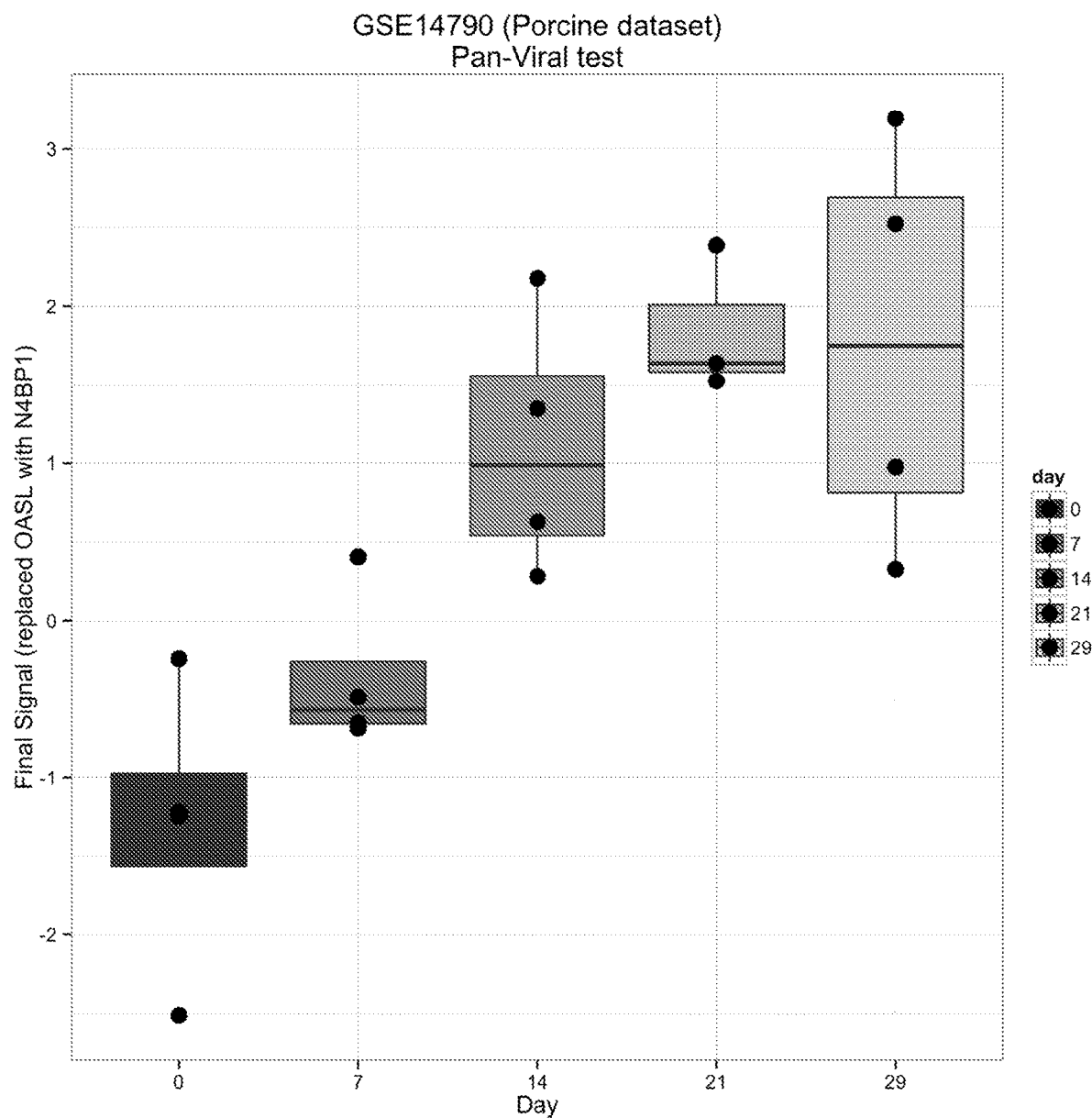
FIG. 15 shows box and whisker plots for a time course study in piglets deliberately infected (Day 0) with porcine circovirus and followed for 29 days. Blood samples were taken prior to inoculation (Day 0) and on Days 7, 14, 21 and 29. The derived biomarkers IL16/ISG15+CD97/N4BP1 were validated in this independent sample set (GSE14790). The alternate biomarker N4BP1 was substituted for OASL because this latter biomarker is not found in pigs. Areas Under Curve (AUCs) for the combined derived biomarkers were 0.812, 1.00, 1.00 and 1.00 for Days 0 vs 7, 0 vs 14, 0 vs 21 and 0 vs 29, respectively.

Validation of Derived Biomarkers IL16/ISG15 and CD97/N4BP1 on a Porcine Sample Set The pair of pan-viral biomarker ratios (IL16/ISG15+ CD97/N4BP1) was validated on an independent sample set (GSE14790) consisting of piglets deliberately infected with porcine circovirus (PCV). PCV is a member of the Baltimore virus classification Group II. Four piglets inoculated with PCV (on Day 0) were followed over time and blood samples were taken on Days 0, 7, 14, 21 and 28. The gene OASL is not present on the microarray used in the GSE14790 study, most likely due to the fact that it is known that the OASL gene product is truncated in pigs (Perelygin, A. A., Zharkikh, A. A., Scherbik, S. V., & Brinton, M. A. (2006). The mammalian 2"-5" oligoadenylate synthetase gene family: evidence for concerted evolution of paralogous Oas1 genes in Rodentia and Artiodactyla. Journal of Molecular Evolution, 63(4), 562-576). As such, the alternate biomarker N4BP1 was substituted for OASL in the derived biomarker of CD97/OASL. N4BP1 is the biomarker with the highest correlation to OASL in Group D (see Table 10). FIG. 15 shows a box and whisker plot of the results of this analysis when using this alternate derived biomarker. Areas Under Curve (AUCs) for the combined derived biomarkers were 0.812, 1.00, 1.00 and 1.00 for Days 0 vs 7, 0 vs 14, 0 vs 21 and 0 vs 29 respectively.

Example 16

Validation of Derived Biomarkers IL16/ISG15 and CD97/OASL on Pediatric Patient Sample Sets with RSV and HRV Infection It is important to demonstrate that the pan-viral signature is not simply an indicator of severity of inflammatory immune response. The present inventors demonstrated that the pan-viral signature is specific to viral infection, rather than severity of inflammation, by analysing two independent datasets in children. Respiratory Syncytial Virus (RSV) has high morbidity and mortality in children and infected children need to be identified, treated and isolated early in the course of the disease process. Human Rhinovirus (HRV) affects both adults and children multiple times during a lifetime and an infection can result in hospitalization or it can be asymptomatic. Some people also act as carriers.

Figure 16:
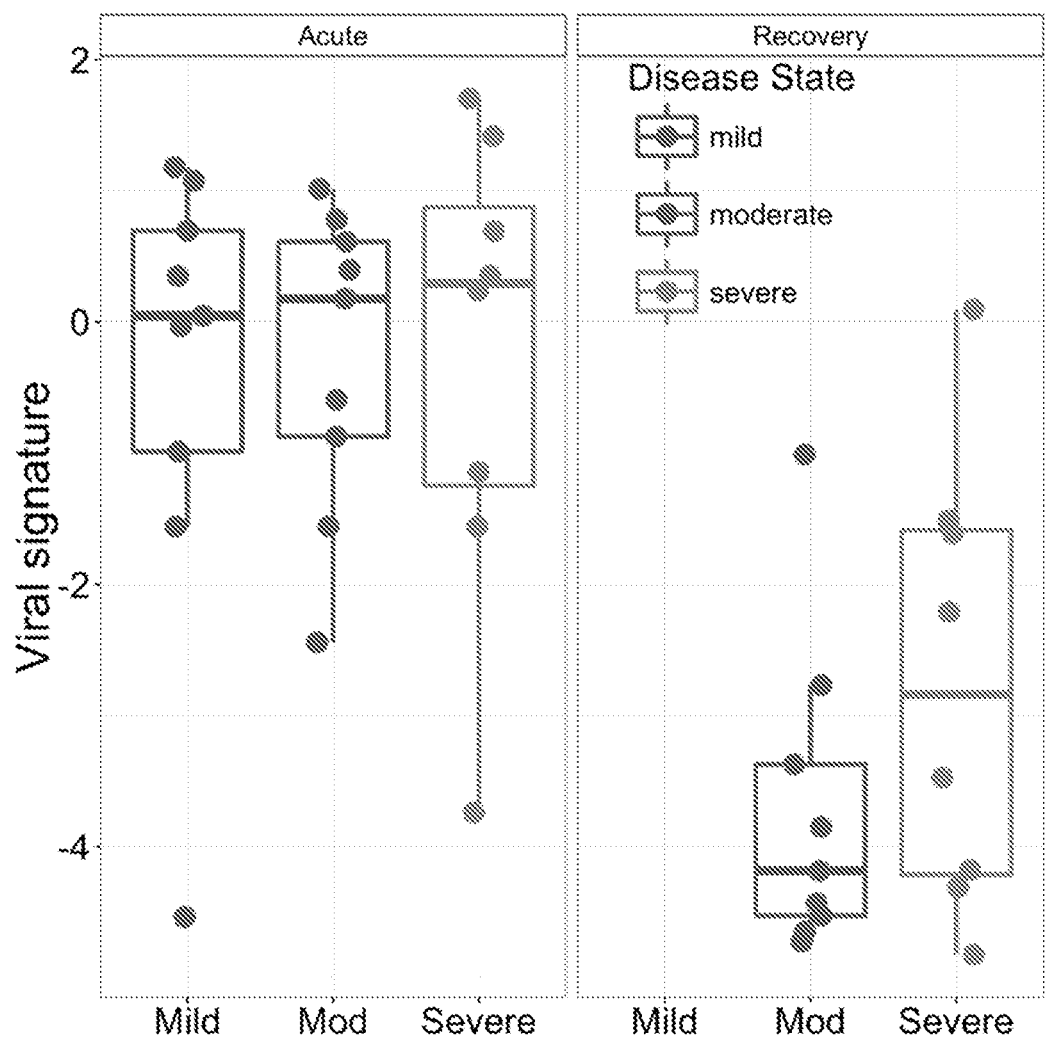
FIG. 16 shows pan-viral signature values for children with acute RSV infection and following recovery (dataset GSE69606). The box and whisker plots show a difference (AUC=0.903) between the pan-viral signature for those children with acute RSV infection (left panel) compared to moderate and severely affected children in recovery 4-6 weeks later (right panel). Little difference can be seen in the pan-viral signature between children with acute mild (n=9), moderate (n=9) or severe (n=8) infection (left panel). The pan-viral signature is therefore not affected by disease severity.

Pan-viral signature values were determined for children with acute RSV infection and following recovery (using dataset GSE69606) (FIG. 16). The box and whisker plots in this figure show a difference (AUC=0.903) between the pan-viral signature for those children with acute RSV infection (left panel) compared to moderate and severely affected children in recovery 4-6 weeks later (right panel). Little difference can be seen in the pan-viral signature between children with acute mild (n=9), moderate (n=9) or severe (n=8) infection (left panel) indicating that the pan-viral signature is not affected by disease severity.

Figure 17:
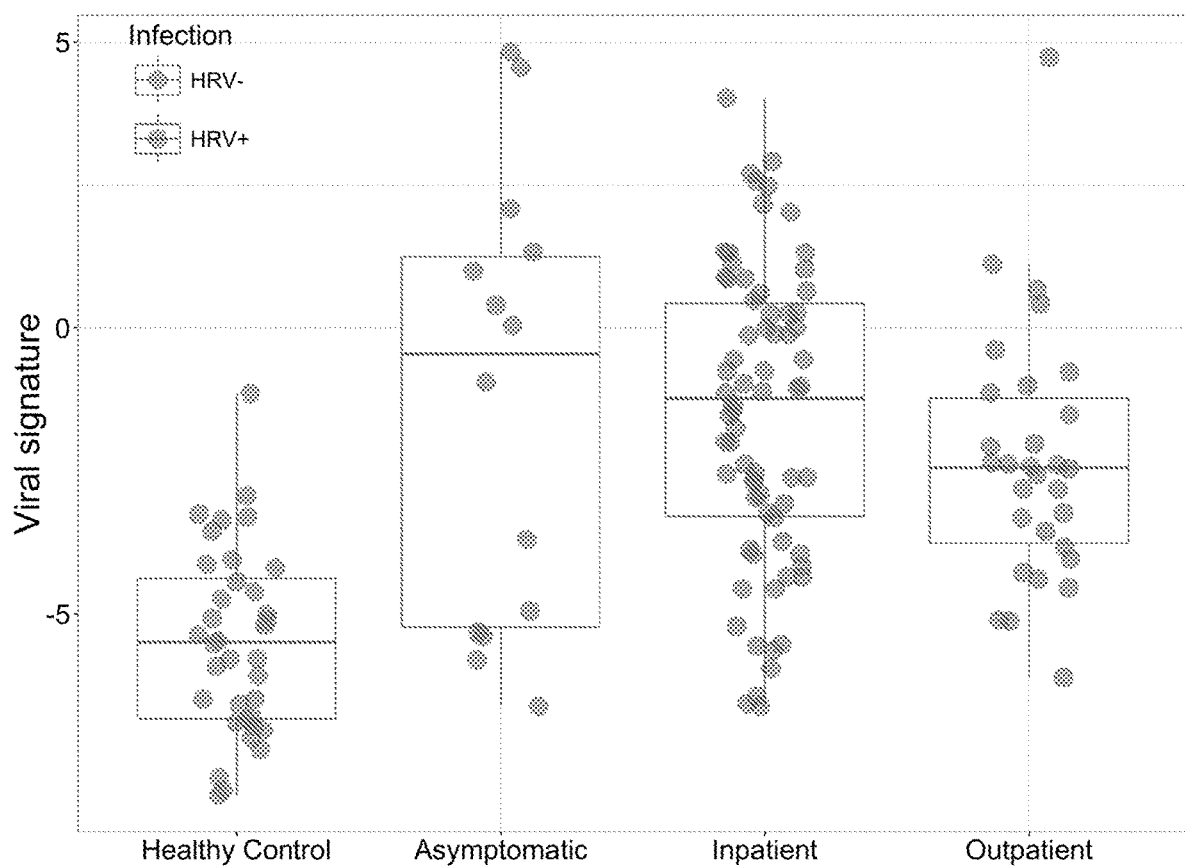
FIG. 17 shows pan-viral signature values for children with and without detectable human rhinovirus (GSE67059). Box and whisker plots of the performance of the pan-viral signature in children (<2 years old). The children were pre-sorted into groups according to presence or absence of HRV in nasopharyngeal swabs, and whether they were asymptomatic, or treated as an inpatient or outpatient. The pan-viral signature AUCs were as follows: 0.884 for all HRV+ versus all HRV−; 0.806 for healthy versus asymptomatic (but confirmed HRV+), 0.896 for healthy versus inpatient; 0.894 for healthy vs. outpatient. The lack of difference in pan-viral signature values for different disease severity, as indicated by whether the patients were asymptomatic or symptomatic, and whether they were treated as an outpatient or inpatient, Indicates that the pan-viral signature is unaffected by disease severity.

Pan-viral signature values were determined for children with and without detectable human rhinovirus (using dataset GSE67059) (FIG. 17). The box and whisker plots in this figure show the performance of the pan-viral signature in children (<2 years old) with and without detectable HRV. The children were pre-sorted into groups according to presence or absence of HRV in nasopharyngeal swabs, and whether they were asymptomatic, or treated as an inpatient or outpatient. The pan-viral signature AUCs were as follows: 0.884 for all HRV+ versus all HRV−; 0.806 for healthy versus asymptomatic (but confirmed HRV+), 0.896 for healthy versus inpatient; 0.894 for healthy versus outpatient.

The results of the pan-viral signature in these two datasets demonstrate specificity for viral infection irrespective of disease severity.

Example 17

Validation of Derived Biomarkers IL16/ISG15 and CD97/OASL in Datasets Indicating Early Diagnostic Performance Early diagnosis of a viral infection is important for a number of reasons including, 1) it enables early treatment, 2) affected patients can be isolated so that they do not infect others, 3) surveillance of a population can be performed in disease outbreaks to aid in containment. Some viral infections can be treated with anti-viral drugs—see Table 17. Earlier treatment in viral infections results in better outcomes. Early diagnosis therefore allows for earlier treatment and better outcomes. Some subjects with viral infections are contagious and it is therefore important to identify and isolate them to reduce viral spread. For example, children with RSV can infect other hospitalized patients and they are therefore isolated. Early diagnosis of patients with a viral infection will allow for better disease containment. In a viral disease outbreak (e.g., Ebola virus in humans, virulent influenza in animals) a population encircling where a known outbreak has occurred can be tested. Those subjects testing positive can be isolated and treated. Testing continues in an ever widening circle until all subjects test negative. Those subjects within the circle can then be vaccinated, or treated appropriately. The present inventors demonstrated early diagnostic performance of the pan-viral signature in two different viral infections (influenza and Marburg) in two species (humans and macaques).

Figure 18:
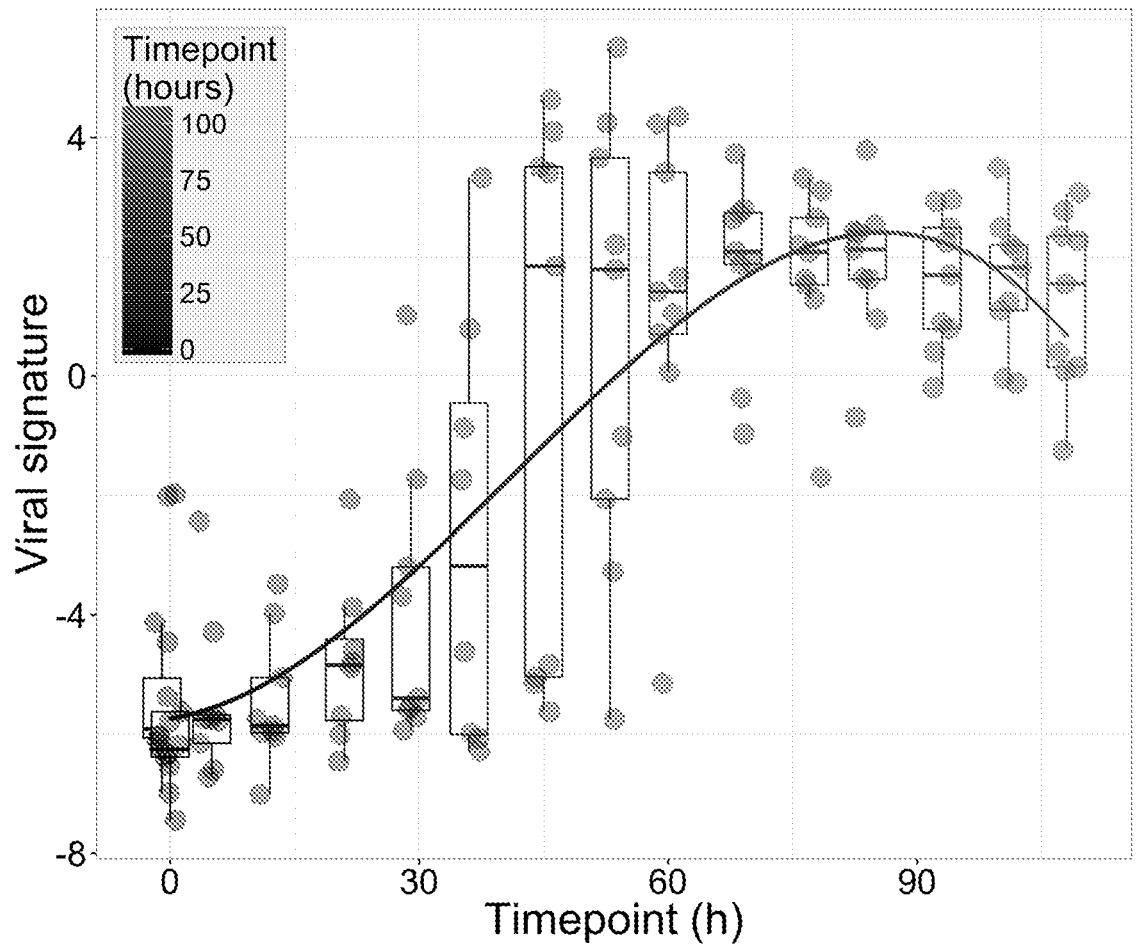
FIG. 18 shows time-course values for the pan-viral signature after intra-nasal infection of human subjects with H3N2 Influenza A (GSE30550). Box and whisker plot showing the pan-viral signature value for symptomatic human subjects, over a 108 hour period following intra-nasal inoculation of influenza H3N2. A difference in pan-viral signature value compared to pre-Inoculation can be seen as early as 36 hours and peaks at 69 hours which precedes recorded clinical signs. Thus, the pan-viral signature is diagnostic for viral Infection early in the disease course. Similar times for earliest detection and peak values were seen in both humans and mice in response to experimental Inoculation with the same strain of influenza virus. A similar time course response in different species to the same virus strain suggests the possibility that similar virus strains have a similar temporal pan-viral signature response.

FIG. 18 shows time-course values for the pan-viral signature in otherwise healthy adult humans following intra-nasal infection with H3N2 influenza A (GSE30550). The box and whisker plot show the pan-viral signature over a 108 hour period following intra-nasal inoculation of influenza strain H3N2. A difference in pan-viral signature value compared to pre-inoculation can be seen as early as 36 hours which is earlier than first recorded clinical symptoms.

Figure 19:
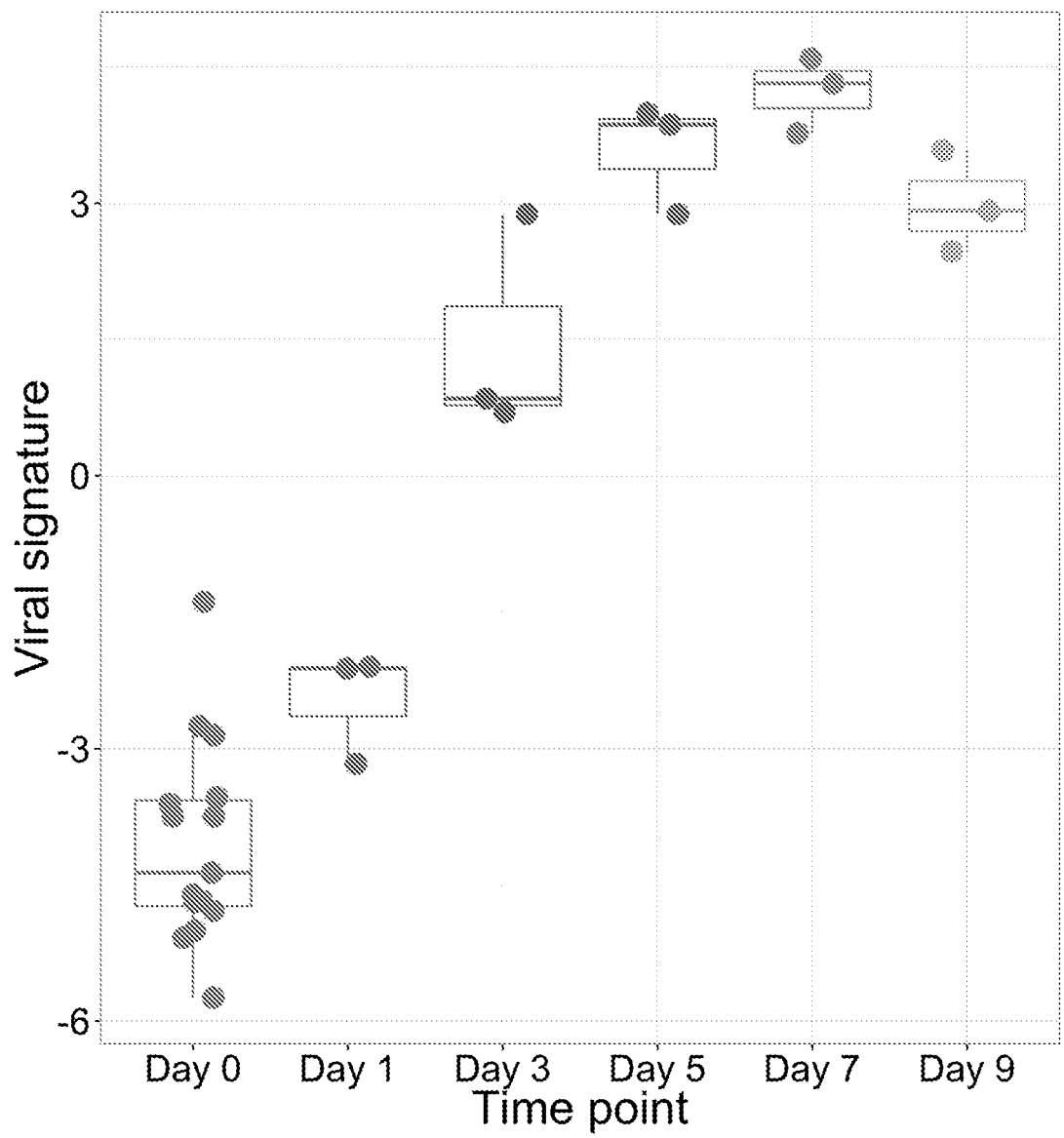
FIG. 19 shows pan-viral signature values over time for macaques Inoculated with Marburg virus (GSE58287). The box and whisker plots showing the pan-viral signature values over 9 days for 15 macaques exposed to aerosolized Marburg virus on day 0. Three macaques were euthanized every two days. Virus was first detected in regional lymph nodes on day 3 post-exposure, viremia was detected on day 4, and the first fever on day 5. Based on these values the pan-viral signature is diagnostic for viral Infection early in the disease course, 2 days before the first appearance of viral antigen in lymph nodes, 3 days before the detection of viremia, and 4 days before clinical signs.

FIG. 19 shows pan-viral signature values over time for macaques inoculated with Marburg virus (dataset GSE58287). The box and whisker plots show the pan-viral signature values over 9 days for 15 macaques exposed to aerosolized Marburg virus on day 0. Three macaques were euthanized every two days. Virus was first detected in regional lymph nodes on day 3 post-exposure, viremia was detected on day 4, and the first fever on day 5. A pan-viral signature response can therefore be detected two days before first detectable antigen, 3 days before detectable viremia, and 4 days before first clinical signs in this animal model of Ebola virus infection. Early diagnosis of subjects infected with Ebola would be important in containment efforts.

The results of the pan-viral signature in these two datasets demonstrate early detection capabilities.

Example 18

Validation of Derived Biomarkers IL16/ISG15 and CD97/OASL in a Dataset Indicating Performance in Tissues Other than Blood Performance of a diagnostic signature in tissues other than blood may be important for clinical practical reasons, or for research purposes. For example, peripheral blood may be difficult to obtain in very low birth weight infants with meningitis. In this instance, cerebrospinal fluid may be easier and safer to obtain. In research, animal models and tissue culture are often used to study the effects of viruses and/or to develop vaccines. The present inventors demonstrated pan-viral signature diagnostic performance in liver biopsies from chimpanzees infected with hepatitis C and E.

Figure 20:
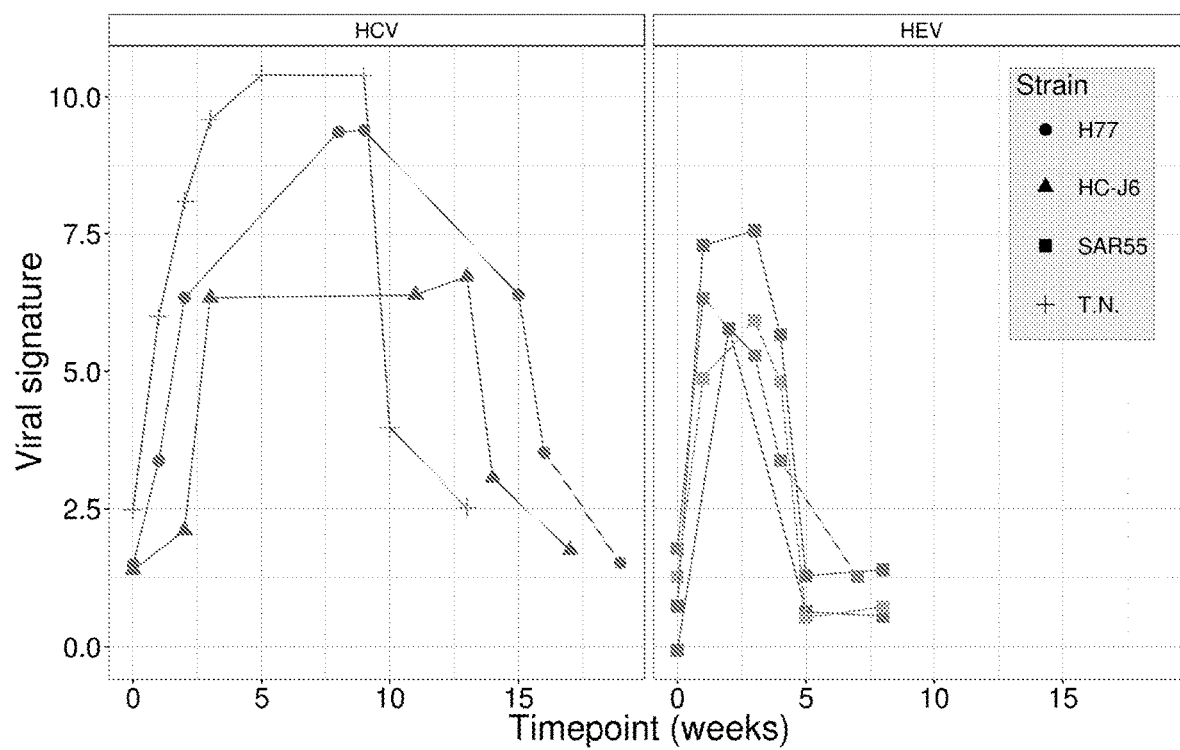
FIG. 20 shows pan-viral signature values over time for liver biopsy tissue from chimpanzees Inoculated with Hepatitis C Virus or Hepatitis E Virus. The box and whisker plots show the pan-viral signature values as a function of time in chimpanzees that were Intravenously Inoculated with either Hepatitis C virus (HCV; N=3) or Hepatitis E virus (HEV; N=4). Liver biopsy samples were analyzed for gene expression at various time points. The pan-viral signature had an AUC>0.96 when comparing all time points post-inoculation to pre-inoculation. The values show that the pan-viral signature can detect a viral response in tissues other than peripheral blood (liver biopsy) and that different viruses (Hepatitis E and C) create a different response in terms of amplitude and time.

FIG. 20 show pan-viral signature values over time for liver biopsy tissue from chimpanzees inoculated with Hepatitis C Virus or Hepatitis E Virus. The box and whisker plots show the pan-viral signature values as a function of time in chimpanzees that were intravenously Inoculated with either Hepatitis C virus (HCV; N=3) or Hepatitis E virus (HEV; N=4). Liver biopsy samples were analyzed for gene expression at various time points. The pan-viral signature had an AUC>0.96 when comparing all time points post-Inoculation to pre-inoculation.

The results of the pan-viral signature in this dataset demonstrates detection capabilities in tissues other than blood.

Example 19

Validation of Derived Biomarkers IL16/ISG15 and CD97/OASL in Adults Presenting to Emergency It is important for the pan-viral signature to have diagnostic performance in various clinical settings, including the emergency room (ER) which has a heterologous patient population with respect to type and prevalence of inflammatory conditions. The present inventors therefore ran a clinical trial that enrolled patients admitted to hospital that presented to ER with fever. Each patient was retrospectively diagnosed as having a bacterial or viral infection, or no infection.

Figure 21:
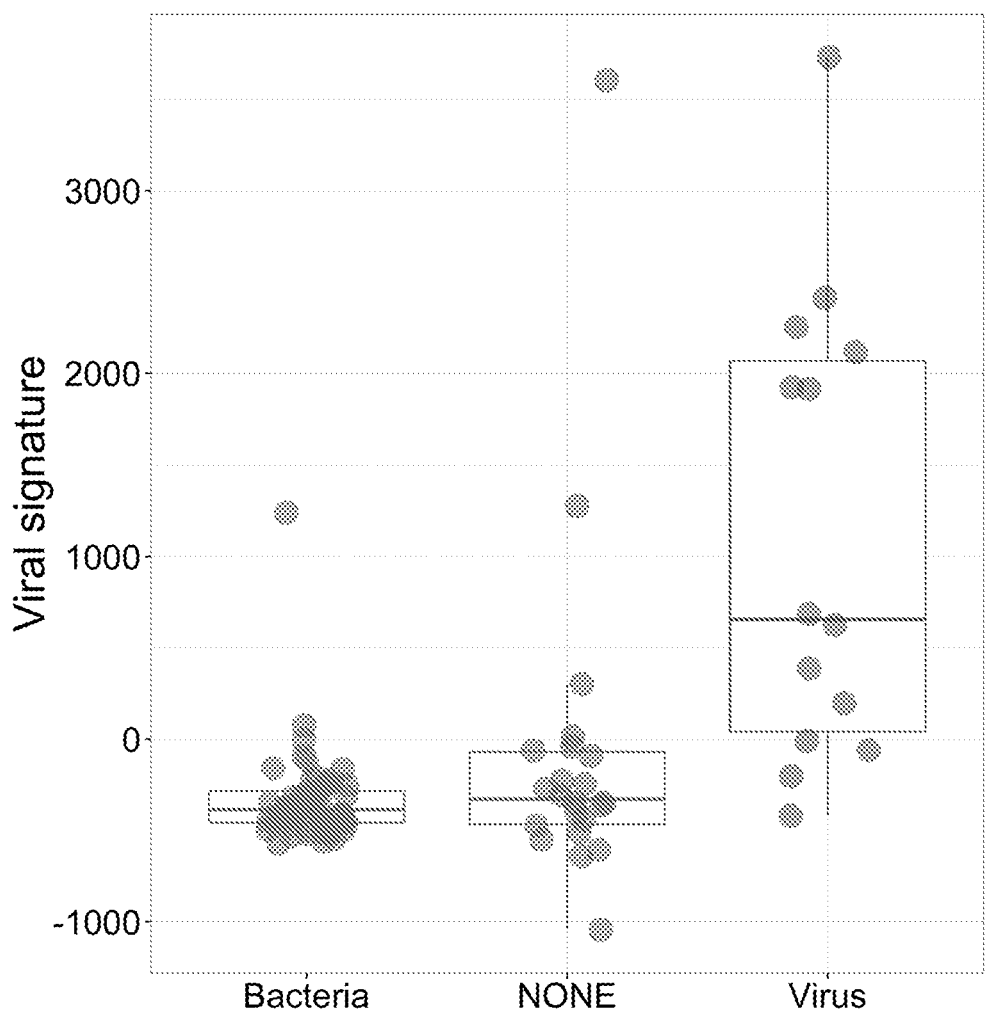
FIG. 21 shows the performance of the pan-viral signature in adult patients presenting to ER with fever. Box and whisker plots for 93 patients in the FEVER study retrospectively diagnosed with either bacterial sepsis (n=55), no Infection (n=22), or viral Infection (n=15). AUCs were 0.934, 0.854 and 0.583 for viral versus bacterial, viral versus uninfected, and bacterial versus uninfected, respectively.

FIG. 21 shows the performance of the pan-viral signature in 93 adult patients presenting to ER with fever. The box and whisker plots for these patients shows clear separation for those retrospectively diagnosed with either bacterial sepsis (n=55), no infection (n=22), or viral infection (n=15). The AUCs were 0.934 (viral versus bacterial), 0.854 (viral versus uninfected) and 0.583 (bacterial versus uninfected).

The results of the pan-viral signature in this dataset demonstrates specificity in a heterologous adult population presenting to ER.

Example 20

Validation of Derived Biomarkers IL16/ISG15 and CD97/OASL in a Dataset Indicating Performance in Response to Therapy It is important for the pan-viral signature to demonstrate diagnostic performance in response to patient therapy. Such performance can then be used to guide clinicians in choice and duration of anti-viral therapies.

Figure 22:
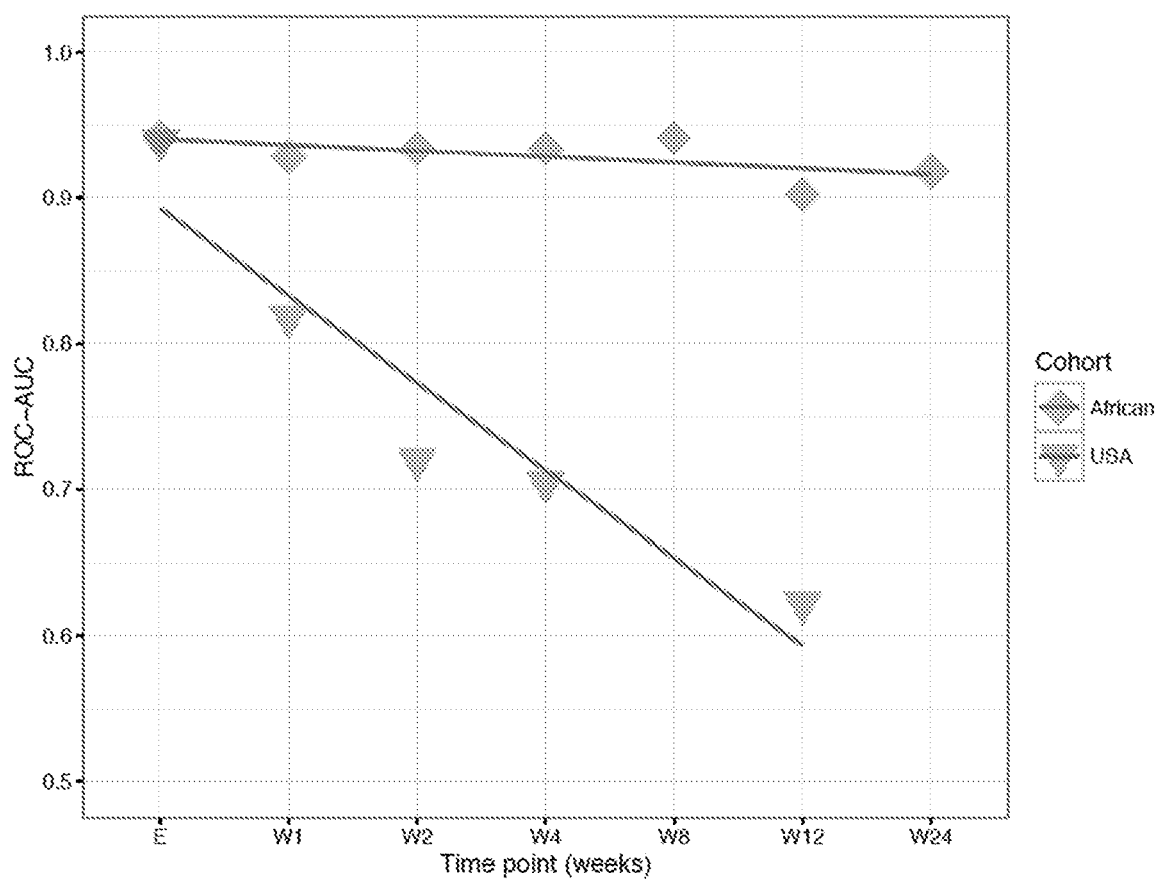
FIG. 22 shows the AUC for the pan-viral signature for two groups of patients diagnosed with HIV located in either Africa (n=43) or the USA (n=15). Patient samples were collected at study enrollment when they had a confirmed acute infection and at weeks 1, 2, 4, 12, and 24. The pan-viral signature AUC when comparing healthy controls to African patients who did not receive any treatment remained at or above 0.9 at all time points, whereas the AUCs when comparing healthy controls to USA patients receiving treatment dropped from above 0.9 at enrolment to less than 0.5 by Week 24. Also, the pan-viral signature scores over time largely reflect the mean HIV viral loads as described in GSE29429.

FIG. 22 shows the AUC for the pan-viral signature for two groups of patients diagnosed with HIV located in either Africa (n=43) or the USA (n=15). Patient samples were collected at study enrollment when they had a confirmed acute infection and at weeks 1, 2, 4, 12, and 24. The pan-viral signature AUC when comparing healthy controls to African patients who did not receive any treatment remained at or above 0.9 at all time points, whereas the AUCs when comparing healthy controls to USA patients receiving treatment dropped from above 0.9 at enrolment to less than 0.5 by Week 24. Also, the pan-viral signature scores over time largely reflect the mean HIV viral loads as described in GSE29429.

Example 21

Validation of Derived Biomarkers IL16/ISG15 and CD97/OASL in a Dataset Indicating Performance in Response to Therapy It is important for the pan-viral signature to demonstrate diagnostic performance in response to live viral vaccination. Such performance can then be used to guide researchers in vaccine development and clinicians in determining whether a subject has had a suitable response to vaccination.

Figure 23:
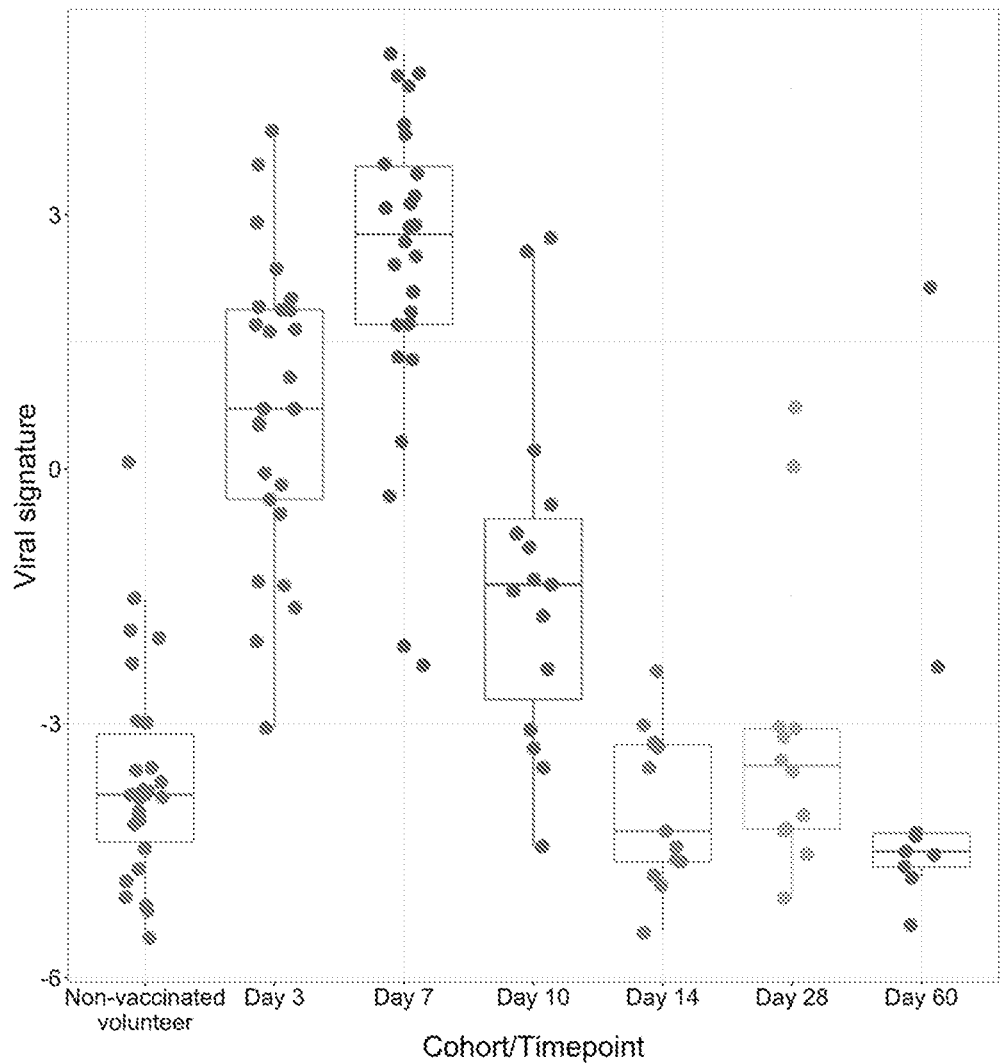
FIG. 23 shows subject response to a live yellow fever vaccine. Two geographically separated groups of volunteers (Lausanne, n=11; Montreal, n=15) were vaccinated subcutaneously on Day 0 with Stamaril (Sanofi-Pasteur YF17D-204 YF-VAX), a vaccine containing live attenuated yellow fever virus which affords protection from 10 days following vaccination. Whole blood samples were collected on days 0, 3 and 7 for the Lausanne cohort and on days 0, 3, 7, 10, 14, 28 and 60 for the Montreal cohort. The pan-viral signature value peaked on Day 7 following vaccination and dropped to pre-vaccination levels by Day 14. The pan-viral signature value largely reflects viremia (viral particles per mL of plasma) as detailed in Gaucher et al. (2008) (Supplemental Material, Table 5). In this study a specific antibody response to vaccination was not detected until 14 days post-vaccination.

In a yellow fever vaccination study (Gaucher et al., 2008) two geographically separated groups of volunteers (Lausanne, n=11; Montreal, n=15) were vaccinated subcutaneously on Day 0 with Stamaril (Sanofi-Pasteur YF17D-204 YF-VAX), a vaccine containing live attenuated yellow fever virus which affords protection from 10 days following vaccination. Whole blood samples were collected on days 0, 3 and 7 for the Lausanne cohort and on days 0, 3, 7, 10, 14, 28 and 60 for the Montreal cohort. The pan-viral signature value peaked on Day 7 following vaccination and dropped to pre-vaccination levels by Day 14 (FIG. 23). The pan-viral signature value largely reflects viremia (viral particles per mL of plasma) as detailed in Gaucher et al. (2008) (Supplemental Material, Table 5). In this study a specific antibody response to vaccination was not detected until 14 days post-vaccination.

The results of the pan-viral signature in this dataset demonstrates diagnostic performance in response to vaccination.

The disclosure of every patent, patent application, and publication cited herein is hereby incorporated herein by reference in its entirety.

The citation of any reference herein should not be construed as an admission that such reference is available as "Prior Art" to the instant application.

Throughout the specification the aim has been to describe the preferred embodiments of the invention without limiting the invention to any one embodiment or specific collection of features. Those of skill in the art will therefore appreciate that, in light of the instant disclosure, various modifications and changes can be made in the particular embodiments exemplified without departing from the scope of the present invention. All such modifications and changes are intended to be included within the scope of the appended claims.

TABLE 1

DIFFERENT TYPES OF VIRUS ANTIGEN EXPOSURE

| Antigen Exposure Type | Example Virus Families | Baltimore Classifications |
|---|---|---|
| Infection Type | | |
| Cytolytic | Reoviridae | III |
| | Herpesviridae | I |
| | Poxviridae | I |
| | Paramyxoviridae | V |
| | Orthomyxoviridae | V |
| | Parvoviridae | II |
| | Flaviviridae | IV |
| | Circoviridae | II |
| Persistent | Paramyxoviridae | V |
| Latent | Herpesviridae | I |
| Integrated | Retroviridae | VI |
| | Herpesviridae | I |
| Mechanism of Spread | | |
| 1° Hematogenous | Flaviviridae | IV |
| | Hepadnaviridae | VII |
| 2° Hematogenous | Herpesviridae | I |
| | Reoviridae | III |
| | Parvoviridae | II |
| | Circoviridae | II |
| Local | Rhinoviridae | IV |
| | Reoviridae | III |
| Nervous | Herpesviridae | I |
| Virus Location | | |
| Systemic | Paramyxoviridae | V |
| | Orthomyxoviridae | V |
| | Parvoviridae | II |
| | Circoviridae | II |
| Local | Rhinoviridae | IV |
| | Reoviridae | III |

TABLE 2

GROUP A BIOMARKERS AND THEIR DIAGNOSTIC PERFORMANCE ACROSS VARIOUS DATASETS

| | | Biomarker | | |
|---|---|---|---|---|
| Dataset Type | Parameter Description | ZBP1 DNA SEQ ID NO: 399 | TMEM62 DNA SEQ ID NO: 414 AUC | CD38 DNA SEQ ID NO: 415 |
| | mean 4 core sets | 0.891 | 0.897 | 0.744 |
| | mean auc of all viral sets | 0.768 | 0.77 | 0.74 |
| | num viral lt75 | 3 | 5 | 5 |
| | num non-viral gt80 | 3 | 1 | 0 |
| core viral | viral GSE51808 dengue | 0.948 | 0.98 | 1 |
| core viral | viral GSE41752 lassa | 0.88 | 0.938 | 0.928 |
| core viral | viral GSE52428 flu | 0.926 | 0.888 | 0.785 |
| core viral | viral GSE40366 herpes | 0.81 | 0.782 | 0.263 |
| validation viral | viral GSE6269 peds_bact_viral | 0.902 | 0.63 | 0.789 |
| validation viral | viral GSE40396 peds_bact_viral | 0.824 | 0.832 | 0.719 |
| validation viral | viral GSE40012 pneumonia | 0.931 | 0.784 | 0.904 |
| validation viral | viral GSE18090 dengue | 0.812 | 0.743 | 0.903 |
| validation viral | viral GSE30550 flu | 0.955 | 0.877 | 0.882 |
| validation viral | viral GSE40224 HepC | 0.888 | 0.981 | 0.619 |
| validation viral | viral GSE5790 LCMV | 0.327 | 0.564 | 0.173 |
| validation viral | viral GSE34205 RSV | 0.652 | 0.686 | 0.654 |
| validation viral | viral GSE5808 measles | 0.4 | 0.6 | 0.933 |
| validation viral | viral GSE2729 rotavirus | 0.5 | 0.5 | 0.808 |
| non-viral inflammation | sirs GSE17755 autoimmune disease | 0.845 | 0.5 | 0.5 |
| non-viral inflammation | sirs GSE19301 asthma | 0.536 | 0.488 | 0.603 |
| non-viral inflammation | sirs GSE47655 anaphlyxis | 0.5 | 0.5 | 0.7 |
| non-viral inflammation | sirs GSE38485 schizophrenia | 0.466 | 0.508 | 0.392 |
| non-viral inflammation | sirs GSE36809 trauma | 0.394 | 0.376 | 0.066 |
| non-viral inflammation | sirs GSE29532 coronary_artery | 0.667 | 0.727 | 0.22 |
| non-viral inflammation | sirs GSE40366 AGE_cmv herpes | 0.815 | 0.897 | 0.323 |
| non-viral inflammation | sirs GSE46743 depression_stress | 0.649 | 0.323 | 0.571 |
| non-viral inflammation | sirs GSE61672 anxiety | 0.557 | 0.445 | 0.515 |
| non-viral inflammation | sirs GSE64813 PTSD | 0.575 | 0.432 | 0.466 |

TABLE 2-continued

GROUP A BIOMARKERS AND THEIR DIAGNOSTIC PERFORMANCE ACROSS VARIOUS DATASETS

| | | Biomarker | | |
|---|---|---|---|---|
| Dataset Type | Parameter Description | ZBP1 DNA SEQ ID NO: 399 | TMEM62 DNA SEQ ID NO: 414 AUC | CD38 DNA SEQ ID NO: 415 |
| non-viral inflammation | triage GSE11908 infections | 0.298 | 0.455 | 0.629 |
| non-viral inflammation | triage GSE16129 staph_peds | 0.4 | 0.736 | 0.462 |
| non-viral inflammation | triage GSE25504 bact_neonatal | 0.522 | 0.748 | 0.365 |
| non-viral inflammation | triage GSE30119 staph_healthy | 0.51 | 0.638 | 0.504 |
| non-viral inflammation | triage GSE33341 staph_ecoli_healthy | 0.777 | 0.754 | 0.573 |
| non-viral inflammation | triage GSE40012 pneumonia | 0.473 | 0.662 | 0.358 |
| non-viral inflammation | triage GSE40396 peds_bact_viral | 0.48 | 0.257 | 0.254 |
| non-viral inflammation | triage GSE40586 bact_peds | 0.279 | 0.476 | 0.507 |
| non-viral inflammation | triage GSE42834 infection | 0.869 | 0.579 | 0.756 |
| non-viral inflammation | triage GSE6269 peds_bact_viral | 0.118 | 0.456 | 0.237 |
| non-viral inflammation | healthy GSE35846.0 race | 0.469 | 0.503 | 0.622 |
| non-viral inflammation | healthy GSE35846.1 age | 0.498 | 0.572 | 0.475 |
| non-viral inflammation | healthy GSE35846.2 gender | 0.615 | 0.493 | 0.528 |
| non-viral inflammation | healthy GSE35846.3 obese | 0.527 | 0.55 | 0.489 |

TABLE 3

DATASETS USED FOR "DISCOVERY" OF PAN-VIRAL BIOMARKERS AND BIOMARKER PROFILES

| Dataset Identifier | Virus name, classification, genome | Study Description |
|---|---|---|
| GSE51808 | Dengue, Flavivirus, RNA | 28 human patients with naturally-acquired Dengue Fever or Dengue Hemorrhagic Fever. Samples collected at 2 and 9 days post onset of symptoms, and at four weeks (convalescent). Nine healthy controls. |
| GSE41752 | Lassa, Arenavirus, RNA | 11 macaques with experimentally-induced Lassa virus infection. Samples collected pre-infection and on Days 2, 3, 6, 8, 10 and 12 post-infection. Total 46 processed samples. |
| GSE52428 | Influenza A, Orthomyxovirus, RNA | 18 human subjects experimentally-infected with Influenza virus A (two strains). Samples taken pre-infection and every eight hours out to 108 hours post-infection. Symptomatic and asymptomatic responses. |
| GSE40366 | Cytomegalovirus, Herpesvirus, DNA | Human subjects with and without a CMV titer (0-42,000). 143 nonagenarians and 30 young subjects (<30 years of age). |

TABLE 4

DATASETS USED FOR "VALIDATION" OF PAN-VIRAL BIOMARKERS AND BIOMARKER PROFILES

| Dataset Identifier | Virus name, classification, genome | Study Description |
|---|---|---|
| GSE6269 | Influenza A, Orthomyxovirus, RNA | Human patients, single sample. Influenza A/B: 30/6 *Staphylococcus aureus*: 50 *Escherichia coli*: 29 *Streptococcus pneumoniae*: 22 Healthy: 6 |
| GSE40396 | Adenovirus, DNA. HHV6, Herpesvirus, DNA. Enterovirus, Picornavirus, RNA. Rhinovirus, Picornavirus, RNA. | Human patients, single sample. Adenovirus: 11 HHV6: 10 Enterovirus: 6 Rhinovirus: 8 *Escherichia coli*: 2 MRSA: 4 Controls: 19 |
| GSE40012 | Influenza A, Orthomyxovirus, RNA | Human patients, single sample. Influenza A: 34 Healthy: 38 |
| GSE18090 | Dengue, Flavivirus, RNA | 26 patients with Dengue fever. Up to five days of clinical symptoms. Patients were afebrile 3 days post-sampling. 8 control patients without Dengue fever. |
| GSE30550 | Influenza A, Orthomyxovirus, RNA | 17 human subjects experimentally-infected with Influenza virus A (H3N2). Samples taken pre-infection and every eight hours out to 108 hours post-infection. Symptomatic and asymptomatic responses. |
| GSE40224 | Hepatitis C, Flavivirus, RNA | Human patients, single sample. Hepatitis C: 10 Healthy: 8 |
| GSE5790 | Lymphocytic choriomeningitis virus, Arenavirus, RNA | 9 macaques experimentally-infected with lethal LCMV. Samples taken pre-infection and on Days 1, 2, 3, 4, 6 and 7 post-infection. |

TABLE 4-continued

DATASETS USED FOR "VALIDATION" OF PAN-VIRAL BIOMARKERS AND BIOMARKER PROFILES

| Dataset Identifier | Virus name, classification, genome | Study Description |
|---|---|---|
| GSE34205 | Respiratory syncytial virus, Paramyxovirus, RNA. Influenza A, Orthomyxovirus, RNA | Human patients, single sample. Healthy: 22 RSV: 51 Influenza: 28 |
| GSE5808 | Measles, Morbillivirus, RNA | 5 patients with measles. Samples taken on hospital entry, at discharge and at one month follow-up. 3 healthy controls. |
| GSE2729 | Rotavirus, Reovirus, RNA | Human patients, single sample. 10 acute infection 5 convalescent 8 healthy controls. |
| GSE14790 | Porcine circovirus, Circovirus, DNA | Four piglets experimentally-infected with porcine circovirus. Samples taken on Days 0, 7, 14, 21 and 28. |
| GSE29429 | Human Immunodeficiency Virus, Retrovirus, RNA | 17 HIV-infected patients with samples taken on study enrolment. 30 healthy controls with samples taken on study enrolment. |
| GSE69606 | Respiratory syncytial virus, Paramyxovirus, RNA. | 9 mild, 9 moderate and 8 severe followed up 4-6 weeks later (for the severe and moderate) |
| GSE67059 | Human rhinovirus, Picornaviridae, RNA | 37 HRV− and 114 HRV+ |
| GSE8287 | Marburg virus, filoviridae, RNA | 15 macaques followed over time |
| GSE22160 | Hepatitis E, Hepeviridae, RNA Hepatitis C, Flaviviridae, RNA | 3 and 4 chimpanzees respectively followed over time |

TABLE 5

CLASSIFICATION OF VIRUS TYPES

| Common Virus Name | Study Group | Genome | Classification (family) | Baltimore Group |
|---|---|---|---|---|
| Dengue | Core | +ssRNA | Flaviviridae | IV |
| Lassa | Core | +/−ssRNA | Arenaviridae | V |
| Influenza A | Core | −ssRNA | Orthomyxoviridae | V |
| Cytomegalovirus | Core | dsDNA | Herpesviridae | I |
| Influenza A | Validation | −ssRNA | Orthomyxoviridae | V |
| Dengue | Validation | +ssRNA | Flaviviridae | IV |
| Lymphocytic choriomeningitis virus | Validation | +/−ssRNA | Arenaviridae | V |
| Adenovirus | Validation | dsDNA | Adenoviridae | I |
| HHV6 | Validation | dsDNA | Herpesviridae | I |
| Enterovirus | Validation | +ssRNA | Picornaviridae | IV |
| Rhinovirus | Validation | +ssRNA | Picornaviridae | IV |
| Hepatitis C | Validation | +ssRNA | Flaviviridae | IV |
| Metapneumovirus | Validation | −ssRNA | Paramyxoviridae | V |
| Respiratory Syncytial Virus (RSV) | Validation | −ssRNA | Paramyxoviridae | V |
| Measles | Validation | −ssRNA | Paramyxoviridae | V |
| Rotavirus | Validation | dsRNA | Reoviridae | III |
| Human Immunodeficiency Virus (HIV) | Validation | +ssRNA | Retroviridae | VI |
| Circovirus (PRV) | Validation | ssDNA | Circoviridae | II |
| Marburg virus | Validation | −ssRNA | Filoviridae | V |
| Hepatitis E | Validation | +ssRNA | Hepeviridae | IV |
| Hepatitis C | Validation | +ssRNA | Flaviviridae | IV |
| Influenza A | MARS | −ssRNA | Orthomyxoviridae | V |
| Respiratory Syncytial Virus (RSV) | MARS | −ssRNA | Paramyxoviridae | V |
| Metapneumovirus | MARS | −ssRNA | Paramyxoviridae | V |
| Adenovirus | MARS | dsDNA | Adenoviridae | I |
| Rhinovirus | MARS | +ssRNA | Picornaviridae | IV |
| BK virus | MARS | dsDNA | Polyomaviridae | I |
| Coronavirus | MARS | +ssRNA | Coronaviridae | IV |
| Hepatitis B | MARS | dsDNA-RT | Hepadnaviridae | VII |
| Rhinovirus | Pediatric | +ssRNA | Picornaviridae | IV |
| Enterovirus | Pediatric | +ssRNA | Picornaviridae | IV |
| Parainfluenza virus 3 | Pediatric | −ssRNA | Paramyxoviridae | V |
| Coronavirus HKU1 | Pediatric | +ssRNA | Coronaviridae | IV |
| Respiratory Syncytial Virus (RSV) | Pediatric | −ssRNA | Paramyxoviridae | V |

TABLE 6

DATASETS USED TO IDENTIFY BIOMARKERS ASSOCIATED WITH NON-VIRAL INFLAMMATION

| Dataset Identifier | Condition | Study Description |
|---|---|---|
| GSE33341 | Bacteremia; *Staphylococcus aureus* or *Escherichia coli* | Human patients and subjects, single time point. *Staphylococcus aureus*: 34 *Escherichia coli*: 15 Healthy: 43 |
| GSE40366 | Age | 143 nonagenarians and 30 young subjects. Comparison of those subjects without CMV titers. |

TABLE 6-continued

DATASETS USED TO IDENTIFY BIOMARKERS ASSOCIATED WITH NON-VIRAL INFLAMMATION

| Dataset Identifier | Condition | Study Description |
|---|---|---|
| GSE42834 | Tuberculosis<br>Sarcoidosis<br>Lung cancer<br>Pneumonia | Human subjects, single time point.<br>Tuberculosis: 66<br>Sarcoidosis (active, 68; non-active, 22)<br>Lung cancer: 16<br>Pneumonia: 16<br>Control: 147 |
| GSE25504 | Neonatal sepsis | Human subjects, single time point.<br>Sepsis: 28<br>Controls: 35 |
| GSE30119 | *Staphylococcus* infection | Human subjects, single time point.<br>*Staphylococcus*: 99<br>Control: 44 |
| GSE17755 | Autoimmune disease | Human subjects, single time point.<br>Rheumatoid arthritis: 112<br>Systemic Lupus Erythematosus: 22<br>Poly juvenile idiopathic arthritis: 6<br>Systemic juvenile idiopathic arthritis: 51<br>Healthy: 53 |
| GSE19301 | Asthma | Human subjects, single time point.<br>500 samples.<br>113 patients, samples taken during quiet, exacerbation or follow-up time points. |
| GSE47655 | Anaphylaxis | Human subjects, multiple time points.<br>Six patients, three time points (arrival, one hour and three hours). |
| GSE38485 | Schizophrenia | Human subjects, single time point.<br>Schizophrenia: 15<br>Control: 22 |
| GSE36809 | Blunt trauma | Human subjects, multiple time points.<br>Patients: 167, 7 time points (up to 28 days post)<br>Controls: 37 |
| GSE29532 | Coronary artery disease | Human subjects, multiple time points.<br>Patients: 49, six time points including admission and up to 48 hours post-treatment.<br>Controls: 6. |
| GSE46743 | Depression/stress | Human subjects, two time points.<br>Patients: 160 males, pre and post dexamethasone. |
| GSE61672 | Anxiety | Human subjects, single time point.<br>Patients: 157<br>Controls: 179. |
| GSE64813 | Post-traumatic stress disorder | Human subjects, two time points.<br>Patients: 94 males, pre and post deployment, 50% with PTSD. |
| GSE11908 | Systemic inflammation | Human subjects, single time point.<br>Systemic juvenile idiopathic arthritis: 47<br>Systemic lupus erythematosus: 40<br>Type I diabetes: 20<br>Metastatic melanoma: 39<br>*Escherichia coli*: 22<br>*Staphylococcus aureus*: 18<br>Influenza A: 16<br>Liver-transplant recipients undergoing immunosuppressive therapy: 37 |
| GSE16129 | *Staphylococcus* infection | Human subjects, single time point.<br>*Staphylococcus aureus*: 97<br>Controls: 29 |
| GSE40012 | Pneumonia | Human subjects, daily samples for up to 5 days.<br>Influenza A: 8<br>Bacterial pneumonia: 16<br>Mixed bacterial and influenza A pneumonia: 3<br>SIRS: 13<br>Healthy: 36 (Days 1 and 5) |
| GSE40396 | Bacterial infection | Human patients, single sample.<br>*Escherichia coli*: 2<br>MRSA: 4<br>Controls: 19 |
| GSE6269 | Bacterial infection | Human patients, single sample.<br>*Staphylococcus aureus*: 50<br>*Escherichia coli*: 29<br>*Streptococcus pneumoniae*: 22<br>Healthy: 6 |
| GSE35846 | Race, age, gender, obesity | Human patients, single sample.<br>189 subjects.<br>65 men and 124 women.<br>Aged 26 and 79 (mean 51).<br>140 Caucasian, 37 African American, 11 Asian, 1 American Indian. |

TABLE 7

DERIVED BIOMARKERS WITH A MEAN AUC OF AT LEAST 0.8 ACROSS AT LEAST 11 OF THE 14 VIRAL DATASETS

| Derived Biomarker | Mean AUC |
|---|---|
| IFI6:IL16 | 0.916 |
| OASL:NR3C1 | 0.915 |
| OASL:EMR2 | 0.914 |
| OASL:SORL1 | 0.908 |
| OASL:SERTAD2 | 0.907 |
| OASL:LPAR2 | 0.904 |
| OASL:ITGAX | 0.902 |
| OASL:TGFBR2 | 0.901 |
| OASL:KIAA0247 | 0.9 |
| OASL:ARHGAP26 | 0.899 |
| OASL:LYN | 0.899 |
| OASL:PCBP2 | 0.898 |
| OASL:TOPORS | 0.898 |
| EIF2AK2:IL16 | 0.896 |
| OASL:NCOA1 | 0.896 |
| OASL:PTGER4 | 0.896 |
| OASL:TLR2 | 0.895 |
| OASL:PACSIN2 | 0.894 |
| OASL:LILRA2 | 0.893 |
| OASL:PTPRE | 0.893 |
| OASL:RPS6KA1 | 0.893 |
| OASL:CASC3 | 0.892 |
| OASL:VEZF1 | 0.892 |
| OASL:CRLF3 | 0.891 |
| OASL:NDEL1 | 0.891 |
| OASL:RASSF2 | 0.891 |
| OASL:TLE4 | 0.891 |
| OASL:CD97 | 0.89 |
| OASL:CEP68 | 0.89 |
| OASL:RXRA | 0.89 |
| OASL:SP3 | 0.89 |
| OASL:ABLIM1 | 0.889 |
| OASL:AOAH | 0.889 |
| OASL:MBP | 0.889 |
| OASL:NLRP1 | 0.889 |
| OASL:PBX3 | 0.889 |
| OASL:PTPN6 | 0.889 |
| OASL:RYBP | 0.889 |
| OASL:IL13RA1 | 0.888 |
| OASL:LCP2 | 0.888 |
| OASL:LRP10 | 0.888 |
| OASL:SYPL1 | 0.888 |
| OASL:VAMP3 | 0.888 |
| IFI44:LTB | 0.887 |
| OASL:ARHGEF2 | 0.887 |
| OASL:CTDSP2 | 0.887 |
| OASL:LST1 | 0.887 |
| OASL:MAPK1 | 0.887 |
| OASL:N4BP1 | 0.887 |
| OASL:STAT5B | 0.887 |
| IFI44:ABLIM1 | 0.886 |
| IFI44:IL6ST | 0.886 |
| OASL:BACH1 | 0.886 |
| OASL:KLF7 | 0.886 |
| OASL:PRMT2 | 0.886 |
| OASL:HCK | 0.885 |
| OASL:ITPKB | 0.885 |
| OASL:MAP4K4 | 0.885 |
| OASL:PPM1F | 0.885 |
| OASL:RAB14 | 0.885 |
| IFI6:ABLIM1 | 0.884 |
| OAS2:FAIM3 | 0.884 |
| OASL:ARHGAP25 | 0.884 |
| OASL:GNA12 | 0.884 |
| OASL:NUMB | 0.884 |
| OASL:CREBBP | 0.883 |
| OASL:PINK1 | 0.883 |
| OASL:PITPNA | 0.883 |
| OASL:SEMA4D | 0.883 |
| OASL:TGFBI | 0.883 |
| OASL:APLP2 | 0.882 |
| OASL:CCNG2 | 0.882 |
| OASL:MKRN1 | 0.882 |
| OASL:RGS14 | 0.882 |
| OASL:LYST | 0.881 |
| OASL:TNRC6B | 0.881 |
| OASL:TYROBP | 0.881 |
| OASL:WDR37 | 0.881 |
| OASL:WDR47 | 0.881 |
| UBE2L6:IL16 | 0.881 |
| OASL:BTG1 | 0.88 |
| OASL:CD93 | 0.88 |
| OASL:DCP2 | 0.88 |
| OASL:FYB | 0.88 |
| OASL:MAML1 | 0.88 |
| OASL:SNRK | 0.88 |
| OASL:USP4 | 0.88 |
| OASL:YTHDF3 | 0.88 |
| OASL:CEP170 | 0.879 |
| OASL:PLEKHO2 | 0.879 |
| OASL:SMAD4 | 0.879 |
| OASL:ST3GAL1 | 0.879 |
| OASL:ZNF292 | 0.879 |
| IFI44:IL4R | 0.878 |
| OASL:HPCAL1 | 0.878 |
| OASL:IGSF6 | 0.878 |
| OASL:MTMR3 | 0.878 |
| OASL:PHF20 | 0.878 |
| OASL:PPARD | 0.878 |
| OASL:PPP4R1 | 0.878 |
| OASL:RBMS1 | 0.878 |
| OASL:RHOG | 0.878 |
| OASL:TIAM1 | 0.878 |
| USP18:IL16 | 0.878 |
| OASL:CBX7 | 0.877 |
| OASL:RAF1 | 0.877 |
| OASL:SERINC5 | 0.877 |
| OASL:UBQLN2 | 0.877 |
| OASL:XPO6 | 0.877 |
| OASL:ATP6V1B2 | 0.876 |
| OASL:CSF2RB | 0.876 |
| OASL:GYPC | 0.876 |
| OASL:IL4R | 0.876 |
| OASL:MMP25 | 0.876 |
| OASL:PSEN1 | 0.876 |
| OASL:SH2B3 | 0.876 |
| OASL:STAT5A | 0.876 |
| ISG15:IL16 | 0.875 |
| MX1:LEF1 | 0.875 |
| OASL:CAMK2G | 0.875 |
| OASL:ETS2 | 0.875 |
| OASL:POLB | 0.875 |
| OASL:STK38L | 0.875 |
| OASL:TFE3 | 0.875 |
| OASL:ICAM3 | 0.874 |
| OASL:ITGB2 | 0.874 |
| OASL:PISD | 0.874 |
| OASL:PLXNC1 | 0.874 |
| OASL:SNX27 | 0.874 |
| OASL:TNIP1 | 0.874 |
| OASL:ZMIZ1 | 0.874 |
| OASL:FOXO3 | 0.873 |
| OASL:IL10RB | 0.873 |
| OASL:MAP3K5 | 0.873 |
| OASL:POLD4 | 0.873 |
| OASL:ARAP1 | 0.872 |
| OASL:CTBP2 | 0.872 |
| OASL:DGKA | 0.872 |
| OASL:NFYA | 0.872 |
| OASL:PCNX | 0.872 |
| OASL:PFDN5 | 0.872 |
| OASL:R3HDM2 | 0.872 |
| OASL:STX6 | 0.872 |
| EIF2AK2:SYPL1 | 0.871 |
| ISG15:ABLIM1 | 0.871 |
| OASL:FOXJ2 | 0.871 |
| OASL:IQSEC1 | 0.871 |
| OASL:LRMP | 0.871 |
| OASL:NAB1 | 0.871 |
| OASL:RAB31 | 0.871 |

TABLE 7-continued

DERIVED BIOMARKERS WITH A MEAN AUC OF AT LEAST 0.8 ACROSS AT LEAST 11 OF THE 14 VIRAL DATASETS

| Derived Biomarker | Mean AUC |
|---|---|
| OASL:WASF2 | 0.871 |
| OASL:ZNF274 | 0.871 |
| OAS2:LEF1 | 0.87 |
| OASL:BRD1 | 0.87 |
| OASL:GNAQ | 0.87 |
| OASL:GSK3B | 0.87 |
| OASL:IL6R | 0.87 |
| OASL:MAPK14 | 0.87 |
| USP18:TGFBR2 | 0.87 |
| ISG15:LTB | 0.869 |
| OASL:INPP5D | 0.869 |
| OASL:MED13 | 0.869 |
| OASL:MORC3 | 0.869 |
| OASL:PTAFR | 0.869 |
| OASL:RBM23 | 0.869 |
| OASL:SNN | 0.869 |
| OASL:ST13 | 0.869 |
| OASL:TFEB | 0.869 |
| OASL:ZFYVE16 | 0.869 |
| EIF2AK2:SATB1 | 0.868 |
| OASL:ABAT | 0.868 |
| OASL:ABI1 | 0.868 |
| OASL:ACVR1B | 0.868 |
| OASL:GPSM3 | 0.868 |
| OASL:MPPE1 | 0.868 |
| OASL:PTEN | 0.868 |
| OASL:SEC62 | 0.868 |
| IFI6:MYC | 0.867 |
| IFI6:PCF11 | 0.867 |
| OASL:AIF1 | 0.867 |
| OASL:CSNK1D | 0.867 |
| OASL:GABARAP | 0.867 |
| OASL:HAL | 0.867 |
| OASL:LAPTM5 | 0.867 |
| OASL:XPC | 0.867 |
| USP18:NFKB1 | 0.867 |
| OASL:ACAP2 | 0.866 |
| OASL:CLEC4A | 0.866 |
| OASL:HIP1 | 0.866 |
| OASL:PIAS1 | 0.866 |
| OASL:PPP3R1 | 0.866 |
| OASL:RALB | 0.866 |
| OASL:RGS19 | 0.866 |
| OASL:TRIOBP | 0.866 |
| EIF2AK2:PDE3B | 0.865 |
| OASL:NCOA4 | 0.865 |
| OASL:RARA | 0.865 |
| OASL:RPS6KA3 | 0.865 |
| OASL:SIRPA | 0.865 |
| OASL:TLE3 | 0.865 |
| OASL:TNFRSF1A | 0.865 |
| DDX60:TGFBR2 | 0.864 |
| OASL:FLOT2 | 0.864 |
| OASL:FNBP1 | 0.864 |
| OASL:MAP3K3 | 0.864 |
| OASL:STX10 | 0.864 |
| OASL:ZDHHC18 | 0.864 |
| OASL:ZNF143 | 0.864 |
| TAP1:TGFBR2 | 0.864 |
| OAS2:ABLIM1 | 0.863 |
| OASL:ARRB2 | 0.863 |
| OASL:IKBKB | 0.863 |
| OASL:KBTBD2 | 0.863 |
| OASL:PHC2 | 0.863 |
| OASL:PUM2 | 0.863 |
| OASL:SSFA2 | 0.863 |
| IFI44:MYC | 0.862 |
| OASL:ABHD2 | 0.862 |
| OASL:CYLD | 0.862 |
| OASL:MAST3 | 0.862 |
| OASL:UBN1 | 0.862 |
| IFI6:IL6ST | 0.861 |
| IFIH1:TGFBR2 | 0.861 |
| OASL:CNPY3 | 0.861 |
| OASL:KIAA0232 | 0.861 |
| USP18:CHMP7 | 0.861 |
| USP18:NECAP2 | 0.861 |
| OASL:CAP1 | 0.86 |
| OASL:HPS1 | 0.86 |
| OASL:IL1RAP | 0.86 |
| OASL:MEF2A | 0.86 |
| OASL:RNF19B | 0.86 |
| OASL:TMEM127 | 0.86 |
| USP18:IL27RA | 0.86 |
| OASL:CDIPT | 0.859 |
| OASL:CREB1 | 0.859 |
| OASL:GPS2 | 0.859 |
| OASL:NDE1 | 0.859 |
| OASL:RAB11FIP1 | 0.859 |
| USP18:ABLIM1 | 0.859 |
| EIF2AK2:TNRC6B | 0.858 |
| OASL:FAM134A | 0.858 |
| OASL:FCGRT | 0.858 |
| OASL:LPIN2 | 0.858 |
| OASL:PECAM1 | 0.858 |
| OASL:WBP2 | 0.858 |
| OASL:ZNF148 | 0.858 |
| OASL:RTN3 | 0.857 |
| OASL:TYK2 | 0.857 |
| USP18:LTB | 0.857 |
| DHX58:IL16 | 0.856 |
| ISG15:IL4R | 0.856 |
| OASL:BRD4 | 0.856 |
| OASL:CCNT2 | 0.856 |
| OASL:FGR | 0.856 |
| OASL:ITSN2 | 0.856 |
| OASL:LYL1 | 0.856 |
| OASL:PHF3 | 0.856 |
| OASL:PSAP | 0.856 |
| OASL:STX3 | 0.856 |
| OASL:TNK2 | 0.856 |
| EIF2AK2:ZNF274 | 0.855 |
| OASL:ACAA1 | 0.855 |
| OASL:CHD3 | 0.855 |
| OASL:FRY | 0.855 |
| OASL:GRB2 | 0.855 |
| OASL:MAP3K11 | 0.855 |
| OASL:NEK7 | 0.855 |
| OASL:PPP2R5A | 0.855 |
| USP18:ST13 | 0.855 |
| XAF1:LEF1 | 0.855 |
| OASL:CASP8 | 0.854 |
| OASL:PCF11 | 0.854 |
| OASL:PRKCD | 0.854 |
| OASL:PSTPIP1 | 0.854 |
| OASL:SLCO3A1 | 0.854 |
| OASL:ZDHHC17 | 0.854 |
| USP18:FOXO1 | 0.854 |
| OASL:ASAP1 | 0.853 |
| OASL:BAZ2B | 0.853 |
| OASL:FAM65B | 0.853 |
| OASL:HHEX | 0.853 |
| OASL:MAX | 0.853 |
| OASL:PHF2 | 0.853 |
| OASL:RNF130 | 0.853 |
| OASL:SOS2 | 0.853 |
| OASL:STAM2 | 0.853 |
| OASL:ZFC3H1 | 0.853 |
| IFI44:CYLD | 0.852 |
| IFIH1:CRLF3 | 0.852 |
| OASL:BANP | 0.852 |
| OASL:CCND3 | 0.852 |
| OASL:DGCR2 | 0.852 |
| OASL:USP15 | 0.852 |
| USP18:EIF3H | 0.852 |
| OASL:LAT2 | 0.851 |
| OASL:ZYX | 0.851 |
| USP18:CAMK1D | 0.851 |
| ZBP1:NDE1 | 0.851 |
| EIF2AK2:IL4R | 0.85 |

TABLE 7-continued

DERIVED BIOMARKERS WITH A MEAN AUC OF AT LEAST 0.8 ACROSS AT LEAST 11 OF THE 14 VIRAL DATASETS

| Derived Biomarker | Mean AUC |
| --- | --- |
| IFI44:SESN1 | 0.85 |
| OASL:CD37 | 0.85 |
| OASL:CST3 | 0.85 |
| OASL:DPEP2 | 0.85 |
| OASL:MYC | 0.85 |
| OASL:RERE | 0.85 |
| OASL:USP10 | 0.85 |
| USP18:LEF1 | 0.85 |
| OASL:MXI1 | 0.849 |
| OASL:PRUNE | 0.849 |
| OASL:VPS8 | 0.849 |
| OASL:CYTH4 | 0.848 |
| OASL:FBXO11 | 0.848 |
| OASL:PRKAA1 | 0.848 |
| OASL:SERINC3 | 0.848 |
| OASL:UBXN2B | 0.848 |
| USP18:DPF2 | 0.848 |
| USP18:NACA | 0.848 |
| USP18:SYPL1 | 0.848 |
| ISG15:DGKA | 0.847 |
| OASL:MARK3 | 0.847 |
| USP18:DIDO1 | 0.846 |
| CUL1:IL16 | 0.845 |
| OASL:DOCK9 | 0.845 |
| USP18:PIK3IP1 | 0.845 |
| OASL:FBXO9 | 0.844 |
| OASL:MKLN1 | 0.844 |
| OASL:PPP1R11 | 0.844 |
| USP18:DGKA | 0.844 |
| USP18:ZNF274 | 0.844 |
| OASL:POLR1D | 0.843 |
| OASL:SETD2 | 0.843 |
| DDX60:ABLIM1 | 0.842 |
| OASL:ARHGAP15 | 0.842 |
| OASL:BCL2 | 0.842 |
| OASL:GOLGA7 | 0.842 |
| OASL:KIAA0513 | 0.842 |
| OASL:MARCH7 | 0.842 |
| USP18:LDLRAP1 | 0.842 |
| C19orf66:IL16 | 0.841 |
| OASL:ARRB1 | 0.841 |
| OASL:BMP2K | 0.841 |
| OASL:LIMK2 | 0.841 |
| OASL:RNASET2 | 0.841 |
| USP18:ATM | 0.841 |
| USP18:CYLD | 0.841 |
| USP18:NOSIP | 0.841 |
| OASL:TNFSF13 | 0.84 |
| OASL:TRIM8 | 0.84 |
| XAF1:IL4R | 0.84 |
| DHX58:ABLIM1 | 0.839 |
| OASL:MANSC1 | 0.839 |
| OASL:MAP1LC3B | 0.839 |
| OASL:OSBPL2 | 0.839 |
| OASL:RAB7A | 0.839 |
| EIF2AK2:ZFC3H1 | 0.838 |
| IFIH1:LTB | 0.838 |
| OASL:FES | 0.838 |
| OASL:HGSNAT | 0.838 |
| OASL:KLF6 | 0.838 |
| OASL:TM2D3 | 0.838 |
| OASL:KLHL2 | 0.837 |
| OASL:MAPRE2 | 0.837 |
| OASL:RNF146 | 0.837 |
| USP18:RPL22 | 0.837 |
| DHX58:LTB | 0.836 |
| OASL:GMIP | 0.836 |
| DDX60:SYPL1 | 0.835 |
| EIF2AK2:IL6ST | 0.835 |
| EIF2AK2:PCF11 | 0.835 |
| ISG15:NOSIP | 0.835 |
| OASL:NRBF2 | 0.835 |
| OASL:RNF141 | 0.835 |
| OASL:VAV3 | 0.835 |
| OASL:ZFAND5 | 0.835 |
| USP18:NDFIP1 | 0.835 |
| USP18:TMEM204 | 0.835 |
| USP18:UBE2D2 | 0.835 |
| OASL:CAMK1D | 0.834 |
| OASL:CLK4 | 0.834 |
| OASL:MCTP2 | 0.834 |
| OASL:MOSPD2 | 0.834 |
| OASL:TSC22D3 | 0.834 |
| USP18:CRLF3 | 0.834 |
| USP18:SESN1 | 0.834 |
| USP18:ZC3HAV1 | 0.834 |
| OASL:MSL1 | 0.833 |
| OASL:TREM1 | 0.833 |
| OASL:YPEL5 | 0.833 |
| USP18:CIAPIN1 | 0.833 |
| USP18:PDCD6IP | 0.833 |
| HERC5:ABLIM1 | 0.832 |
| OASL:OSBPL11 | 0.832 |
| OASL:PLEKHO1 | 0.832 |
| USP18:CRTC3 | 0.832 |
| HERC6:ATM | 0.831 |
| ISG15:SESN1 | 0.831 |
| OAS2:MYC | 0.831 |
| OASL:OGFRL1 | 0.831 |
| OASL:ZXDC | 0.831 |
| USP18:CCR7 | 0.831 |
| OASL:APBB1IP | 0.83 |
| OASL:CHST11 | 0.83 |
| OASL:GPBP1L1 | 0.83 |
| USP18:SSBP2 | 0.83 |
| OASL:RC3H2 | 0.829 |
| USP18:UTP14A | 0.829 |
| OASL:GCC2 | 0.828 |
| USP18:LRMP | 0.828 |
| USP18:TRIB2 | 0.828 |
| OASL:GPR97 | 0.827 |
| EIF2AK2:BTG1 | 0.826 |
| EIF2AK2:CYLD | 0.826 |
| OASL:PAFAH1B1 | 0.826 |
| USP18:BTG1 | 0.826 |
| USP18:NCBP2 | 0.826 |
| USP18:PPP1R2 | 0.826 |
| LAP3:MAP4K4 | 0.825 |
| OASL:ERBB2IP | 0.825 |
| OASL:NOD2 | 0.825 |
| OASL:RIN3 | 0.825 |
| OASL:TMBIM1 | 0.825 |
| ZBP1:XPO6 | 0.825 |
| ISG15:LDLRAP1 | 0.824 |
| OASL:CHMP1B | 0.824 |
| OASL:LILRB3 | 0.824 |
| OASL:PHF20L1 | 0.823 |
| USP18:PCF11 | 0.823 |
| OASL:ANKRD49 | 0.822 |
| OASL:DOK3 | 0.822 |
| OASL:PRKAG2 | 0.822 |
| OASL:SOAT1 | 0.822 |
| USP18:IL6ST | 0.822 |
| USP18:RPL10A | 0.822 |
| LAP3:SYPL1 | 0.82 |
| OASL:MARCH8 | 0.819 |
| TAP1:TNRC6B | 0.819 |
| OASL:KLF3 | 0.818 |
| PHF11:ZNF274 | 0.818 |
| OASL:PGS1 | 0.817 |
| OASL:ZNF238 | 0.817 |
| STAT1:PCBP2 | 0.817 |
| OASL:SH2D3C | 0.816 |
| USP18:SAFB2 | 0.816 |
| EIF2AK2:CAMK1D | 0.815 |
| LAP3:CNPY3 | 0.815 |
| LAP3:NDFIP1 | 0.815 |
| LAP3:TRAK1 | 0.815 |
| OASL:NPL | 0.815 |
| OASL:NSUN3 | 0.815 |

TABLE 7-continued

DERIVED BIOMARKERS WITH A MEAN AUC OF AT LEAST 0.8 ACROSS AT LEAST 11 OF THE 14 VIRAL DATASETS

| Derived Biomarker | Mean AUC |
|---|---|
| OASL:ATAD2B | 0.814 |
| ZBP1:KLF7 | 0.813 |
| ZBP1:PCF11 | 0.813 |
| LAP3:ABLIM1 | 0.812 |
| OASL:CSAD | 0.812 |
| PHF11:IL16 | 0.812 |
| USP18:BEX4 | 0.812 |
| USP18:METTL3 | 0.812 |
| RTP4:ABLIM1 | 0.811 |
| HERC6:MYC | 0.81 |
| USP18:ALDH3A2 | 0.81 |
| OASL:RAB4B | 0.809 |
| USP18:ATF7IP2 | 0.809 |
| TAP1:TGOLN2 | 0.807 |
| PARP12:ABLIM1 | 0.806 |
| RSAD2:CAMK1D | 0.806 |
| ZBP1:CYLD | 0.806 |
| STAT1:FBXO11 | 0.805 |
| ZBP1:ZFC3H1 | 0.805 |
| OASL:SIRPB1 | 0.804 |
| OASL:C2orf68 | 0.802 |
| RTP4:SYPL1 | 0.802 |
| LAP3:JAK1 | 0.801 |

TABLE 8

PERFORMANCE OF EIGHT EXAMPLE DERIVED BIOMARKERS WITH UNIQUE NUMERATORS AND DENOMINATORS (OF A TOTAL OF 473 DERIVED BIOMARKERS) ACROSS THE VARIOUS INDIVIDUAL DATASETS ("DISCOVERY", "VALIDATION", "NON-VIRAL")

| Category | Data Type/Dataset | IFI6:IL16 | OASL:EMR2 | EIF2AK2:IL16 | IFI44:ABLIM1 | OAS2:FAIM3 | ISG15:IL16 | MX1:LEF1 | USP18:NFKB1 |
|---|---|---|---|---|---|---|---|---|---|
| Statistic | Mean AUC over all viral datasets | 0.916 | 0.914 | 0.896 | 0.886 | 0.884 | 0.875 | 0.875 | 0.867 |
| Statistic | Number viral datasets with mean AUC less than 0.75 | 0 | 0 | 1 | 0 | 1 | 1 | 0 | 0 |
| Statistic | Number of non-viral datasets with a mean AUC greater than 0.8 | 3 | 0 | 3 | 2 | 3 | 2 | 3 | 1 |
| Core Viral | GSE51808 | 1 | 1 | 0.992 | 0.996 | 0.948 | 1 | 0.976 | 1 |
| Core Viral | GSE41752 | 0.971 | 0.928 | 0.933 | 0.986 | 0.995 | 0.986 | 0.967 | 0.947 |
| Core Viral | GSE52428 | 0.947 | 0.97 | 0.978 | 0.932 | 0.943 | 0.966 | 0.913 | 0.951 |
| Core Viral | GSE40366 | 0.829 | 0.807 | 0.823 | 0.842 | 0.827 | 0.782 | 0.851 | 0.87 |
| Validation | GSE6269 | 0.845 | 0.916 | 0.913 | 0.927 | 0.847 | 0.909 | 0.906 | 0.965 |
| Validation | GSE40396 | 0.787 | 0.818 | 0.737 | 0.771 | 0.838 | 0.792 | 0.781 | 0.769 |
| Validation | GSE40012 | 0.988 | 0.974 | 0.961 | 0.952 | 0.937 | 0.981 | 0.897 | 0.807 |
| Validation | GSE18090 | 0.799 | 0.799 | 0.812 | 0.764 | 0.819 | 0.785 | 0.778 | 0.792 |
| Validation | GSE30550 | 0.946 | 0.94 | 0.951 | 0.95 | 0.959 | 0.95 | 0.944 | 0.953 |
| Validation | GSE40224 | 0.875 | 0.938 | 0.888 | 0.9 | 0.875 | 0.888 | 0.875 | 0.862 |
| Validation | GSE5790 | 1 | 1 | 0.955 | 0.755 | 1 | 0.6 | 0.973 | 0.982 |
| Validation | GSE34205 | 0.843 | 0.871 | 0.793 | 0.824 | 0.81 | 0.792 | 0.816 | 0.812 |
| Validation | GSE5808 | 1 | 0.933 | 0.933 | 0.933 | 0.867 | 0.867 | 0.8 | 0.933 |
| Validation | GSE2729 | 1 | 0.908 | 0.869 | 0.877 | 0.715 | 0.954 | 0.777 | N/A |
| Non-viral | GSE33341 | 0.864 | 0.647 | 0.91 | 0.924 | 0.911 | 0.824 | 0.898 | 0.296 |
| Non-viral | GSE40366 | 0.924 | 0.667 | 0.901 | 0.922 | 0.93 | 0.863 | 0.937 | 0.86 |
| Non-viral | GSE42834 | 0.787 | 0.631 | 0.799 | 0.795 | 0.866 | 0.799 | 0.826 | 0.503 |
| Non-viral | GSE25504 | 0.628 | 0.414 | 0.788 | 0.778 | 0.709 | 0.725 | 0.718 | N/A |
| Non-viral | GSE30119 | 0.432 | 0.28 | 0.727 | 0.632 | 0.723 | 0.448 | 0.636 | 0.456 |
| Non-viral | GSE17755 | 0.885 | N/A | 0.636 | N/A | N/A | N/A | N/A | N/A |
| Non-viral | GSE19301 | 0.614 | 0.536 | 0.598 | 0.636 | 0.592 | 0.637 | 0.612 | 0.6 |
| Non-viral | GSE47655 | N/A | 0.667 | N/A | 0.6 | 0.633 | N/A | 0.733 | N/A |
| Non-viral | GSE38485 | 0.517 | 0.447 | 0.532 | 0.577 | 0.494 | 0.488 | 0.436 | N/A |
| Non-viral | GSE36809 | 0.464 | 0.302 | 0.867 | 0.445 | 0.234 | 0.401 | 0.522 | 0.243 |
| Non-viral | GSE29532 | N/A | N/A | N/A | 0.54 | 0.46 | N/A | 0.6 | N/A |
| Non-viral | GSE46743 | 0.545 | 0.478 | 0.743 | 0.763 | 0.469 | 0.452 | 0.647 | N/A |
| Non-viral | GSE61672 | 0.528 | 0.534 | 0.515 | 0.511 | 0.438 | 0.562 | 0.463 | N/A |
| Non-viral | GSE64813 | N/A | 0.535 | N/A | 0.631 | 0.659 | N/A | 0.641 | 0.477 |
| Non-viral | GSE11908 | 0.589 | 0.536 | 0.421 | 0.242 | 0.398 | 0.383 | 0.287 | 0.356 |
| Non-viral | GSE16129 | 0.712 | 0.355 | 0.595 | 0.481 | 0.645 | 0.586 | 0.476 | 0.236 |
| Non-viral | GSE40012 | 0.479 | 0.41 | 0.513 | 0.649 | 0.585 | 0.604 | 0.552 | N/A |
| Non-viral | GSE40396 | 0.303 | 0.226 | 0.544 | 0.616 | 0.421 | 0.316 | 0.511 | 0.16 |
| Non-viral | GSE40586 | N/A | 0.189 | N/A | 0.618 | 0.697 | N/A | 0.717 | 0.172 |
| Non-viral | GSE6269 | 0.33 | 0.184 | 0.255 | 0.224 | 0.319 | 0.216 | 0.199 | 0.099 |
| Non-viral | GSE35846 (race) | 0.575 | 0.488 | 0.632 | 0.534 | 0.45 | 0.589 | 0.559 | N/A |
| Non-viral | GSE35846 (age) | 0.537 | 0.445 | 0.514 | 0.543 | 0.591 | 0.523 | 0.563 | N/A |
| Non-viral | GSE35846 (gender) | 0.554 | 0.56 | 0.56 | 0.529 | 0.46 | 0.561 | 0.527 | N/A |
| Non-viral | GSE35846 (obesity) | 0.523 | 0.523 | 0.539 | 0.482 | 0.451 | 0.513 | 0.489 | N/A |

TABLE 9

PERFORMANCE (AUC) OF THE TOP EIGHT DERIVED BIOMARKERS INDIVIDUALLY AND WHEN ADDED SEQUENTIALLY TO THE TOP PERFORMING DERIVED BIOMARKERS FOR THE COMBINED DATASETS

| N | Derived Biomarker | Individual AUC | Combined AUC |
|---|---|---|---|
| 1 | ISG15:IL16 | 0.92 | 0.92 |
| 2 | OASL:CD97 | 0.865 | 0.936 |
| 3 | TAP1:TGFBR2 | 0.879 | 0.945 |
| 4 | IFIH1:CRLF3 | 0.873 | 0.946 |
| 5 | IFI44:IL4R | 0.867 | 0.947 |
| 6 | EIF2AK2:SYPL1 | 0.859 | 0.947 |
| 7 | OAS2:LEF1 | 0.875 | 0.946 |
| 8 | STAT1:PCBP2 | 0.844 | 0.944 |

TABLE 10

LIST OF 413 INDIVIDUAL BIOMARKERS (THAT ARE PART OF A DERIVED BIOMARKER WITH AN AUC >0.8) AND THEIR RESPECTIVE CORRELATION COEFFICIENT TO THE COMPONENT BIOMARKERS OF THE TOP PERFORMING TWO DERIVED-BIOMARKER SIGNATURE OF ISG15, IL16, OASL AND CD97. EACH LIST OF BIOMARKERS CONSTITUTES GROUPS B, C, D, AND E

| Group B | | | Group C | | | Group D | | | Group E | | |
|---|---|---|---|---|---|---|---|---|---|---|---|
| Correlation to ISG15 | HUGO Gene Name | SEQ ID | Correlation to IL16 | HUGO Gene Name | SEQ ID | Correlation to OASL | HUGO Gene Name | SEQ ID | Correlation to CD97 | HUGO Gene Name | SEQ ID |
| 1.000 | ISG15 | 142 | 1.000 | IL16 | 134 | 1.000 | OASL | 227 | 1.000 | CD97 | 49 |
| 0.915 | IFI44 | 127 | 0.661 | ITPKB | 145 | 0.529 | N4BP1 | 205 | 0.634 | CYTH4 | 73 |
| 0.915 | RSAD2 | 308 | 0.600 | CAMK2G | 38 | 0.460 | NOD2 | 219 | 0.599 | HCK | 118 |
| 0.913 | HERC5 | 119 | 0.567 | CTDSP2 | 70 | 0.455 | RNF19B | 303 | 0.582 | ARHGAP26 | 17 |
| 0.906 | MX1 | 202 | 0.555 | DPEP2 | 82 | 0.437 | PRKAG2 | 268 | 0.555 | RARA | 289 |
| 0.895 | HERC6 | 120 | 0.551 | LTB | 170 | 0.413 | IGSF6 | 130 | 0.547 | XPO6 | 396 |
| 0.894 | OAS2 | 226 | 0.549 | CBX7 | 42 | 0.352 | MEF2A | 192 | 0.534 | TNFRSF1A | 362 |
| 0.894 | XAF1 | 394 | 0.535 | FNBP1 | 98 | 0.343 | LPIN2 | 166 | 0.527 | SLCO3A1 | 326 |
| 0.892 | IFI6 | 128 | 0.534 | FOXO1 | 100 | 0.341 | PPP1R11 | 262 | 0.526 | ICAM3 | 126 |
| 0.873 | PARP12 | 233 | 0.531 | MAST3 | 187 | 0.316 | USP15 | 382 | 0.521 | PTPN6 | 278 |
| 0.872 | EIF2AK2 | 84 | 0.529 | LDLRAP1 | 160 | 0.308 | BACH1 | 26 | 0.519 | PRKCD | 269 |
| 0.849 | DHX58 | 78 | 0.529 | TMEM204 | 361 | 0.307 | SSFA2 | 336 | 0.518 | RAB11FIP1 | 282 |
| 0.844 | UBE2L6 | 377 | 0.526 | FAIM3 | 89 | 0.299 | MKLN1 | 194 | 0.514 | CSF2RB | 66 |
| 0.838 | DDX60 | 75 | 0.516 | RGS14 | 295 | 0.270 | FYB | 103 | 0.512 | LCP2 | 159 |
| 0.819 | USP18 | 383 | 0.516 | IKBKB | 131 | 0.250 | NSUN3 | 224 | 0.509 | TYROBP | 375 |
| 0.817 | RTP4 | 310 | 0.516 | ZXDC | 412 | 0.232 | MAX | 188 | 0.499 | PHC2 | 243 |
| 0.815 | PHF11 | 244 | 0.508 | PHF20 | 246 | 0.218 | STAM2 | 339 | 0.496 | RHOG | 297 |
| 0.812 | IFIH1 | 129 | 0.507 | DGKA | 77 | 0.209 | HHEX | 122 | 0.496 | PSAP | 272 |
| 0.792 | ZBP1 | 399 | 0.501 | XPC | 395 | 0.207 | CLEC4A | 58 | 0.496 | LYN | 172 |
| 0.766 | STAT1 | 340 | 0.499 | PPARD | 260 | 0.197 | ZFAND5 | 404 | 0.494 | TMEM127 | 360 |
| 0.765 | LAP3 | 156 | 0.499 | C2orf68 | 36 | 0.188 | ABI1 | 3 | 0.492 | LILRA2 | 162 |
| 0.755 | TAP1 | 348 | 0.494 | NLRP1 | 218 | 0.144 | MORC3 | 197 | 0.485 | AOAH | 11 |
| 0.741 | C19orf66 | 35 | 0.488 | IL27RA | 136 | 0.142 | RC3H2 | 293 | 0.476 | FGR | 96 |
| 0.617 | CUL1 | 71 | 0.480 | ABLIM1 | 4 | 0.137 | MAP1LC3B | 176 | 0.470 | PLEKHO2 | 255 |
| 0.453 | POLB | 257 | 0.477 | JAK1 | 147 | 0.120 | TM2D3 | 358 | 0.470 | ARAP1 | 14 |
| 0.395 | ZC3HAV1 | 401 | 0.475 | METTL3 | 193 | 0.100 | CHST11 | 56 | 0.468 | RBM23 | 291 |
| | | | 0.474 | SAFB2 | 313 | 0.097 | NAB1 | 206 | 0.462 | PTPRE | 279 |
| | | | 0.474 | PPM1F | 261 | 0.014 | KLF3 | 152 | 0.459 | KLF6 | 153 |
| | | | 0.473 | TYK2 | 374 | −0.030 | YPEL5 | 397 | 0.458 | LIMK2 | 164 |
| | | | 0.471 | BANP | 27 | −0.063 | MXI1 | 203 | 0.456 | LILRB3 | 163 |
| | | | 0.470 | CRTC3 | 64 | | | | 0.454 | TLR2 | 357 |
| | | | 0.468 | ATM | 24 | | | | 0.451 | GPR97 | 111 |
| | | | 0.453 | PAFAH1B1 | 232 | | | | 0.451 | GMIP | 106 |
| | | | 0.447 | PIK3IP1 | 250 | | | | 0.446 | SIRPA | 324 |
| | | | 0.445 | WDR37 | 392 | | | | 0.444 | LRP10 | 168 |
| | | | 0.444 | TGFBR2 | 352 | | | | 0.444 | LPAR2 | 165 |
| | | | 0.442 | ZNF274 | 410 | | | | 0.442 | TREM1 | 369 |
| | | | 0.429 | STAT5B | 342 | | | | 0.441 | IL13RA1 | 133 |
| | | | 0.427 | MAML1 | 174 | | | | 0.439 | ITGAX | 143 |
| | | | 0.420 | SATB1 | 314 | | | | 0.435 | ARHGAP25 | 16 |
| | | | 0.419 | DOCK9 | 80 | | | | 0.433 | SIRPB1 | 325 |
| | | | 0.417 | CHMP7 | 55 | | | | 0.433 | ZDHHC18 | 403 |
| | | | 0.413 | BRD1 | 32 | | | | 0.433 | TLE3 | 355 |
| | | | 0.410 | BTG1 | 34 | | | | 0.432 | ITGB2 | 144 |
| | | | 0.408 | ATF7IP2 | 23 | | | | 0.432 | SNX27 | 330 |
| | | | 0.408 | DIDO1 | 79 | | | | 0.431 | PGS1 | 242 |
| | | | 0.407 | LEF1 | 161 | | | | 0.429 | ATP6V1B2 | 25 |
| | | | 0.407 | TNRC6B | 366 | | | | 0.428 | RAB31 | 284 |
| | | | 0.405 | SERTAD2 | 319 | | | | 0.427 | MAP3K11 | 177 |
| | | | 0.405 | CEP68 | 52 | | | | 0.427 | PACSIN2 | 231 |
| | | | 0.398 | BCL2 | 29 | | | | 0.427 | KIAA0513 | 151 |

TABLE 10-continued

LIST OF 413 INDIVIDUAL BIOMARKERS (THAT ARE PART OF A DERIVED BIOMARKER WITH
AN AUC >0.8) AND THEIR RESPECTIVE CORRELATION COEFFICIENT TO THE COMPONENT
BIOMARKERS OF THE TOP PERFORMING TWO DERIVED-BIOMARKER SIGNATURE OF ISG15, IL16,
OASL AND CD97. EACH LIST OF BIOMARKERS CONSTITUTES GROUPS B, C, D, AND E

| Group B | | | Group C | | | Group D | | | Group E | | |
|---|---|---|---|---|---|---|---|---|---|---|---|
| Correlation to ISG15 | HUGO Gene Name | SEQ ID | Correlation to IL16 | HUGO Gene Name | SEQ ID | Correlation to OASL | HUGO Gene Name | SEQ ID | Correlation to CD97 | HUGO Gene Name | SEQ ID |
| | | | 0.397 | VPS8 | 389 | | | | 0.426 | EMR2 | 86 |
| | | | 0.396 | CHD3 | 53 | | | | 0.426 | RERE | 294 |
| | | | 0.393 | PUM2 | 280 | | | | 0.426 | NUMB | 225 |
| | | | 0.390 | TGOLN2 | 353 | | | | 0.425 | RALB | 288 |
| | | | 0.383 | NDE1 | 211 | | | | 0.425 | ETS2 | 88 |
| | | | 0.382 | CCR7 | 46 | | | | 0.422 | STAT5A | 341 |
| | | | 0.381 | PSTPIP1 | 274 | | | | 0.421 | LST1 | 169 |
| | | | 0.379 | TIAM1 | 354 | | | | 0.417 | RIN3 | 298 |
| | | | 0.376 | PECAM1 | 240 | | | | 0.417 | TNK2 | 365 |
| | | | 0.374 | PDE3B | 239 | | | | 0.416 | IQSEC1 | 141 |
| | | | 0.374 | MYC | 204 | | | | 0.413 | PISD | 252 |
| | | | 0.371 | FOXJ2 | 99 | | | | 0.412 | SORL1 | 332 |
| | | | 0.370 | PRMT2 | 270 | | | | 0.412 | FES | 95 |
| | | | 0.370 | CSNK1D | 67 | | | | 0.411 | KIAA0247 | 150 |
| | | | 0.357 | RPL10A | 304 | | | | 0.404 | IL6R | 138 |
| | | | 0.356 | SERINC5 | 318 | | | | 0.404 | LAPTM5 | 157 |
| | | | 0.354 | ARHGEF2 | 18 | | | | 0.402 | VAMP3 | 386 |
| | | | 0.352 | HGSNAT | 121 | | | | 0.400 | FAM65B | 91 |
| | | | 0.350 | TRAK1 | 368 | | | | 0.398 | MAP3K5 | 179 |
| | | | 0.350 | PHF2 | 245 | | | | 0.396 | TRIM8 | 371 |
| | | | 0.349 | PBX3 | 234 | | | | 0.396 | ZYX | 413 |
| | | | 0.349 | SESN1 | 320 | | | | 0.388 | MAPK14 | 182 |
| | | | 0.341 | DPF2 | 83 | | | | 0.387 | PLEKHO1 | 254 |
| | | | 0.338 | IL4R | 137 | | | | 0.387 | NCOA1 | 209 |
| | | | 0.334 | NOSIP | 220 | | | | 0.384 | RNASET2 | 299 |
| | | | 0.331 | MPPE1 | 199 | | | | 0.383 | APBB1IP | 12 |
| | | | 0.321 | NR3C1 | 222 | | | | 0.381 | RXRA | 311 |
| | | | 0.320 | ABAT | 1 | | | | 0.375 | PTAFR | 275 |
| | | | 0.320 | GCC2 | 105 | | | | 0.373 | CNPY3 | 60 |
| | | | 0.316 | ZFC3H1 | 405 | | | | 0.373 | TNFSF13 | 363 |
| | | | 0.311 | SETD2 | 321 | | | | 0.368 | RPS6KA1 | 306 |
| | | | 0.308 | ITSN2 | 146 | | | | 0.367 | OSBPL2 | 230 |
| | | | 0.306 | R3HDM2 | 281 | | | | 0.367 | MTMR3 | 201 |
| | | | 0.302 | ARHGAP15 | 15 | | | | 0.362 | TMBIM1 | 359 |
| | | | 0.301 | PCF11 | 236 | | | | 0.359 | TFEB | 350 |
| | | | 0.301 | MAPRE2 | 183 | | | | 0.359 | TFE3 | 349 |
| | | | 0.299 | ST3GAL1 | 338 | | | | 0.358 | RAF1 | 287 |
| | | | 0.299 | NACA | 207 | | | | 0.357 | STX3 | 345 |
| | | | 0.299 | WDR47 | 393 | | | | 0.357 | LAT2 | 158 |
| | | | 0.298 | SSBP2 | 335 | | | | 0.356 | GRB2 | 114 |
| | | | 0.293 | CLK4 | 59 | | | | 0.355 | NDEL1 | 212 |
| | | | 0.289 | EIF3H | 85 | | | | 0.355 | SEMA4D | 316 |
| | | | 0.287 | FRY | 102 | | | | 0.353 | FCGRT | 94 |
| | | | 0.286 | ZNF238 | 409 | | | | 0.353 | DOK3 | 81 |
| | | | 0.286 | PTGER4 | 277 | | | | 0.353 | HIP1 | 123 |
| | | | 0.285 | PCNX | 237 | | | | 0.353 | UBN1 | 378 |
| | | | 0.283 | NECAP2 | 214 | | | | 0.352 | PLXNC1 | 256 |
| | | | 0.279 | CASC3 | 40 | | | | 0.351 | NRBF2 | 223 |
| | | | 0.279 | MSL1 | 200 | | | | 0.348 | INPP5D | 140 |
| | | | 0.278 | VEZF1 | 388 | | | | 0.347 | SH2D3C | 323 |
| | | | 0.275 | KIAA0232 | 149 | | | | 0.347 | MMP25 | 196 |
| | | | 0.274 | RASSF2 | 290 | | | | 0.342 | IL10RB | 132 |
| | | | 0.268 | RPL22 | 305 | | | | 0.340 | FLOT2 | 97 |
| | | | 0.265 | ACAA1 | 5 | | | | 0.339 | PIAS1 | 249 |
| | | | 0.263 | MAP4K4 | 180 | | | | 0.338 | PITPNA | 253 |
| | | | 0.263 | BEX4 | 30 | | | | 0.334 | APLP2 | 13 |
| | | | 0.263 | NCBP2 | 208 | | | | 0.333 | CTBP2 | 69 |
| | | | 0.262 | LRMP | 167 | | | | 0.332 | GPSM3 | 113 |
| | | | 0.259 | CAMK1D | 37 | | | | 0.331 | RNF130 | 300 |
| | | | 0.257 | UTP14A | 385 | | | | 0.326 | DGCR2 | 76 |
| | | | 0.253 | STX6 | 346 | | | | 0.326 | ZMIZ1 | 407 |
| | | | 0.253 | RPS6KA3 | 307 | | | | 0.320 | CAP1 | 39 |
| | | | 0.249 | PRKAA1 | 267 | | | | 0.319 | GSK3B | 115 |
| | | | 0.240 | GOLGA7 | 109 | | | | 0.318 | RGS19 | 296 |
| | | | 0.239 | ZNF143 | 408 | | | | 0.317 | RAB7A | 286 |
| | | | 0.237 | SNRK | 329 | | | | 0.316 | CREBBP | 62 |
| | | | 0.233 | SYPL1 | 347 | | | | 0.313 | RBMS1 | 292 |
| | | | 0.229 | CYLD | 72 | | | | 0.310 | IL1RAP | 135 |
| | | | 0.228 | PRUNE | 271 | | | | 0.308 | RTN3 | 309 |

TABLE 10-continued

LIST OF 413 INDIVIDUAL BIOMARKERS (THAT ARE PART OF A DERIVED BIOMARKER WITH
AN AUC >0.8) AND THEIR RESPECTIVE CORRELATION COEFFICIENT TO THE COMPONENT
BIOMARKERS OF THE TOP PERFORMING TWO DERIVED-BIOMARKER SIGNATURE OF ISG15, IL16,
OASL AND CD97. EACH LIST OF BIOMARKERS CONSTITUTES GROUPS B, C, D, AND E

| Group B | | | Group C | | | Group D | | | Group E | | |
|---|---|---|---|---|---|---|---|---|---|---|---|
| Correlation to ISG15 | HUGO Gene Name | SEQ ID | Correlation to IL16 | HUGO Gene Name | SEQ ID | Correlation to OASL | HUGO Gene Name | SEQ ID | Correlation to CD97 | HUGO Gene Name | SEQ ID |
| | | | 0.224 | CRLF3 | 63 | | | | 0.308 | PPP4R1 | 266 |
| | | | 0.223 | CD93 | 48 | | | | 0.307 | TRIOBP | 372 |
| | | | 0.223 | GPS2 | 112 | | | | 0.306 | GABARAP | 104 |
| | | | 0.221 | FBXO11 | 92 | | | | 0.305 | MCTP2 | 190 |
| | | | 0.217 | UBE2D2 | 376 | | | | 0.304 | NFKB1 | 216 |
| | | | 0.217 | USP10 | 381 | | | | 0.303 | CST3 | 68 |
| | | | 0.216 | CCNG2 | 44 | | | | 0.292 | ABHD2 | 2 |
| | | | 0.212 | SOS2 | 333 | | | | 0.285 | SH2B3 | 322 |
| | | | 0.211 | ARRB1 | 19 | | | | 0.284 | STX10 | 344 |
| | | | 0.207 | CEP170 | 51 | | | | 0.282 | TSC22D3 | 373 |
| | | | 0.206 | SMAD4 | 327 | | | | 0.280 | TLE4 | 356 |
| | | | 0.205 | CIAPIN1 | 57 | | | | 0.277 | HAL | 117 |
| | | | 0.204 | KLF7 | 154 | | | | 0.277 | ARRB2 | 20 |
| | | | 0.198 | PHF20L1 | 247 | | | | 0.276 | MAP3K3 | 178 |
| | | | 0.194 | ALDH3A2 | 9 | | | | 0.274 | NPL | 221 |
| | | | 0.193 | PDCD6IP | 238 | | | | 0.265 | CCND3 | 43 |
| | | | 0.185 | WASF2 | 390 | | | | 0.265 | SERINC3 | 317 |
| | | | 0.184 | TGFBI | 351 | | | | 0.263 | GNAQ | 108 |
| | | | 0.175 | GPBP1L1 | 110 | | | | 0.262 | USP4 | 384 |
| | | | 0.174 | PCBP2 | 235 | | | | 0.261 | PSEN1 | 273 |
| | | | 0.166 | DCP2 | 74 | | | | 0.256 | KBTBD2 | 148 |
| | | | 0.165 | LYST | 173 | | | | 0.254 | LYL1 | 171 |
| | | | 0.154 | ERBB2IP | 87 | | | | 0.241 | AIF1 | 8 |
| | | | 0.146 | ANKRD49 | 10 | | | | 0.239 | MBP | 189 |
| | | | 0.145 | NDFIP1 | 213 | | | | 0.238 | ACVR1B | 7 |
| | | | 0.141 | ATAD2B | 22 | | | | 0.238 | RAB4B | 285 |
| | | | 0.138 | ZNF292 | 411 | | | | 0.232 | PTEN | 276 |
| | | | 0.137 | CCNT2 | 45 | | | | 0.231 | ASAP1 | 21 |
| | | | 0.134 | MARCH7 | 184 | | | | 0.231 | MANSC1 | 175 |
| | | | 0.133 | ACAP2 | 6 | | | | 0.228 | RYBP | 312 |
| | | | 0.132 | MED13 | 191 | | | | 0.225 | CSAD | 65 |
| | | | 0.131 | IL6ST | 139 | | | | 0.223 | UBXN2B | 380 |
| | | | 0.131 | PHF3 | 248 | | | | 0.223 | TNIP1 | 364 |
| | | | 0.129 | SP3 | 334 | | | | 0.222 | WBP2 | 391 |
| | | | 0.110 | SEC62 | 315 | | | | 0.211 | OGFRL1 | 228 |
| | | | 0.098 | ZFYVE16 | 406 | | | | 0.209 | SNN | 328 |
| | | | 0.095 | NEK7 | 215 | | | | 0.205 | HPCAL1 | 124 |
| | | | 0.094 | POLD4 | 258 | | | | 0.196 | CD37 | 47 |
| | | | 0.091 | GNA12 | 107 | | | | 0.194 | RNF146 | 302 |
| | | | 0.087 | TRIB2 | 370 | | | | 0.184 | RAB14 | 283 |
| | | | 0.086 | YTHDF3 | 398 | | | | 0.177 | TOPORS | 367 |
| | | | 0.082 | PPP2R5A | 264 | | | | 0.176 | NFYA | 217 |
| | | | 0.081 | PPP1R2 | 263 | | | | 0.172 | FOXO3 | 101 |
| | | | 0.076 | ZDHHC17 | 402 | | | | 0.171 | CREB1 | 61 |
| | | | 0.060 | STK38L | 343 | | | | 0.170 | MAPK1 | 181 |
| | | | 0.057 | ST13 | 337 | | | | 0.170 | SOAT1 | 331 |
| | | | 0.046 | FAM134A | 90 | | | | 0.168 | UBQLN2 | 379 |
| | | | 0.022 | PFDN5 | 241 | | | | 0.166 | OSBPL11 | 229 |
| | | | 0.015 | MARCH8 | 185 | | | | 0.165 | KLHL2 | 155 |
| | | | −0.041 | POLR1D | 259 | | | | 0.153 | VAV3 | 387 |
| | | | | | | | | | 0.135 | BRD4 | 33 |
| | | | | | | | | | 0.130 | MARK3 | 186 |
| | | | | | | | | | 0.114 | BAZ2B | 28 |
| | | | | | | | | | 0.112 | ZNF148 | 409 |
| | | | | | | | | | 0.110 | CASP8 | 41 |
| | | | | | | | | | 0.108 | CHMP1B | 54 |
| | | | | | | | | | 0.105 | HPS1 | 125 |
| | | | | | | | | | 0.099 | RNF141 | 301 |
| | | | | | | | | | 0.096 | MOSPD2 | 198 |
| | | | | | | | | | 0.081 | PINK1 | 251 |
| | | | | | | | | | 0.080 | CDIPT | 50 |
| | | | | | | | | | 0.060 | NCOA4 | 210 |
| | | | | | | | | | 0.059 | PPP3R1 | 265 |
| | | | | | | | | | 0.014 | MKRN1 | 195 |
| | | | | | | | | | 0.005 | GYPC | 116 |
| | | | | | | | | | −0.021 | BMP2K | 31 |
| | | | | | | | | | −0.058 | FBXO9 | 93 |

TABLE 11

FREQUENCY OF NUMERATORS (N > 2) IN THE 473 DERIVED BIOMARKERS

| Numerator | Count |
|---|---|
| OASL | 344 |
| USP18 | 50 |
| EIF2AK2 | 13 |
| ISG15 | 8 |
| IFI44 | 7 |
| LAP3 | 7 |
| ZBP1 | 6 |
| IFI6 | 5 |
| OAS2 | 4 |
| DDX60 | 3 |
| DHX58 | 3 |
| IFIH1 | 3 |
| TAP1 | 3 |
| 12 other biomarkers | 17 derived biomarkers |

TABLE 12

FREQUENCY OF DENOMINATORS (N > 2) IN THE 473 DERIVED BIOMARKERS

| Denominator | Count |
|---|---|
| ABLIM1 | 12 |
| IL16 | 9 |
| SYPL1 | 6 |
| CYLD | 5 |
| IL4R | 5 |
| LTB | 5 |
| MYC | 5 |
| PCF11 | 5 |
| TGFBR2 | 5 |
| CAMK1D | 4 |
| IL6ST | 4 |
| LEF1 | 4 |
| ZNF274 | 4 |
| BTG1 | 3 |
| CRLF3 | 3 |
| DGKA | 3 |
| SESN1 | 3 |
| TNRC6B | 3 |
| ZFC3H1 | 3 |
| 369 other biomarkers | 382 derived biomarkers |

TABLE 13

PERFORMANCE (AUC) OF THE 473 DERIVED BIOMARKERS ACROSS THE FOUR CORE DATASETS

| Derived Biomarkers # 1-237 | Mean | GSE 51808 dengue | GSE 41752 lassa | GSE 52428 flu | GSE 40366 herpes | Derived Biomarkers # 238-473 | Mean | GSE 51808 dengue | GSE 41752 lassa | GSE 52428 flu | GSE 40366 herpes |
|---|---|---|---|---|---|---|---|---|---|---|---|
| OASL:DPEP2 | 0.973 | 1.000 | 0.995 | 0.974 | 0.922 | OASL:CDIPT | 0.936 | 0.905 | 0.995 | 0.957 | 0.887 |
| OASL:KLF7 | 0.969 | 0.996 | 1.000 | 0.969 | 0.912 | OASL:ZFC3H1 | 0.936 | 0.889 | 0.990 | 0.961 | 0.904 |
| OASL:RARA | 0.969 | 1.000 | 1.000 | 0.958 | 0.916 | OAS2:MYC | 0.936 | 0.976 | 1.000 | 0.900 | 0.868 |
| OASL:XPO6 | 0.967 | 0.992 | 0.995 | 0.971 | 0.911 | EIF2AK2:IL6ST | 0.936 | 0.948 | 0.986 | 0.916 | 0.893 |
| OASL:CYLD | 0.966 | 0.972 | 0.986 | 0.959 | 0.945 | OASL:C2orf68 | 0.936 | 0.913 | 0.976 | 0.960 | 0.894 |
| OASL:TLR2 | 0.965 | 1.000 | 1.000 | 0.961 | 0.900 | OASL:LPAR2 | 0.936 | 0.996 | 0.990 | 0.958 | 0.799 |
| OASL:CAMK1D | 0.963 | 0.980 | 0.981 | 0.939 | 0.952 | USP18:PCF11 | 0.936 | 1.000 | 0.976 | 0.947 | 0.820 |
| OASL:ITGAX | 0.963 | 0.996 | 0.986 | 0.953 | 0.916 | OASL:VAMP3 | 0.936 | 0.933 | 0.986 | 0.957 | 0.866 |
| OASL:PINK1 | 0.963 | 1.000 | 0.990 | 0.937 | 0.924 | OASL:CD93 | 0.936 | 1.000 | 0.895 | 0.966 | 0.881 |
| OASL:ARHGAP26 | 0.962 | 1.000 | 0.981 | 0.962 | 0.906 | OASL:RPS6KA3 | 0.936 | 0.925 | 0.976 | 0.954 | 0.887 |
| OASL:LIMK2 | 0.961 | 0.988 | 0.986 | 0.958 | 0.913 | OASL:MCTP2 | 0.936 | 0.905 | 0.976 | 0.952 | 0.909 |
| OASL:FRY | 0.961 | 0.992 | 0.976 | 0.966 | 0.910 | PHF11:ZNF274 | 0.936 | 0.992 | 0.957 | 0.975 | 0.818 |
| OASL:RGS14 | 0.960 | 0.964 | 0.990 | 0.961 | 0.926 | OASL:PCNX | 0.935 | 0.944 | 0.976 | 0.975 | 0.846 |
| OASL:PLXNC1 | 0.960 | 1.000 | 0.995 | 0.966 | 0.880 | OASL:ACAP2 | 0.935 | 0.937 | 0.928 | 0.953 | 0.923 |
| OASL:TNFRSF1A | 0.960 | 0.996 | 1.000 | 0.949 | 0.895 | USP18:PPP1R2 | 0.935 | 0.992 | 1.000 | 0.927 | 0.822 |
| OASL:PBX3 | 0.960 | 0.972 | 0.990 | 0.954 | 0.923 | OASL:ATP6V1B2 | 0.935 | 0.937 | 0.971 | 0.956 | 0.876 |
| OASL:GPR97 | 0.959 | 1.000 | 0.967 | 0.967 | 0.903 | OASL:IQSEC1 | 0.935 | 0.929 | 0.981 | 0.967 | 0.862 |
| OASL:PGS1 | 0.959 | 0.976 | 0.995 | 0.958 | 0.908 | USP18:FOXO1 | 0.935 | 1.000 | 0.947 | 0.947 | 0.845 |
| OASL:RAB11FIP1 | 0.959 | 1.000 | 0.995 | 0.966 | 0.875 | USP18:UBE2D2 | 0.935 | 1.000 | 0.971 | 0.944 | 0.824 |
| OASL:CLEC4A | 0.959 | 0.992 | 0.995 | 0.960 | 0.888 | ZBP1:PCF11 | 0.935 | 0.972 | 0.943 | 0.908 | 0.916 |
| OASL:GYPC | 0.958 | 1.000 | 0.990 | 0.947 | 0.893 | OASL:MED13 | 0.935 | 0.921 | 0.957 | 0.950 | 0.910 |
| OASL:SIRPB1 | 0.958 | 0.996 | 0.986 | 0.968 | 0.880 | OASL:PHF3 | 0.935 | 0.881 | 0.981 | 0.963 | 0.913 |
| OASL:LILRB3 | 0.957 | 0.988 | 0.995 | 0.967 | 0.879 | OASL:LRP10 | 0.935 | 0.925 | 0.995 | 0.959 | 0.859 |
| OASL:ABLIM1 | 0.957 | 0.964 | 0.976 | 0.957 | 0.930 | OASL:TNFSF13 | 0.935 | 0.909 | 1.000 | 0.959 | 0.870 |
| OASL:BTG1 | 0.957 | 0.937 | 0.976 | 0.967 | 0.947 | OASL:LPIN2 | 0.934 | 0.960 | 0.947 | 0.972 | 0.858 |
| OASL:TGFBR2 | 0.957 | 0.972 | 0.967 | 0.969 | 0.918 | OASL:RC3H2 | 0.934 | 0.901 | 0.976 | 0.961 | 0.899 |
| OASL:MKRN1 | 0.956 | 1.000 | 0.990 | 0.933 | 0.902 | OASL:ANKRD49 | 0.934 | 0.913 | 0.981 | 0.961 | 0.882 |
| OASL:LYL1 | 0.956 | 1.000 | 1.000 | 0.952 | 0.873 | OASL:LILRA2 | 0.934 | 0.996 | 0.967 | 0.971 | 0.802 |
| OASL:CAMK2G | 0.956 | 0.988 | 0.981 | 0.972 | 0.882 | OASL:XPC | 0.934 | 0.845 | 0.981 | 0.965 | 0.945 |
| OASL:BACH1 | 0.956 | 0.976 | 0.990 | 0.942 | 0.914 | OASL:KLF6 | 0.934 | 0.952 | 0.995 | 0.968 | 0.821 |
| OASL:PTEN | 0.956 | 0.964 | 0.986 | 0.962 | 0.910 | OASL:DOK3 | 0.934 | 0.960 | 0.909 | 0.959 | 0.908 |
| OASL:WBP2 | 0.956 | 0.992 | 0.990 | 0.934 | 0.906 | OASL:PFDN5 | 0.934 | 0.917 | 0.990 | 0.921 | 0.907 |
| OASL:MXI1 | 0.956 | 1.000 | 0.981 | 0.936 | 0.905 | OASL:RGS19 | 0.934 | 0.929 | 0.995 | 0.970 | 0.841 |
| OASL:SERINC5 | 0.955 | 0.948 | 0.995 | 0.957 | 0.921 | OASL:PRKCD | 0.934 | 0.913 | 0.986 | 0.952 | 0.884 |
| OASL:ITPKB | 0.955 | 0.948 | 0.986 | 0.967 | 0.918 | USP18:LDLRAP1 | 0.934 | 1.000 | 0.962 | 0.955 | 0.818 |
| OASL:ZNF238 | 0.955 | 0.984 | 0.967 | 0.955 | 0.912 | USP18:TRIB2 | 0.934 | 1.000 | 0.957 | 0.936 | 0.842 |
| OASL:TOPORS | 0.954 | 0.980 | 0.995 | 0.949 | 0.893 | PHF11:IL16 | 0.934 | 1.000 | 0.986 | 0.986 | 0.763 |
| OASL:BANP | 0.954 | 0.952 | 0.990 | 0.971 | 0.904 | ISG15:IL16 | 0.934 | 1.000 | 0.986 | 0.966 | 0.782 |
| OASL:CYTH4 | 0.954 | 0.996 | 0.981 | 0.967 | 0.872 | OASL:WASF2 | 0.934 | 0.929 | 0.967 | 0.961 | 0.877 |
| OASL:RNF141 | 0.954 | 0.988 | 0.995 | 0.952 | 0.881 | USP18:NACA | 0.934 | 1.000 | 0.957 | 0.944 | 0.833 |
| USP18:LEF1 | 0.954 | 1.000 | 0.990 | 0.923 | 0.902 | OASL:MANSC1 | 0.934 | 0.984 | 0.885 | 0.955 | 0.910 |
| OASL:IL4R | 0.954 | 0.944 | 0.986 | 0.951 | 0.934 | USP18:LRMP | 0.934 | 1.000 | 0.952 | 0.956 | 0.826 |
| OASL:HGSNAT | 0.954 | 0.948 | 0.981 | 0.973 | 0.912 | OASL:CNPY3 | 0.933 | 0.921 | 1.000 | 0.966 | 0.846 |

TABLE 13-continued

PERFORMANCE (AUC) OF THE 473 DERIVED BIOMARKERS ACROSS THE FOUR CORE DATASETS

| Derived Biomarkers # 1-237 | Mean | GSE 51808 dengue | GSE 41752 lassa | GSE 52428 flu | GSE 40366 herpes | Derived Biomarkers # 238-473 | Mean | GSE 51808 dengue | GSE 41752 lassa | GSE 52428 flu | GSE 40366 herpes |
|---|---|---|---|---|---|---|---|---|---|---|---|
| OASL:MPPE1 | 0.953 | 0.984 | 0.976 | 0.975 | 0.878 | EIF2AK2:TNRC6B | 0.933 | 1.000 | 0.986 | 0.970 | 0.777 |
| OASL:ABHD2 | 0.953 | 0.940 | 1.000 | 0.974 | 0.898 | USP18:EIF3H | 0.933 | 1.000 | 0.971 | 0.927 | 0.835 |
| OASL:PTPN6 | 0.953 | 0.933 | 0.990 | 0.967 | 0.921 | OASL:FOXJ2 | 0.933 | 0.913 | 0.967 | 0.969 | 0.884 |
| OASL:LRMP | 0.953 | 0.929 | 0.967 | 0.974 | 0.941 | USP18:CYLD | 0.933 | 1.000 | 0.976 | 0.942 | 0.814 |
| OASL:GNAQ | 0.953 | 0.996 | 0.995 | 0.958 | 0.862 | OASL:MAML1 | 0.933 | 0.929 | 0.967 | 0.972 | 0.864 |
| OASL:CEP68 | 0.953 | 0.937 | 0.995 | 0.956 | 0.922 | USP18:RPL10A | 0.933 | 1.000 | 0.962 | 0.931 | 0.839 |
| OASL:MAP4K4 | 0.952 | 0.940 | 1.000 | 0.964 | 0.903 | LAP3:SYPL1 | 0.933 | 0.996 | 0.933 | 0.971 | 0.832 |
| OASL:KIAA0247 | 0.951 | 0.972 | 0.967 | 0.966 | 0.899 | OASL:KLF3 | 0.933 | 0.937 | 0.952 | 0.956 | 0.887 |
| OASL:NDEL1 | 0.951 | 0.964 | 1.000 | 0.967 | 0.873 | OASL:DCP2 | 0.933 | 0.917 | 0.986 | 0.951 | 0.877 |
| OASL:MSL1 | 0.951 | 0.992 | 0.976 | 0.961 | 0.875 | USP18:CHMP7 | 0.933 | 1.000 | 0.971 | 0.941 | 0.819 |
| OASL:BMP2K | 0.951 | 0.996 | 0.971 | 0.946 | 0.890 | OASL:RNF146 | 0.933 | 0.948 | 0.967 | 0.955 | 0.861 |
| OASL:NR3C1 | 0.951 | 0.972 | 0.990 | 0.958 | 0.883 | OASL:CTDSP2 | 0.933 | 0.940 | 0.952 | 0.964 | 0.874 |
| OASL:STAT5B | 0.951 | 0.984 | 0.986 | 0.965 | 0.868 | USP18:IL16 | 0.933 | 1.000 | 0.971 | 0.969 | 0.790 |
| OASL:KIAA0232 | 0.951 | 0.968 | 0.962 | 0.967 | 0.906 | OASL:SNX27 | 0.933 | 0.913 | 0.986 | 0.961 | 0.870 |
| OASL:GPSM3 | 0.951 | 0.948 | 0.986 | 0.966 | 0.902 | OASL:PIAS1 | 0.933 | 0.905 | 0.971 | 0.967 | 0.887 |
| OASL:TFEB | 0.951 | 0.972 | 0.990 | 0.951 | 0.889 | ISG15:NOSIP | 0.933 | 0.972 | 0.981 | 0.951 | 0.826 |
| OASL:NDE1 | 0.951 | 0.960 | 0.990 | 0.967 | 0.885 | USP18:CRLF3 | 0.933 | 1.000 | 0.962 | 0.937 | 0.831 |
| OASL:SOS2 | 0.950 | 0.956 | 0.981 | 0.959 | 0.905 | OASL:GPBP1L1 | 0.933 | 0.877 | 0.990 | 0.964 | 0.899 |
| OASL:PACSIN2 | 0.950 | 0.980 | 0.947 | 0.963 | 0.908 | OASL:NRBF2 | 0.932 | 0.972 | 0.947 | 0.930 | 0.880 |
| OASL:CLK4 | 0.950 | 0.948 | 0.957 | 0.971 | 0.922 | EIF2AK2:ZNF274 | 0.932 | 1.000 | 0.957 | 0.970 | 0.802 |
| OASL:CD97 | 0.950 | 0.976 | 1.000 | 0.970 | 0.852 | OASL:SSFA2 | 0.932 | 0.929 | 0.990 | 0.934 | 0.875 |
| OASL:PISD | 0.950 | 0.988 | 0.962 | 0.972 | 0.876 | OASL:PPP1R11 | 0.932 | 0.869 | 1.000 | 0.957 | 0.902 |
| TAP1:TGFBR2 | 0.950 | 1.000 | 0.986 | 0.944 | 0.868 | OASL:RXRA | 0.932 | 0.960 | 0.962 | 0.954 | 0.852 |
| OASL:MARCH8 | 0.949 | 1.000 | 0.947 | 0.945 | 0.905 | OAS2:LEF1 | 0.932 | 0.988 | 0.986 | 0.885 | 0.869 |
| EIF2AK2:CYLD | 0.949 | 1.000 | 0.990 | 0.959 | 0.846 | OASL:APLP2 | 0.932 | 0.929 | 1.000 | 0.969 | 0.829 |
| OASL:TLE3 | 0.949 | 0.964 | 0.967 | 0.971 | 0.892 | OASL:TYROBP | 0.932 | 0.964 | 0.976 | 0.962 | 0.825 |
| C19orf66:IL16 | 0.949 | 0.992 | 0.986 | 0.973 | 0.843 | OASL:SERINC3 | 0.932 | 0.893 | 0.990 | 0.959 | 0.885 |
| OASL:ZNF274 | 0.949 | 0.940 | 0.976 | 0.969 | 0.909 | LAP3:CNPY3 | 0.932 | 1.000 | 0.995 | 0.974 | 0.758 |
| OASL:PCF11 | 0.948 | 0.913 | 0.990 | 0.956 | 0.934 | LAP3:ABLIM1 | 0.932 | 0.996 | 0.947 | 0.967 | 0.817 |
| OASL:CHST11 | 0.948 | 0.925 | 1.000 | 0.958 | 0.910 | OASL:TGFBI | 0.932 | 0.944 | 0.967 | 0.949 | 0.867 |
| OASL:SORL1 | 0.948 | 0.988 | 0.981 | 0.962 | 0.860 | OASL:USP15 | 0.932 | 0.937 | 0.990 | 0.964 | 0.836 |
| OASL:BAZ2B | 0.948 | 0.996 | 0.962 | 0.962 | 0.871 | USP18:SSBP2 | 0.932 | 1.000 | 0.962 | 0.942 | 0.823 |
| OASL:CRLF3 | 0.948 | 0.921 | 0.971 | 0.959 | 0.939 | ZBP1:ZFC3H1 | 0.932 | 0.984 | 0.976 | 0.923 | 0.844 |
| OASL:UBXN2B | 0.948 | 0.968 | 0.976 | 0.956 | 0.890 | EIF2AK2:IL16 | 0.932 | 0.992 | 0.933 | 0.978 | 0.823 |
| OASL:TFE3 | 0.947 | 0.944 | 1.000 | 0.959 | 0.886 | OASL:MORC3 | 0.932 | 0.933 | 0.976 | 0.934 | 0.883 |
| ISG15:ABLIM1 | 0.947 | 1.000 | 0.986 | 0.956 | 0.846 | IFI6:PCF11 | 0.932 | 1.000 | 1.000 | 0.927 | 0.799 |
| OASL:CTBP2 | 0.947 | 0.960 | 0.995 | 0.969 | 0.864 | ZBP1:NDE1 | 0.932 | 0.980 | 0.990 | 0.954 | 0.802 |
| USP18:RPL22 | 0.947 | 1.000 | 1.000 | 0.928 | 0.860 | OASL:DOCK9 | 0.932 | 0.909 | 0.943 | 0.951 | 0.923 |
| OASL:RAB4B | 0.947 | 0.937 | 1.000 | 0.964 | 0.887 | OASL:GOLGA7 | 0.932 | 0.909 | 0.986 | 0.956 | 0.875 |
| OASL:SYPL1 | 0.947 | 0.944 | 0.957 | 0.961 | 0.925 | DHX58:LTB | 0.932 | 0.976 | 0.986 | 0.939 | 0.825 |
| OASL:RTN3 | 0.947 | 0.964 | 1.000 | 0.963 | 0.859 | USP18:PDCD6IP | 0.932 | 1.000 | 0.971 | 0.960 | 0.795 |
| OASL:CCNG2 | 0.946 | 0.968 | 0.957 | 0.959 | 0.901 | EIF2AK2:BTG1 | 0.932 | 0.992 | 0.962 | 0.969 | 0.803 |
| OASL:RNF19B | 0.946 | 1.000 | 0.990 | 0.944 | 0.850 | USP18:BTG1 | 0.932 | 1.000 | 0.971 | 0.962 | 0.793 |
| OASL:NCOA1 | 0.946 | 0.984 | 0.976 | 0.970 | 0.854 | ZBP1:XPO6 | 0.932 | 0.992 | 0.962 | 0.943 | 0.829 |
| OASL:PITPNA | 0.946 | 0.913 | 1.000 | 0.967 | 0.903 | OASL:MBP | 0.931 | 0.984 | 0.990 | 0.949 | 0.802 |
| OASL:RNASET2 | 0.946 | 0.976 | 0.995 | 0.929 | 0.882 | IFI44:IL6ST | 0.931 | 0.944 | 1.000 | 0.921 | 0.860 |
| OASL:PRMT2 | 0.946 | 0.940 | 0.995 | 0.971 | 0.876 | OASL:RAB31 | 0.931 | 0.980 | 0.962 | 0.965 | 0.818 |
| OASL:MAST3 | 0.946 | 0.980 | 0.995 | 0.976 | 0.831 | OASL:FNBP1 | 0.931 | 0.897 | 0.981 | 0.967 | 0.880 |
| OASL:FAM65B | 0.946 | 0.976 | 0.943 | 0.974 | 0.889 | OASL:RBMS1 | 0.931 | 0.937 | 0.967 | 0.952 | 0.869 |
| OASL:LAT2 | 0.946 | 0.972 | 0.976 | 0.959 | 0.875 | OASL:INPP5D | 0.931 | 0.889 | 0.967 | 0.968 | 0.901 |
| OASL:SERTAD2 | 0.945 | 0.976 | 0.990 | 0.957 | 0.858 | OASL:TRIOBP | 0.931 | 0.929 | 0.981 | 0.962 | 0.853 |
| OASL:POLD4 | 0.945 | 0.913 | 1.000 | 0.948 | 0.920 | ISG15:LDLRAP1 | 0.931 | 0.968 | 0.981 | 0.951 | 0.825 |
| OASL:ABAT | 0.945 | 0.956 | 0.962 | 0.958 | 0.905 | USP18:LTB | 0.931 | 1.000 | 0.967 | 0.934 | 0.823 |
| OASL:HHEX | 0.945 | 0.984 | 0.976 | 0.941 | 0.880 | USP18:CAMK1D | 0.931 | 1.000 | 0.957 | 0.926 | 0.841 |
| OASL:IL13RA1 | 0.945 | 1.000 | 0.990 | 0.965 | 0.825 | OASL:MARK3 | 0.931 | 0.933 | 0.981 | 0.956 | 0.854 |
| OASL:FYB | 0.945 | 0.948 | 0.967 | 0.958 | 0.907 | DDX60:ABLIM1 | 0.931 | 0.968 | 0.990 | 0.928 | 0.838 |
| OASL:NUMB | 0.945 | 0.960 | 0.981 | 0.972 | 0.867 | USP18:CRTC3 | 0.931 | 1.000 | 0.962 | 0.958 | 0.804 |
| OASL:HIP1 | 0.945 | 0.913 | 0.995 | 0.970 | 0.901 | OASL:MAP3K11 | 0.931 | 0.869 | 0.990 | 0.969 | 0.896 |
| OASL:RALB | 0.945 | 0.972 | 0.990 | 0.948 | 0.869 | EIF2AK2:PCF11 | 0.931 | 0.988 | 0.952 | 0.958 | 0.826 |
| OASL:ZDHHC18 | 0.945 | 0.996 | 0.990 | 0.967 | 0.826 | OASL:POLB | 0.931 | 0.917 | 0.967 | 0.938 | 0.901 |
| OASL:FAM134A | 0.945 | 0.976 | 0.995 | 0.956 | 0.852 | OASL:SEC62 | 0.931 | 0.877 | 0.967 | 0.959 | 0.920 |
| OASL:TNIP1 | 0.945 | 0.972 | 0.995 | 0.961 | 0.850 | OASL:CSNK1D | 0.931 | 0.937 | 0.990 | 0.967 | 0.829 |
| OASL:RBM23 | 0.945 | 0.909 | 0.990 | 0.963 | 0.916 | USP18:NOSIP | 0.931 | 1.000 | 0.962 | 0.930 | 0.831 |
| OASL:USP10 | 0.945 | 0.972 | 0.976 | 0.960 | 0.870 | OASL:CHMP1B | 0.931 | 0.972 | 1.000 | 0.957 | 0.794 |
| OASL:FOXO3 | 0.944 | 0.976 | 1.000 | 0.964 | 0.837 | IFI6:ABLIM1 | 0.931 | 1.000 | 0.952 | 0.931 | 0.839 |
| OASL:STAT5A | 0.944 | 0.956 | 0.981 | 0.961 | 0.879 | OASL:STX3 | 0.931 | 0.996 | 0.900 | 0.966 | 0.860 |
| OASL:SH2B3 | 0.944 | 0.948 | 0.981 | 0.959 | 0.888 | OASL:MARCH7 | 0.931 | 0.893 | 0.986 | 0.941 | 0.902 |
| OASL:ITSN2 | 0.944 | 0.909 | 0.995 | 0.959 | 0.913 | OASL:ZFAND5 | 0.931 | 0.897 | 0.986 | 0.961 | 0.878 |
| OASL:RAB7A | 0.944 | 0.940 | 0.990 | 0.959 | 0.887 | OASL:OSBPL11 | 0.931 | 0.937 | 0.971 | 0.964 | 0.850 |
| OASL:MYC | 0.944 | 0.905 | 0.986 | 0.950 | 0.934 | OASL:ZNF292 | 0.931 | 0.925 | 0.971 | 0.933 | 0.893 |
| OASL:HCK | 0.944 | 0.996 | 0.981 | 0.962 | 0.836 | OASL:LYN | 0.930 | 0.964 | 0.990 | 0.941 | 0.826 |
| OASL:STX6 | 0.944 | 0.933 | 0.971 | 0.961 | 0.910 | OASL:ZMIZ1 | 0.930 | 0.897 | 0.990 | 0.956 | 0.878 |
| OASL:FCGRT | 0.944 | 1.000 | 0.986 | 0.965 | 0.824 | OASL:FES | 0.930 | 0.897 | 1.000 | 0.955 | 0.869 |
| OASL:TIAM1 | 0.944 | 0.944 | 0.990 | 0.958 | 0.882 | OASL:RASSF2 | 0.930 | 0.980 | 0.981 | 0.954 | 0.805 |

TABLE 13-continued

PERFORMANCE (AUC) OF THE 473 DERIVED BIOMARKERS ACROSS THE FOUR CORE DATASETS

| Derived Biomarkers # 1-237 | Mean | GSE 51808 dengue | GSE 41752 lassa | GSE 52428 flu | GSE 40366 herpes | Derived Biomarkers # 238-473 | Mean | GSE 51808 dengue | GSE 41752 lassa | GSE 52428 flu | GSE 40366 herpes |
|---|---|---|---|---|---|---|---|---|---|---|---|
| OASL:STK38L | 0.944 | 0.925 | 0.990 | 0.946 | 0.913 | OASL:ST3GAL1 | 0.930 | 0.889 | 0.990 | 0.959 | 0.882 |
| OASL:ZDHHC17 | 0.944 | 0.948 | 0.986 | 0.955 | 0.885 | OASL:CASP8 | 0.930 | 0.956 | 0.986 | 0.936 | 0.842 |
| OASL:PLEKHO1 | 0.944 | 0.964 | 0.976 | 0.959 | 0.875 | OASL:TRIM8 | 0.930 | 0.917 | 0.990 | 0.967 | 0.846 |
| OASL:CST3 | 0.943 | 0.940 | 0.995 | 0.957 | 0.881 | ZBP1:KLF7 | 0.930 | 0.992 | 0.971 | 0.950 | 0.807 |
| OASL:BRD1 | 0.943 | 0.937 | 0.986 | 0.967 | 0.882 | STAT1:FBXO11 | 0.930 | 1.000 | 0.957 | 0.951 | 0.812 |
| OASL:CCNT2 | 0.943 | 0.913 | 0.976 | 0.942 | 0.941 | OASL:PPP2R5A | 0.930 | 0.901 | 0.981 | 0.944 | 0.893 |
| DHX58:ABLIM1 | 0.943 | 0.980 | 0.995 | 0.942 | 0.854 | OASL:WDR47 | 0.930 | 0.937 | 0.967 | 0.951 | 0.864 |
| OASL:OSBPL2 | 0.943 | 0.921 | 0.990 | 0.971 | 0.889 | USP18:BEX4 | 0.930 | 1.000 | 0.976 | 0.927 | 0.816 |
| OASL:TMBIM1 | 0.943 | 0.940 | 0.995 | 0.965 | 0.871 | OASL:PHF20 | 0.930 | 0.929 | 0.919 | 0.971 | 0.899 |
| HERC6:MYC | 0.943 | 0.976 | 0.995 | 0.916 | 0.884 | USP18:PIK3IP1 | 0.930 | 1.000 | 0.957 | 0.956 | 0.805 |
| OASL:SNN | 0.943 | 0.992 | 0.995 | 0.966 | 0.817 | OASL:MAP1LC3B | 0.930 | 0.937 | 0.976 | 0.961 | 0.844 |
| OASL:CASC3 | 0.943 | 0.964 | 0.938 | 0.968 | 0.900 | STAT1:PCBP2 | 0.930 | 1.000 | 0.990 | 0.947 | 0.781 |
| OASL:HPCAL1 | 0.943 | 0.933 | 1.000 | 0.962 | 0.875 | USP18:ALDH3A2 | 0.930 | 0.937 | 0.976 | 0.941 | 0.864 |
| OASL:R3HDM2 | 0.943 | 0.940 | 0.995 | 0.951 | 0.884 | LAP3:JAK1 | 0.930 | 0.996 | 0.990 | 0.977 | 0.755 |
| OASL:APBB1IP | 0.943 | 0.940 | 0.981 | 0.956 | 0.893 | DDX60:TGFBR2 | 0.929 | 0.980 | 0.990 | 0.936 | 0.811 |
| OASL:SEMA4D | 0.942 | 0.956 | 0.919 | 0.972 | 0.922 | OASL:ZNF148 | 0.929 | 0.921 | 0.971 | 0.959 | 0.866 |
| OASL:ACVR1B | 0.942 | 0.897 | 0.986 | 0.971 | 0.915 | XAF1:LEF1 | 0.929 | 0.956 | 0.967 | 0.911 | 0.883 |
| OASL:FLOT2 | 0.942 | 0.960 | 0.995 | 0.950 | 0.864 | OASL:PRKAA1 | 0.929 | 0.913 | 0.990 | 0.956 | 0.858 |
| OASL:BRD4 | 0.942 | 0.937 | 0.990 | 0.952 | 0.890 | OASL:IL1RAP | 0.929 | 1.000 | 0.880 | 0.964 | 0.873 |
| USP18:UTP14A | 0.942 | 0.980 | 0.957 | 0.949 | 0.883 | USP18:DGKA | 0.929 | 1.000 | 0.952 | 0.952 | 0.813 |
| OASL:RAF1 | 0.942 | 0.940 | 0.976 | 0.962 | 0.890 | OAS2:ABLIM1 | 0.929 | 0.992 | 0.990 | 0.933 | 0.801 |
| USP18:NFKB1 | 0.942 | 1.000 | 0.947 | 0.951 | 0.870 | IFIH1:TGFBR2 | 0.929 | 0.996 | 0.967 | 0.971 | 0.782 |
| OASL:CD37 | 0.942 | 0.933 | 0.976 | 0.948 | 0.911 | DHX58:IL16 | 0.929 | 0.972 | 0.995 | 0.954 | 0.795 |
| OASL:VPS8 | 0.942 | 0.933 | 0.962 | 0.959 | 0.914 | OASL:N4BP1 | 0.929 | 0.952 | 0.938 | 0.960 | 0.866 |
| OASL:FBXO11 | 0.942 | 0.948 | 0.976 | 0.954 | 0.890 | OASL:LAPTM5 | 0.929 | 0.889 | 0.995 | 0.956 | 0.876 |
| OASL:GMIP | 0.942 | 0.933 | 0.981 | 0.970 | 0.884 | OASL:SOAT1 | 0.929 | 0.921 | 0.952 | 0.947 | 0.896 |
| OASL:PLEKHO2 | 0.942 | 0.996 | 0.957 | 0.968 | 0.847 | OASL:IL10RB | 0.929 | 0.877 | 0.981 | 0.959 | 0.898 |
| OASL:SH2D3C | 0.942 | 0.948 | 0.923 | 0.955 | 0.942 | OASL:PTAFR | 0.929 | 0.996 | 0.995 | 0.959 | 0.765 |
| OASL:RPS6KA1 | 0.942 | 0.948 | 0.990 | 0.964 | 0.865 | OASL:KBTBD2 | 0.929 | 0.933 | 0.976 | 0.956 | 0.850 |
| OASL:ARHGEF2 | 0.942 | 0.913 | 0.986 | 0.956 | 0.912 | OASL:ARRB2 | 0.929 | 0.996 | 0.990 | 0.942 | 0.787 |
| OASL:ARAP1 | 0.942 | 0.952 | 1.000 | 0.962 | 0.853 | OASL:CAP1 | 0.929 | 0.857 | 0.990 | 0.961 | 0.907 |
| OASL:PPM1F | 0.942 | 0.980 | 0.995 | 0.966 | 0.825 | OASL:MEF2A | 0.929 | 0.857 | 0.986 | 0.962 | 0.910 |
| USP18:ABLIM1 | 0.942 | 1.000 | 0.962 | 0.951 | 0.853 | OASL:TNK2 | 0.929 | 0.897 | 0.986 | 0.964 | 0.868 |
| OASL:RERE | 0.942 | 0.956 | 0.971 | 0.968 | 0.871 | OASL:PSTPIP1 | 0.929 | 0.913 | 0.990 | 0.967 | 0.845 |
| OASL:ATAD2B | 0.942 | 0.929 | 0.986 | 0.945 | 0.906 | OASL:MAX | 0.929 | 0.944 | 0.995 | 0.934 | 0.841 |
| IFI44:MYC | 0.941 | 0.968 | 0.995 | 0.910 | 0.892 | IFI44:LTB | 0.929 | 0.980 | 0.995 | 0.929 | 0.810 |
| OASL:LCP2 | 0.941 | 0.964 | 0.981 | 0.966 | 0.854 | OASL:IGSF6 | 0.929 | 0.992 | 0.986 | 0.949 | 0.787 |
| OASL:GNA12 | 0.941 | 0.913 | 0.995 | 0.949 | 0.908 | OASL:DGCR2 | 0.929 | 0.905 | 0.981 | 0.964 | 0.864 |
| OASL:SMAD4 | 0.941 | 0.901 | 0.986 | 0.949 | 0.929 | LAP3:NDFIP1 | 0.929 | 0.996 | 0.981 | 0.971 | 0.766 |
| OASL:DGKA | 0.941 | 0.929 | 0.962 | 0.958 | 0.915 | OASL:AIF1 | 0.929 | 0.968 | 0.957 | 0.952 | 0.837 |
| OASL:UBN1 | 0.941 | 0.944 | 0.986 | 0.957 | 0.877 | OASL:ZNF143 | 0.929 | 0.897 | 0.967 | 0.957 | 0.893 |
| OASL:CBX7 | 0.941 | 0.968 | 0.986 | 0.966 | 0.844 | OAS2:FAIM3 | 0.928 | 0.948 | 0.995 | 0.943 | 0.827 |
| OASL:YPEL5 | 0.941 | 0.952 | 1.000 | 0.949 | 0.863 | OASL:USP4 | 0.928 | 0.905 | 0.976 | 0.966 | 0.866 |
| USP18:IL6ST | 0.941 | 1.000 | 0.981 | 0.911 | 0.872 | OASL:CEP170 | 0.928 | 0.917 | 0.957 | 0.952 | 0.887 |
| USP18:CCR7 | 0.941 | 0.992 | 0.947 | 0.942 | 0.882 | OASL:PECAM1 | 0.928 | 0.929 | 0.995 | 0.971 | 0.818 |
| OASL:ICAM3 | 0.941 | 0.956 | 1.000 | 0.966 | 0.841 | OASL:PHF2 | 0.928 | 0.897 | 0.981 | 0.961 | 0.874 |
| OASL:NFYA | 0.941 | 0.905 | 0.990 | 0.959 | 0.909 | EIF2AK2:IL4R | 0.928 | 1.000 | 0.900 | 0.948 | 0.865 |
| OASL:NAB1 | 0.941 | 0.921 | 0.990 | 0.959 | 0.893 | OASL:GABARAP | 0.928 | 0.897 | 0.995 | 0.957 | 0.864 |
| OASL:PRKAG2 | 0.941 | 0.960 | 0.986 | 0.959 | 0.858 | IFI44:IL4R | 0.928 | 0.996 | 0.995 | 0.924 | 0.797 |
| OASL:CSAD | 0.941 | 0.968 | 0.981 | 0.948 | 0.866 | TAP1:TGOLN2 | 0.928 | 0.996 | 0.986 | 0.957 | 0.773 |
| USP18:SYPL1 | 0.941 | 1.000 | 0.957 | 0.938 | 0.868 | OASL:LST1 | 0.928 | 0.992 | 0.990 | 0.964 | 0.766 |
| OASL:SLCO3A1 | 0.941 | 0.988 | 0.990 | 0.972 | 0.812 | OASL:GSK3B | 0.928 | 0.905 | 0.986 | 0.964 | 0.857 |
| OASL:ZYX | 0.941 | 1.000 | 1.000 | 0.966 | 0.796 | USP18:TGFBR2 | 0.928 | 1.000 | 0.957 | 0.956 | 0.799 |
| OASL:PCBP2 | 0.941 | 0.909 | 0.995 | 0.956 | 0.902 | OASL:PSAP | 0.928 | 0.865 | 1.000 | 0.967 | 0.880 |
| OASL:PTPRE | 0.941 | 0.956 | 0.986 | 0.962 | 0.858 | OASL:KLHL2 | 0.928 | 0.996 | 0.967 | 0.961 | 0.788 |
| OASL:CSF2RB | 0.941 | 0.984 | 0.914 | 0.958 | 0.906 | LAP3:TRAK1 | 0.928 | 0.988 | 0.986 | 0.971 | 0.767 |
| OASL:SNRK | 0.941 | 0.940 | 0.990 | 0.967 | 0.865 | OASL:MMP25 | 0.928 | 1.000 | 0.981 | 0.964 | 0.766 |
| OASL:SIRPA | 0.940 | 0.992 | 0.981 | 0.974 | 0.814 | EIF2AK2:PDE3B | 0.928 | 0.996 | 0.957 | 0.955 | 0.803 |
| OASL:VAV3 | 0.940 | 0.960 | 0.995 | 0.967 | 0.839 | CUL1:IL16 | 0.928 | 1.000 | 0.943 | 0.953 | 0.815 |
| OASL:WDR37 | 0.940 | 0.933 | 0.981 | 0.959 | 0.887 | OASL:POLR1D | 0.928 | 0.905 | 0.971 | 0.935 | 0.900 |
| OASL:SP3 | 0.940 | 0.901 | 0.995 | 0.946 | 0.918 | USP18:ATM | 0.928 | 1.000 | 0.967 | 0.949 | 0.795 |
| OASL:MAPK1 | 0.940 | 0.948 | 0.986 | 0.965 | 0.861 | OASL:NLRP1 | 0.928 | 0.980 | 0.923 | 0.969 | 0.838 |
| OASL:RAB14 | 0.940 | 0.909 | 0.986 | 0.959 | 0.905 | OASL:PPARD | 0.928 | 0.869 | 0.976 | 0.960 | 0.905 |
| USP18:ST13 | 0.940 | 1.000 | 0.986 | 0.942 | 0.831 | IFI6:IL6ST | 0.928 | 0.972 | 0.967 | 0.908 | 0.863 |
| OASL:BCL2 | 0.940 | 0.913 | 0.990 | 0.957 | 0.899 | IFIH1:CRLF3 | 0.928 | 0.921 | 0.957 | 0.957 | 0.875 |
| OASL:MTMR3 | 0.940 | 0.976 | 0.990 | 0.968 | 0.824 | IFI44:SESN1 | 0.928 | 0.996 | 0.976 | 0.936 | 0.802 |
| OASL:PPP4R1 | 0.940 | 1.000 | 0.971 | 0.964 | 0.823 | OASL:TREM1 | 0.928 | 1.000 | 0.995 | 0.955 | 0.760 |
| OASL:MKLN1 | 0.940 | 0.937 | 0.986 | 0.959 | 0.876 | OASL:NOD2 | 0.928 | 1.000 | 0.861 | 0.941 | 0.908 |
| OASL:LYST | 0.939 | 0.984 | 0.981 | 0.966 | 0.826 | TAP1:TNRC6B | 0.928 | 1.000 | 1.000 | 0.946 | 0.764 |
| OASL:ITGB2 | 0.939 | 0.909 | 0.990 | 0.970 | 0.888 | USP18:ATF7IP2 | 0.928 | 0.992 | 0.971 | 0.952 | 0.795 |
| ISG15:LTB | 0.939 | 1.000 | 0.976 | 0.952 | 0.829 | USP18:ZNF274 | 0.927 | 1.000 | 0.952 | 0.960 | 0.797 |
| IFI44:ABLIM1 | 0.939 | 0.996 | 0.986 | 0.932 | 0.842 | USP18:NDFIP1 | 0.927 | 1.000 | 0.986 | 0.946 | 0.777 |
| EIF2AK2:SYPL1 | 0.939 | 0.992 | 0.962 | 0.950 | 0.852 | RTP4:SYPL1 | 0.927 | 1.000 | 0.885 | 0.944 | 0.880 |
| OASL:NCOA4 | 0.939 | 0.956 | 0.967 | 0.954 | 0.879 | EIF2AK2:SATB1 | 0.927 | 0.996 | 0.947 | 0.962 | 0.803 |

TABLE 13-continued

PERFORMANCE (AUC) OF THE 473 DERIVED BIOMARKERS ACROSS THE FOUR CORE DATASETS

| Derived Biomarkers # 1-237 | Mean | GSE 51808 dengue | GSE 41752 lassa | GSE 52428 flu | GSE 40366 herpes | Derived Biomarkers # 238-473 | Mean | GSE 51808 dengue | GSE 41752 lassa | GSE 52428 flu | GSE 40366 herpes |
|---|---|---|---|---|---|---|---|---|---|---|---|
| OASL:FGR | 0.939 | 0.976 | 0.957 | 0.957 | 0.866 | OASL:ACAA1 | 0.927 | 0.837 | 1.000 | 0.962 | 0.909 |
| OASL:PHF20L1 | 0.939 | 0.929 | 0.947 | 0.961 | 0.919 | ISG15:SESN1 | 0.927 | 1.000 | 0.962 | 0.950 | 0.796 |
| OASL:ABI1 | 0.939 | 0.893 | 0.990 | 0.956 | 0.916 | OASL:UBQLN2 | 0.927 | 0.893 | 0.962 | 0.950 | 0.903 |
| OASL:STAM2 | 0.939 | 0.940 | 0.957 | 0.950 | 0.908 | OASL:SETD2 | 0.927 | 0.857 | 0.976 | 0.971 | 0.904 |
| OASL:PHC2 | 0.939 | 0.996 | 0.990 | 0.972 | 0.796 | OASL:RYBP | 0.927 | 0.889 | 0.990 | 0.967 | 0.861 |
| OASL:TLE4 | 0.939 | 0.913 | 0.957 | 0.973 | 0.911 | UBE2L6:IL16 | 0.927 | 1.000 | 0.904 | 0.970 | 0.833 |
| PARP12:ABLIM1 | 0.939 | 0.960 | 0.990 | 0.945 | 0.859 | MX1:LEF1 | 0.927 | 0.976 | 0.967 | 0.913 | 0.851 |
| OASL:TMEM127 | 0.938 | 0.921 | 0.995 | 0.975 | 0.862 | USP18:IL27RA | 0.927 | 1.000 | 0.952 | 0.956 | 0.799 |
| OASL:OGFRL1 | 0.938 | 1.000 | 0.995 | 0.968 | 0.790 | OASL:ARHGAP15 | 0.927 | 0.873 | 0.986 | 0.943 | 0.905 |
| OASL:CREB1 | 0.938 | 0.968 | 0.947 | 0.959 | 0.878 | USP18:SESN1 | 0.927 | 1.000 | 0.952 | 0.946 | 0.809 |
| OASL:ST13 | 0.938 | 0.905 | 0.967 | 0.952 | 0.928 | RSAD2:CAMK1D | 0.927 | 0.929 | 1.000 | 0.935 | 0.843 |
| OASL:ARRB1 | 0.938 | 0.940 | 0.995 | 0.964 | 0.853 | XAF1:IL4R | 0.927 | 0.992 | 0.986 | 0.927 | 0.801 |
| OASL:TSC22D3 | 0.938 | 0.996 | 0.990 | 0.974 | 0.792 | USP18:METTL3 | 0.927 | 1.000 | 0.947 | 0.958 | 0.801 |
| OASL:RIN3 | 0.938 | 0.925 | 0.967 | 0.972 | 0.888 | OASL:MAP3K5 | 0.927 | 0.925 | 0.995 | 0.972 | 0.814 |
| OASL:CREBBP | 0.938 | 0.937 | 0.986 | 0.969 | 0.859 | OASL:ZXDC | 0.927 | 0.865 | 0.971 | 0.971 | 0.899 |
| OASL:MAP3K3 | 0.938 | 0.956 | 0.990 | 0.963 | 0.842 | OASL:HPS1 | 0.927 | 0.921 | 0.995 | 0.942 | 0.848 |
| OASL:GCC2 | 0.938 | 0.893 | 0.995 | 0.952 | 0.911 | OASL:GRB2 | 0.927 | 0.881 | 0.995 | 0.961 | 0.869 |
| OASL:NSUN3 | 0.938 | 0.901 | 0.976 | 0.963 | 0.911 | USP18:DPF2 | 0.927 | 1.000 | 0.957 | 0.962 | 0.787 |
| OASL:STX10 | 0.938 | 0.940 | 0.976 | 0.959 | 0.875 | OASL:EMR2 | 0.926 | 1.000 | 0.928 | 0.970 | 0.807 |
| OASL:IKBKB | 0.938 | 0.929 | 0.971 | 0.962 | 0.888 | IFI6:MYC | 0.926 | 0.988 | 0.923 | 0.911 | 0.882 |
| OASL:ASAP1 | 0.938 | 0.988 | 0.971 | 0.958 | 0.833 | OASL:GPS2 | 0.926 | 0.833 | 0.990 | 0.956 | 0.925 |
| OASL:RNF130 | 0.938 | 0.992 | 0.990 | 0.959 | 0.809 | USP18:SAFB2 | 0.926 | 1.000 | 0.971 | 0.965 | 0.768 |
| OASL:FBXO9 | 0.938 | 0.972 | 0.947 | 0.932 | 0.899 | OASL:HAL | 0.926 | 1.000 | 0.914 | 0.959 | 0.830 |
| OASL:TM2D3 | 0.938 | 0.921 | 0.990 | 0.948 | 0.891 | USP18:DIDO1 | 0.926 | 1.000 | 0.971 | 0.956 | 0.776 |
| OASL:TNRC6B | 0.937 | 0.893 | 0.976 | 0.966 | 0.914 | ISG15:DGKA | 0.926 | 1.000 | 0.957 | 0.951 | 0.795 |
| OASL:PRUNE | 0.937 | 0.901 | 0.990 | 0.963 | 0.895 | HERC5:ABLIM1 | 0.926 | 0.881 | 0.990 | 0.953 | 0.879 |
| OASL:PTGER4 | 0.937 | 0.980 | 0.995 | 0.971 | 0.802 | HERC6:ATM | 0.926 | 0.980 | 0.990 | 0.946 | 0.787 |
| OASL:PSEN1 | 0.937 | 0.913 | 0.990 | 0.952 | 0.893 | OASL:CHD3 | 0.926 | 0.877 | 0.981 | 0.954 | 0.890 |
| OASL:IL6R | 0.937 | 0.929 | 0.981 | 0.956 | 0.882 | OASL:MAPRE2 | 0.926 | 0.837 | 0.990 | 0.971 | 0.904 |
| OASL:KIAA0513 | 0.937 | 0.937 | 0.976 | 0.974 | 0.861 | USP18:ZC3HAV1 | 0.926 | 1.000 | 0.976 | 0.951 | 0.775 |
| EIF2AK2:ZFC3H1 | 0.937 | 0.996 | 1.000 | 0.967 | 0.785 | IFIH1:LTB | 0.925 | 0.980 | 0.976 | 0.934 | 0.811 |
| LAP3:MAP4K4 | 0.937 | 1.000 | 1.000 | 0.976 | 0.772 | DDX60:SYPL1 | 0.925 | 0.937 | 0.990 | 0.911 | 0.863 |
| OASL:AOAH | 0.937 | 1.000 | 0.990 | 0.967 | 0.791 | OASL:PAFAH1B1 | 0.925 | 0.873 | 0.981 | 0.961 | 0.886 |
| OASL:RHOG | 0.937 | 0.940 | 0.990 | 0.962 | 0.856 | OASL:CCND3 | 0.925 | 0.849 | 1.000 | 0.971 | 0.881 |
| IFI6:IL16 | 0.937 | 1.000 | 0.971 | 0.947 | 0.829 | USP18:NECAP2 | 0.925 | 1.000 | 0.981 | 0.942 | 0.777 |
| OASL:ARHGAP25 | 0.937 | 0.968 | 0.981 | 0.972 | 0.826 | USP18:NCBP2 | 0.925 | 1.000 | 0.971 | 0.937 | 0.792 |
| ISG15:IL4R | 0.937 | 1.000 | 0.995 | 0.939 | 0.813 | OASL:TYK2 | 0.925 | 0.905 | 0.981 | 0.962 | 0.852 |
| OASL:MAPK14 | 0.937 | 0.885 | 0.990 | 0.967 | 0.904 | OASL:PUM2 | 0.925 | 0.841 | 0.981 | 0.953 | 0.924 |
| OASL:ZFYVE16 | 0.937 | 0.980 | 0.962 | 0.956 | 0.848 | USP18:TMEM204 | 0.924 | 1.000 | 0.943 | 0.922 | 0.832 |
| OASL:PPP3R1 | 0.936 | 0.933 | 0.995 | 0.934 | 0.883 | IFI44:CYLD | 0.924 | 1.000 | 0.995 | 0.929 | 0.772 |
| OASL:NEK7 | 0.936 | 0.944 | 0.990 | 0.944 | 0.867 | OASL:ERBB2IP | 0.924 | 0.861 | 0.971 | 0.952 | 0.912 |
| USP18:CIAPIN1 | 0.936 | 0.992 | 0.971 | 0.943 | 0.839 | EIF2AK2:CAMK1D | 0.924 | 1.000 | 0.933 | 0.922 | 0.841 |
| OASL:NPL | 0.936 | 0.996 | 0.986 | 0.966 | 0.797 | OASL:YTHDF3 | 0.924 | 0.861 | 0.981 | 0.952 | 0.901 |
| ZBP1:CYLD | 0.936 | 0.984 | 0.962 | 0.902 | 0.897 | OASL:ETS2 | 0.923 | 0.992 | 1.000 | 0.960 | 0.741 |
| OASL:MOSPD2 | 0.936 | 0.984 | 0.947 | 0.951 | 0.862 | RTP4:ABLIM1 | 0.923 | 1.000 | 0.890 | 0.941 | 0.861 |
| OASL:VEZF1 | 0.936 | 0.901 | 0.990 | 0.961 | 0.892 | | | | | | |

TABLE 14

LIST OF BIOMARKER RATIOS WITH AN AUC GREATER THAN 0.8 IN THE MARS DATASET

| Biomarker Ratio | AUC |
|---|---|
| IFIH1:LTB | 0.863 |
| OASL:TGFBI | 0.859 |
| DDX60:ABLIM1 | 0.850 |
| IFI44:IL4R | 0.843 |
| OASL:NLRP1 | 0.842 |
| DDX60:TGFBR2 | 0.836 |
| OAS2:ABLIM1 | 0.833 |
| IFI6:IL16 | 0.831 |
| IFI44:LTB | 0.829 |
| OASL:TREM1 | 0.825 |
| OASL:ZDHHC18 | 0.823 |
| IFI44:ABLIM1 | 0.821 |
| RSAD2:CAMK1D | 0.820 |
| USP18:BTG1 | 0.820 |
| IFIH1:TGFBR2 | 0.818 |
| OASL:CST3 | 0.817 |
| PHF11:IL16 | 0.817 |
| USP18:CRTC3 | 0.816 |
| ISG15:LTB | 0.815 |
| USP18:IL16 | 0.815 |
| OASL:SNN | 0.815 |
| HERC5:ABLIM1 | 0.815 |
| OASL:UBN1 | 0.814 |
| XAF1:IL4R | 0.814 |
| ISG15:IL16 | 0.811 |
| IFI6:ABLIM1 | 0.809 |
| ISG15:ABLIM1 | 0.808 |
| IFIH1:CRLF3 | 0.807 |
| ISG15:IL4R | 0.805 |
| OASL:TIAM1 | 0.805 |
| OASL:TLE3 | 0.805 |
| USP18:NOSIP | 0.804 |
| ISG15:NOSIP | 0.804 |
| UBE2L6:IL16 | 0.804 |

TABLE 14-continued

LIST OF BIOMARKER RATIOS WITH AN AUC GREATER THAN 0.8 IN THE MARS DATASET

| Biomarker Ratio | AUC |
| --- | --- |
| OASL:LPAR2 | 0.803 |
| OASL:FCGRT | 0.801 |
| OASL:MAST3 | 0.800 |
| ISG15:LDLRAP1 | 0.800 |

TABLE 15

KEY HUMAN VIRAL PATHOGENS (BY VIRUS NAME AND TYPE) THAT ARE KNOWN TO CAUSE SYSTEMIC INFLAMMATION GROUPED BASED ON MAJOR CLINICAL SIGNS. UNDERLINED VIRUS TYPES ARE THOSE DEMONSTRABLY DETECTED USING THE VIR BIOMARKER SIGNATURE

| Clinical Signs | Virus Name | Virus Type |
| --- | --- | --- |
| Respiratory | Respiratory Syncytial Virus | Paramyxovirus |
| | Influenza A and B | Orthomyxovirus |
| | Adenovirus | Adenovirus |
| | Parainfluenza virus 1, 2, 3 and 4 | Paramyxovirus |
| | Human Coronavirus types 229e, OC43, HKU1, NL-63 | Coronavirus |
| | Rhinovirus | |
| | SARS Coronavirus | Rhinovirus |
| | Enterovirus | Coronavirus |
| Respiratory/Gastrointestinal Fever/Rash/Aches/Generalised | BK virus | Picovirus |
| | Polyomavirus | Polyomavirus |
| | Bocavirus | Parvovirus |
| | Rotavirus | Reovirus |
| | Measles | Morbillivirus |
| | Hantavirus | Bunyavirus |
| | Cytomegalovirus | Herpesvirus |
| | Varicella Zoster Virus | Herpesvirus |
| | Herpes Simplex Virus | Herpesvirus |
| | Epstein Barr Virus | Herpesvirus |
| | Parechovirus | Picornavirus |
| | Human immunodeficiency virus | Lentivirus |
| | Hepatitis B virus | Orthohepadnavirus |
| | HTLV1 and 2 | Retrovirus |
| | Vaccinia virus | Poxvirus |
| | West Nile Virus | Flavivirus |
| | Coxsackie virus | Picornavirus |
| | Parvovirus B19 | Parvovirus |
| | Dengue | Flavivirus |
| Few Clinical Signs | TTV (torque teno virus) | Anellovirus |
| | Hepatitis C virus | Flavivirus |

TABLE 16

COMMON HUMAN VIRUSES THAT CAUSE SIRS AND A VIREMIA AS PART OF THEIR PATHOGENESIS AND AN ASSOCIATED REFERENCE

| Virus | Reference |
| --- | --- |
| Measles | de Vries R D, Mesman A W, Geijtenbeek T B H, Duprex W P, de Swart R L (2012) The pathogenesis of measles. Curr Opin Virol 2: 248-255. |
| Respiratory Syncytial Virus (RSV) | Rohwedder A, Keminer O, Forster J, Schneider K, Schneider E, et al. (1998) Detection of respiratory syncytial virus RNA in blood of neonates by polymerase chain reaction. J Med Virol 54: 320-327. |
| Influenza A and B | Wootton S H, Aguilera E A, Wanger A, Jewell A, Patel K, et al. (2014) Detection of NH1N1 influenza virus in nonrespiratory sites among children. Pediatr Infect Dis J 33: 95-96. |
| Hepatitis B virus Hepatitis C virus Human immunodeficiency virus 1 and 2 HTLV1 and 2 Vaccinia virus West Nile Virus | Pripuzova N, Wang R, Tsai S, Li B, Hung G-C, et al. (2012) Development of Real-Time PCR Array for Simultaneous Detection of Eight Human Blood-Borne Viral Pathogens. PLoS ONE 7: e43246. |
| Cytomegalovirus Varicella Zoster Virus Herpes Simplex Virus Epstein Barr Virus | Johnson G, Nelson S, Petric M, Tellier R (2000) Comprehensive PCR-based assay for detection and species identification of human herpesviruses. Journal of Clinical Microbiology 38: 3274-3279. |
| Rhinovirus | Xatzipsalti M, Kyrana S, Tsolia M, Psarras S, Bossios A, et al. (2005) Rhinovirus viremia in children with respiratory infections. American Journal of Respiratory and Critical Care Medicine 172: 1037-1040. |
| Adenovirus Bocavirus Human Coronavirus types 229e, OC43, HKU1, NL-63 SARS coronavirus | Dunn J J, Miller M B (2014) Emerging respiratory viruses other than influenza. Clin Lab Med 34: 409-430. |
| Hantavirus | Evander M, Eriksson I, Pettersson L, Juto P, Ahlm C, et al. (2007) Puumala Hantavirus Viremia Diagnosed by Real-Time Reverse Transcriptase PCR Using Samples from Patients with Hemorrhagic Fever and Renal Syndrome. Journal of Clinical Microbiology 45: 2491-2497. |
| Enterovirus | Cheng H-Y, Huang Y-C, Yen T-Y, Hsia S-H, Hsieh Y-C, et al. (2014) The correlation between the presence of viremia and clinical severity in patients with enterovirus 71 infection: a multi-center cohort study. BMC Infect Dis 14: 417. |
| Parechovirus | Abed Y, Boivin G (2006) Human parechovirus infections in Canada. Emerging Infectious Diseases 12: 969. |
| BK virus | Erard V, Storer B, Corey L, Nollkamper J, Huang M-L, et al. (2004) BK virus infection in hematopoietic stem cell transplant recipients: frequency, risk factors, and association with postengraftment hemorrhagic cystitis. Clin Infect Dis 39: 1861-1865. |

TABLE 16-continued

COMMON HUMAN VIRUSES THAT CAUSE SIRS AND A VIREMIA AS PART OF THEIR PATHOGENESIS AND AN ASSOCIATED REFERENCE

| Virus | Reference |
|---|---|
| Parainfluenza virus 1, 2, 3 and 4 | Gerkowicz T, Szajner-Milart I, Szczygielska J, Blaszynska M, Karska M, et al. (1979) [Clinical manifestations of viremia during infections caused by adenoviruses and parainfluenza viruses]. Pediatr Pol 54: 41-45. |
| SARS coronavirus | Wang W K, Fang C T, Chen H L, Yang C F, Chen Y C, et al. (2005) Detection of Severe Acute Respiratory Syndrome Coronavirus RNA in Plasma during the Course of Infection. Journal of Clinical Microbiology 43: 962-965. |
| TTV (torque teno virus) | Walton A H, Muenzer J T, Rasche D, Boomer J S, Sato B, et al. (2014) Reactivation of multiple viruses in patients with sepsis. PLoS ONE 9: e98819. |
| Coxsackie virus | Clem A L, Sims J, Telang S, Eaton J W, Chesney J (2007) Virus detection and identification using random multiplex (RT)-PCR with 3'-locked random primers. Virol J 4: 65. |
| Parvovirus B19 | Juhl D, Steppat D, Görg S, Hennig H (2014) Parvovirus B19 Infections and Blood Counts in Blood Donors. Transfus Med Hemother 41: 6-6. |
| Dengue | La Cruz Hernandez De S I, Flores-Aguilar H, Gonzalez-Mateos S, Lopez-Martinez I, Ortiz-Navarrete V, et al. (2013) Viral load in patients infected with dengue is modulated by the presence of anti-dengue IgM antibodies. J Clin Virol 58: 258-261. |

TABLE 17

COMMON HUMAN VIRUSES THAT CAUSE SIRS AND A VIREMIA AS PART OF THEIR PATHOGENESIS AND FOR WHICH THERE ARE SPECIFIC ANTI-VIRAL TREATMENTS

| Virus | Reference |
|---|---|
| Influenza A and B | Wootton S H, Aguilera E A, Wanger A, Jewell A, Patel K, et al. (2014) Detection of NH1N1 influenza virus in nonrespiratory sites among children. Pediatr Infect Dis J 33: 95-96. |
| Hepatitis B virus Hepatitis C virus Human immunodeficiency virus 1 and 2 Cytomegalovirus Varicella Zoster Virus Herpes Simplex Virus Epstein Barr Virus | Pripuzova N, Wang R, Tsai S, Li B, Hung G-C, et al. (2012) Development of Real-Time PCR Array for Simultaneous Detection of Eight Human Blood-Borne Viral Pathogens. PLoS ONE 7: e43246. Johnson G, Nelson S, Petric M, Tellier R (2000) Comprehensive PCR-based assay for detection and species identification of human herpesviruses. Journal of Clinical Microbiology 38: 3274-3279. |

TABLE 18

COMMON AND LESS COMMON VIRUSES ASSOCIATED WITH PNEUMONIA IN ADULTS AND CHILDREN

| Common | Less Common (or in specific hosts or settings) |
|---|---|
| Respiratory Syncytial Virus (RSV) | Measles |
| Influenza A and B | Cytomegalovirus |
| Human Metapneumovirus | Varicella Zoster Virus |
| Adenovirus | Herpes Simplex Virus |
| Parainfluenza virus 1, 2, 3 and 4 | Epstein Barr Virus |
| Human Coronavirus types 229e, OC43, HKU1, NL-63 | Hantavirus |
| Rhinovirus | Enterovirus |
| Bocavirus | Parechovirus |
|  | SARS Coronavirus |

TABLE 19

SEQUENCE ID NUMBERS, BIOMARKER GENE SYMBOLS AND ENSEMBL TRANSCRIPT IDS

| SEQ ID | Gene Symbol | Ensembl Transcript ID |
|---|---|---|
| 1 | ABAT | ENST00000396600 |
| 2 | ABHD2 | ENST00000565973 |
| 3 | ABI1 | ENST00000376142 |
| 4 | ABLIM1 | ENST00000277895 |
| 5 | ACAA1 | ENST00000333167 |
| 6 | ACAP2 | ENST00000326793 |
| 7 | ACVR1B | ENST00000257963 |
| 8 | AIF1 | ENST00000413349 |
| 9 | ALDH3A2 | ENST00000579855 |
| 10 | ANKRD49 | ENST00000544612 |
| 11 | AOAH | ENST00000617537 |
| 12 | APBB1IP | ENST00000376236 |
| 13 | APLP2 | ENST00000263574 |
| 14 | ARAP1 | ENST00000334211 |
| 15 | ARHGAP15 | ENST00000295095 |
| 16 | ARHGAP25 | ENST00000409030 |
| 17 | ARHGAP26 | ENST00000274498 |
| 18 | ARHGEF2 | ENST00000313695 |
| 19 | ARRB1 | ENST00000420843 |
| 20 | ARRB2 | ENST00000269260 |
| 21 | ASAP1 | ENST00000518721 |
| 22 | ATAD2B | ENST00000238789 |
| 23 | ATF7IP2 | ENST00000396560 |
| 24 | ATM | ENST00000278616 |
| 25 | ATP6V1B2 | ENST00000276390 |
| 26 | BACH1 | ENST00000286800 |
| 27 | BANP | ENST00000355022 |
| 28 | BAZ2B | ENST00000392783 |
| 29 | BCL2 | ENST00000398117 |
| 30 | BEX4 | ENST00000372695 |
| 31 | BMP2K | ENST00000502871 |
| 32 | BRD1 | ENST00000216267 |
| 33 | BRD4 | ENST00000371835 |
| 34 | BTG1 | ENST00000256015 |
| 35 | C19orf66 | ENST00000253110 |
| 36 | C2orf68 | ENST00000306336 |
| 37 | CAMK1D | ENST00000378845 |
| 38 | CAMK2G | ENST00000351293 |
| 39 | CAP1 | ENST00000372797 |
| 40 | CASC3 | ENST00000264645 |
| 41 | CASP8 | ENST00000264275 |
| 42 | CBX7 | ENST00000216133 |
| 43 | CCND3 | ENST00000372991 |
| 44 | CCNG2 | ENST00000316355 |
| 45 | CCNT2 | ENST00000295238 |
| 46 | CCR7 | ENST00000246657 |
| 47 | CD37 | ENST00000323906 |
| 48 | CD93 | ENST00000246006 |
| 49 | CD97 | ENST00000358600 |
| 50 | CDIPT | ENST00000219789 |
| 51 | CEP170 | ENST00000612450 |

TABLE 19-continued

SEQUENCE ID NUMBERS, BIOMARKER GENE SYMBOLS AND ENSEMBL TRANSCRIPT IDS

| SEQ ID | Gene Symbol | Ensembl Transcript ID |
|---|---|---|
| 52 | CEP68 | ENST00000377990 |
| 53 | CHD3 | ENST00000358181 |
| 54 | CHMP1B | ENST00000526991 |
| 55 | CHMP7 | ENST00000397677 |
| 56 | CHST11 | ENST00000303694 |
| 57 | CIAPIN1 | ENST00000394391 |
| 58 | CLEC4A | ENST00000229332 |
| 59 | CLK4 | ENST00000316308 |
| 60 | CNPY3 | ENST00000372836 |
| 61 | CREB1 | ENST00000353267 |
| 62 | CREBBP | ENST00000262367 |
| 63 | CRLF3 | ENST00000324238 |
| 64 | CRTC3 | ENST00000268184 |
| 65 | CSAD | ENST00000267085 |
| 66 | CSF2RB | ENST00000403662 |
| 67 | CSNK1D | ENST00000314028 |
| 68 | CST3 | ENST00000376925 |
| 69 | CTBP2 | ENST00000337195 |
| 70 | CTDSP2 | ENST00000398073 |
| 71 | CUL1 | ENST00000325222 |
| 72 | CYLD | ENST00000311559 |
| 73 | CYTH4 | ENST00000248901 |
| 74 | DCP2 | ENST00000389063 |
| 75 | DDX60 | ENST00000393743 |
| 76 | DGCR2 | ENST00000263196 |
| 77 | DGKA | ENST00000331886 |
| 78 | DHX58 | ENST00000251642 |
| 79 | DIDO1 | ENST00000370371 |
| 80 | DOCK9 | ENST00000376460 |
| 81 | DOK3 | ENST00000357198 |
| 82 | DPEP2 | ENST00000393847 |
| 83 | DPF2 | ENST00000528416 |
| 84 | EIF2AK2 | ENST00000395127 |
| 85 | EIF3H | ENST00000521861 |
| 86 | EMR2 | ENST00000315576 |
| 87 | ERBB2IP | ENST00000380943 |
| 88 | ETS2 | ENST00000360938 |
| 89 | FAIM3 | ENST00000367091 |
| 90 | FAM134A | ENST00000430297 |
| 91 | FAM65B | ENST00000259698 |
| 92 | FBXO11 | ENST00000402508 |
| 93 | FBXO9 | ENST00000244426 |
| 94 | FCGRT | ENST00000426395 |
| 95 | FES | ENST00000328850 |
| 96 | FGR | ENST00000374005 |
| 97 | FLOT2 | ENST00000394908 |
| 98 | FNBP1 | ENST00000446176 |
| 99 | FOXJ2 | ENST00000162391 |
| 100 | FOXO1 | ENST00000379561 |
| 101 | FOXO3 | ENST00000406360 |
| 102 | FRY | ENST00000542859 |
| 103 | FYB | ENST00000505428 |
| 104 | GABARAP | ENST00000302386 |
| 105 | GCC2 | ENST00000309863 |
| 106 | GMIP | ENST00000203556 |
| 107 | GNA12 | ENST00000275364 |
| 108 | GNAQ | ENST00000286548 |
| 109 | GOLGA7 | ENST00000520817 |
| 110 | GPBP1L1 | ENST00000355105 |
| 111 | GPR97 | ENST00000333493 |
| 112 | GPS2 | ENST00000389167 |
| 113 | GPSM3 | ENST00000383269 |
| 114 | GRB2 | ENST00000316804 |
| 115 | GSK3B | ENST00000316626 |
| 116 | GYPC | ENST00000259254 |
| 117 | HAL | ENST00000261208 |
| 118 | HCK | ENST00000534862 |
| 119 | HERC5 | ENST00000264350 |
| 120 | HERC6 | ENST00000264346 |
| 121 | HGSNAT | ENST00000379644 |
| 122 | HHEX | ENST00000282728 |
| 123 | HIP1 | ENST00000336926 |
| 124 | HPCAL1 | ENST00000307845 |
| 125 | HPS1 | ENST00000325103 |
| 126 | ICAM3 | ENST00000160262 |
| 127 | IFI44 | ENST00000370747 |
| 128 | IFI6 | ENST00000361157 |
| 129 | IFIH1 | ENST00000263642 |
| 130 | IGSF6 | ENST00000268389 |
| 131 | IKBKB | ENST00000520810 |
| 132 | IL10RB | ENST00000290200 |
| 133 | IL13RA1 | ENST00000371666 |
| 134 | IL16 | ENST00000394652 |
| 135 | IL1RAP | ENST00000447382 |
| 136 | IL27RA | ENST00000263379 |
| 137 | IL4R | ENST00000395762 |
| 138 | IL6R | ENST00000368485 |
| 139 | IL6ST | ENST00000381298 |
| 140 | INPP5D | ENST00000359570 |
| 141 | IQSEC1 | ENST00000273221 |
| 142 | ISG15 | ENST00000379389 |
| 143 | ITGAX | ENST00000268296 |
| 144 | ITGB2 | ENST00000302347 |
| 145 | ITPKB | ENST00000429204 |
| 146 | ITSN2 | ENST00000355123 |
| 147 | JAK1 | ENST00000342505 |
| 148 | KBTBD2 | ENST00000304056 |
| 149 | KIAA0232 | ENST00000307659 |
| 150 | KIAA0247 | ENST00000342745 |
| 151 | KIAA0513 | ENST00000258180 |
| 152 | KLF3 | ENST00000261438 |
| 153 | KLF6 | ENST00000497571 |
| 154 | KLF7 | ENST00000309446 |
| 155 | KLHL2 | ENST00000226725 |
| 156 | LAP3 | ENST00000618908 |
| 157 | LAPTM5 | ENST00000294507 |
| 158 | LAT2 | ENST00000344995 |
| 159 | LCP2 | ENST00000046794 |
| 160 | LDLRAP1 | ENST00000374338 |
| 161 | LEF1 | ENST00000265165 |
| 162 | LILRA2 | ENST00000251376 |
| 163 | LILRB3 | ENST00000617251 |
| 164 | LIMK2 | ENST00000331728 |
| 165 | LPAR2 | ENST00000407877 |
| 166 | LPIN2 | ENST00000261596 |
| 167 | LRMP | ENST00000354454 |
| 168 | LRP10 | ENST00000359591 |
| 169 | LST1 | ENST00000376093 |
| 170 | LTB | ENST00000429299 |
| 171 | LYL1 | ENST00000264824 |
| 172 | LYN | ENST00000519728 |
| 173 | LYST | ENST00000389793 |
| 174 | MAML1 | ENST00000292599 |
| 175 | MANSC1 | ENST00000535902 |
| 176 | MAP1LC3B | ENST00000268607 |
| 177 | MAP3K11 | ENST00000309100 |
| 178 | MAP3K3 | ENST00000361733 |
| 179 | MAP3K5 | ENST00000359015 |
| 180 | MAP4K4 | ENST00000350198 |
| 181 | MAPK1 | ENST00000215832 |
| 182 | MAPK14 | ENST00000229795 |
| 183 | MAPRE2 | ENST00000300249 |
| 184 | MARCH7 | ENST00000259050 |
| 185 | MARCH8 | ENST00000319836 |
| 186 | MARK3 | ENST00000303622 |
| 187 | MAST3 | ENST00000262811 |
| 188 | MAX | ENST00000358664 |
| 189 | MBP | ENST00000359645 |
| 190 | MCTP2 | ENST00000357742 |
| 191 | MED13 | ENST00000397786 |
| 192 | MEF2A | ENST00000354410 |
| 193 | METTL3 | ENST00000298717 |
| 194 | MKLN1 | ENST00000352689 |
| 195 | MKRN1 | ENST00000255977 |
| 196 | MMP25 | ENST00000336577 |
| 197 | MORC3 | ENST00000400485 |
| 198 | MOSPD2 | ENST00000380492 |
| 199 | MPPE1 | ENST00000588072 |
| 200 | MSL1 | ENST00000579565 |
| 201 | MTMR3 | ENST00000401950 |

TABLE 19-continued

SEQUENCE ID NUMBERS, BIOMARKER GENE SYMBOLS AND ENSEMBL TRANSCRIPT IDS

| SEQ ID | Gene Symbol | Ensembl Transcript ID |
|---|---|---|
| 202 | MX1 | ENST00000398598 |
| 203 | MXI1 | ENST00000239007 |
| 204 | MYC | ENST00000613283 |
| 205 | N4BP1 | ENST00000262384 |
| 206 | NAB1 | ENST00000337386 |
| 207 | NACA | ENST00000356769 |
| 208 | NCBP2 | ENST00000321256 |
| 209 | NCOA1 | ENST00000348332 |
| 210 | NCOA4 | ENST00000585132 |
| 211 | NDE1 | ENST00000396354 |
| 212 | NDEL1 | ENST00000334527 |
| 213 | NDFIP1 | ENST00000253814 |
| 214 | NECAP2 | ENST00000337132 |
| 215 | NEK7 | ENST00000367385 |
| 216 | NFKB1 | ENST00000226574 |
| 217 | NFYA | ENST00000341376 |
| 218 | NLRP1 | ENST00000269280 |
| 219 | NOD2 | ENST00000300589 |
| 220 | NOSIP | ENST00000596358 |
| 221 | NPL | ENST00000367553 |
| 222 | NR3C1 | ENST00000394464 |
| 223 | NRBF2 | ENST00000277746 |
| 224 | NSUN3 | ENST00000314622 |
| 225 | NUMB | ENST00000557597 |
| 226 | OAS2 | ENST00000392583 |
| 227 | OASL | ENST00000257570 |
| 228 | OGFRL1 | ENST00000370435 |
| 229 | OSBPL11 | ENST00000296220 |
| 230 | OSBPL2 | ENST00000358053 |
| 231 | PACSIN2 | ENST00000403744 |
| 232 | PAFAH1B1 | ENST00000397195 |
| 233 | PARP12 | ENST00000263549 |
| 234 | PBX3 | ENST00000373489 |
| 235 | PCBP2 | ENST00000359462 |
| 236 | PCF11 | ENST00000298281 |
| 237 | PCNX | ENST00000304743 |
| 238 | PDCD6IP | ENST00000307296 |
| 239 | PDE3B | ENST00000282096 |
| 240 | PECAM1 | ENST00000563924 |
| 241 | PFDN5 | ENST00000551018 |
| 242 | PGS1 | ENST00000262764 |
| 243 | PHC2 | ENST00000373418 |
| 244 | PHF11 | ENST00000378319 |
| 245 | PHF2 | ENST00000359246 |
| 246 | PHF20 | ENST00000374012 |
| 247 | PHF20L1 | ENST00000395386 |
| 248 | PHF3 | ENST00000393387 |
| 249 | PIAS1 | ENST00000249636 |
| 250 | PIK3IP1 | ENST00000215912 |
| 251 | PINK1 | ENST00000321556 |
| 252 | PISD | ENST00000266095 |
| 253 | PITPNA | ENST00000313486 |
| 254 | PLEKHO1 | ENST00000369124 |
| 255 | PLEKHO2 | ENST00000323544 |
| 256 | PLXNC1 | ENST00000258526 |
| 257 | POLB | ENST00000265421 |
| 258 | POLD4 | ENST00000312419 |
| 259 | POLR1D | ENST00000302979 |
| 260 | PPARD | ENST00000360694 |
| 261 | PPM1F | ENST00000263212 |
| 262 | PPP1R11 | ENST0000448378 |
| 263 | PPP1R2 | ENST00000618156 |
| 264 | PPP2R5A | ENST00000261461 |
| 265 | PPP3R1 | ENST00000234310 |
| 266 | PPP4R1 | ENST00000400555 |
| 267 | PRKAA1 | ENST00000397128 |
| 268 | PRKAG2 | ENST00000287878 |
| 269 | PRKCD | ENST00000330452 |
| 270 | PRMT2 | ENST00000397638 |
| 271 | PRUNE | ENST00000271620 |
| 272 | PSAP | ENST00000394936 |
| 273 | PSEN1 | ENST00000324501 |
| 274 | PSTPIP1 | ENST00000558012 |
| 275 | PTAFR | ENST00000373857 |
| 276 | PTEN | ENST00000371953 |
| 277 | PTGER4 | ENST00000302472 |
| 278 | PTPN6 | ENST00000318974 |
| 279 | PTPRE | ENST00000254667 |
| 280 | PUM2 | ENST00000338086 |
| 281 | R3HDM2 | ENST00000358907 |
| 282 | RAB11FIP1 | ENST00000287263 |
| 283 | RAB14 | ENST00000373840 |
| 284 | RAB31 | ENST00000578921 |
| 285 | RAB4B | ENST00000357052 |
| 286 | RAB7A | ENST00000265062 |
| 287 | RAF1 | ENST00000251849 |
| 288 | RALB | ENST00000272519 |
| 289 | RARA | ENST00000254066 |
| 290 | RASSF2 | ENST00000379400 |
| 291 | RBM23 | ENST00000399922 |
| 292 | RBMS1 | ENST00000348849 |
| 293 | RC3H2 | ENST00000423239 |
| 294 | RERE | ENST00000337907 |
| 295 | RGS14 | ENST00000408923 |
| 296 | RGS19 | ENST00000395042 |
| 297 | RHOG | ENST00000351018 |
| 298 | RIN3 | ENST00000216487 |
| 299 | RNASET2 | ENST00000508775 |
| 300 | RNF130 | ENST00000521389 |
| 301 | RNF141 | ENST00000265981 |
| 302 | RNF146 | ENST00000608991 |
| 303 | RNF19B | ENST00000373456 |
| 304 | RPL10A | ENST00000322203 |
| 305 | RPL22 | ENST00000234875 |
| 306 | RPS6KA1 | ENST00000374168 |
| 307 | RPS6KA3 | ENST00000379565 |
| 308 | RSAD2 | ENST00000382040 |
| 309 | RTN3 | ENST00000537981 |
| 310 | RTP4 | ENST00000259030 |
| 311 | RXRA | ENST00000481739 |
| 312 | RYBP | ENST00000477973 |
| 313 | SAFB2 | ENST00000252542 |
| 314 | SATB1 | ENST00000338745 |
| 315 | SEC62 | ENST00000337002 |
| 316 | SEMA4D | ENST00000438547 |
| 317 | SERINC3 | ENST00000342374 |
| 318 | SERINC5 | ENST00000509193 |
| 319 | SERTAD2 | ENST00000313349 |
| 320 | SESN1 | ENST00000436639 |
| 321 | SETD2 | ENST00000409792 |
| 322 | SH2B3 | ENST00000341259 |
| 323 | SH2D3C | ENST00000373277 |
| 324 | SIRPA | ENST00000356025 |
| 325 | SIRPB1 | ENST00000381605 |
| 326 | SLCO3A1 | ENST00000318445 |
| 327 | SMAD4 | ENST00000342988 |
| 328 | SNN | ENST00000329565 |
| 329 | SNRK | ENST00000296088 |
| 330 | SNX27 | ENST00000368843 |
| 331 | SOAT1 | ENST00000367619 |
| 332 | SORL1 | ENST00000260197 |
| 333 | SOS2 | ENST00000216373 |
| 334 | SP3 | ENST00000310015 |
| 335 | SSBP2 | ENST00000320672 |
| 336 | SSFA2 | ENST00000320370 |
| 337 | ST13 | ENST00000216218 |
| 338 | ST3GAL1 | ENST00000521180 |
| 339 | STAM2 | ENST00000263904 |
| 340 | STAT1 | ENST00000361099 |
| 341 | STAT5A | ENST00000345506 |
| 342 | STAT5B | ENST00000293328 |
| 343 | STK38L | ENST00000389032 |
| 344 | STX10 | ENST00000587230 |
| 345 | STX3 | ENST00000337979 |
| 346 | STX6 | ENST00000258301 |
| 347 | SYPL1 | ENST00000011473 |
| 348 | TAP1 | ENST00000428324 |
| 349 | TFE3 | ENST00000315869 |
| 350 | TFEB | ENST00000230323 |
| 351 | TGFBI | ENST00000442011 |

TABLE 19-continued

SEQUENCE ID NUMBERS, BIOMARKER GENE
SYMBOLS AND ENSEMBL TRANSCRIPT IDS

| SEQ ID | Gene Symbol | Ensembl Transcript ID |
|---|---|---|
| 352 | TGFBR2 | ENST00000295754 |
| 353 | TGOLN2 | ENST00000377386 |
| 354 | TIAM1 | ENST00000286827 |
| 355 | TLE3 | ENST00000558939 |
| 356 | TLE4 | ENST00000376552 |
| 357 | TLR2 | ENST00000260010 |
| 358 | TM2D3 | ENST00000347970 |
| 359 | TMBIM1 | ENST00000258412 |
| 360 | TMEM127 | ENST00000258439 |
| 361 | TMEM204 | ENST00000566264 |
| 362 | TNFRSF1A | ENST00000162749 |
| 363 | TNFSF13 | ENST00000338784 |
| 364 | TNIP1 | ENST00000521591 |
| 365 | TNK2 | ENST00000333602 |
| 366 | TNRC6B | ENST00000335727 |
| 367 | TOPORS | ENST00000360538 |
| 368 | TRAK1 | ENST00000341421 |
| 369 | TREM1 | ENST00000244709 |
| 370 | TRIB2 | ENST00000155926 |
| 371 | TRIM8 | ENST00000302424 |
| 372 | TRIOBP | ENST00000403663 |
| 373 | TSC22D3 | ENST00000372397 |
| 374 | TYK2 | ENST00000525621 |
| 375 | TYROBP | ENST00000262629 |
| 376 | UBE2D2 | ENST00000398733 |
| 377 | UBE2L6 | ENST00000287156 |
| 378 | UBN1 | ENST00000262376 |
| 379 | UBQLN2 | ENST00000338222 |
| 380 | UBXN2B | ENST00000399598 |
| 381 | USP10 | ENST00000219473 |
| 382 | USP15 | ENST00000353364 |
| 383 | USP18 | ENST00000215794 |
| 384 | USP4 | ENST00000265560 |
| 385 | UTP14A | ENST00000394422 |
| 386 | VAMP3 | ENST00000054666 |
| 387 | VAV3 | ENST00000370056 |
| 388 | VEZF1 | ENST00000581208 |
| 389 | VPS8 | ENST00000436792 |
| 390 | WASF2 | ENST00000618852 |
| 391 | WBP2 | ENST00000254806 |
| 392 | WDR37 | ENST00000263150 |
| 393 | WDR47 | ENST00000369965 |
| 394 | XAF1 | ENST00000361842 |
| 395 | XPC | ENST00000285021 |
| 396 | XPO6 | ENST00000304658 |
| 397 | YPEL5 | ENST00000261353 |
| 398 | YTHDF3 | ENST00000539294 |
| 399 | ZBP1 | ENST00000371173 |
| 400 | ZBTB18 | ENST00000622512 |
| 401 | ZC3HAV1 | ENST00000242351 |
| 402 | ZDHHC17 | ENST00000426126 |
| 403 | ZDHHC18 | ENST00000374142 |
| 404 | ZFAND5 | ENST00000376960 |
| 405 | ZFC3H1 | ENST00000378743 |
| 406 | ZFYVE16 | ENST00000338008 |
| 407 | ZMIZ1 | ENST00000334512 |
| 408 | ZNF143 | ENST00000396602 |
| 409 | ZNF148 | ENST00000360647 |
| 410 | ZNF274 | ENST00000424679 |
| 411 | ZNF292 | ENST00000369577 |
| 412 | ZXDC | ENST00000389709 |
| 413 | ZYX | ENST00000322764 |
| 414 | TMEM62 | ENST00000260403 |
| 415 | CD38 | ENST00000226279 |

TABLE 20

SEQUENCE ID NUMBERS AND
GENBANK ACCESSION NUMBERS

| SEQ ID | GenBank Accession |
|---|---|
| 416 | NP_000654 |
| 417 | NP_008942 |
| 418 | NP_005461 |
| 419 | NP_002304 |
| 420 | NP_001598 |
| 421 | NP_036419 |
| 422 | NP_004293 |
| 423 | NP_001614 |
| 424 | NP_000373 |
| 425 | NP_060174 |
| 426 | NP_001628 |
| 427 | NP_061916 |
| 428 | NP_001633 |
| 429 | NP_056057 |
| 430 | NP_060930 |
| 431 | NP_055697 |
| 432 | NP_055886 |
| 433 | NP_004714 |
| 434 | NP_004032 |
| 435 | NP_004304 |
| 436 | NP_060952 |
| 437 | NP_060022 |
| 438 | NP_079273 |
| 439 | NP_000042 |
| 440 | NP_001684 |
| 441 | NP_001177 |
| 442 | NP_060339 |
| 443 | NP_038478 |
| 444 | NP_000624 |
| 445 | NP_001073894 |
| 446 | NP_060063 |
| 447 | NP_055392 |
| 448 | NP_055114 |
| 449 | NP_001722 |
| 450 | NP_060851 |
| 451 | NP_001013671 |
| 452 | NP_065130 |
| 453 | NP_001213 |
| 454 | NP_006358 |
| 455 | NP_031385 |
| 456 | NP_001219 |
| 457 | NP_783640 |
| 458 | NP_001751 |
| 459 | NP_004345 |
| 460 | NP_001232 |
| 461 | NP_001829 |
| 462 | NP_001765 |
| 463 | NP_036204 |
| 464 | NP_001775 |
| 465 | NP_006310 |
| 466 | NP_055627 |
| 467 | NP_055962 |
| 468 | NP_005843 |
| 469 | NP_065145 |
| 470 | NP_689485 |
| 471 | NP_060883 |
| 472 | NP_064709 |
| 473 | NP_057268 |
| 474 | NP_065717 |
| 475 | NP_006577 |
| 476 | NP_004370 |
| 477 | NP_004371 |
| 478 | NP_057070 |
| 479 | NP_073606 |
| 480 | NP_057073 |
| 481 | NP_000386 |
| 482 | NP_001884 |
| 483 | NP_000090 |
| 484 | NP_001320 |
| 485 | NP_005721 |
| 486 | NP_003583 |
| 487 | NP_056062 |
| 488 | NP_037517 |
| 489 | NP_689837 |
| 490 | NP_060101 |

TABLE 20-continued

SEQUENCE ID NUMBERS AND GENBANK ACCESSION NUMBERS

| SEQ ID | GenBank Accession |
|---|---|
| 491 | NP_005128 |
| 492 | NP_001336 |
| 493 | NP_077024 |
| 494 | NP_071388 |
| 495 | NP_056111 |
| 496 | NP_079148 |
| 497 | NP_071750 |
| 498 | NP_006259 |
| 499 | NP_002750 |
| 500 | NP_003747 |
| 501 | NP_038475 |
| 502 | NP_061165 |
| 503 | NP_005230 |
| 504 | NP_005440 |
| 505 | NP_077269 |
| 506 | NP_055537 |
| 507 | NP_079409 |
| 508 | NP_036479 |
| 509 | NP_004098 |
| 510 | NP_001996 |
| 511 | NP_005239 |
| 512 | NP_004466 |
| 513 | NP_055848 |
| 514 | NP_060886 |
| 515 | NP_002006 |
| 516 | NP_001446 |
| 517 | NP_075463 |
| 518 | NP_001456 |
| 519 | NP_009209 |
| 520 | NP_852118 |
| 521 | NP_057657 |
| 522 | NP_031379 |
| 523 | NP_002063 |
| 524 | NP_057183 |
| 525 | NP_067652 |
| 526 | NP_740746 |
| 527 | NP_004480 |
| 528 | NP_071390 |
| 529 | NP_002077 |
| 530 | NP_002084 |
| 531 | NP_002092 |
| 532 | NP_002099 |
| 533 | NP_002101 |
| 534 | NP_057407 |
| 535 | NP_060382 |
| 536 | NP_689632 |
| 537 | NP_002720 |
| 538 | NP_005329 |
| 539 | NP_002140 |
| 540 | NP_000186 |
| 541 | NP_002153 |
| 542 | NP_006408 |
| 543 | NP_002029 |
| 544 | NP_071451 |
| 545 | NP_005840 |
| 546 | NP_001547 |
| 547 | NP_000619 |
| 548 | NP_001551 |
| 549 | NP_004504 |
| 550 | NP_002173 |
| 551 | NP_004834 |
| 552 | NP_000409 |
| 553 | NP_000556 |
| 554 | NP_002175 |
| 555 | NP_005532 |
| 556 | NP_055684 |
| 557 | NP_005092 |
| 558 | NP_000878 |
| 559 | NP_000202 |
| 560 | NP_002212 |
| 561 | NP_006268 |
| 562 | NP_002218 |
| 563 | NP_056298 |
| 564 | NP_055558 |
| 565 | NP_055549 |
| 566 | NP_055547 |
| 567 | NP_057615 |
| 568 | NP_001291 |
| 569 | NP_003700 |
| 570 | NP_009177 |
| 571 | NP_056991 |
| 572 | NP_006753 |
| 573 | NP_054865 |
| 574 | NP_005556 |
| 575 | NP_056442 |
| 576 | NP_057353 |
| 577 | NP_006857 |
| 578 | NP_006855 |
| 579 | NP_005560 |
| 580 | NP_004711 |
| 581 | NP_055461 |
| 582 | NP_006143 |
| 583 | NP_054764 |
| 584 | NP_009092 |
| 585 | NP_002332 |
| 586 | NP_005574 |
| 587 | NP_002341 |
| 588 | NP_000072 |
| 589 | NP_055572 |
| 590 | NP_060520 |
| 591 | NP_073729 |
| 592 | NP_002410 |
| 593 | NP_002392 |
| 594 | NP_005914 |
| 595 | NP_004825 |
| 596 | NP_002736 |
| 597 | NP_001306 |
| 598 | NP_055083 |
| 599 | NP_073737 |
| 600 | NP_659458 |
| 601 | NP_002367 |
| 602 | NP_055831 |
| 603 | NP_002373 |
| 604 | NP_002376 |
| 605 | NP_060819 |
| 606 | NP_005112 |
| 607 | NP_005578 |
| 608 | NP_062826 |
| 609 | NP_037387 |
| 610 | NP_038474 |
| 611 | NP_071913 |
| 612 | NP_056173 |
| 613 | NP_689794 |
| 614 | NP_075563 |
| 615 | NP_001012241 |
| 616 | NP_066576 |
| 617 | NP_002453 |
| 618 | NP_005953 |
| 619 | NP_002458 |
| 620 | NP_694574 |
| 621 | NP_005957 |
| 622 | NP_001106673 |
| 623 | NP_031388 |
| 624 | NP_003734 |
| 625 | NP_005428 |
| 626 | NP_060138 |
| 627 | NP_110435 |
| 628 | NP_085048 |
| 629 | NP_060560 |
| 630 | NP_598001 |
| 631 | NP_003989 |
| 632 | NP_002496 |
| 633 | NP_055737 |
| 634 | NP_071445 |
| 635 | NP_057037 |
| 636 | NP_110396 |
| 637 | NP_000167 |
| 638 | NP_110386 |
| 639 | NP_071355 |
| 640 | NP_003735 |

TABLE 20-continued

SEQUENCE ID NUMBERS AND
GENBANK ACCESSION NUMBERS

| SEQ ID | GenBank Accession |
|---|---|
| 641 | NP_002526 |
| 642 | NP_003724 |
| 643 | NP_078852 |
| 644 | NP_073613 |
| 645 | NP_055650 |
| 646 | NP_009160 |
| 647 | NP_000421 |
| 648 | NP_073587 |
| 649 | NP_006186 |
| 650 | NP_005007 |
| 651 | NP_056969 |
| 652 | NP_055797 |
| 653 | NP_037506 |
| 654 | NP_000913 |
| 655 | NP_000433 |
| 656 | NP_002615 |
| 657 | NP_077733 |
| 658 | NP_004418 |
| 659 | NP_001035533 |
| 660 | NP_005383 |
| 661 | NP_057520 |
| 662 | NP_057102 |
| 663 | NP_055968 |
| 664 | NP_057250 |
| 665 | NP_443112 |
| 666 | NP_115785 |
| 667 | NP_055153 |
| 668 | NP_006215 |
| 669 | NP_057358 |
| 670 | NP_079477 |
| 671 | NP_005752 |
| 672 | NP_002681 |
| 673 | NP_066996 |
| 674 | NP_057056 |
| 675 | NP_006229 |
| 676 | NP_055449 |
| 677 | NP_068778 |
| 678 | NP_006232 |
| 679 | NP_006234 |
| 680 | NP_000936 |
| 681 | NP_005125 |
| 682 | NP_006242 |
| 683 | NP_057287 |
| 684 | NP_006245 |
| 685 | NP_001526 |
| 686 | NP_067045 |
| 687 | NP_002769 |
| 688 | NP_000012 |
| 689 | NP_003969 |
| 690 | NP_000943 |
| 691 | NP_000305 |
| 692 | NP_000949 |
| 693 | NP_002822 |
| 694 | NP_006495 |
| 695 | NP_056132 |
| 696 | NP_055740 |
| 697 | NP_079427 |
| 698 | NP_057406 |
| 699 | NP_006859 |
| 700 | NP_057238 |
| 701 | NP_004628 |
| 702 | NP_002871 |
| 703 | NP_002872 |
| 704 | NP_000955 |
| 705 | NP_055552 |
| 706 | NP_060577 |
| 707 | NP_002888 |
| 708 | NP_061323 |
| 709 | NP_036234 |
| 710 | NP_006471 |
| 711 | NP_005864 |
| 712 | NP_001656 |
| 713 | NP_079108 |
| 714 | NP_003721 |
| 715 | NP_060904 |

TABLE 20-continued

SEQUENCE ID NUMBERS AND
GENBANK ACCESSION NUMBERS

| SEQ ID | GenBank Accession |
|---|---|
| 716 | NP_057506 |
| 717 | NP_112225 |
| 718 | NP_699172 |
| 719 | NP_009035 |
| 720 | NP_000974 |
| 721 | NP_002944 |
| 722 | NP_004577 |
| 723 | NP_542388 |
| 724 | NP_006045 |
| 725 | NP_071430 |
| 726 | NP_002948 |
| 727 | NP_036366 |
| 728 | NP_055464 |
| 729 | NP_002962 |
| 730 | NP_003253 |
| 731 | NP_006369 |
| 732 | NP_006802 |
| 733 | NP_840060 |
| 734 | NP_055570 |
| 735 | NP_055269 |
| 736 | NP_054878 |
| 737 | NP_005466 |
| 738 | NP_005480 |
| 739 | NP_542970 |
| 740 | NP_006056 |
| 741 | NP_037404 |
| 742 | NP_005350 |
| 743 | NP_003489 |
| 744 | NP_060189 |
| 745 | NP_112180 |
| 746 | NP_003092 |
| 747 | NP_003096 |
| 748 | NP_008870 |
| 749 | NP_003102 |
| 750 | NP_036578 |
| 751 | NP_006742 |
| 752 | NP_003923 |
| 753 | NP_003024 |
| 754 | NP_005834 |
| 755 | NP_009330 |
| 756 | NP_003143 |
| 757 | NP_036580 |
| 758 | NP_055815 |
| 759 | NP_003756 |
| 760 | NP_004168 |
| 761 | NP_005810 |
| 762 | NP_006745 |
| 763 | NP_000584 |
| 764 | NP_006512 |
| 765 | NP_009093 |
| 766 | NP_000349 |
| 767 | NP_003233 |
| 768 | NP_006455 |
| 769 | NP_003244 |
| 770 | NP_005069 |
| 771 | NP_008936 |
| 772 | NP_003255 |
| 773 | NP_079417 |
| 774 | NP_071435 |
| 775 | NP_060319 |
| 776 | NP_078876 |
| 777 | NP_001056 |
| 778 | NP_003799 |
| 779 | NP_006049 |
| 780 | NP_005772 |
| 781 | NP_055903 |
| 782 | NP_005793 |
| 783 | NP_055780 |
| 784 | NP_061113 |
| 785 | NP_067675 |
| 786 | NP_112174 |
| 787 | NP_008963 |
| 788 | NP_004080 |
| 789 | NP_003322 |
| 790 | NP_003323 |

TABLE 20-continued

SEQUENCE ID NUMBERS AND GENBANK ACCESSION NUMBERS

| SEQ ID | GenBank Accession |
|---|---|
| 791 | NP_003330 |
| 792 | NP_004214 |
| 793 | NP_001072982 |
| 794 | NP_038472 |
| 795 | NP_001071087 |
| 796 | NP_005144 |
| 797 | NP_006304 |
| 798 | NP_059110 |
| 799 | NP_003354 |
| 800 | NP_006640 |
| 801 | NP_004772 |
| 802 | NP_006104 |
| 803 | NP_009077 |
| 804 | NP_056118 |
| 805 | NP_008921 |
| 806 | NP_036610 |
| 807 | NP_054742 |
| 808 | NP_055784 |
| 809 | NP_059993 |
| 810 | NP_004619 |
| 811 | NP_055986 |
| 812 | NP_057145 |
| 813 | NP_689971 |
| 814 | NP_110403 |
| 815 | NP_006343 |
| 816 | NP_064504 |
| 817 | NP_056151 |
| 818 | NP_115659 |
| 819 | NP_005998 |
| 820 | NP_659419 |
| 821 | NP_055548 |
| 822 | NP_065071 |
| 823 | NP_003433 |
| 824 | NP_068799 |
| 825 | NP_057408 |
| 826 | NP_055836 |
| 827 | NP_079388 |
| 828 | NP_003452 |
| 829 | NP_079232 |
| 830 | NP_001766 |

SEQUENCE LISTING

The patent contains a lengthy sequence listing. A copy of the sequence listing is available in electronic form from the USPTO web site (https://seqdata.uspto.gov/?pageRequest=docDetail&DocID=US11884978B2). An electronic copy of the sequence listing will also be available from the USPTO upon request and payment of the fee set forth in 37 CFR 1.19(b)(3).

What is claimed is:

1. A method for treating a virus-associated inflammatory response syndrome (VaSIRS) in a human subject, wherein the human subject has at least one clinical sign of SIRS, the method comprising:
   (1) in a blood sample taken from the subject, measuring an expression level for a polynucleotide expression product of ISG15 and an expression level for a polynucleotide expression product of IL16;
   (2) determining a derived biomarker value for the blood sample, wherein the derived biomarker value being a ratio of the expression level of the polynucleotide expression product of ISG15 to the expression level of the polynucleotide expression product of IL16;
   (3) determining whether the derived biomarker value for the blood sample is greater than a reference derived biomarker value determined from expression levels for the polynucleotide expression product of ISG15 and the expression levels for the polynucleotide expression product of IL16 in samples from non-VaSIRS control subjects; and
   (4) if the derived biomarker value for the blood sample is greater than the reference derived biomarker value, administering to the subject an effective amount of a VaSIRS therapeutic agent.

2. The method of claim 1, wherein
the derived biomarker value of (2) is a first derived biomarker value, the method further comprising:
   (5) in the blood sample taken from the subject, measuring an expression level for an expression product of OASL and an expression level for an expression product of CD97;
   (6) determining a second derived biomarker value for the blood sample, the second derived biomarker value being a ratio of the expression level of the expression product of OASL to the expression level of the expression product of CD97;
   (7) combining the first derived biomarker value and the second derived biomarker value into a combined biomarker value;
   (8) determining whether the combined biomarker value for the blood sample is greater than a reference combined biomarker value determined from expression levels for a polynucleotide expression product of ISG15, a polynucleotide expression product of IL16, an expression product of OASL, and an expression product of CD97 in samples from non-VaSIRS control subjects; and
   (4) if the combined biomarker value for the blood sample is greater than the reference combined biomarker value, administering to the subject an effective amount of a VaSIRS therapeutic agent.

3. The method of claim 2, comprising combining the derived biomarker values using a combining function, wherein the combining function is at least one of: an additive model; a linear model; a support vector machine; a neural network model; a random forest model; a regression model;

a genetic algorithm; an annealing algorithm; a weighted sum; a nearest neighbor model; and a probabilistic model.

4. The method of claim 1, wherein the virus associated with the VaSIRS is selected from any one of Baltimore virus classification Groups I, II, III, IV, V, VI and VII, which is capable of inducing at least one of the clinical signs of SIRS.

5. The method of claim 1, wherein the VaSIRS therapeutic agent comprises an anti-viral agent.

6. The method of claim 5, wherein the anti-viral agent is selected from the group consisting of abacavir, acyclovir, acyclovir, adefovir, amantadine, amprenavir, ampligen, arbidol, asunaprevir, atazanavir, atripla, boceprevir, cidofovir, combivir, complera, daclatasvir, darunavir, delavirdine, didanosine, docosanol, dolutegravir, edoxudine, efavirenz, emtricitabine, enfuvirtide, entecavir, famciclovir, fomivirsen, fosamprenavir, foscarnet, fosfonet, ganciclovir, ibacitabine, immunovir, idoxuridine, imiquimod, indinavir, inosine, interferon type III, interferon type II, interferon type I, lamivudine, lopinavir, loviride, maraviroc, moroxydine, methisazone, nelfinavir, nevirapine, nexavir, neuraminidase blocking agents, oseltamivir, peginterferon alfa-2a, penciclovir, peramivir, pleconaril, podofilox, podophyllin, podophyllotoxin, raltegravir, monoclonal antibody respigams, ribavirin, inhaled rhibovirons, rimantadine, ritonavir, pyrimidine, saquinavir, stavudine, stribild, tenofovir, tenofovir disoproxil, tenofovir alafenamide fumarate (TAF), tipranavir, trifluridine, trizivir, tromantadine, truvada, valaciclovir, valganciclovir, vicriviroc, vidarabine, viperin, viramidine, zalcitabine, zanamivir, zidovudine, or salts and combinations thereof.

7. The method of claim 1, wherein the VaSIRS therapeutic agent is administered in concert with an adjunctive or palliative therapy.

8. The method of claim 7, wherein the adjunctive or palliative therapy is to increase oxygen supply to major organs, increase blood flow to major organs or to reduce the inflammatory response.

9. The method of claim 7, wherein the adjunctive or palliative therapy is selected from the group consisting of non-steroidal-anti-inflammatory drugs (NSAIDs), intravenous saline and oxygen.

10. The method of claim 4, wherein the virus is from a family selected from the group consisting of Reoviridae, Retroviridae, Rhinoviridae, Herpesviridae, Poxviridae, Paramyxoviridae, Orthomyxoviridae, Parvoviridae, Flaviviridae and Circoviridae.

11. The method of claim 4, wherein the virus is selected from the group consisting of Adenovirus, BK virus, Circovirus, Coronavirus, Cytomegalovirus, Dengue, Enterovirus, Hepatitis B, Hepatitis C, Hepatitis E, Herpes virus, Human Immunodeficiency Virus (HIV), Influenza, Lassa, Lymphocytic Choriomeningitis virus, Marburg virus, Measles, Metapneumovirus, Parainfluenza virus 3, Respiratory Syncytial Virus (RSV) and Rhinovirus.

12. The method of claim 4, wherein the virus is Influenza virus, Lassa virus, Cytomegalovirus or Dengue virus.

13. The method of claim 1, wherein the blood sample is a peripheral blood sample.

* * * * *